US012810636B2

(12) United States Patent

Comiter et al.

(10) Patent No.: US 12,810,636 B2

(45) Date of Patent: Nov. 24, 2026

(54) LIVE-CELL LABEL-FREE PREDICTION OF SINGLE-CELL OMICS PROFILES BY MICROSCOPY

(71) Applicants: The Broad Institute, Inc., Cambridge, MA (US); The General Hospital Corporation, Boston, MA (US); MASSACHUSETTS INSTITUTE OF TECHNOLOGY, Cambridge, MA (US)

(72) Inventors: Charles Comiter, Cambridge, MA (US); Jian Shu, Boston, MA (US); Aviv Regev, Cambridge, MA (US); Koseki Kobayashi-Kirschvink, Cambridge, MA (US); Tommaso Biancalani, Cambridge, MA (US)

(73) Assignees: The Broad Institute, Inc., Cambridge, MA (US); General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 221 days.

(21) Appl. No.: 18/664,872

(22) Filed: May 15, 2024

(65) Prior Publication Data

US 2024/0371184 A1 Nov. 7, 2024

Related U.S. Application Data

(63) Continuation of application No. PCT/US2022/079989, filed on Nov. 16, 2022.

(Continued)

(51) Int. Cl.

*G06V 20/69* (2022.01)
*G06V 10/774* (2022.01)

(Continued)

(52) U.S. Cl.

CPC .......... *G06V 20/698* (2022.01); *G06V 10/774* (2022.01); *G06V 10/82* (2022.01); *G16B 25/10* (2019.02); *G16B 40/20* (2019.02)

(58) Field of Classification Search

CPC .... G06V 20/698; G06V 10/774; G06V 10/82; G16B 25/10; G16B 40/20; G06N 3/0455;

(Continued)

(56) References Cited

U.S. PATENT DOCUMENTS 6,479,626 B1 11/2002 Kim et al.
6,534,261 B1 3/2003 Cox et al.

(Continued)

FOREIGN PATENT DOCUMENTS

WO WO-2014/093622 A2 6/2014
WO WO-2014/210353 A2 12/2014

(Continued)

OTHER PUBLICATIONS

Shao et al, ("scDeepSort: a pre-trained cell-type annotation method for single-cell transcriptomics using deep learning with a weighted graph neural network", Nucleic acids research 2021, vol. 49, No. 21; Sep. 9, 2021) (Year: 2021).*

(Continued)

*Primary Examiner* — Amara Abdi

(74) *Attorney, Agent, or Firm* — Sunit Talapatra; Foley & Lardner LLP

(57) ABSTRACT

Computer-implemented methods, computer program products, and systems determine an omics profiles of a cell using microscopy imaging data. In one aspect, a computer-implemented method determines an omics profiles of a cell using microscopy imaging data by a) receiving microscopy imaging data of a cell or a population of cells; b) determining a targeted expression profile of a set of target genes from the microscopy imaging data using a first machine learning (Continued)

200 model, the target genes identifying a cell type or cell state of interest; and c) determining a single-cell omics profile for the population of cells using a second machine learning algorithm model. The targeted expression profile and a reference single-cell RNA-seq data set are used as inputs for the second machine learning model. Computer-implemented methods, computer program products, and systems described herein also provide for determining single-cell omics profile from microscopy, such as Raman microscopy, or expression profiles, such as H&E stains.

20 Claims, 94 Drawing Sheets

Specification includes a Sequence Listing.

Related U.S. Application Data

(60) Provisional application No. 63/347,496, filed on May 31, 2022, provisional application No. 63/280,112, filed on Nov. 16, 2021.

(51) Int. Cl.
*G06V 10/82* (2022.01)
*G16B 25/10* (2019.01)
*G16B 40/20* (2019.01)

(58) Field of Classification Search
CPC .... G06N 3/0464; G06N 3/0475; G06N 3/088; G06N 3/094; G06N 5/01; G06N 20/20; G16H 20/10; G16H 20/60; G16H 30/20; G16H 30/40; G16H 40/67; G16H 50/20; G16H 50/30; G16H 50/70
See application file for complete search history.

(56) References Cited

U.S. PATENT DOCUMENTS

| | | | |
|---|---|---|---|
| 6,746,838 | B1 | 6/2004 | Choo et al. |
| 6,794,136 | B1 | 9/2004 | Eisenberg et al. |
| 6,866,997 | B1 | 3/2005 | Choo et al. |
| 6,933,113 | B2 | 8/2005 | Case et al. |
| 6,979,539 | B2 | 12/2005 | Cox et al. |
| 7,013,219 | B2 | 3/2006 | Case et al. |
| 7,030,215 | B2 | 4/2006 | Liu et al. |
| 7,241,573 | B2 | 7/2007 | Choo et al. |
| 7,241,574 | B2 | 7/2007 | Choo et al. |
| 7,585,849 | B2 | 9/2009 | Liu et al. |
| 8,021,867 | B2 | 9/2011 | Smith et al. |
| 8,119,361 | B2 | 2/2012 | Smith et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 9,708,648 | B2 | 7/2017 | Dekker et al. |
| 10,059,990 | B2 | 8/2018 | Boyden et al. |
| 10,851,358 | B2 | 12/2020 | Jantz et al. |
| 11,001,829 | B2 | 5/2021 | Zhang et al. |
| 11,214,797 | B2 | 1/2022 | Regev et al. |
| 2003/0147558 | A1 | 8/2003 | Loui et al. |
| 2009/0263002 | A1* | 10/2009 | Cremer .................. B82Y 20/00 382/133 |
| 2010/0310531 | A1 | 12/2010 | Wagner et al. |
| 2013/0296535 | A1 | 11/2013 | Church et al. |
| 2016/0060691 | A1 | 3/2016 | Giresi et al. |
| 2016/0208323 | A1 | 7/2016 | Bernstein et al. |
| 2017/0148226 | A1 | 5/2017 | Zhang et al. |
| 2017/0321251 | A1 | 11/2017 | Nolan |
| 2017/0329892 | A1 | 11/2017 | Fan et al. |
| 2017/0362649 | A1 | 12/2017 | Lieberman-Aiden et al. |
| 2018/0057810 | A1 | 3/2018 | Zhang et al. |
| 2018/0245154 | A1* | 8/2018 | Tsalik .................. C12Q 1/6883 |
| 2018/0320224 | A1 | 11/2018 | Gaublomme et al. |
| 2018/0340939 | A1 | 11/2018 | Gaublomme et al. |
| 2019/0285644 | A1 | 9/2019 | Regev et al. |
| 2020/0152289 | A1 | 5/2020 | Cleary et al. |
| 2020/0239544 | A1 | 7/2020 | Jantz et al. |
| 2020/0248255 | A1 | 8/2020 | Buenrostro et al. |
| 2020/0283843 | A1 | 9/2020 | Regev et al. |
| 2021/0366577 | A1* | 11/2021 | Koller .................... G16B 40/20 |
| 2023/0026291 | A1* | 1/2023 | Meade ................... G16H 50/30 |
| 2023/0257587 | A1* | 8/2023 | Mao ..................... C07D 487/14 548/426 |

FOREIGN PATENT DOCUMENTS

| | | | |
|---|---|---|---|
| WO | WO-2016/040476 | A1 | 3/2016 |
| WO | WO-2016/168584 | A1 | 10/2016 |
| WO | WO-2017/156336 | A1 | 9/2017 |
| WO | WO-2017/164936 | A1 | 9/2017 |
| WO | WO-2019/094984 | A1 | 5/2019 |
| WO | WO-2020/033601 | A1 | 2/2020 |
| WO | WO-2020/047005 | A1 | 3/2020 |
| WO | WO-2020/047007 | A2 | 3/2020 |
| WO | WO-2020/077236 | A1 | 4/2020 |
| WO | WO-2020/123317 | A2 | 6/2020 |
| WO | WO-2020/160044 | A1 | 8/2020 |
| WO | WO-2020/176788 | A1 | 9/2020 |
| WO | WO-2020/190509 | A9 | 9/2020 |
| WO | WO-2020/206231 | A1 | 10/2020 |
| WO | WO-2021/041922 | A1 | 3/2021 |

OTHER PUBLICATIONS

Chlis et al, ("Predicting single-cell gene expression profiles of imaging flow cytometry data with machine learning", Nucleic Acids Research, 2020, vol. 48, No. 20, pp. 11335-11346, Oct. 20, 2020) (Year: 2020).*

Arisdakessian et al, ("DeepImpute: an accurate, fast, and scalable deep neural network method to impute single-cell RNA-seq data", Genome Biology 2019, pp. 1-14) (Year: 2019).*

Wu et al, ("BABEL enables cross-modality translation between multiomic profiles at single-cell resolution", PNAS 2021 vol. 118 No. 15, pp. 1-11), (Year: 2021).*

Satija et al, ("Spatial reconstruction of single-cell gene expression data", Nature Biotechnology, vol. 33, No. 5, May 2015) (Year: 2015).*

Achim et al., "High-Throughput Spatial Mapping of Single-Cell RNA-Seq Data to Tissue of Origin," Nature Biotechnology, May 2015, vol. 33, No. 5 (pp. 503-509).

Ackloo et al., "Chemical probes targeting epigenetic proteins: Applications beyond oncology," Epigenetics, 2017, vol. 12, No. 5 (pp. 378-400).

Adamson et al., "A Multiplexed Single-Cell CRISPR Screening Platform Enables Systematic Dissection of the Unfolded Protein Response," Cell, Dec. 15, 2016, vol. 167 (pp. 1867-1882) (38 pages).

Adhikari et al., "Photothermal Microscopy: Imaging the Optical Absorption of Single Nanoparticles and Single Molecules," ACS Nano, 2020, vol. 14 (pp. 16414-16445).

Ahn et al., "Introduction to Single-Cell DNA Methylation Profiling Methods," 2021, vol. 11, No. 7 (20 pages).

Al et al., "Multispectral Optoacoustic Imaging of Dynamic Redox Correlation and Pathophysiological Progression Utilizing Upconversion Nanoprobes," Nature Communications, 2019, vol. 10, No. 1087 (11 pages).

Alon et al., "Expansion Sequencing: Spatially Precise In Situ Transcriptomics in Intact Biological Systems," Science. Jan. 29, 2021, vol. 371, No. 6528 (pp. 1-29).

Altschul et al., "Basic local alignment search tool," Journal of Molecular Biology, 1990, vol. 215 (pp. 403-410).

Angelo et al., "Multiplexed ion beam imaging of human breast tumors," Nature Medicine, Apr. 2014, vol. 20, No. 4 (pp. 436-442).

Anzalone et al., "Search-and-replace genome editing without double-strand breaks or donor DNA," Nature, Dec. 2019, vol. 576, No. 7785 (pp. 149-157).

(56) References Cited

OTHER PUBLICATIONS

Bai et al., "Ultrafast chemical imaging by widefield photothermal sensing of infrared absorption," Science Advances, 2019, vol. 5, No. 7 (8 pages).
Beerli et al., "Toward Controlling Gene Expression at Will: Specific Regulation of the ERBB-2/HER-2 Promoter by Using Polydactyl Zinc Finger Proteins Constructed from Modular Building Blocks," Proceedings of the National Academy of Sciences, USA, 1998, vol. 95, No. 25 (pp. 14628-14633).
Bergen et al., "Generalizing RNA velocity to transient cell states through dynamical modeling," bioRxiv, URL: https://www.biorxiv.org/content/10.1101/820936v1, 2019 (26 pages).
Bernstein et al., "TALE-mediated epigenetic suppression of CDKN2A increases replication in human fibroblasts," The Journal of Clinical Investigation, 2015, vol. 125, No. 5 (pp. 1998-2006).
Biancalani et al., "Deep learning and alignment of spatially resolved single-cell transcriptomes with Tangram," Nature Methods, Nov. 2021, vol. 18 (25 pages).
Biancalani et al., "Deep learning and alignment of spatially-resolved whole transcriptomes of single cells in the mouse brain with Tangram," bioRxiv, 2020 (62 pages).
Biswass et al., "CRISPRTarget: bioinformatic prediction and analysis of crRNA targets," RNA Biology, May 2013, vol. 10 (pp. 817-827).
Black et al., "Targeted Epigenetic Remodeling of Endogenous Loci by CRISPR/Cas9-Based Transcriptional Activators Directly Converts Fibroblasts to Neuronal Cells," Cell Stem Cell, Sep. 1, 2016, vol. 19, No. 3 (10 pages).
Boch, et al., "Breaking the Code of DNA Binding Specificity of TAL-Type III Effectors," Science, Dec. 11, 2009, vol. 326 (pp. 1509-1512).
Bondeson et al., "Targeted Protein Degradation by Small Molecules," Annual Review of Pharmacology and Toxicology, Jan. 6, 2017, vol. 57 (pp. 107-123).
Bray et al., "Cell Painting, a high-content image-based assay for morphological profiling using multiplexed fluorescent dyes," Nature Protocols, 2016, vol. 11, No. 9 (42 pages).
Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).
Buenrostro et al., "Integrated Single-Cell Analysis Maps the Continuous Regulatory Landscape of Human Hematopoietic Differentiation," Cell, 2018, vol. 173, No. 6 (pp. 1535-1548).
Buenrostro et al., "Single-cell chromatin accessibility reveals principles of regulatory variation," Nature, Jul. 23, 2015, vol. 523, No. 7561 (pp. 486-490).
Burlingame et al., "Mass spectrometry," Analytical Chemistry, Aug. 15, 1998, vol. 70, No. 16 (pp. 647-716).
Cadwell et al., "Electrophysiological, transcriptomic and morphologic profiling of single neurons using Patch-seq," Nature Biotechnology, Feb. 2016, vol. 34, No. 2 (pp. 199-203).
Cano-Rodriguez et al., "Writing of H3K4Me3 overcomes epigenetic silencing in a sustained but context-dependent manner," Nature Communications, 2016, vol. 7, No. 12284 (11 pages).
Cao et al., "Comprehensive single cell transcriptional profiling of a multicellular organism by combinatorial indexing," bioRxiv, URL: https://www.biorxiv.org/content/10.1101/104844v1, preprint first posted online Feb. 2, 2017 (35 pages).
Cao et al., "Comprehensive single-cell transcriptional profiling of a multicellular organism," Science, Aug. 18, 2017, vol. 357, No. 6352 (pp. 661-667).
Carr et al., "Genome Engineering," Nature Biotechnology, Dec. 2009, vol. 27, No. 12 (pp. 1151-1162).
Cermak et al., "Efficient Design and Assembly of Custom Talen and Other Tal Effector-Based Constructs for DNA Targeting", Nucleic Acids Research, 2011, vol. 39, No. 12 (pp. 1-11).
Chavez et al., "Highly efficient Cas9-mediated transcriptional programming," Nature Methods, Apr. 2015, vol. 12, No. 4 (pp. 326-328).
Chen et al., "Efficient in situ barcode sequencing using padlock probe-based BaristaSeq," Nucleic Acids Research, 2018, vol. 46, No. 4 (10 pages).
Chen et al., "RNA Imaging. Spatially Resolved, Highly Multiplexed RNA Profiling in Single Cells," Science, Apr. 24, 2015, vol. 348, No. 6233 (pp. 1-14).
Chen et al., "Single Molecule Fluorescence In Situ Hybridization (SmFISH) Analysis in Budding Yeast Vegetative Growth and Meiosis," Journal of Visual Experiments, 2018, 135 (14 pages).
Chen et al., "Expansion Microscopy," Science, Jan. 30, 2015, vol. 47, No. 6221 (pp. 543-548).
Choi et al., "Third-generation in situ hybridization chain reaction: multiplexed, quantitative, sensitive, versatile, robust," Development, 2018, 145 (10 pages).
Choudhury et al., "CRISPR-dCas9 mediated TET1 targeting for selective DNA demethylation at BRCA1 promoter," Oncotarget, 2016, vol. 7, No. 29 (pp. 46545-46556).
Clark et al., "Genome-wide base-resolution mapping of DNA methylation in single cells using single-cell bisulfite sequencing (scBS-seq)," Nature Protocols, 2017, vol. 12, No. 3 (pp. 534-547).
Cleary et al., "Compressed sensing for highly efficient imaging transcriptomics," Nature Biotechnology, 2021, vol. 39 (pp. 936-942).
Cleary et al., "Compressed sensing for imaging transcriptomics," bioRxiv preprint, URL: https://www.biorxiv.org/content/10.1101/743039v2, 2019 (42 pages).
Codeluppi et al., "Spatial organization of the somatosensory cortex revealed by cyclic smFISH," bioRxiv preprint doi: https://doi.org/10.1101/276097; this version posted Mar. 4, 2018 (pp. 1-8).
Cong et al. "Comprehensive interrogation of natural TALE DNA-binding modules and transcriptional repressor domains," Nature Communications, Jul. 24, 2012, vol. 3 (pp. 968-973).
Cui et al., "Fluorescence In Situ Hybridization: Cell-Based Genetic Diagnostic and Research Applications," Frontiers in Cell and Developmental Biology, Sep. 2016, vol. 4, Art. 89 (11 pages).
Cusanovich et al., "Multiplex single-cell profiling of chromatin accessibility by combinatorial cellular indexing" Science, May 22, 2015, vol. 348, No. 6237 (34 pages—Supplementary materials).
Datlinger et al., "Pooled CRISPR screening with single-cell transcriptome readout," Nature Methods, Mar. 2016, vol. 14, No. 3 (pp. 297-301).
Datta et al., "Fluorescence lifetime imaging microscopy: fundamentals and advances in instrumentation, analysis, and applications," Journal of Biomedical Optics, Jul. 2020, vol. 25, No. 7 (44 pages).
Dawson et al., "Cancer epigenetics: from mechanism to therapy," Cell, Jul. 6, 2012, vol. 150, No. 1 (pp. 12-27).
Diamant et al., "Patient contrastive learning: A performant, expressive, and practical approach to electrocardiogram modeling," PLOS Computational Biology, 2022 (16 pages).
Ding et al., "Emerging New Concepts of Degrader Technologies," Trends Pharmacological Sciences, Jul. 2020, vol. 41, No. 7 (pp. 464-474).
Dixit et al., "Perturb-Seq: Dissecting Molecular Circuits with Scalable Single-Cell RNA Profiling of Pooled Genetic Screens," Cell, Dec. 15, 2016, vol. 167, No. 7 (pp. 1853-1866).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Doyon et al., "Enhancing zinc-finger-nuclease activity with improved obligate heterodimeric architectures," Nature Methods, Jan. 2011, vol. 8, No. 1 (pp. 74-79).
Drokhlyansky et al., "The enteric nervous system of the human and mouse colon at a single-cell resolution," bioRxiv, 746743, this version posted Sep. 4, 2019 (90 pages).
Drokhlyansky et al., "The Human and Mouse Enteric Nervous System at Single-Cell Resolution," Cell, Sep. 17, 2020, vol. 182 (pp. 1606-1622).
Edelstein et al., "Computer control of microscopes using µManager," Current Protocols Molecular Biology, Oct. 2010, Chapter: Unit 14.20 (22 pages).

(56) References Cited

OTHER PUBLICATIONS

Eng et al., "Transcriptome-Scale Super-Resolved Imaging in Tissues by RNA seqFISH+," Nature, Apr. 2019, vol. 568, No. 7751 (pp. 235-239).
Esvelt et al., "Orthogonal Cas9 proteins for RNA-guided gene regulation and editing," Nature Methods, Nov. 2013, vol. 10, No. 11 (pp. 1116-1121).
Fantoni et al., "Laser Line Scanning for Fluorescence Reflectance Imaging: A Phantom Study and In Vivo Validation of the Enhancement of Contrast and Resolution," Journal of Biomedical Optics, Oct. 2014, vol. 19, No. 10 (12 pages).
Farlik et al., "Single-cell DNA methylome sequencing and bioinformatic inference of epigenomic cell-state dynamics," Cell Reports, Mar. 3, 2015, vol. 10, No. 8 (pp. 1386-1397) (22 pages).
Farzadfard et al., "Tunable and multifunctional eukaryotic transcription factors based on CRISPR/Cas," ACS Synthetic Biology, 2013, vol. 2 (pp. 604-613).
Frangieh et al., "Multimodal pooled Perturb-CITE-seq screens in patient models define mechanisms of cancer immune evasion," Nature Genetics, 2021, vol. 53, No. 3 (pp. 332-341) (36 pages).
Freudiger et al., "Label-free biomedical imaging with high sensitivity by stimulated Raman scattering microscopy," Science, 2008, vol. 322 (pp. 1857-1861) (11 pages).
Gao et al., "Engineered Cpf1 Enzymes with Altered PAM Specificities," Nature Biotechnology, Aug. 2017, vol. 35, No. 8 (pp. 789-792).
Gatys et al., "Image Style Transfer Using Convolutional Neural Networks," 2016 IEEE Conference on Computer Vision and Pattern Recognition (CVPR), Las Vegas, NV, USA, Jun. 27-30, 2016 (10 pages).
Geiss et al., "Direct multiplexed measurement of gene expression with color-coded probe pairs," Nature Biotechnology, 2008, vol. 26, No. 3 (pp. 317-325).
Germond et al., "Following Embryonic Stem Cells, Their Differentiated Progeny, and Cell-State Changes During iPS Reprogramming by Raman Spectroscopy," Analytical Chemistry, Oct. 2020, vol. 92 (9 pages).
Gierahn et al., "Seq-Well: Portable, Low-Cost RNA Sequencing of Single Cells at High Throughput," Nature Methods, Apr. 2017, vol. 14, No. 4 (8 pages).
Gilbert et al., "CRISPR-Mediated Modular RNA-Guided Regulation of Transcription in Eukaryotes," Cell, Jul. 18, 2013, vol. 154 (pp. 442-451).
Gleditzsch et al., "PAM identification by CRISPR-Cas effector complexes: diversified mechanisms and structures," RNA Biology, 2019, vol. 16, No. 4 (pp. 504-517).
Goodfellow et al., "Generative Adversarial Networks," Advances in Neural Information Processing Systems, Jun. 2014 (10 pages).
Gregory et al., "Specific transcriptional enhancement of inducible nitric oxide synthase by targeted promoter demethylation," Epigenetics, 2013, vol. 8, No. 11 (17 pages).
Grissa et al., "CRISPRFinder: a web tool to identify clustered regularly interspaced short palindromic repeats," Nucleic Acids Research, 2007, vol. 35 (pp. W52-W57).
Gruber et al., "The Vienna RNA Websuite," Nucleic Acids Research, Apr. 19, 2008, vol. 36 (pp. W70-W74).
Habib et al., "Div-Seq: Single-nucleus RNA-Seq reveals dynamics of rare adult newborn neurons," Science, Aug. 26, 2016, vol. 353, No. 6302 (pp. 925-928).
Habib et al., "Massively parallel single-nucleus RNA-seq with DroNc-seq," Nature Methods, Oct. 2017, vol. 14, No. 10 (pp. 955-958).
Hariri et al., "In Vivo Optical Coherence Tomography: The Role of the Pathologist," Archives of Pathology & Laboratory Medicine, 2012, vol. 136 (1492-1501).
Hartman et al., "Immune monitoring using mass cytometry and related high-dimensional imaging approaches," Nature Reviews Rheumatology, 2020, vol. 16 (pp. 87-99) (28 pages).
Hashimshony, et al., "CEL-Seq: Single-Cell RNA-Seq by Multiplexed Linear Amplification," Cell Reports, 2012, vol. 2, No. 3 (pp. 666-673).
He et al., "Deep residual learning for image recognition", In Proceedings of the IEEE Conference on Computer Vision and Pattern Recognition, pp. 770-778, (2016).
He et al., "High-plex Multiomic Analysis in FFPE at Subcellular Level by Spatial Molecular Imaging," URL: https://doi.org/10.1101/2021.11.03.467020, 2020 (67 pages).
Hill et al., "On the design of CRISPR-based single cell molecular screens," Nature Methods, Apr. 2018, vol. 15, No. 4 (pp. 271-274).
Ho et al., "Rapid identification of pathogenic bacteria using Raman spectroscopy and deep learning," Nature Communications, 2019, vol. 10, Art. 4927 (8 pages).
Holzscheck et al., "Modeling transcriptomic age using knowledge-primed artificial neural networks," npj Aging and Mechanisms of Disease, 2021, vol. 7, No. 15 (13 pages).
Huang et al., "Multimodal unsupervised image-to-image translation," Proceedings of the European Conference on Computer Vision (ECCV), 2018 (18 pages).
Hughes et al., "Highly Efficient, Massively-Parallel Single-Cell RNA-Seq Reveals Cellular States and Molecular Features of Human Skin Pathology," bioRxiv, 689273, this version posted Jul. 2, 2019 (51 pages).
Iafrate et al., "How Non-Invasive in Vivo Cell Tracking Supports the Development and Translation of Cancer Immunotherapies," Frontiers in Physiology, Apr. 2020, vol. 11, Art. 154 (30 pages).
Ichimura et al., Visualizing cell state transition using Raman spectroscopy. PLoS One, Jan. 2014, vol. 9, No. 1 (8 pages).
Islam et al., "Characterization of the single-cell transcriptional landscape by highly multiplex RNA-seq," Genome Research, 2011, vol. 21, No. 7 (pp. 1160-1167).
Isola et al., "Image-to-image translation with conditional adversarial networks," 2017 IEEE Conference on Computer Vision and Pattern Recognition (CVPR), Jul. 21-26, 2017 (10 pages).
Ji et al., "Engineered zinc-finger transcription factors activate OCT4 (POU5F1), SOX2, KLF4, c-MYC (MYC) and miR302/367," Nucleic Acids Research, 2014, vol. 42, No. 10 (pp. 6158-6167).
Jiang et al., "RNA-guided editing of bacterial genomes using CRISPR-Cas systems," Nature Biotechnology, Mar. 2013, vol. 31 [including supplementary information—30 pages] (pp. 233-239).
Jumper, et al., "Highly accurate protein structure prediction with AlphaFold," Nature, 2021, vol. 596 (pp. 583-589) (12 pages).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Kamentsky et al., "Improved structure, function and compatibility for CellProfiler: modular high-throughput image analysis software," Bioinformatics, 2011, vol. 27, No. 8 (pp. 1179-1180).
Kane et al., "Epigenetic changes during aging and their reprogramming potential," Critical Reviews in Biochemistry and Molecular Biology, 2019, vol. 54, No. 1 (37 pages).
Kang et al., "Regulation of gene expression by altered promoter methylation using a CRISPR/Cas9-mediated epigenetic editing system," Science Reports, 2019, vol. 9, Art. 11960 (12 pages).
Karemaker et al., "Single-Cell DNA Methylation Profiling: Technologies and Biological Applications," Trends in Biotechnology, 2018, vol. 36, No. 9 (pp. 952-965).
Kaya, M., "Deep metric learning: A survey," Symmetry, 2019, vol. 11 (26 pages).
Ke et al., "In situ sequencing for RNA analysis in preserved tissue and cells," Nature Methods, Sep. 2013, vol. 10, No. 9 (pp. 857-862).
Kearns et al., "Functional annotation of native enhancers with a Cas9-histone demethylase fusion," Nature Methods, 2015, vol. 12 (13 pages).
Kelly, R., "Single-cell Proteomics: Progress and Prospects," Molecular Cell Proteomics, 2020, vol. 19, No. 11 (pp. 1739-1748).
Kim et al., "Hybrid restriction enzymes: Zinc finger fusions to Fok I cleavage domain," Proceedings of the National Academy of Science, USA, Feb. 1996, vol. 93, No. 3 (pp. 1156-1160).

(56) References Cited

OTHER PUBLICATIONS

Kim et al., "Chimeric restriction endonuclease.," Proceedings of the National Academy of Sciences, USA, Feb. 1994, vol. 91, No. 3 (pp. 883-887).
Kingma et al., "Auto-Encoding Variational Bayes," arXiv, URL: https://arxiv.org/pdf/1312.6114.pdf, 2022 (14 pages).
Kingma et al., A method for stochastic Optimization, 3rd International Conference for Learning Representations, San Diego, USA, URL: https://arXiv:1412.6980v9, 2015 (15 pages).
Klein et al., "Droplet Barcoding for Single-Cell Transcriptomics Applied to Embryonic Stem Cells," Cell, 2015, vol. 161, No. 5 (pp. 1187-1201).
Kleinstiver et al., "Engineered CRISPR-Cas9 nucleases with altered PAM specificities," Nature, Jul. 23, 2015, vol. 523, No. 7561 (pp. 481-485).
Klompe et al., "Transposon-encoded CRISPR-Cas systems direct RNA-guided DNA integration," Nature, Jul. 2019, vol. 571, No. 7764 (pp. 219-225).
Kobayashi-Kirschvink et al., "Linear Regression Links Transcriptomic Data and Cellular Raman Spectra," Cell Systems, 2018, vol. 7 (26 pages).
Kobayashi-Kirschvink et al., "Raman2RNA: Live-cell label-free prediction of single-cell RNA expression profiles by Raman microscopy," BioRxiv, URL: https://doi.org/10.1101/2021.11.30.470655, 2021 (46 pages).
Komor et al., "Programmable editing of a target base in genomic DNA without double-stranded DNA cleavage," Nature, 2016, vol. 533 (pp. 420-424).
Konermann et al., "Genome-scale transcriptional activation by an engineered CRISPR-Cas9 complex," Nature, 2015, vol. 517 (pp. 583-588) [Including Supplemental information, 12 pages].
Konermann et al., "Optical control of mammalian endogenous transcription and epigenetic states," Nature, Aug. 22, 2013, vol. 500, Includes Supplemental Information (pp. 472-476).
Koonin et al., "Origins and evolution of CRISPR-Cas systems," Philosophical Transactions of the Royal Society B., May 13, 2019, vol. 374, No. 1772 (16 pages).
Kumamoto et al., "Label-Free Molecular Imaging and Analysis by Raman Spectroscopy," ACTA Histochemica et Cytochemica, 2018, vol. 51, No. 3 (101-110).
Kumar et al., "Deep learning based assistive technology on audio visual speech recognition for hearing impaired," International Journal of Cognitive Computing in Engineering, 2022, vol. 3 (pp. 24-30).
La Manno et al., "RNA velocity of single cells," Nature, 2018, vol. 560, No. 7719 (36 pages).
Laber et al., "Discovering cellular programs of intrinsic and extrinsic drivers of metabolic traits using LipocyteProfiler," BioRxiv, URL: https://www.biorxiv.org/content/10.1101/2021.07.17.452050v1, 2021 (121 pages).
Lahnemann et al., "Eleven grand challenges in single-cell data science," Genome Biology, 2020, vol. 21, Art. 31 (35 pages).
Lai et al., "Modular PROTAC Design for the Degradation of Oncogenic BCR-ABL," Angewandte Chemie International Edition [Engl] Jan. 11, 2016, vol. 55, No. 2 (pp. 807-810).
Lal et al., "Deep learning-based enhancement of epigenomics data with AtacWorks," Nature Communications, 2021, vol. 12., Art. 1507 (11 pages).
Lamb et al., "The Connectivity Map: Using Gene-Expression Signatures to Connect Small Molecules, Genes, and Disease," Science, Sep. 29, 2006, vol. 313, No. 5795 (pp. 1929-1935).
Lamb, "The Connectivity Map: A New Tool for Biomedical Research," Nature Reviews, Cancer, Jan. 2007, vol. 7, No. 1 (pp. 54-60).
Lee et al., "Highly multiplexed subcellular RNA sequencing in situ," Science, Mar. 21, 2014, vol. 343, No. 6177 (pp. 1360-1363).
Lee et al., "Single-cell multiomics: technologies and data analysis methods," Experimental & Molecular Medicine, 2020, vol. 52 (pp. 1428-1442).
Leenay et al., "Identifying and Visualizing Functional PAM Diversity across CRISPR-Cas Systems," Molecular Cell, Apr. 7, 2016, vol. 62, No. 1 (pp. 137-147).
Li et al., "A Simple and Robust Method for Simultaneous Dual-Omics Profiling with Limited Numbers of Cells," Cell Reports Methods, 2021, vol. 1, No. 3 (8 pages).
Li et al., "Base editing with a Cpf1-cytidine deaminase fusion," Nature Biotechnology, Apr. 2018, vol. 36, No. 4 (pp. 324-327).
Li et al., "Cistrome-GO: a web server for functional enrichment analysis of transcription factor ChIP-seq peaks," Nucleic Acids Research, 2019, vol. 47 (pp. W206-W211).
Li et al., "From bulk, single-cell to spatial RNA sequencing," International Journal of Oral Science, 2021, vol. 13, Article 36 (6 pages).
Li et al., "Hematoxylin and eosin staining of intact tissues via delipidation and ultrasound," Scientific Reports, 2018, vol. 8, No. 12259 (8 pages).
Li et al., "In Vivo Diffuse Optical Tomography and Fluorescence Molecular Tomography," Journal of Healthcare Engineering, 2010, vol. 1, No. 3 (pp. 477-507).
Li et al., "Programmable human histone phosphorylation and gene activation using a CRISPR/Cas9-based chromatin kinase," Nature Communications, 2021, vol. 12, Art. 896 (10 pages).
Liu et al., "Editing DNA Methylation in the Mammalian Genome," Cell, 2016, vol. 167 (pp. 39 pages).
Liu et al., "Regulation of an endogenous locus using a panel of designed zinc finger proteins targeted to accessible chromatin regions, Activation of Vascular Endothelial Growth Factor A*," Journal of Biological Chemistry, 2001, 276, No. 14 (pp. 11323-11334).
Lubeck et al., "Single-Cell in Situ RNA Profiling by Sequential Hybridization," Nature Methods, 2014, vol. 11 (3 pages).
Luecken et al., "Benchmarking atlas-level data integration in single-cell genomics," bioRxiv, URL: https://www.biorxiv.org/content/10.1101/2020.05.22.111161v2.full.pdf, 2020 (61 pages).
Ma et al., "Chromatin potential identified by shared single cell profiling of RNA and chromatin," Cell, Nov. 12, 2020, vol. 183, No. 4 (pp. 1103-1116).
Ma et al., "Targeted AID-mediated mutagenesis (TAM) enables efficient genomic diversification in mammalian cells," Nature Methods, Dec. 2016, vol. 13, No. 12 (pp. 1029-1035).
Macosko et al., "Highly Parallel Genome-wide Expression Profiling of Individual Cells Using Nanoliter Droplets," Cell, May 21, 2015, vol. 161 (pp. 1202-1214).
Maeder et al., "CRISPR RNA-guided activation of endogenous human genes," Nature Methods, 2013, vol. 10 (pp. 977-979).
Makarova et al., "Classification and nomenclature of CRISPR-Cas systems: where from here?," The CRISPR Journal, 2018, vol. 1, No. 5 (pp. 325-336).
Makarova et al., "Evolutionary classification of CRISPR-Cas systems: a burst of class 2 and derived variants," Nature Reviews, Microbiology, Feb. 2020, vol. 18, No. 2 (pp. 67-83).
Makhzani et al., "Adversarial Autoencoders", arXiv, URL: https://arxiv.org/abs/1511.05644v1, Nov. 18, 2015 (10 pages).
Marraffini et al., "Self vs. non-self discrimination during CRISPR RNA-directed immunity," Nature, 2010, vol. 463 (pp. 568-571).
Mayeux et al., "Biomarkers: Potential uses and Limitations", NeuroRX: The Journal of the American Society for Experimental Neuro Therapeutics, 2004, vol. 1 (pp. 182-188).
Mcinnes et al., "UMAP: Uniform Manifold Approximation and Projection for Dimension Reduction," ArXiv, Sep. 21, 2020 (pp. 1-63).
Mcinnes et al., "UMAP: Uniform Manifold Approximation and Projection," Journal of Open Source Software, 2018, vol. 3 (2 pages).
Mojica et al., "Short Motif Sequences Determine the Targets of the Prokaryotic CRISPR Defence System," Microbiology, 2009, vol. 155 (pp. 733-740).
Moscou et al., "A Simple Cipher Governs DNA Recognition by TAL Effectors", Science, Dec. 11, 2009, vol. 326 (pp. 1501-1512).
Mulqueen et al., "Highly scalable generation of DNA methylation profiles in single cells," Nature Biotechnology, 2018, vol. 36 (16 pages).

(56) References Cited

OTHER PUBLICATIONS

Ngiam et al., "Multimodal deep learning", Proceedings of the 28th International Conference on Machine Learning, 2011, retrieved Jul. 7, 2021 from URL: https://icml.cc/2011/papers/399_icmlpaper.pdf (8 pages).
Nishida et al., "Targeted nucleotide editing using hybrid prokaryotic and vertebrate adaptive immune systems," Science, Sep. 16, 2016, vol. 353, No. 6305 (9 Pages).
Nolan et al., "Spectral Flow Cytometry," Current Protocols in Cytometry, 2013 (18 pages).
O'Shea et al., "An Introduction to Convolutional Neural Networks," ArXiv, URL: https://doi.org/10.48550/arXiv.1511.08458, 2015 (11 pages).
Odena et al., "Conditional Image Synthesis with Auxiliary Classifier GANs," Proceedings of the 34th International Conference on Machine Learning, Sydney, Australia, PMLR 70, 2017 (12 pages).
Oki et al., "ChIP-Atlas: a data-mining suite powered by full integration of public ChIP-seq data," EMBO Reports, 2018 (10 pages).
Ounkomol et al., Label-free prediction of three-dimensional fluorescence images from transmitted-light microscopy, Nature Methods, 2018, vol. 15 (13 pages).
Paszke et al., "PyTorch: An Imperative Style, High-Performance Deep Learning Library," 33rd Conference on Neural Information Processing Systems (NeurIPS 2019), Vancouver, Canada, 2019 (12 pages).
Pattanayak et al., "High-throughput profiling of off-target DNA cleavage reveals RNA-programmed Cas9 nuclease specificity," Nature Biotechnology, 2013, vol. 31 (pp. 839-843) [Including Supplementary Materials].
Perez-Pinera et al., "Synergistic and tunable human gene activation by combinations of synthetic transcription factors," Nature Methods, 2013, vol. 10, No. 3 (pp. 239-242).
Peters et al., "Recruitment of CRISPR-Cas systems by Tn7-like transposons," Proceedings of the National Academy of Sciences, U.S.A, Online Aug. 15, 2017, vol. 29, No. 114 (pp. E7358-E7366).
Pflueger et al., "A modular dCas9-SunTag DNMT3A epigenome editing system overcomes pervasive off-target activity of direct fusion dCas9-DNMT3A constructs," Genome Research, 2018, vol. 28 (pp. 1193-1206).
Picelli et al. "Full-length RNA-seq from single cells using Smart-seq2," Nature Protocols, Jan. 2014, vol. 9, No. 1 (pp. 171-181).
Prokhorenkova et al., "CatBoost: unbiased boosting with categorical features," ArXiv, URL: https://doi.org/10.48550/arXiv.1706.09516, Jan. 20, 2019 (23 pages).
Qi et al., "HEDD: the human epigenetic drug database," Database, 2016 (pp. 1-10).
Qi et al., "Single-cell sequencing and its applications in head and neck cancer," Oral Oncology, Dec. 2019, vol. 99 (32 pages).
Qi et al., "Repurposing CRISPR as an RNA-Guided Platform for Sequence-Specific Control of Gene Expression," Cell, 2013, vol. 152 (pp. 1173-1183).
Qui et al., "Mutation detection using Surveyor™ nuclease," BioTechniques, Apr. 2004, vol. 36 (pp. 702-707).
Radford et al., "Learning Transferable Visual Models from Natural Language Supervision." arXiv, URL: https://doi.org/10.48550/arXiv.2103.00020, Feb. 26, 2021 (48 pages).
Ramani et al., "Sci-Hi-C: A single-cell Hi-C method for mapping 3D genome organization in large number of single cells," Methods, 2020, vol. 170 (pp. 61-68).
Ramesh et al., "Hierarchical text-conditional image generation with CLIP latents," URL: https://arxiv.org/abs/2204.06125, Apr. 13, 2022 (27 pages).
Ramirez et al., "OptiJ: Open-Source Optical Projection Tomography of Large Organ Samples," Scientific Reports, 2019 (9 pages).
Ramskold et al., "Full-length mRNA-Seq from single-cell levels of RNA and individual circulating tumor cells," Nature Biotechnology, Aug. 2012, vol. 30, No. 8 (pp. 777-782).
Rao et al., "A 3D map of the human genome at kilobase resolution reveals principles of chromatin looping," Cell, Dec. 18, 2014, vol. 159, No. 7 (pp. 1665-1680).
Rappez et al., "SpaceM reveals metabolic states of single cells," Nature Methods, 2021, vol. 18, No. 7 (pp. 799-805).
Rees et al., "Base editing: precision chemistry on the genome and transcriptome of living cells," Nature Reviews Genetics, Dec. 2018, vol. 19, No. 12 (pp. 770-788).
Regev et al., "Science Forum: The Human Cell Atlas," eLife, Dec. 5, 2017, vol. 6 (pp. 1-30).
Regev et al., "The human cell atlas white paper," White Paper, The HCA Consortium, Oct. 18, 2017 (109 pages).
Replogle et al., "Combinatorial single-cell CRISPR screens by direct guide RNA capture and targeted sequencing," Nature Biotechnology, Aug. 2020, vol. 38, No. 8 (pp. 954-961).
Reyes et al., "Simultaneous Profiling of Gene Expression and Chromatin Accessibility in Single Cells," Advanced Biosystems, 2019, vol. 3, No. 11 (12 pages).
Rhyasen et al., "AZD5153: A Novel Bivalent BET Bromodomain Inhibitor Highly Active against Hematologic Malignancies," Molecular Cancer Therapeutics, Nov. 2016, vol. 15, No. 11 (pp. 2563-2574).
Rivenbark et al., "Epigenetic reprogramming of cancer cells via targeted DNA methylation," Epigenetics, Apr. 1, 2012, vol. 7, No. 4 (pp. 350-360).
Rodriques et al., "Slide-seq: A Scalable Technology for Measuring Genome-Wide Expression at High Spatial Resolution," Science, 2019, vol. 363, No. 6434 (pp. 1463-1467).
Rosenberg et al., "Scaling single cell transcriptomics through split pool barcoding," bioRxiv preprint first posted online Feb. 2, 2017 (13 pages).
Rosenberg et al., "Single-cell profiling of the developing mouse brain and spinal cord with split-pool barcoding," Science, Single Cell Genomics, 2018, vol. 360 (pp. 176-182).
Rotem et al., "Single-cell ChIP-seq reveals cell subpopulations defined by chromatin state," Nature Biotechnology, Oct. 12, 2015, vol. 33, No. 11 (pp. 1165-1172).
Rozenblatt-Rosen et al., "The Human Cell Atlas: from vision to reality," Nature, Oct. 26, 2017, vol. 550 (pp. 451-453).
Rozenblatt-Rosen et al., "The Human Tumor Atlas Network: Charting Tumor Transitions across Space and Time at Single-Cell Resolution," Cell 181, 236-249 (2020).
Sanderson et al., "Fluorescence Microscopy," Cold Spring Harbor Protocols, 2014 (24 pages).
Satija et a al., "Spatial reconstruction of single-cell gene expression data," Nature Biotechnology, May 2015, vol. 33, No. 5 (pp. 495-502).
Schmauch et al., "A deep learning model to predict RNA-Seq expression of tumours from whole slide images," Nature Communications, 2020, vol. 11, Art. 3877 (15 pages).
Schofield et al., "TimeLapse-seq: adding a temporal dimension to RNA sequencing through nucleoside recoding," Nature Methods, 2018, vol. 15 (21 pages).
Schraivogel et al., "Targeted Perturb-seq enables genome-scale genetic screens in single cells," Nature Methods, 2020, vol. 17 (36 pages).
Schwarz et al., "Motion Correction in Optoacoustic Mesoscopy," Scientific Reports, 2017, vol. 7, No. 1 (9 pages).
Semrau, et al., "Dynamics of lineage commitment revealed by single-cell transcriptomics of differentiating embryonic stem cells," Nature Communications, 2017, vol. 8, Art. 1096 (16 pages).
Sharma et al., "The Aging Metabolome-Biomarkers to Hub Metabolites," Proteomics, 2020, vol. 20 (8 pages).
Sherstinsky et al., "Fundamentals of Recurrent Neural Network (RNN) and Long Short-Term Memory (LSTM) Network," arXiv, URL: https://arxiv.org/pdf/1808.03314, Jul. 31, 2023 (43 pages).
Shiebinger et al., "Optimal-Transport Analysis of Single-Cell Gene Expression Identifies Developmental Trajectories in Reprogramming," Cell, Feb. 7, 2019, vol. 176 (pp. 928-943).
Siddique et al., "Targeted methylation and gene silencing of VEGF-A in human cells by using a designed Dnmt3a-Dnmt3L single-chain fusion protein with increased DNA methylation activity," Journal of Molecular Biology, 2013, vol. 425, No. 3 (pp. 479-491).

(56) References Cited

OTHER PUBLICATIONS

Singh et al., "Label-free characterization of ultra violet-radiation-induced changes in skin fibroblasts with Raman spectroscopy and quantitative phase microscopy," Scientific Reports, 2017, vol. 7 (8 pages).
Stadtfeld et al., "A reprogrammable mouse strain from gene-targeted embryonic stem cells," Nature Methods, 2010, vol. 7 (pp. 53-55).
Stahl et al., "Visualization and analysis of gene expression in tissue sections by spatial transcriptomics" Science, Jul. 2016, vol. 353, No. 6294 (pp. 78-82).
Stegmaier et al., "Gene expression-based high-throughput screening (GE-HTS) and application to leukemia differentiation," Nature Genetics, 2004, vol. 36 (pp. 257-263).
Stepper et al., "Efficient targeted DNA methylation with chimeric dCas9-Dnmt3a-Dnmt3L methyltransferase," Nucleic Acids Research, 2017, vol. 45, No. 4 (pp. 1703-1713).
Stoeckius et al., "Simultaneous Epitope and Transcriptome Measurement in Single Cells", Nature Methods, Jul. 31, 2017, vol. 14, No. 9 (10 pages).
Strecker et al., "RNA-guided DNA insertion with CRISPR-associated transposases," Science, Jul. 2019, vol. 365, No. 6448 (pp. 48-53).
Strimbu et al., "What are Biomarkers?", Current Opinion in HIV and AIDS, Nov. 2010, vol. 5, No. 6 (pp. 463-466).
Stuart et al., "Comprehensive Integration of Single-Cell Data," Cell, 2019, vol. 177, No. 7 (37 pages).
Sulubacak et al., "Multimodal machine translation through visuals and speech," Machine Translation, 2020, vol. 34 (pp. 97-147).
Suzuki et al., "In vivo genome editing via CRISPR/Cas9 mediated homology-independent targeted integration," Nature, Dec. 1, 2016, vol. 540, No. 7631 (pp. 144-149).
Swiech et al., "In vivo interrogation of gene function in the mammalian brain using CRISPR-Cas9," Nature Biotechnology, 2014, vol. 33 (pp. 102-106) [Including Supplemental information, 4 pages].
Syding et al., "CRISPR/Cas9 Epigenome Editing Potential for Rare Imprinting Diseases: A Review," Cells, Review, Apr. 16, 2020, vol. 9, No. 993 (pp. 1-25).
Tamamitsu et la., "Quantitative phase imaging with molecular vibrational sensitivity," Optics Letters, 2019, vol. 44, No. 15 (5 pages).
Tanaka et al., "Plasma proteomic signature of age in healthy humans," Aging Cell, 2018, vol. 17 (13 pages).
Tanay et al., "Scaling single-cell genomics from phenomenology to mechanism," Nature, Jan. 18, 2017, vol. 541, No. 7637 (pp. 331-338).
Tang et al., "mRNA-Seq whole-transcriptome analysis of a single cell," Nature Methods, May 2009, vol. 6, No. 5 (pp. 377-382).
Tang et al., "RNA-Seq analysis to capture the transcriptome landscape of a single cell," Nature Protocols, Mar. 2010, vol. 5, No. 3 (pp. 516-535).
Tang et al., "The single-cell sequencing: new developments and medical applications," Cell & Bioscience, 2019, vol. 9, Art. 53 (9 pages).
Thakore et al. Highly specific epigenome editing by CRISPR-Cas9 repressors for silencing of distal regulatory elements. Nature Methods, Dec. 2015, vol. 12, No. 12 (pp. 1143-1149).
Thakore et al., "Editing the epigenome: technologies for programmable transcription and epigenetic modulation," Nature Methods, 2016, vol. 13, No. 2 (pp. 127-137).
The ENCODE Project Consortium, "Expanded encyclopaedias of DNA elements in the human and mouse genomes," Nature, 2020, vol. 583 (pp. 699-710) (27 pages).
Tian et al., "Fluorescence Correlation Spectroscopy: A Review of Biochemical and Microfluidic Applications," Applied Spectroscopy, 2011, vol. 65, No. 4 (pp. 115A-124A).
Tian et al., "What makes for good views for contrastive learning?" Advances in Neural Information Processing Systems 33 (NeurIPS 2020), 2020 (13 pages).
Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).
Ulicna et al., "Automated Deep Lineage Tree Analysis Using a Bayesian Single Cell Tracking Approach," Frontiers in Computer Science, 2021, vol. 3, Art. 734559 (14 pages).
Van Den Hurk et al., "Patch-Seq Protocol to Analyze the Electrophysiology, Morphology and Transcriptome of Whole Single Neurons Derived from Human Pluripotent Stem Cells," Frontiers in Molecular Neuroscience, Aug. 2018, vol. 11, No. 261 (pp. 1-19).
Van Der Laak et al., "Deep learning in histopathology: the path to the clinic," Nature Medicine, 2021, vol. 27 (pp. 775-784).
Vickovic et al., "High-Definition Spatial Transcriptomics for in Situ Tissue Profiling," Nature Methods, Oct. 2019, vol. 16, No. 10 (pp. 987-990).
Vickovic et al., "SM-Omics: An automated platform for high-throughput spatial multi-omics," bioRxiv, URL: https://doi.org/10.1101/2020.10.14.338418, Oct. 15, 2020 (40 pages).
Vitak et al., "Sequencing thousands of single-cell genomes with combinatorial indexing," Nature Methods, Mar. 2017, vol. 14, No. 3 (pp. 302-308).
Vo et al., "Unbiased profiling of CRISPR RNA-guided transposition products by long-read sequencing," URL: https://doi.org/10.1101/2021.02.11.430876, Apr. 26, 2021 (21 pages).
Volpi et al., "FISH Glossary: An Overview of the Fluorescence in Situ Hybridization Technique," BioTechniques, 2008, vol. 45, No. 4 (pp. 385-409).
Wagner et al., "Lineage tracing meets single-cell omics: opportunities and challenges," Nature Review Genetics, 2020, vol. 21 (39 pages).
Wagner et al., "Metabolic modeling of single Th17 cells reveals regulators of autoimmunity," Cell, 2021, vol. 184 (40 pages).
Wang et al., "Photoacoustic Tomography: In Vivo Imaging from Organelles to Organs," Science, 2012, vol. 335, No. 6075 (12 pages).
Wang et al., "Three-dimensional intact-tissue sequencing of single-cell transcriptional states," Science, Jul. 27, 2018, vol. 361, No. 6400 (22 pages).
Wei et al., "Super-multiplex vibrational imaging," Nature, 2017, vol. 544 (19 pages).
Weigert et al., "Star-convex Polyhedra for 3D Object Detection and Segmentation in Microscopy," 2020 IEEE Winter Conference on Applications of Computer Vision (WACV), 2020 (pp. 3655-3662).
Wolf et al., "SCANPY: Large-scale single-cell gene expression data analysis," Genome Biology, 2018, vol. 19, No. 15 (pp. 1-5).
Wolf et al., "Transformers: State-of-the-Art Natural Language Processing," Proceedings of the 2020 Conference on Empirical Methods in Natural Language Processing: System Demonstrations, Oct. 2020 (pp. 38-45).
Xu et al., "A CRISPR-based approach for targeted DNA demethylation," Cell Discovery, May 2016, vol. 2 (pp. 1-12).
Yamashita et al., "Convolutional neural networks: an overview and application in radiology," Insights into Imaging, 2018, vol. 9 (pp. 611-629).
Yang et al., "Deep Profiling of Cellular Heterogeneity by Emerging Single-Cell Proteomic Technologies," Proteomics, 2020, vol. 20, No. 13 (24 pages).
Yang et al., "Engineering and optimising deaminase fusions for genome editing," Nature Communications, 2017 vol. 7. No. 13330 (pp. 1-12).
Yang et al., "Lipidomics: Techniques, Applications, and Outcomes Related to Biomedical Sciences," Trends in Biochemical Sciences, 2016, vol. 41, No. 11 (26 pages).
Yang et al., "Multi-domain translation between single-cell imaging and sequencing data using autoencoders," Nature Communications, 2021, vol. 12, Art. 31 (10 pages).
Yang et al., "Multi-Domain Translation by Learning Uncoupled Autoencoders," arXiv, URL: https://doi.org/10.48550/arXiv.1902.03515 2019, Feb. 9, 2019 (13 pages).
Yann et al., "Deep learning," Nature, 2015, vol. 521 (10 pages).
Yeo et al., "An enhanced CRISPR repressor for targeted mammalian gene regulation," Nature Methods, Aug. 2018, vol. 15, No. 8 (pp. 611-616).

(56) References Cited

OTHER PUBLICATIONS

Yu et al., "Elucidating transcriptomic profiles from single-cell RNA sequencing data using nature-inspired compressed sensing," Briefings in Bioinformatics, 2021, vol. 22, No. 5 (16 pages).
Zetsche at el., "Cpfl Is a Single RNA-Guided Endonuclease of a Class 2 CRISPR-Cas System," Cell, Oct. 22, 2015, vol. 163, No. 3 (pp. 759-771).
Zhang et al., "Efficient Construction of Sequence-Specific TAL Effectors for Modulating Mammalian Transcription," Nature Biotechnology, Feb. 2011, vol. 29, No. 2 (pp. 149-154).
Zhang, Y., "Transcriptional regulation by histone ubiquitination and deubiquitination," Genes & Development, 2003, vol. 17, No. 22 (pp. 2733-2740).
Zheng et al. "Haplotyping germline and cancer genomes with high-throughput linked-read sequencing," Nature Biotechnology, Feb. 1, 2016, vol. 34, No. 3 (pp. 303-311) [with Supplemental Material].
Zheng et al., "Massively parallel digital transcriptional profiling of single cells," Nature Communications, Jan. 16, 2017, vol. 8, No. 14049 (12 pages).
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, vol. 61 (pp. 462-481).
Zhu et al., "Deep Audio-visual Learning: A Survey," International Journal of Automation and Computing, Jun. 2021, vol. 18, No. 3 (pp. 351-376).
Zhu et al., "Long short-term memory over recursive structures," ICML'15: Proceedings of the 32nd International Conference on International Conference on Machine Learning, 2015, vol. 37 (pp. 1604-1612).
Zhu et al., "Unpaired image-to-image translation using cycle-consistent adversarial networks", Computer Vision (ICCV), 2017 IEEE International Conference on Computer Vision, Oct. 22-29, 2017 (18 pages).
Ziegenhain et al., "Comparative Analysis of Single-Cell RNA Sequencing Methods," Molecular Cell, vol. 65, Feb. 16, 2017 (18 pages).
Zilionis et al., "Single-cell barcoding and sequencing using droplet microfluidics," Nature Protocols, 2017, vol. 12, No. 1 (pp. 44-73).
Zuker et al., "Optimal computer folding of large RNA sequences using thermodynamics and auxiliary information," Nucleic Acids Research, Jan. 10, 1981, vol. 9, No. 1 (pp. 133-148).
Chlis et al. "Predicting single-cell gene expression profiles of imaging flow cytometry data with machine learning," Nucleic Acids Research, Nov. 18, 2020, vol. 48, No. 20 (pp. 11335-11346).
International Search report for Appl. Ser. No. PCT/US22/79989 dated Feb. 23, 2023 (6 pages).
Schultz et al., "Tip Enhanced Raman Spectroscopy and Imaging: an Apical Illumination Geometry," Applied Spectroscopy, Nov. 2008, vol. 62, No. 11 (pp. 1173-1179).
Shao et al., "scDeepSort: a pre-trained cell-type annotation method for single-cell transcriptomics using deep learning with a weighted graph neural network," Nucleic Acids Research, 2021, vol. 49, No. 21 (13 pages).

* cited by examiner

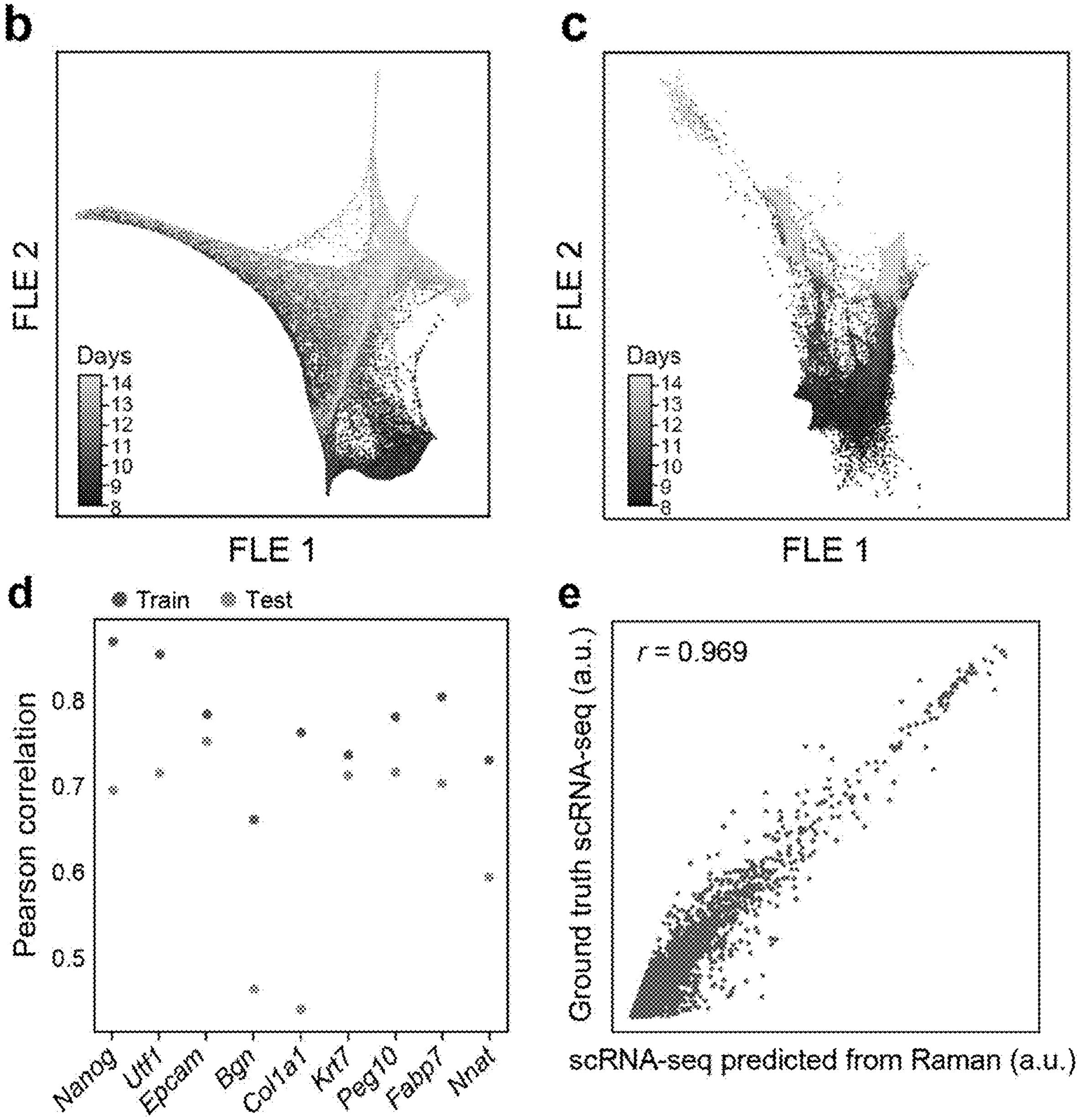
FIG. 6b-e

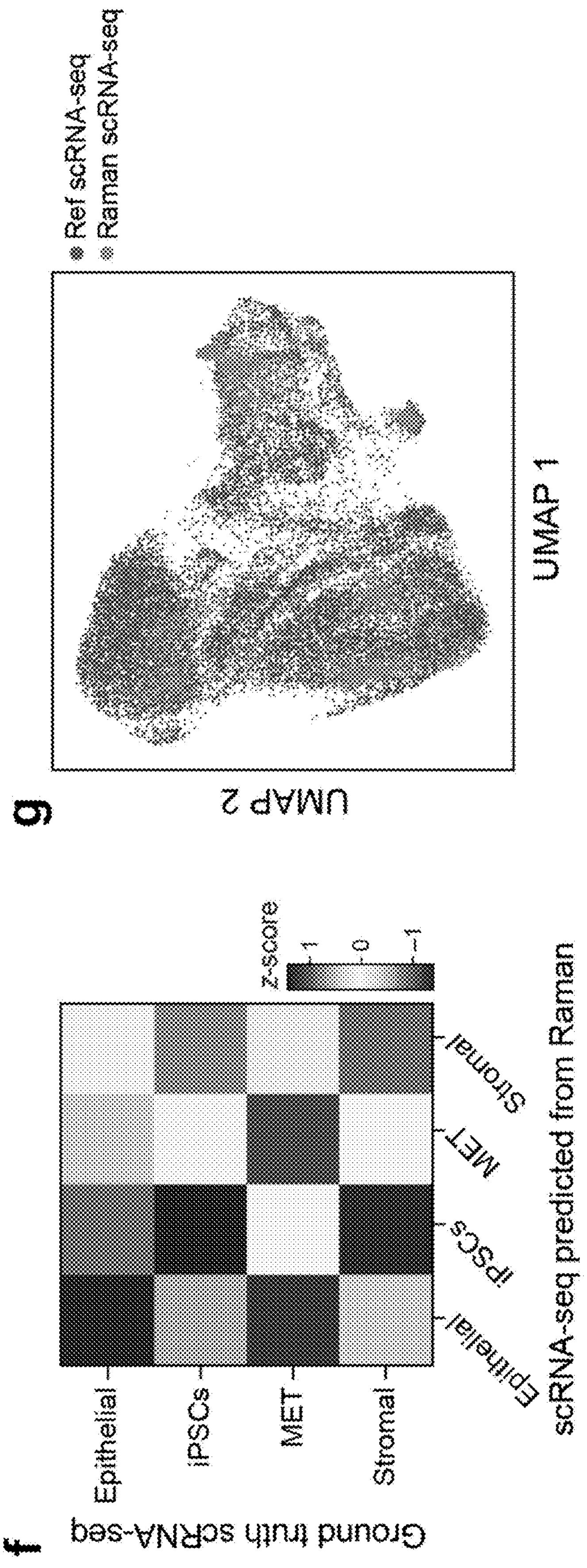
FIG. 6f-g

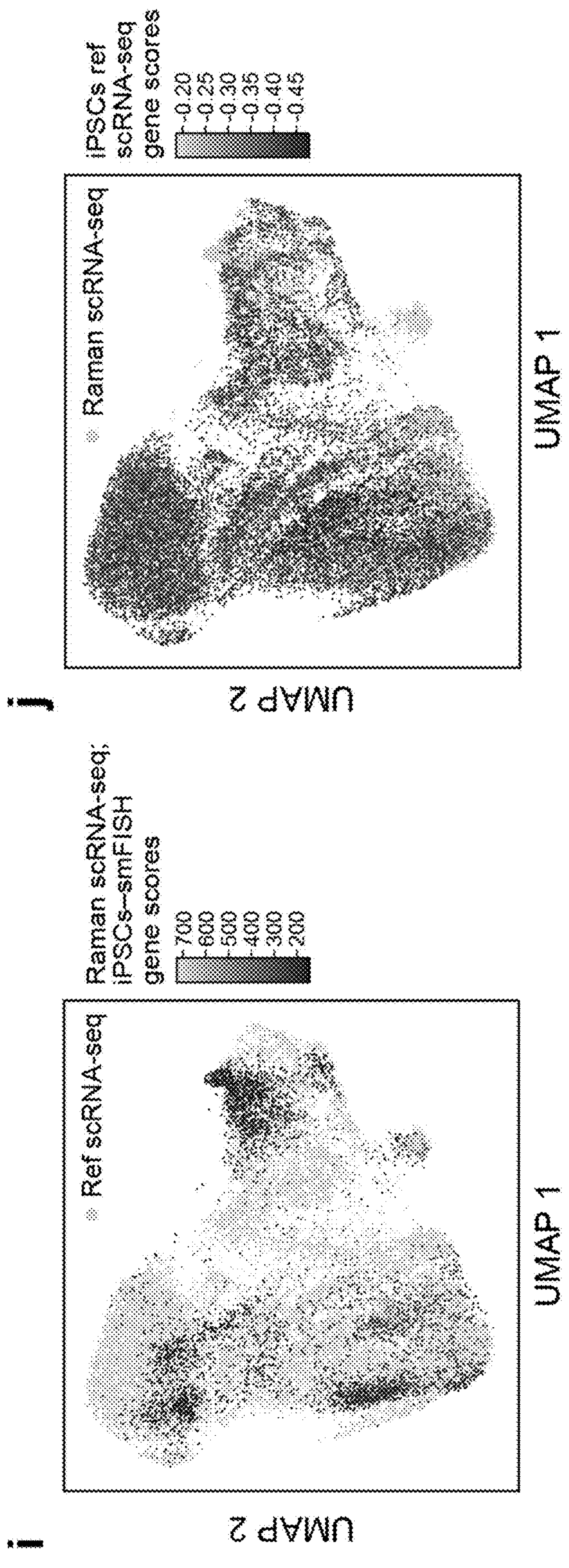
FIG. 6i-j

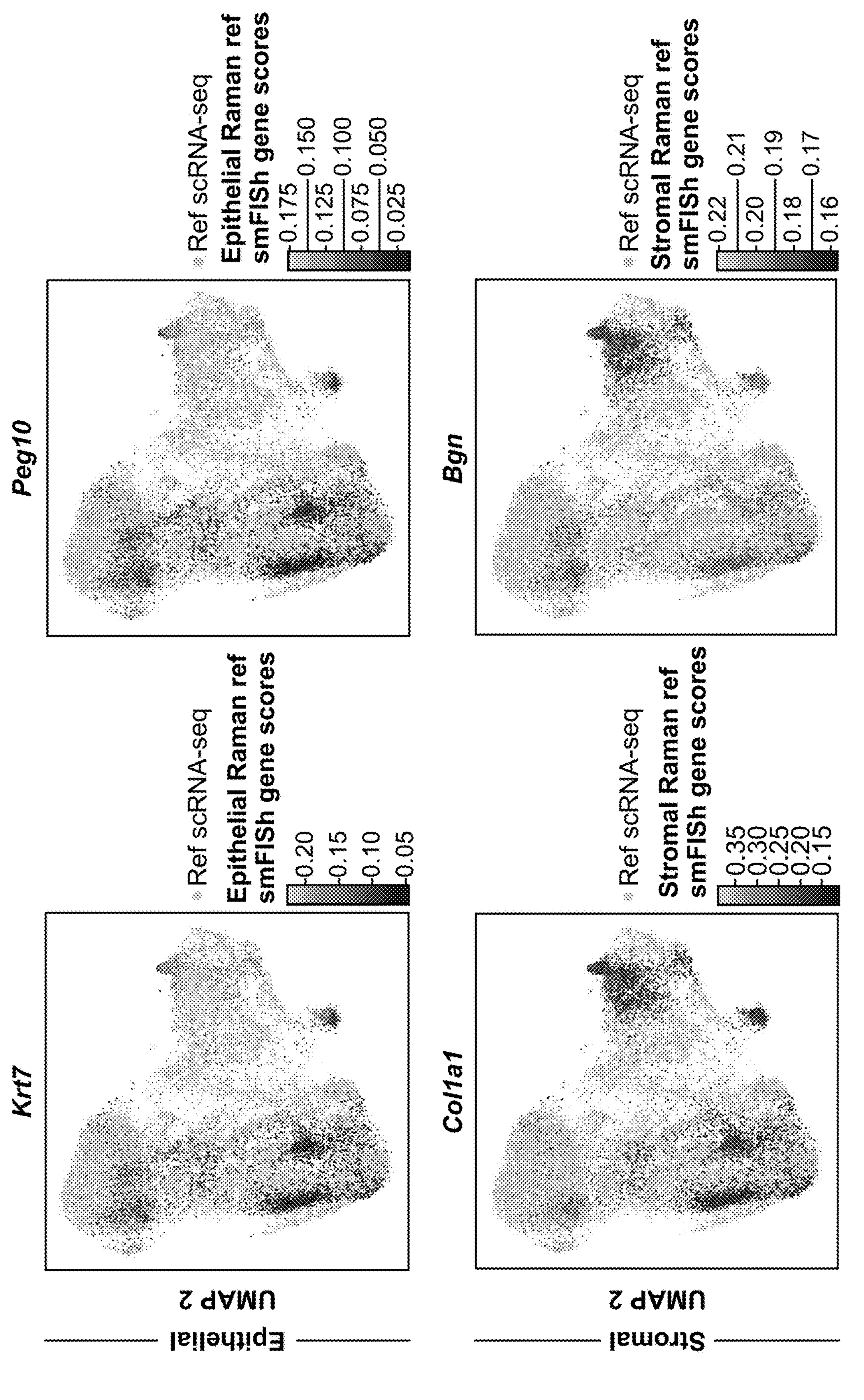
FIG. 36 (Cont. 1)

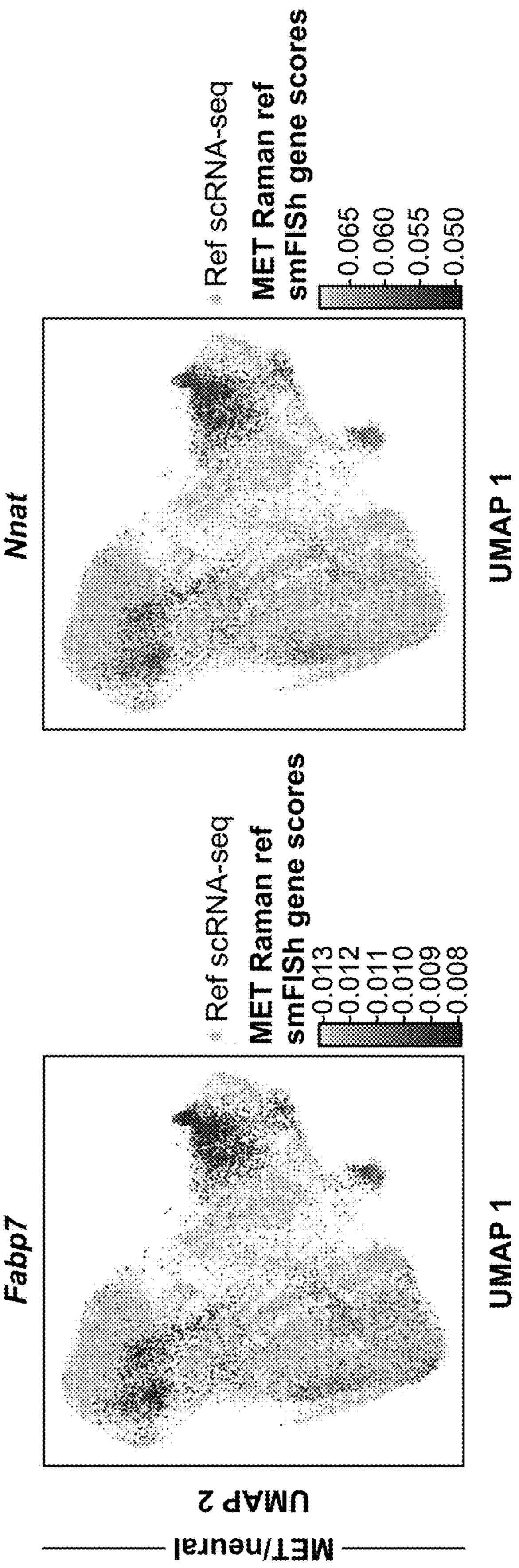
FIG. 36 (Cont. 2)

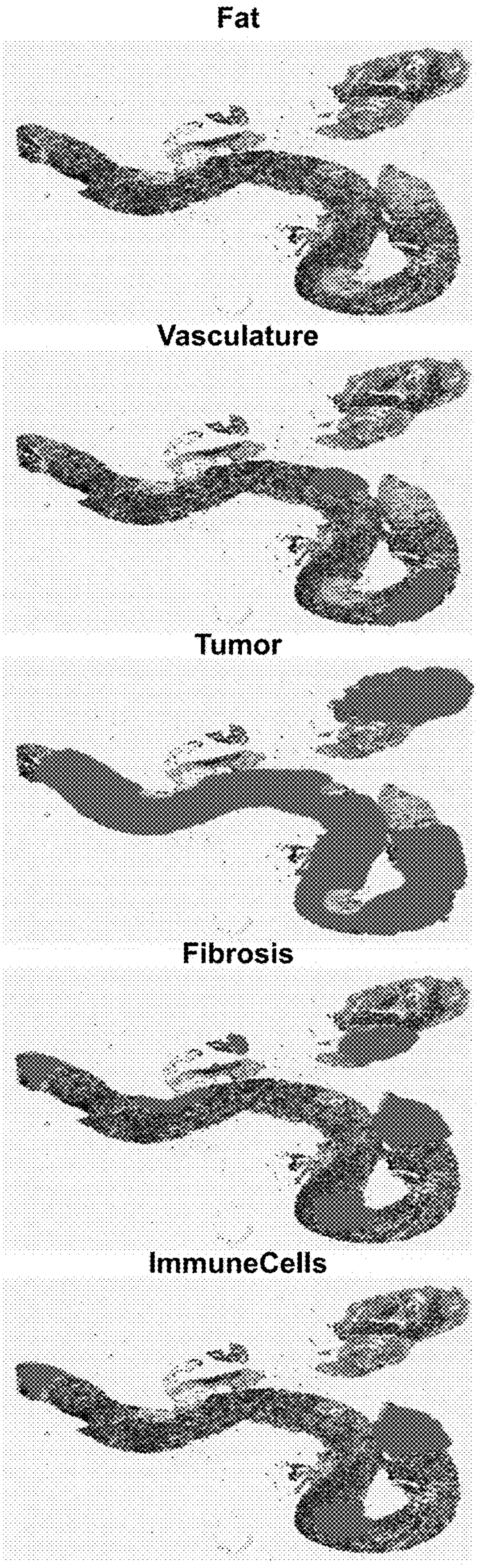
FIG. 52D (Cont. 1)

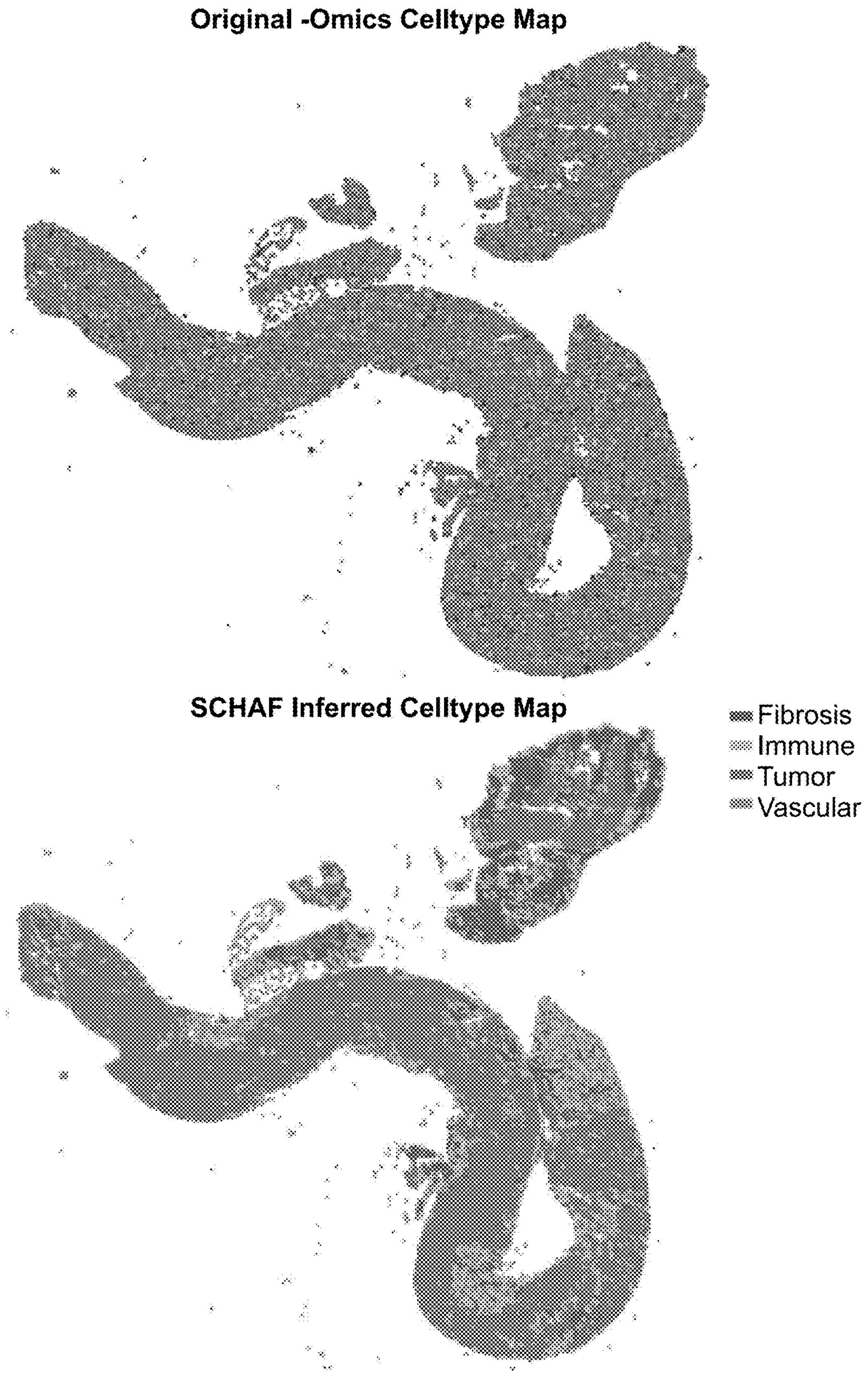
FIG. 52D (Cont. 2)

LIVE-CELL LABEL-FREE PREDICTION OF SINGLE-CELL OMICS PROFILES BY MICROSCOPY

CROSS-REFERENCE TO RELATED APPLICATIONS

This application is a continuation of International Application No. PCT/US2022/079989, filed Nov. 16, 2022, which claims priority under 35 U.S.C. § 119 (e) of U.S. Provisional Patent Application Nos. 63/280,112, filed on Nov. 16, 2021, and 63/347,496, filed May 31, 2022, the contents of which are incorporated by reference herein in their entireties.

STATEMENT AS TO FEDERALLY SPONSORED RESEARCH

This invention was made with government support under grant numbers CA275687, HD096049, and TR004354 awarded by the National Institutes of Health. The government has certain rights in the invention.

TECHNICAL FIELD

The subject matter disclosed herein is generally directed to determining an omics profile of a cell utilizing microscopy data, expression data, or a combination thereof of the cell.

REFERENCE TO AN ELECTRONIC SEQUENCE LISTING

The instant application contains a Sequence Listing which has been submitted electronically in XML format and is hereby incorporated by reference in its entirety. Said XML copy, created on May 13, 2024, is named 114203-2373_SL.xml and is 18,858 bytes in size.

BACKGROUND

Cellular states and functions are determined by a dynamic balance between intrinsic and extrinsic programs. Dynamic processes such as cell growth, stress responses, differentiation, and reprogramming are not determined by a single gene, but by the orchestrated temporal expression and function of multiple genes organized in programs and their interactions with other cells and the surrounding environment[1]. To understand how cells change their states in physiological and pathological conditions it is essential to decipher the dynamics of the underlying gene programs.

Despite major advances in single cell genomics and microscopy, Applicants still cannot track live cells and tissues at the genomic level. On the one hand, single cell and spatial genomics have provided a view of gene programs and cell states at unprecedented scale and resolution[1], but these measurement methods are destructive, and involve tissue fixation and freezing and/or cell lysis, precluding Applicants from directly tracking the dynamics of full molecular profiles in live cells or organisms. While advanced computational methods, such as pseudo-time algorithms (e.g., Monocle[2], Waddington-OT[3]) and velocity-based methods (e.g., velocyto[4], scVelo[5]), can infer dynamics from snapshots of molecular profiles, they rely on assumptions that remain challenging to verify experimentally[6]. On the other hand, fluorescent reporters can be used to monitor the dynamics of individual genes and programs within live cells, but are limited in the number of targets they can report[7], must be chosen ahead of the experiment and often involve genetically engineered cells. Moreover, the vast majority of dyes and reporters require fixation or can interfere with nascent biochemical processes and alter the natural state of the gene of interest[7]. Therefore, it remains technically challenging to dynamically monitor the activity of a large number of genes simultaneously.

Raman microscopy opens a unique opportunity for monitoring live cells and tissues, as it collectively reports on the vibrational energy levels of molecules in a label-free and non-destructive manner at a subcellular spatial resolution, thus providing molecular fingerprints of cells[8]. Pioneering research has demonstrated that Raman microscopy can be used for characterizing cell types and cell states[8], non-destructively diagnosing pathological specimens such as tumors[9], characterizing the developmental states of embryos[10], and identifying bacteria with antibiotic resistance[11]. However, the complex and high-dimensional nature of the spectra, the spectral overlaps of biomolecules such as proteins and nucleic acids, and the lack of unified computational frameworks have hindered the decomposition of the underlying molecular profiles[7,8].

Citation or identification of any document in this application is not an admission that such a document is available as prior art to the present invention.

SUMMARY

In example embodiments, the technology described herein includes computer-implemented methods, computer program products, and systems to determine an omics profiles of a cell using microscopy imaging data. In one aspect, a computer-implemented method determines an omics profiles of a cell using microscopy imaging data, comprising: a) receiving, by at least one computing device, microscopy imaging data of a cell or a population of cells; b) determining, by the at least one computing device, a targeted expression profile of a set of target genes from the microscopy imaging data using a first machine learning model, the target genes identifying a cell type or cell state of interest; and c) determining, by the at least one computing device, a single-cell omics profile for the population of cells using a second machine learning algorithm model, wherein the targeted expression profile from b), and a reference single-cell RNA-seq data set are used as inputs for the second machine learning model.

In example embodiments, the targeted expression profile is targeted spatial expression profile. In example embodiments, the microscopy method is a label-free microscopy method. The cell or population of cells may be a live cell or a population of live cells. In example embodiments, the cell or population of cells are fixed. The microscopy imaging data may be vibrational hyperspectral imaging data. The vibrational hyperspectral imaging data may be Raman imaging data. The Raman imaging data may be Spontaneous/far-field Raman spectroscopy, Enhanced/near-field Raman spectroscopy, Non-linear Raman spectroscopy, Morphologically-Directed Raman Spectroscopy, or Correlative Raman imaging. The Spontaneous/far-field Raman spectroscopy technique may comprise Resonance Raman, Angle-resolved Raman, Optical tweezer Raman, Spatially offset Raman, Transmission Raman, or Micro-cavity Raman. The Enhanced/near-field Raman spectroscopy technique may comprise Surface-Enhanced Raman, Surface-Enhanced Resonance Raman, Tip-Enhanced Raman, or Surface Plasmon Polariton Enhanced Raman Scattering. The Non-linear Raman spectroscopy technique may comprise Hyper Raman, Stimulated Raman, Inverse Raman, or Coherent anti-stokes Raman. In example embodiments, the microscopy imaging data comprises Cell Painting or Cell Profiler.

The microscopy imaging data may be in vivo imaging data. The in vivo imaging data may be Positron Emission Tomography (PET), Single Photon Emission Computed Tomography (SPECT), computed tomography (CT), bioluminescence imaging (BLI), fluorescent lifetime imaging (FLI), fluorescent reflectance imaging (FRI), fluorescence molecular tomography (FMT), optical coherence tomography (OCT), optical projection tomography (OPT), photoacoustic tomography (PAT), multispectral optoacoustic tomography (MSOT), raster-scan optoacoustic mesoscopy (RSOM), magnetic resonance imaging (MRI), ultrasound (US).

The first machine learning model may be trained using Raman imaging spectra obtained from a sample cell or population of cells as training inputs, and gene expression data obtained for the set of target genes as ground truths. The gene expression data may be sequencing based omics data, imaging based omics data, or spatial omics data. The imaging based omics data or spatial omics data may comprise smFISH, seqFISH, merFISH, STARmap, ExSeq, Slide-seq, FISSEQ, BOLORAMIS, Slide-seq, DBiT-seq, sci-Space, 10× Genomics Visium, Saber, or a combination thereof. The first machine learning model may comprise gradient boosting. The gradient boosting method may be gradient boosted decision trees. The second machine learning model may comprise neural networks. The neural network may be a deep learning neural network.

The second machine learning model may comprise unsupervised deep learning nonlinear optimization. The unsupervised deep learning non-linear optimization may use one or more similarity functions. The one or more similarity functions may comprise Kullback-Leibler (KL) divergence and cosine similarity.

In one aspect, a system to determine an omics profiles of a cell using microscopy imaging data comprises a storage device and a processor communicatively coupled to the storage device, wherein the processor executes application code instructions that are stored in the storage device to cause the system to a) receive microscopy imaging data of a cell or a population of cells; b) determine a targeted expression profile of a set of target genes from the microscopy imaging data using a first machine learning model, the target genes identify cell type or cell state of interest; and determine a single-cell omics profile for the population of cells using a second machine learning algorithm model, wherein the targeted expression profile from b), and a reference single-cell RNA-seq data set are used as inputs for the second machine learning model.

In example embodiment, the targeted expression profile is targeted spatial expression profile. In example embodiments, the microscopy method is label-free. The cell or population of cells may be a live cell or a population of live cells or fixed cell or population of fixed cells. The microscopy imaging data may be vibrational hyperspectral imaging data. The vibrational hyperspectral imaging data may be Raman imaging data. The Raman imaging data may be Spontaneous/far-field Raman spectroscopy, Enhanced/near-field Raman spectroscopy, Non-linear Raman spectroscopy, Morphologically-Directed Raman Spectroscopy, or Correlative Raman imaging. The Spontaneous/far-field Raman spectroscopy technique may comprise Resonance Raman, Angle-resolved Raman, Optical tweezer Raman, Spatially offset Raman, Transmission Raman, or Micro-cavity Raman. The Enhanced/near-field Raman spectroscopy technique may comprises Surface-Enhanced Raman, Surface-Enhanced Resonance Raman, Tip-Enhanced Raman, or Surface Plasmon Polariton Enhanced Raman Scattering. The Non-linear Raman spectroscopy technique may comprise Hyper Raman, Stimulated Raman, Inverse Raman, or Coherent anti-stokes Raman. In example embodiment, the microscopy imaging data comprises Cell Painting or Cell Profiler.

The microscopy imaging data may be in vivo imaging data. The in vivo imaging data may be Positron Emission Tomography (PET), Single Photon Emission Computed Tomography (SPECT), computed tomography (CT), bioluminescence imaging (BLI), fluorescent lifetime imaging (FLI), fluorescent reflectance imaging (FRI), fluorescence molecular tomography (FMT), optical coherence tomography (OCT), optical projection tomography (OPT), photoacoustic tomography (PAT), multispectral optoacoustic tomography (MSOT), raster-scan optoacoustic mesoscopy (RSOM), magnetic resonance imaging (MRI), ultrasound (US).

The first machine learning model may be trained using Raman imaging spectra obtained from a sample cell or population of cells as training inputs, and gene expression data obtained for the set of target genes as ground truths. The gene expression data may be sequencing based omics data, imaging based omics data, or spatial omics data. The imaging based omics data or spatial omics data may comprise smFISH, seqFISH, merFISH, STARmap, ExSeq, Slide-seq, FISSEQ, BOLORAMIS, Slide-seq, DBiT-seq, sci-Space, 10× Genomics Visium, Saber, or a combination thereof. The first machine learning model may comprise gradient boosting. The gradient boosting method may be gradient boosted decision tree. The second machine learning model may comprise neural networks. The neural network may be a deep learning neural network.

The second machine learning model may comprise unsupervised deep learning nonlinear optimization. The unsupervised deep learning non-linear optimization may use one or more similarity functions. The one or more similarity functions may comprise Kullback-Leibler (KL) divergence and cosine similarity.

In one aspect, a computer program product comprises a non-transitory computer-readable storage device having computer-executable program instructions embodied thereon that when executed by a computer cause the computer to determine an omics profiles of a cell using microscopy imaging data, the computer-executable program instructions comprising: a) computer-executable program instructions to receive microscopy imaging data of a cell or a population of cells; b) computer-executable program instructions to determine a targeted expression profile of a set of target genes from the microscopy imaging data using a first machine learning model, the target genes identify cell type or cell state of interest; and c) computer-executable program instructions to determine a single-cell omics profile for the population of cells using a second machine learning algorithm model, wherein the targeted expression profile and a reference single-cell RNA-seq data set are used as inputs for the second machine learning model.

In example embodiments, the targeted expression profile is targeted spatial expression profile. In example embodiments, the microscopy method is label-free. The cell or population of cells may be a live cell or a population of live cells or fixed cell or a population of fixed cells. The microscopy imaging data may be vibrational hyperspectral imaging data. The vibrational hyperspectral imaging data may be Raman imaging data. The Raman imaging data may be Spontaneous/far-field Raman spectroscopy, Enhanced/near-field Raman spectroscopy, Non-linear Raman spectroscopy, Morphologically-Directed Raman Spectroscopy, or Correlative Raman imaging. The Spontaneous/far-field Raman spectroscopy technique may comprise Resonance Raman, Angle-resolved Raman, Optical tweezer Raman, Spatially offset Raman, Transmission Raman, or Micro-cavity Raman. The Enhanced/near-field Raman spectroscopy technique may comprise Surface-Enhanced Raman, Surface-Enhanced Resonance Raman, Tip-Enhanced Raman, or Surface Plasmon Polariton Enhanced Raman Scattering. The Non-linear Raman spectroscopy technique may comprise Hyper Raman, Stimulated Raman, Inverse Raman, or Coherent anti-stokes Raman. In example embodiments, the microscopy imaging data comprises Cell Painting or Cell Profiler The microscopy imaging data may be in vivo imaging data. The in vivo imaging data may be Positron Emission Tomography (PET), Single Photon Emission Computed Tomography (SPECT), computed tomography (CT), bioluminescence imaging (BLI), fluorescent lifetime imaging (FLI), fluorescent reflectance imaging (FRI), fluorescence molecular tomography (FMT), optical coherence tomography (OCT), optical projection tomography (OPT), photoacoustic tomography (PAT), multispectral optoacoustic tomography (MSOT), raster-scan optoacoustic mesoscopy (RSOM), magnetic resonance imaging (MRI), ultrasound (US).

The first machine learning model may be trained using Raman imaging spectra obtained from a sample cell or population of cells as training inputs, and gene expression data obtained for the set of target genes as ground truths. The gene expression data may be sequencing based omics data, imaging based omics data, or spatial omics data. The imaging based omics data or spatial omics data may comprise smFISH, seqFISH, merFISH, STARmap, ExSeq, Slide-seq, FISSEQ, BOLORAMIS, Slide-seq, DBiT-seq, sci-Space, 10× Genomics Visium, Saber, or a combination thereof. The first machine learning model may comprise gradient boosting. The gradient boosting method may be gradient boosted decision tree. The second machine learning model may comprise neural networks. The neural network may be a deep learning neural network.

The second machine learning model may comprise unsupervised deep learning nonlinear optimization. The unsupervised deep learning non-linear optimization may use one or more similarity functions. The one or more similarity functions may comprise Kullback-Leibler (KL) divergence and cosine similarity.

In one aspect, as described herein, a computer-implemented method to determine an omics profile of a cell using microscopy imaging data, comprising: receiving, by at least one computing device, microscopy imaging data of a cell or a population of cells; and determining, by the at least one computing device, a single-cell omics profile for the cell or the population of cells from the microscopy imaging data using a machine learning model. In example embodiments, the microscopy imaging data is obtained from a label-free microscopy method. In example embodiments, the cell or population of cells is a live cell or a population of live cells. In example embodiments, the cell or population of cells are fixed.

In example embodiments, the microscopy imaging data is vibrational hyperspectral imaging data. In example embodiments, the vibrational hyperspectral imaging data is Raman imaging data. In example embodiments, the Raman imaging data is Spontaneous/far-field Raman spectroscopy, Enhanced/near-field Raman spectroscopy, Non-linear Raman spectroscopy, Morphologically-Directed Raman Spectroscopy, or Correlative Raman imaging. In example embodiments, the Spontaneous/far-field Raman spectroscopy technique comprises Resonance Raman, Angle-resolved Raman, Optical tweezer Raman, Spatially offset Raman, Transmission Raman, or Micro-cavity Raman. In example embodiments, the Enhanced/near-field Raman spectroscopy technique comprises Surface-Enhanced Raman, Surface-Enhanced Resonance Raman, Tip-Enhanced Raman, or Surface Plasmon Polariton Enhanced Raman Scattering. In example embodiments, the Non-linear Raman spectroscopy technique comprises Hyper Raman, Stimulated Raman, Inverse Raman, or Coherent anti-stokes Raman. In example embodiments, the microscopy imaging data comprises Cell Painting or Cell Profiler.

In example embodiments, the microscopy imaging data is obtained using an in vivo imaging method. In example embodiments, the in vivo imaging method comprises Positron Emission Tomography (PET), Single Photon Emission Computed Tomography (SPECT), computed tomography (CT), bioluminescence imaging (BLI), fluorescent lifetime imaging (FLI), fluorescent reflectance imaging (FRI), fluorescence molecular tomography (FMT), optical coherence tomography (OCT), optical projection tomography (OPT), photoacoustic tomography (PAT), multispectral optoacoustic tomography (MSOT), raster-scan optoacoustic mesoscopy (RSOM), magnetic resonance imaging (MRI), ultrasound (US), photo-thermal microscopy, or a combination thereof.

In example embodiments, the method further comprises training the machine learning model using Raman imaging spectra obtained from a sample cell or population of cells as training inputs, and single-cell omics profiles as ground truths. In example embodiments, the machine learning model comprises gradient boosting. In example embodiments, the gradient boosting method is a gradient boosted decision tree. In example embodiments, the machine learning model comprises neural networks. In example embodiments, the neural network is a deep learning neural network. In example embodiments, the deep learning neural network comprises an autoencoder. In example embodiments, the autoencoder is an adversarial autoencoder. In example embodiments, the machine learning model comprises unsupervised deep learning nonlinear optimization. In example embodiments, the unsupervised deep learning non-linear optimization uses one or more similarity functions. In example embodiments, the one or more similarity functions comprise Kullback-Leibler (KL) divergence and cosine similarity.

In one aspect, as described herein, a system to determine an omics profiles of a cell using microscopy imaging data, comprising: a storage device; and a processor communicatively coupled to the storage device, wherein the processor executes application code instructions that are stored in the storage device to cause the system to carry out the methods described herein.

In one aspect, as described herein a computer program product, comprising: a non-transitory computer-readable storage device having computer-executable program instructions embodied thereon that when executed by a computer cause the computer to determine an omics profiles of a cell using microscopy imaging data, the computer-executable program instructions comprising the methods described herein.

A computer-implemented method to determine an omics profile of a cell using expression profile data, comprising: receiving, by at least one computing device, an expression profile of a cell or a population of cells; and determining, by the at least one computing device, a single-cell omics profile for the population of cells from the expression profile using a machine learning model. In example embodiments, the expression profile is targeted spatial expression profile. In example embodiments, the cell or population of cells is a live cell or a population of live cells. In example embodiments, the cell or population of cells are fixed.

In example embodiments, the method further comprises training the machine learning model using expression profiles obtained from a sample cell or population of cells as training inputs, and single-cell omics profile as ground truths. In example embodiments, the expression profile is imaging-based omics data or spatial omics data. In example embodiments, the imaging-based omics data or spatial omics data comprises smFISH, seqFISH, merFISH, STAR-map, ExSeq, Slide-seq, FISSEQ, BOLORAMIS, Slide-seq, DBiT-seq, sci-Space, 10× Genomics Visium, Saber, Hematoxylin-and-Eosin (H&E) stains or a combination thereof. In example embodiments, the imaging bases omics data comprise H&E stains.

In example embodiments, the machine learning model comprises gradient boosting. In example embodiments, the gradient boosting method is a gradient boosted decision tree. In example embodiments, the machine learning model comprises neural networks. In example embodiments, the neural network is a deep learning neural network. In example embodiments, the deep learning neural network is a convolutional neural network. In example embodiments, the convolutional neural network is a convolutional autoencoder. In example embodiments, the convolutional neural network is a convolutional neural network. In example embodiments, the machine learning model comprises unsupervised deep learning nonlinear optimization. In example embodiments, the unsupervised deep learning non-linear optimization uses one or more similarity functions. In example embodiments, the one or more similarity functions comprise Kullback-Leibler (KL) divergence and cosine similarity.

In one aspect, as described herein, a system to determine an omics profiles of a cell using microscopy imaging data, comprising: a storage device; and a processor communicatively coupled to the storage device, wherein the processor executes application code instructions that are stored in the storage device to cause the system to carry out the methods described herein.

In one aspect, as described herein, A computer program product, comprising: a non-transitory computer-readable storage device having computer-executable program instructions embodied thereon that when executed by a computer cause the computer to determine an omics profiles of a cell using microscopy imaging data, the computer-executable program instructions comprising the methods described herein.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 6*a*-6*k*—Raman2RNA predicts single-cell RNA profiles across cell types during reprogramming of mouse fibroblasts to iPSCs. 6*a*) Approach overview. From left: Mouse fibroblasts were reprogrammed into induced pluripotent stem cells (iPSCs) over the course of 14.5 days ('D'), and, at half-day intervals from days 8 to 14.5, spatial Raman spectra, smFISH for nine anchor genes, and nuclei stain by fluorescence imaging were measured for each plate. Machine learning and multi-modal data integration methods (Catboost and Tangram) were used to predict single-cell RNA-seq profiles from Raman spectra using smFISH as anchor. 6*b,c*) Low dimensionality embedding of single-cell Raman spectra captures progress in reprogramming. Force-directed layout embedding (FLE) of Raman spectra (b, dots) or scRNA-seq (c, dots) colored by days of measurement (colorbar). 6*d*) Correct prediction of smFISH anchors from Raman spectra. Pearson correlation coefficient (y axis)

between measured (smFISH) and Raman-predicted levels for each smFISH anchor (x axis) in leave-one-out cross-validation where 8 out of 9 smFISH anchor genes were used for training, and the left-out gene was predicted. 6*e-f*) Raman2RNA accurately predicts pseudo-bulk expression profiles of major cell types. 6*e*) scRNA-seq measured (y axis) and R2R-predicted (x axis) for each gene (dot) in pseudo-bulk RNA profiles averaged across iPSCs. 6*f*) Pair-wise correlation (color bar) between Raman-predicted and scRNA-seq measured pseudo-bulk profiles in each cell types (rows, columns). 6*g-j*) Co-embedding highlights agreement between real and R2R inferred single cell profiles. UMAP co-embedding of Raman predicted RNA profiles and measured scRNA-seq profiles (dots) colored by data source 6*g*) Raman predicted in orange; measured scRNA-seq in blue), cell type annotations 6*h*) or by iPSC gene signature scores (calculated by averaging expression of genes Nanog and Utf1, and subtracting the average of a randomly selected set of reference genes; Methods) of Raman-predicted profiles 6*i*) or of real scRNA-seq 6*j*). 6*k*) Feature importance scores of Raman spectra in predicting expression profiles. Feature scores for iPSC related marker genes (y axis) along the Raman spectrum (x axis). Known Raman peaks[32] were annotated.

Figure 7:
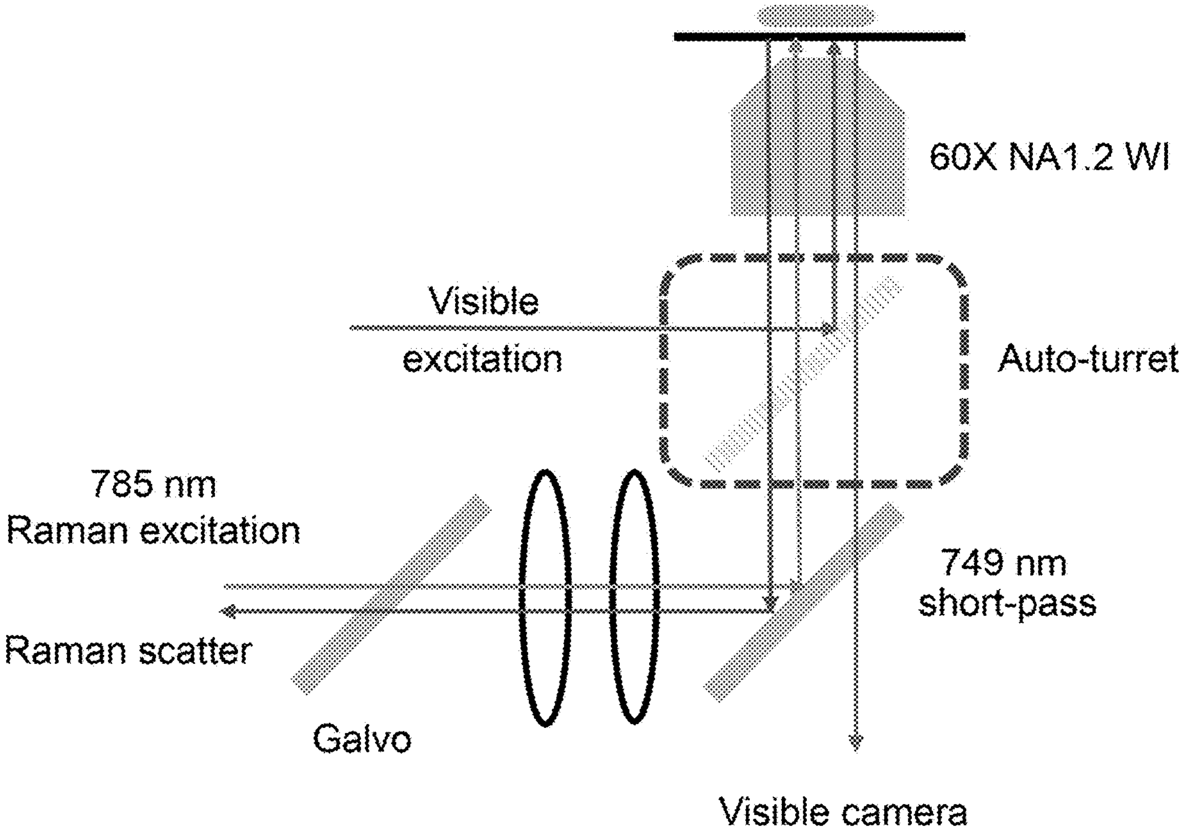

FIG. 7—A multi-modal Raman microscope capable of fluorescence imaging and Raman microscopy. Schematic of a Raman microscope integrated with a wide-field fluorescence microscope for simultaneous detection of nuclei staining, bright field, fluorescence channels, and Raman images.

Figure 8:
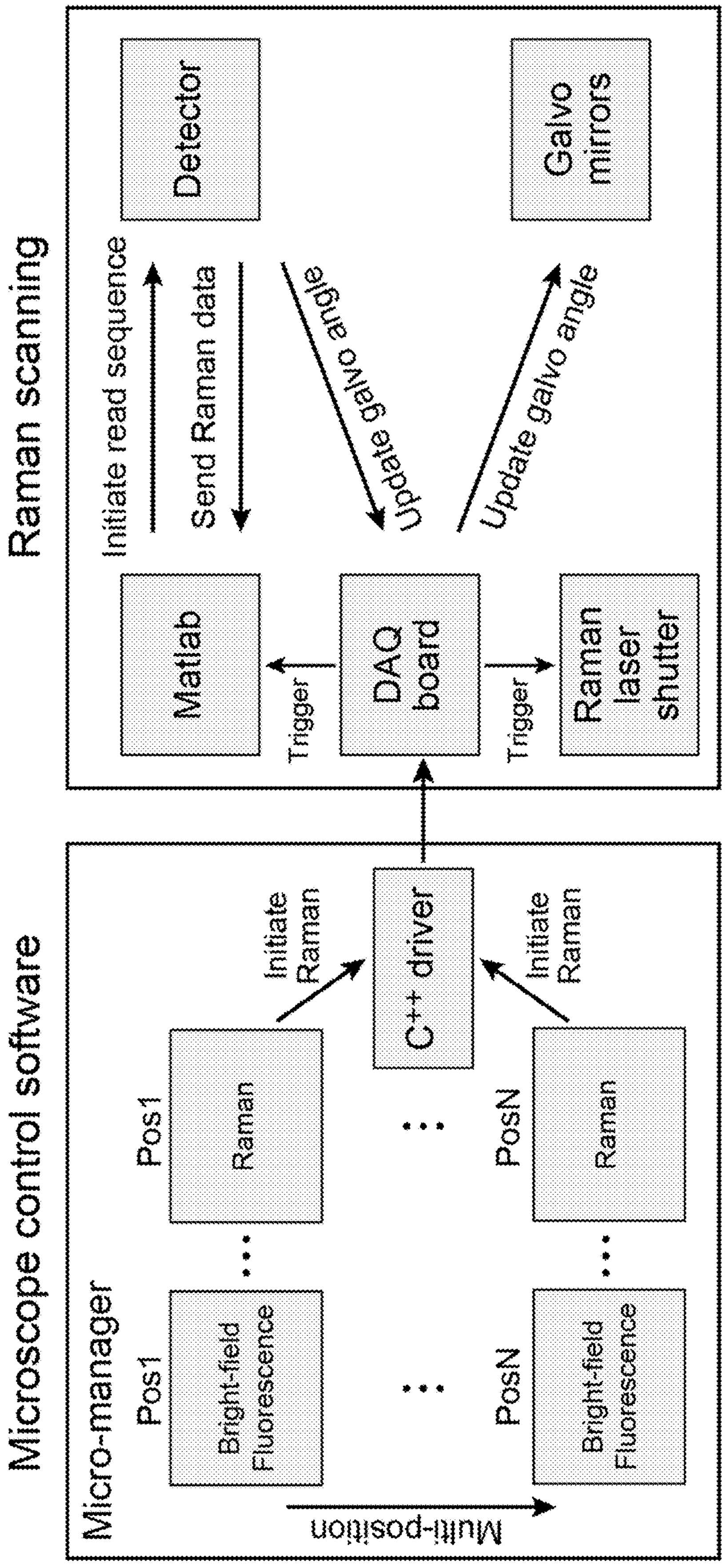

FIG. 8—Overview of high-throughput Raman imaging software used in the study. A general-purpose microscope control software Micro-manager and a custom MATLAB script were combined to enable automated multi-modal measurements. Under Micro-manager, a Raman channel was registered as a 'dummy' channel along with brightfield and fluorescence channels. Micro-manager was responsible for changing the field of view (FOV) and imaging modality. During the Raman sequence, Micro-manager communicated with a digital acquisition (DAQ) board, through which a transistor-to-transistor logic (TTL) signal was generated to initiate the scanning sequence. Upon detection of the TTL signal, the MATLAB script controlled the Raman detector, laser shutter, and updated the galvo mirror angles through the DAQ board.

Figure 9:
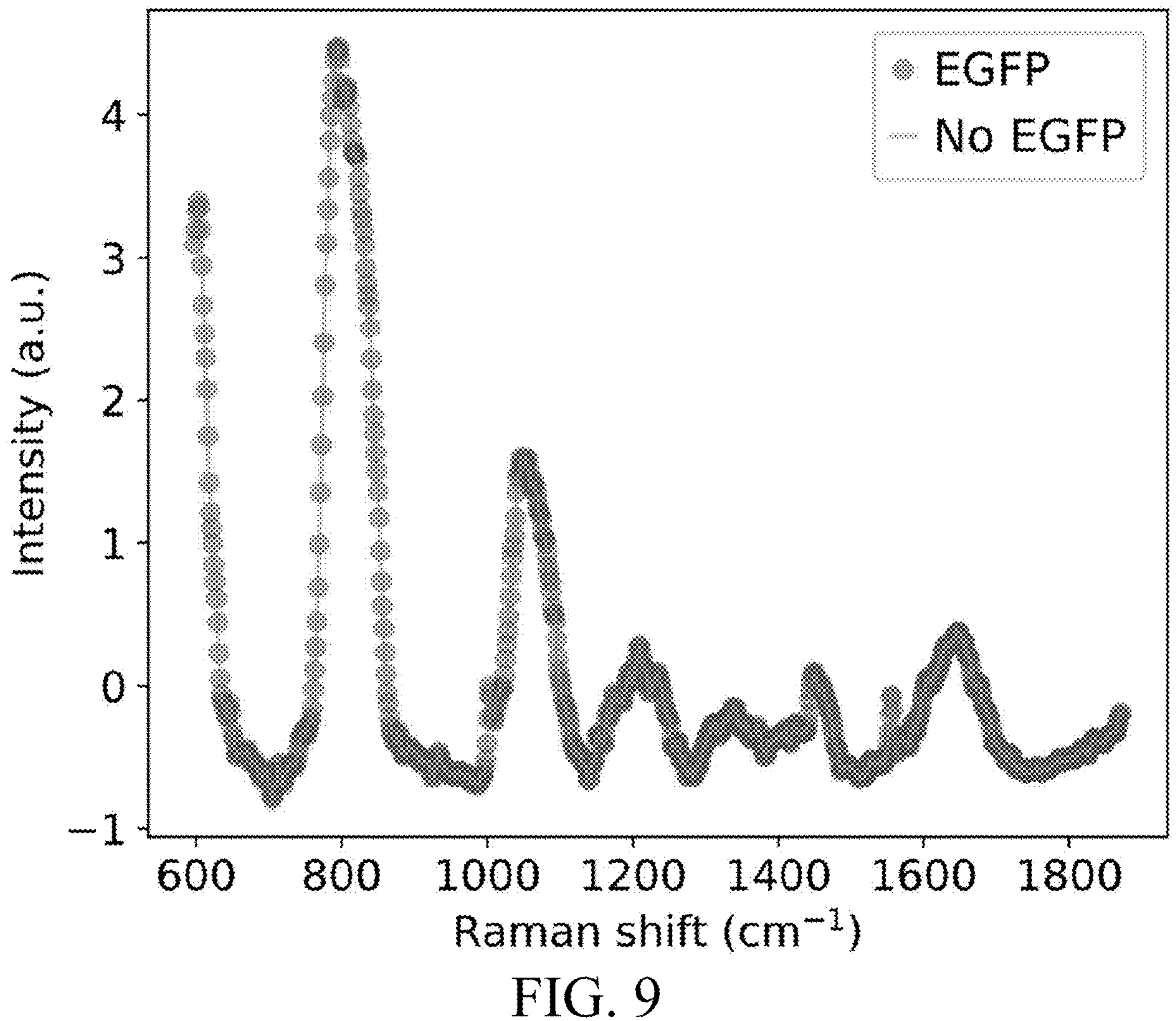

FIG. 9—GFP does not interfere in Raman spectra measurement. Raman spectra of culture media with (blue) and without (orange) GFP at physiological concentration.

Figure 10:
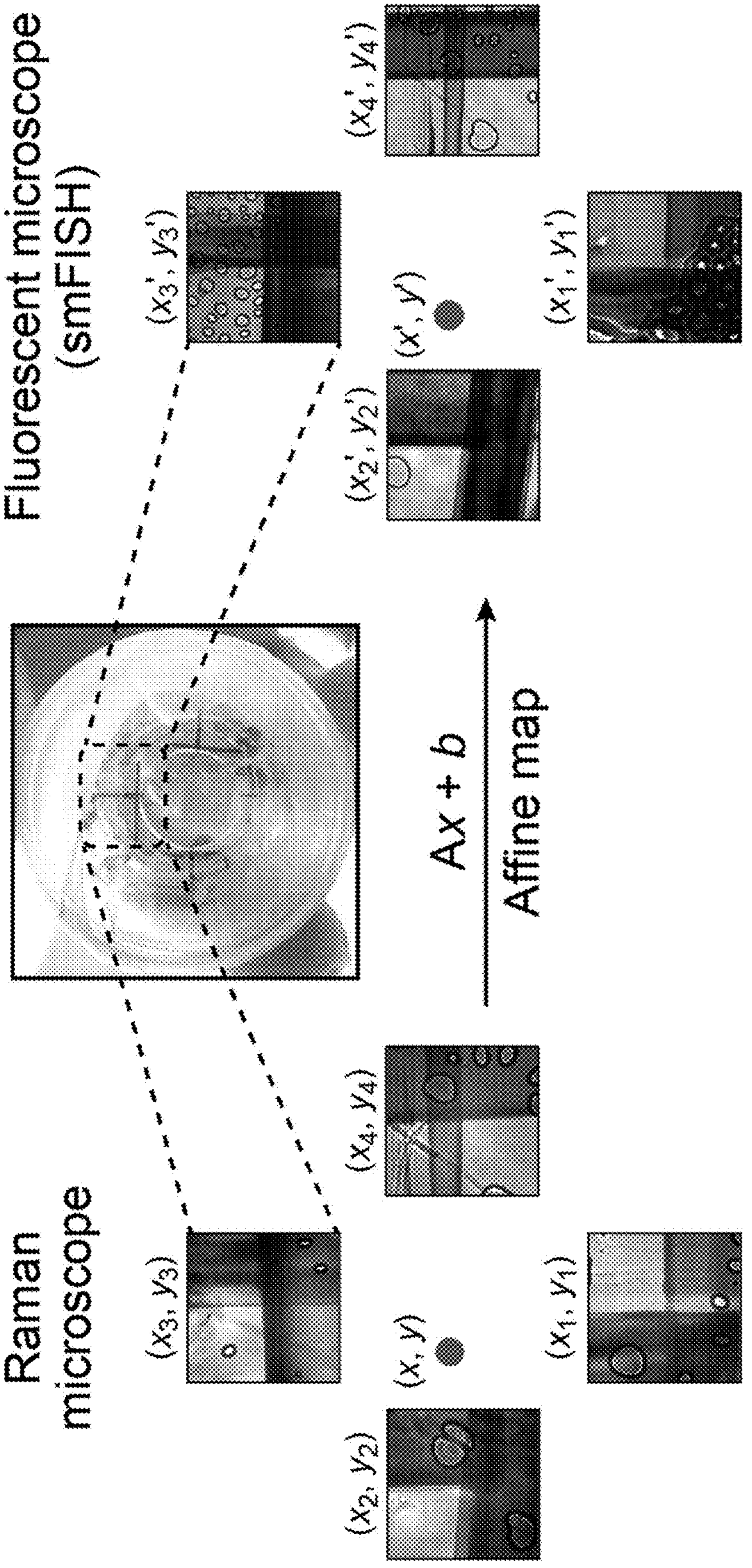

FIG. 10—Image registration between the Raman and smFISH microscope using control points. Control points were inscribed under petri dishes with permanent markers and the coordinates were measured prior to any data acquisition. After Raman measurement and smFISH processing, samples were placed back to the microscope and control point coordinates were remeasured. Then, affine mapping was used to update the FOV coordinates to locate the exact same cells.

Figure 11:
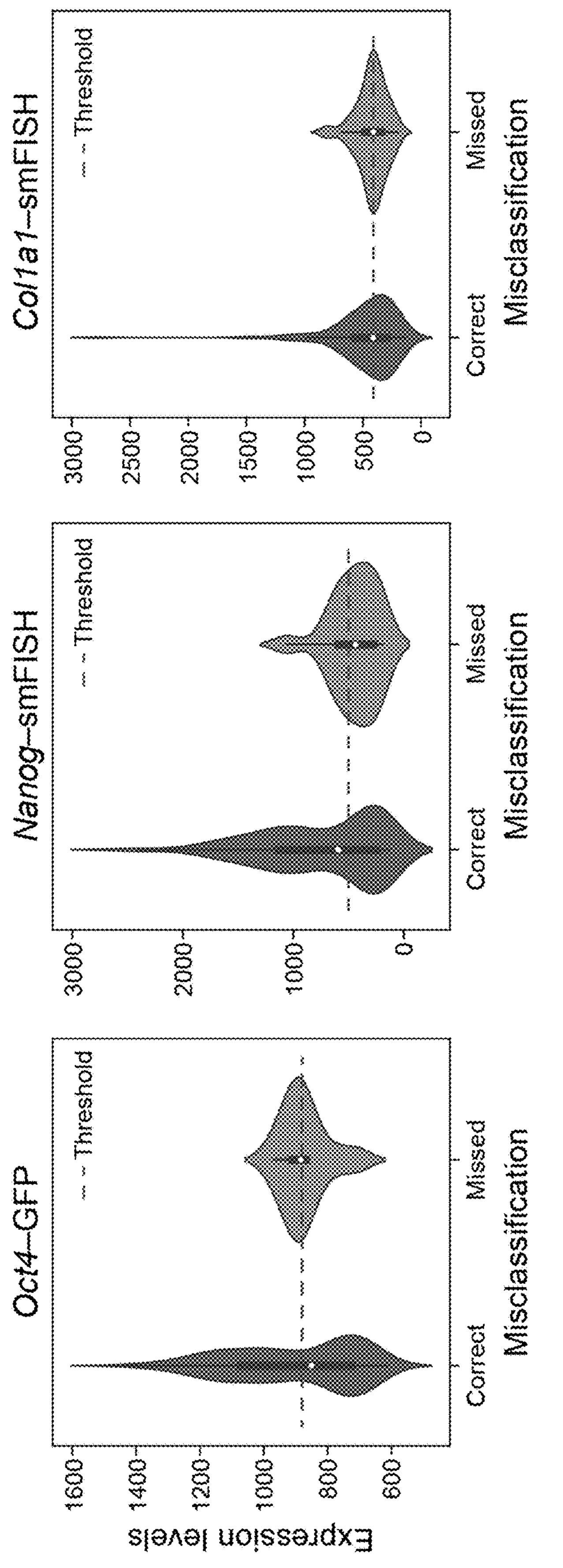

FIG. 11—Misclassification of genes in the cell mixture classification experiment occurs when the ground truth smFISH is near the expression threshold. Distribution of measured smFISH expression level (y axis) for cells correctly (blue) or incorrectly (orange) classified by their Raman spectra for the expression of that gene. Horizontal line: an example threshold used for the logistic regression classifier.

Figure 12:
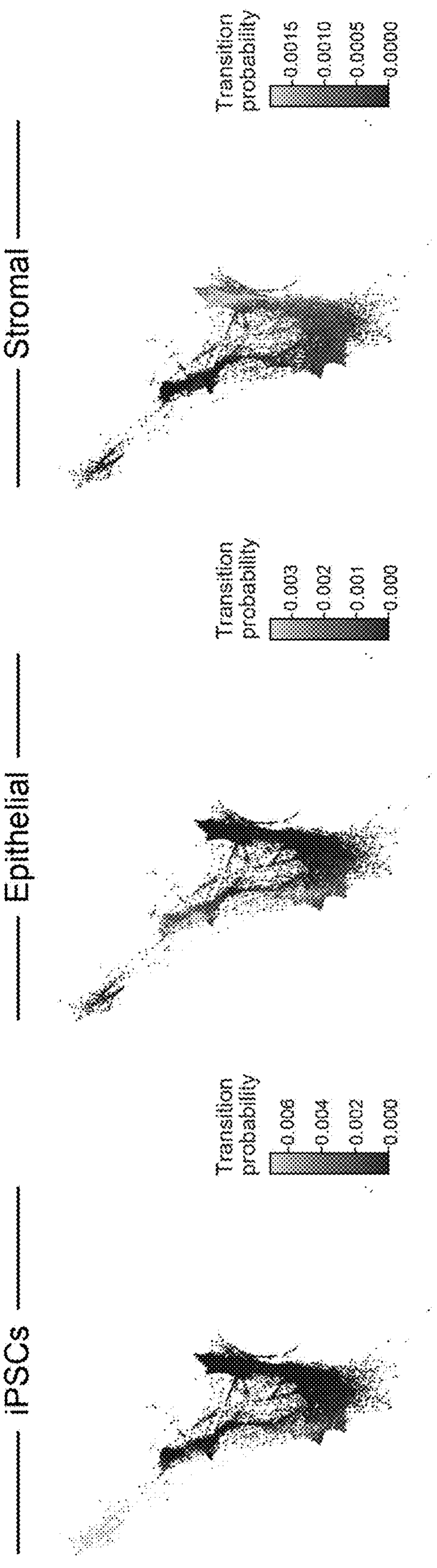

FIG. 12—Cell transition probabilities inferred by Waddington-OT from scRNA-seq during reprogramming. Force-directed layout embedding (FLE) of scRNA-seq profiles (dots) from days 8 to 14.5 of reprogramming (dots) colored by the transition probability of each cell as inferred by Waddington-OT to be an ancestor of iPSCs (left), epithelial cells (middle) or stromal cells (right) at day 14.5.

Figure 13:
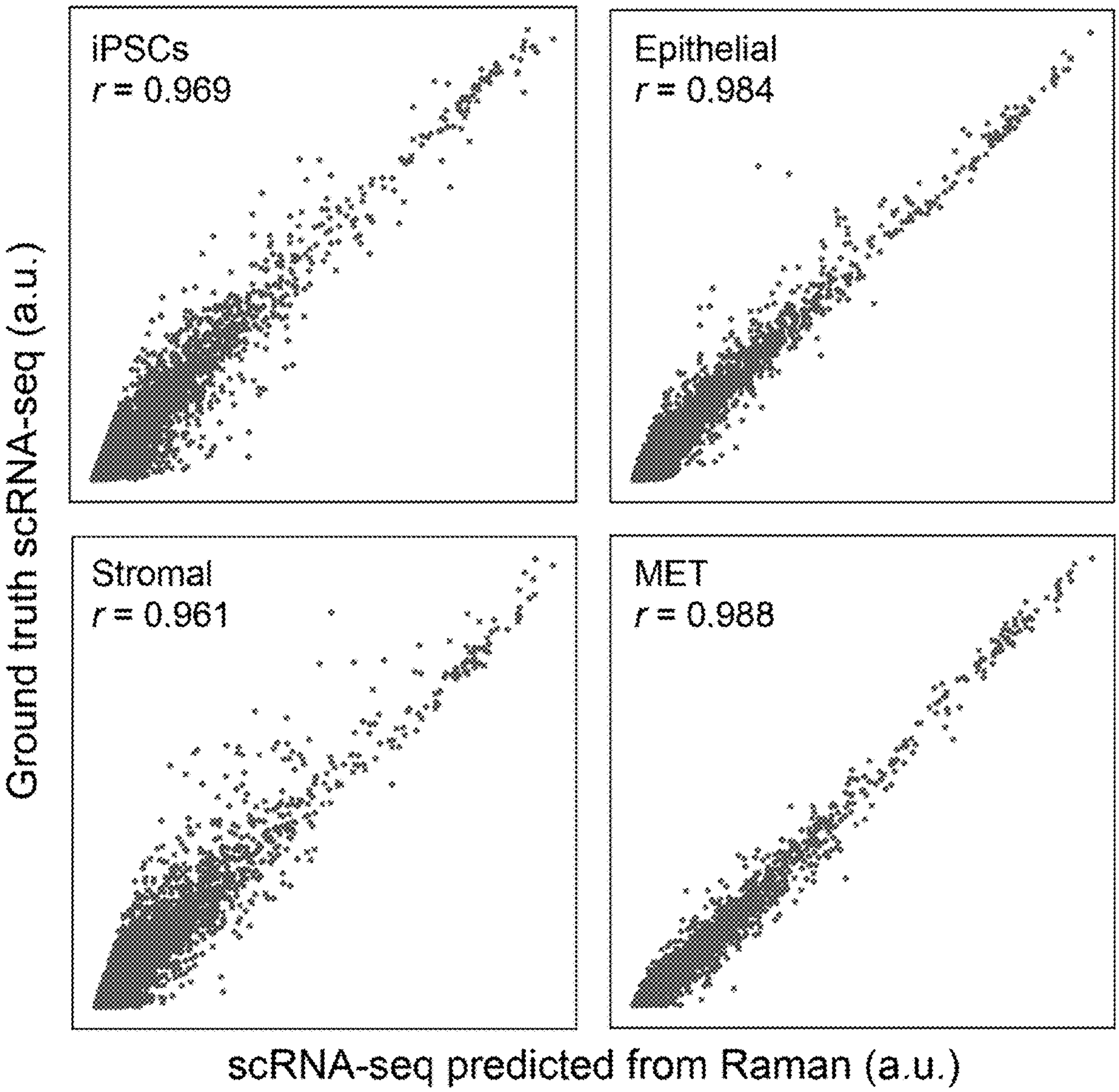

FIG. 13—Raman-predicted and scRNA-seq measured pseudo-bulk profiles are well correlated across cell types. ScRNA-seq measured (y axis) and R2R-predicted (x axis) expression for each gene (dot) in pseudo-bulk RNA profiles averaged across cells labeled as iPSC (top left), epithelial (top right), stromal (bottom left) and MET (bottom right). Pearson's r is denoted at the top left corner.

Figure 14:
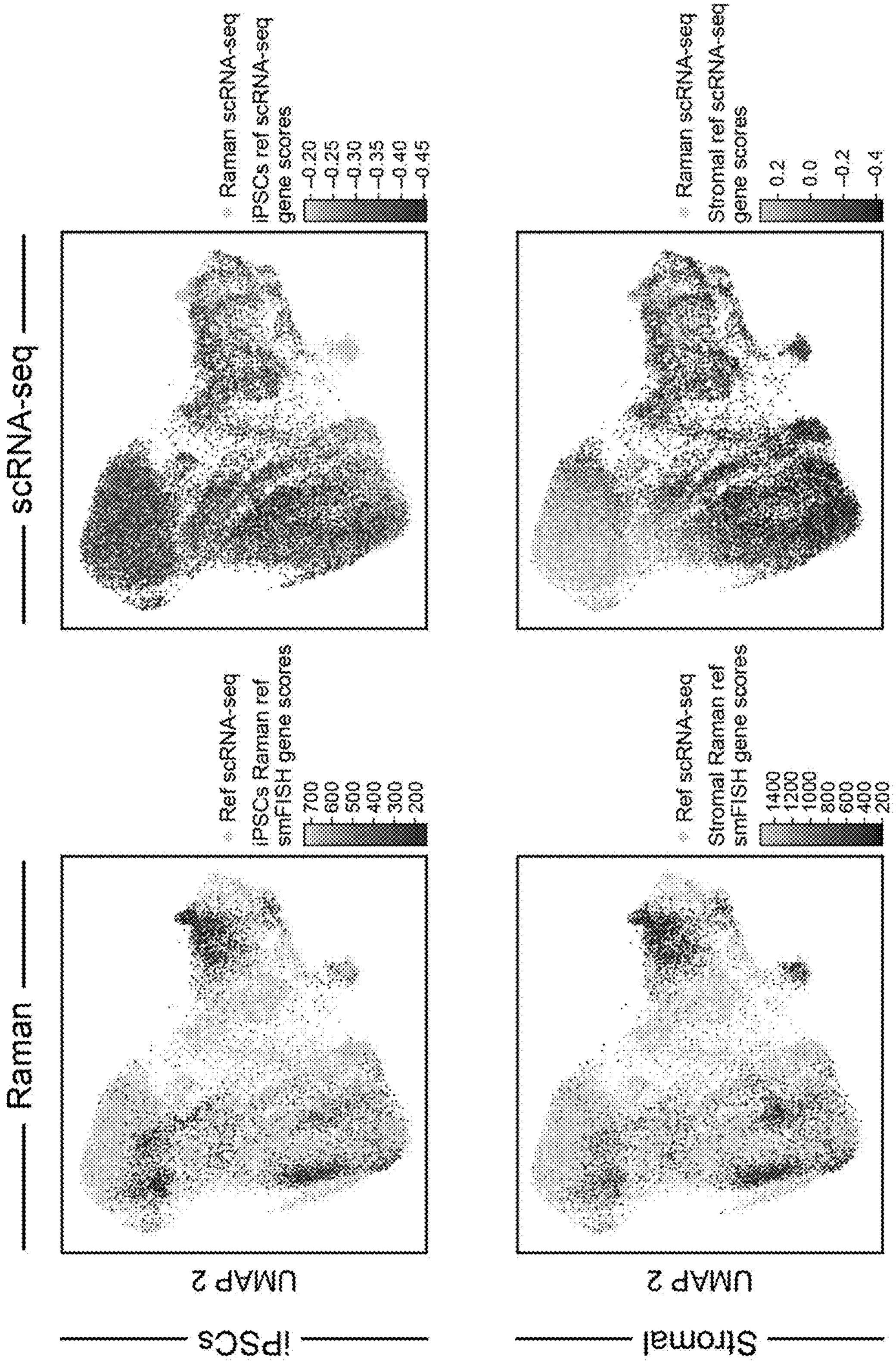
Figure 14:
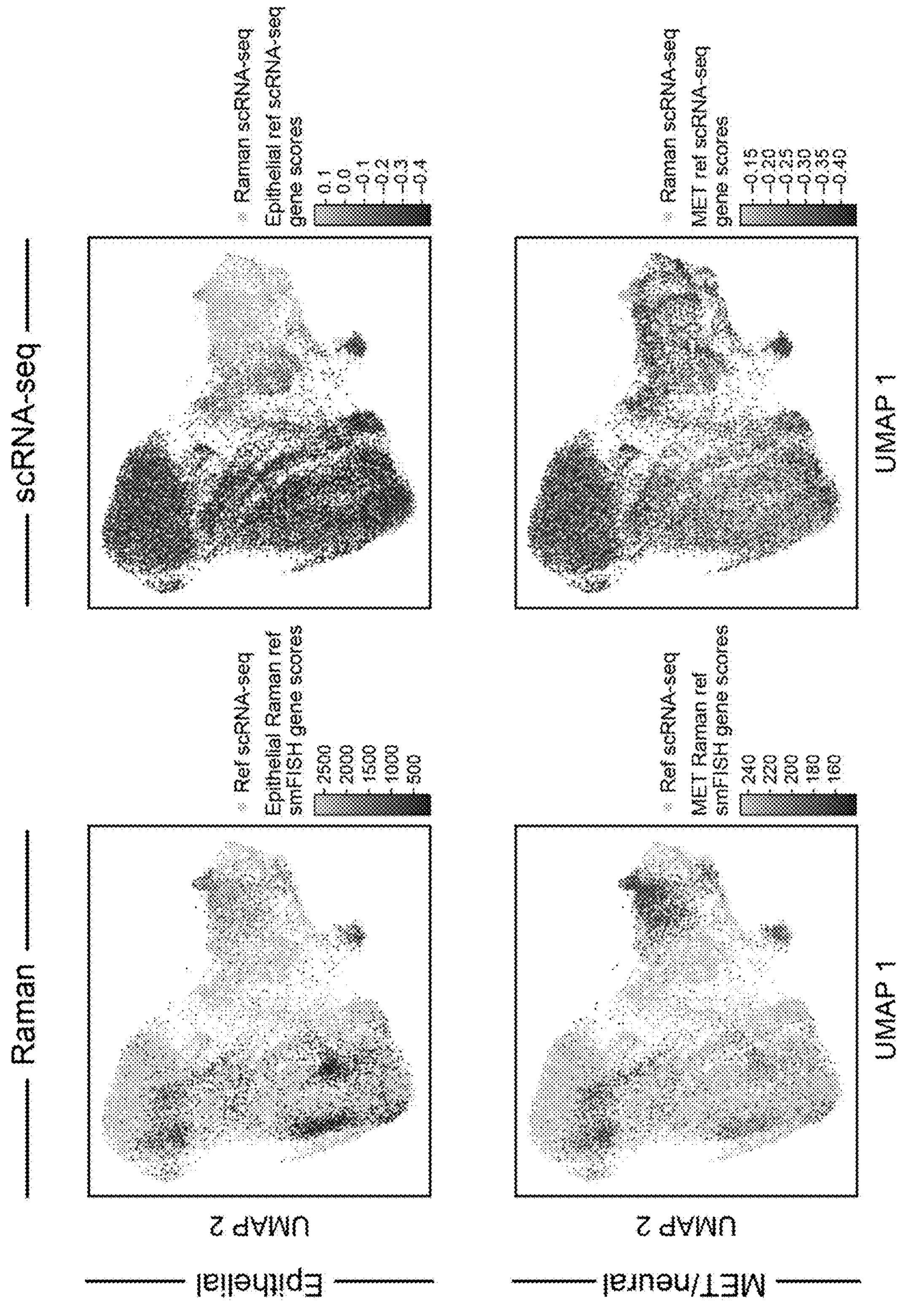

FIG. 14—Measured and Raman-predicted single cell profiles co-embed well as reflected by gene scores for each cell type. UMAP co-embedding of Raman predicted RNA profiles and measured scRNA-seq profiles (dots) colored by scores of marker gene for different cell types (rows) determined by smFISH measurements (left, for cells with Raman-predicted profiles) or real scRNA-seq measurements (right, for cells with scRNA-seq profiles).

Figure 15:
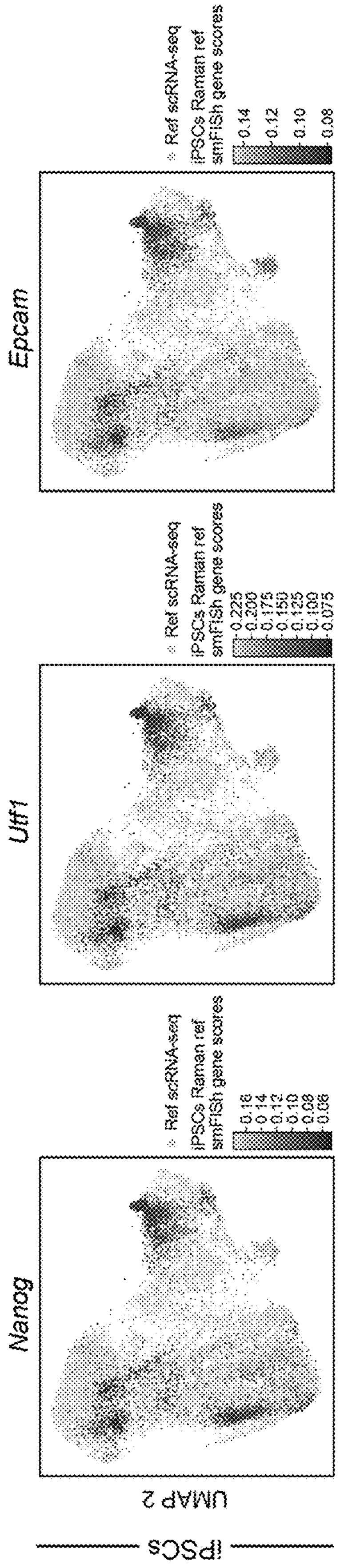
Figure 15:
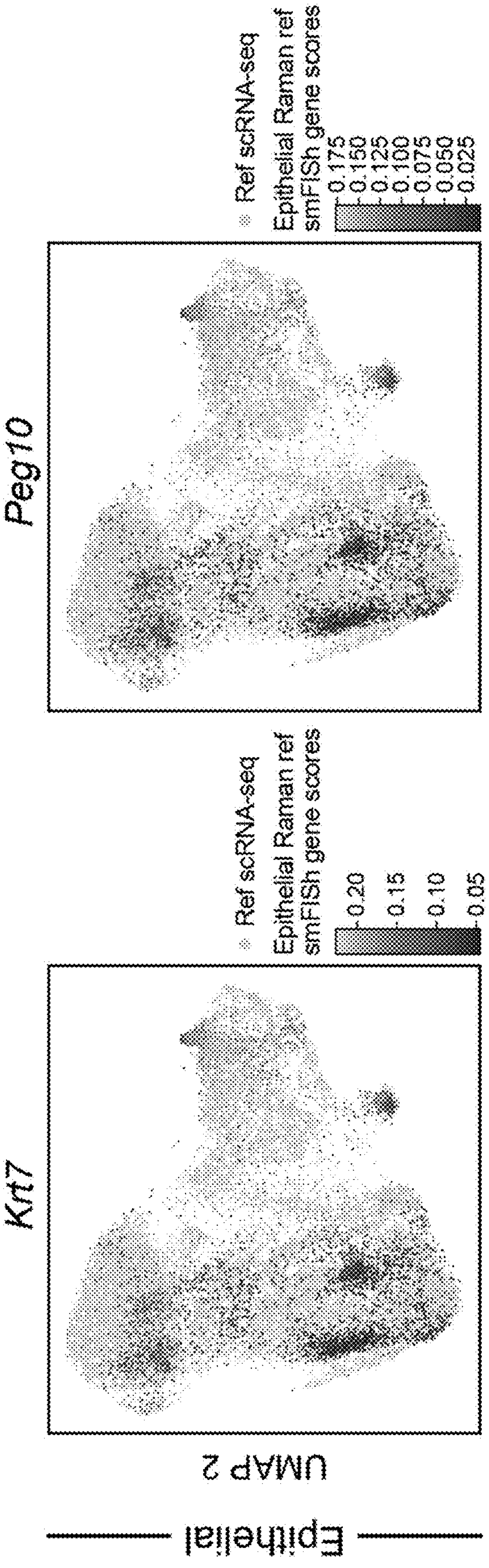
Figure 15:
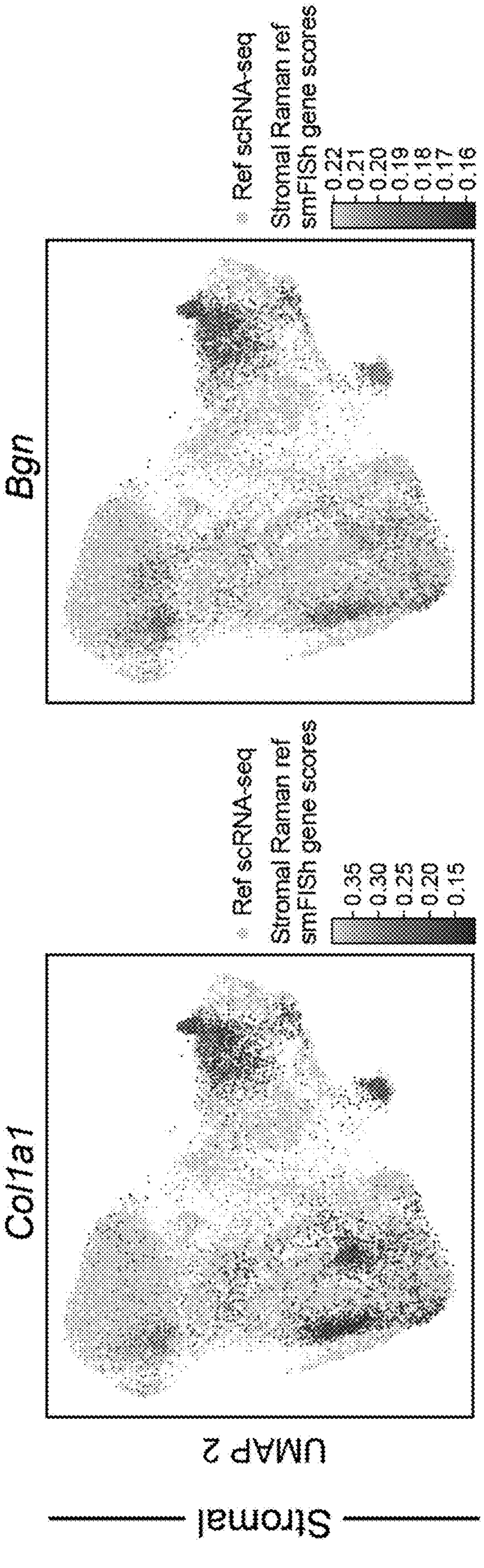
Figure 15:
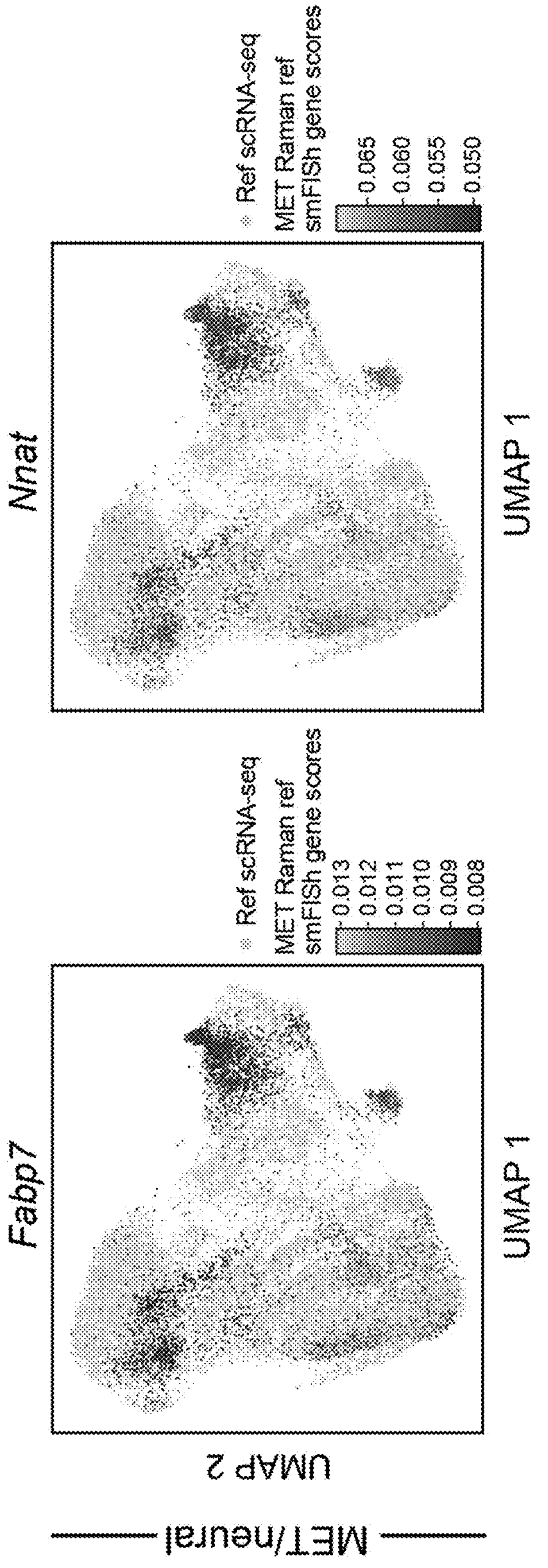

FIG. 15—Measured and Raman-predicted single cell profiles co-embed well as reflected by smFISH measurement of Raman cells. UMAP co-embedding of Raman predicted RNA profiles and measured scRNA-seq profiles (dots) where the Raman cells are colored by smFISH measurement of each of nine anchor genes.

Figure 16:
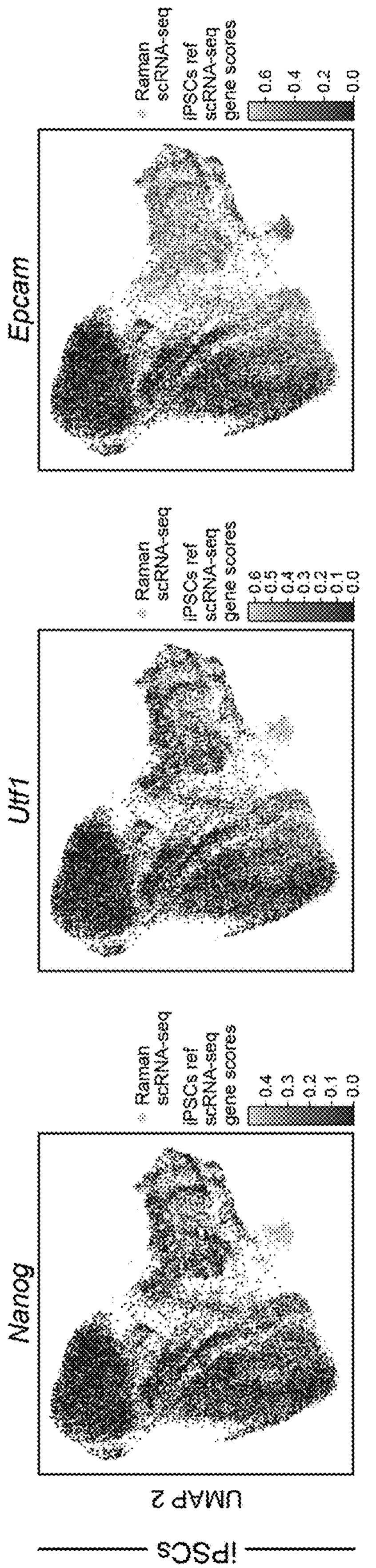
Figure 16:
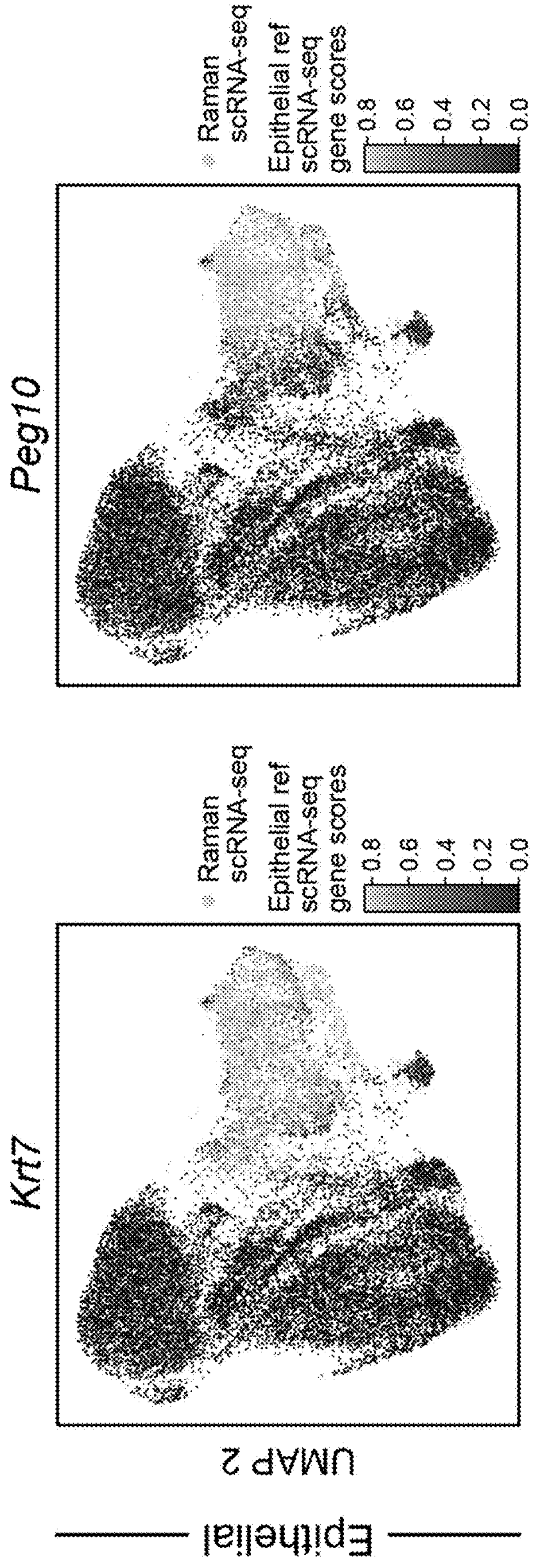
Figure 16:
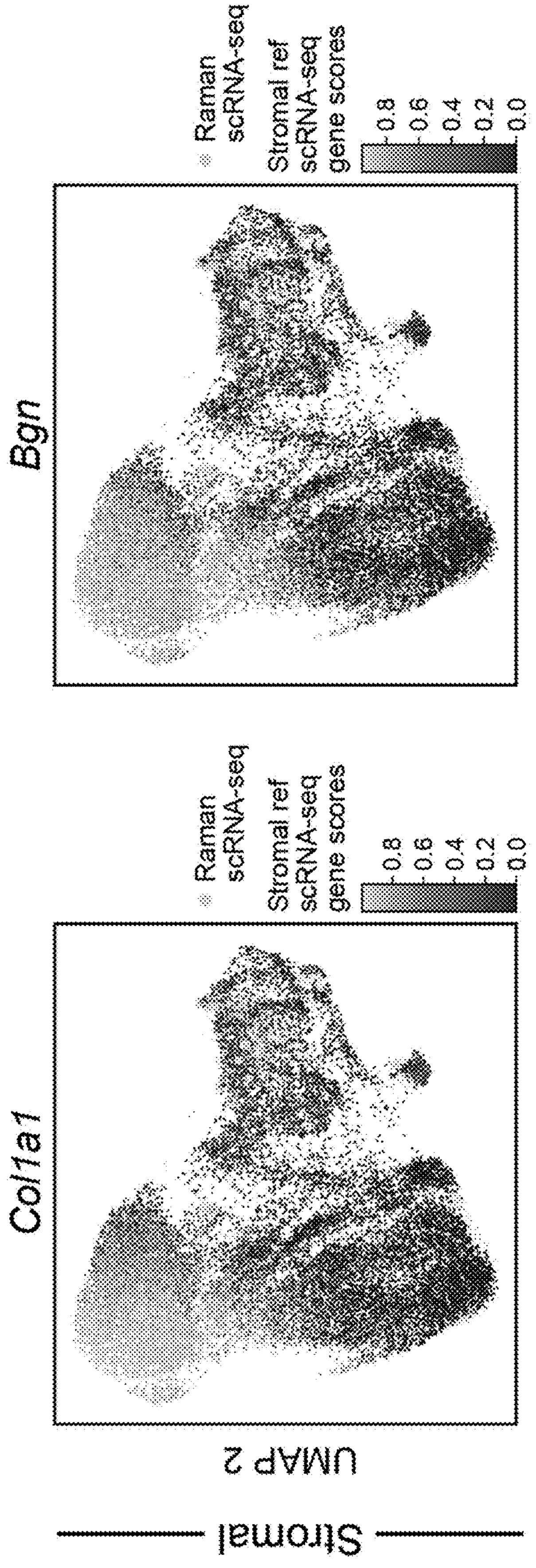
Figure 16:
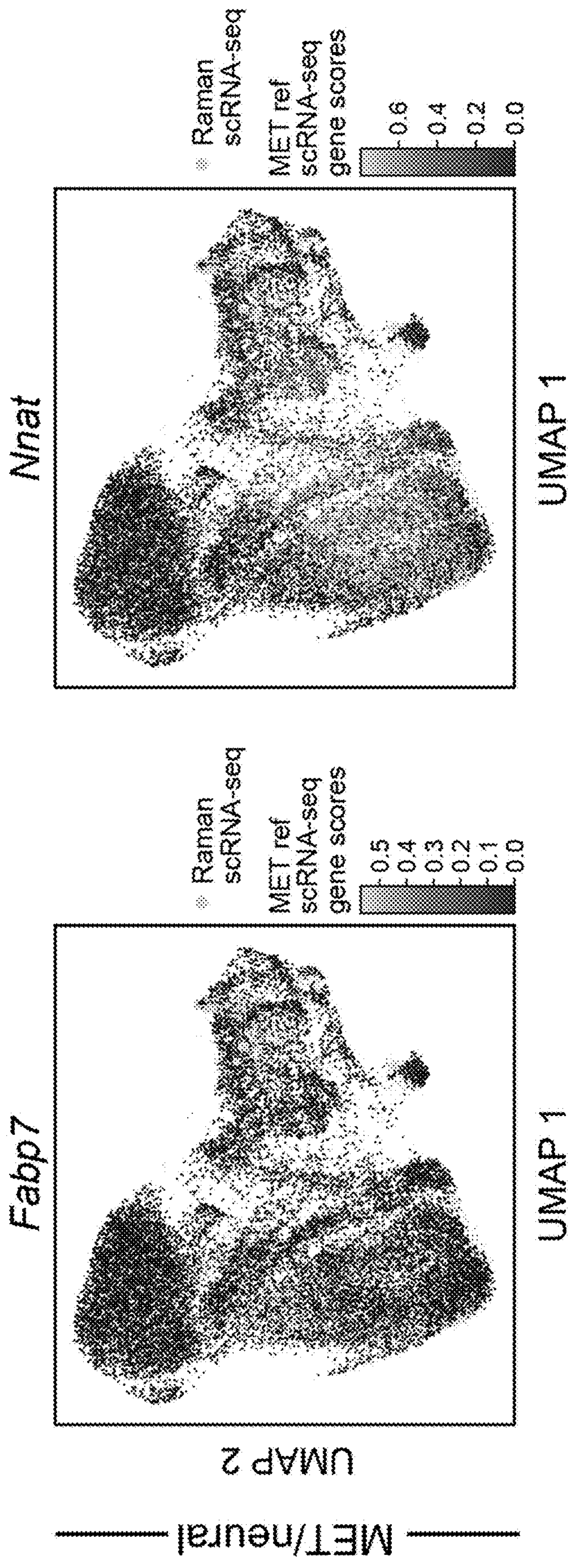

FIG. 16—Measured and Raman-predicted single cell profiles co-embed well as reflected by scRNA-seq based expression of nine anchor genes. UMAP co-embedding of Raman predicted RNA profiles and measured scRNA-Seq profiles (dots) where the scRNA-seq profiled cells are colored by scRNA-seq measured expression of each of nine anchor genes.

Figure 17:
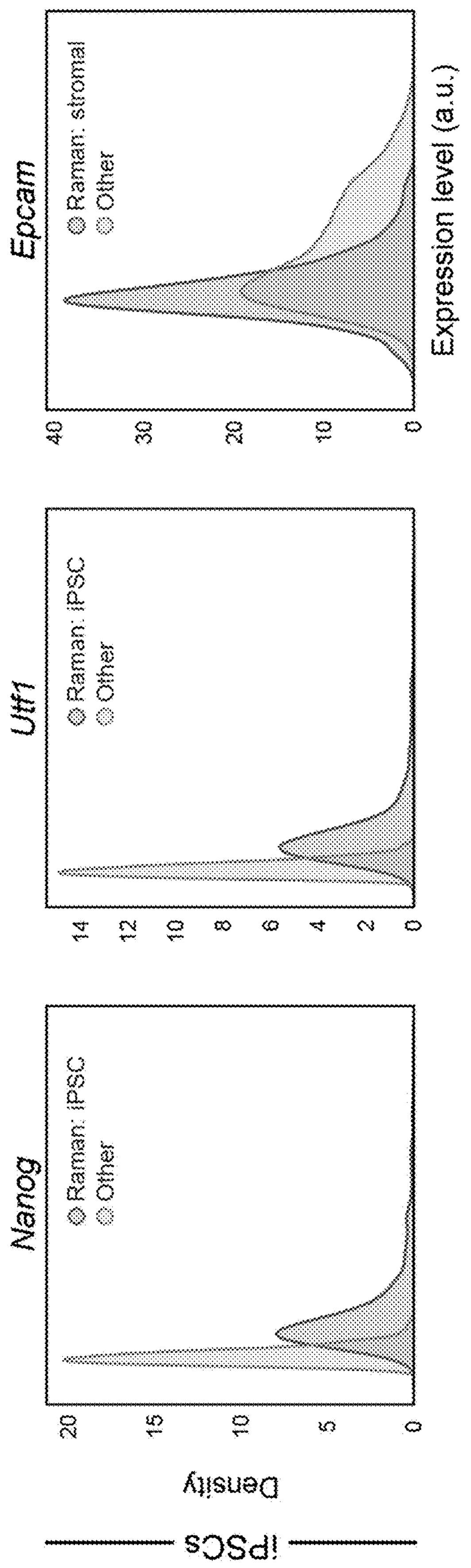
Figure 17:
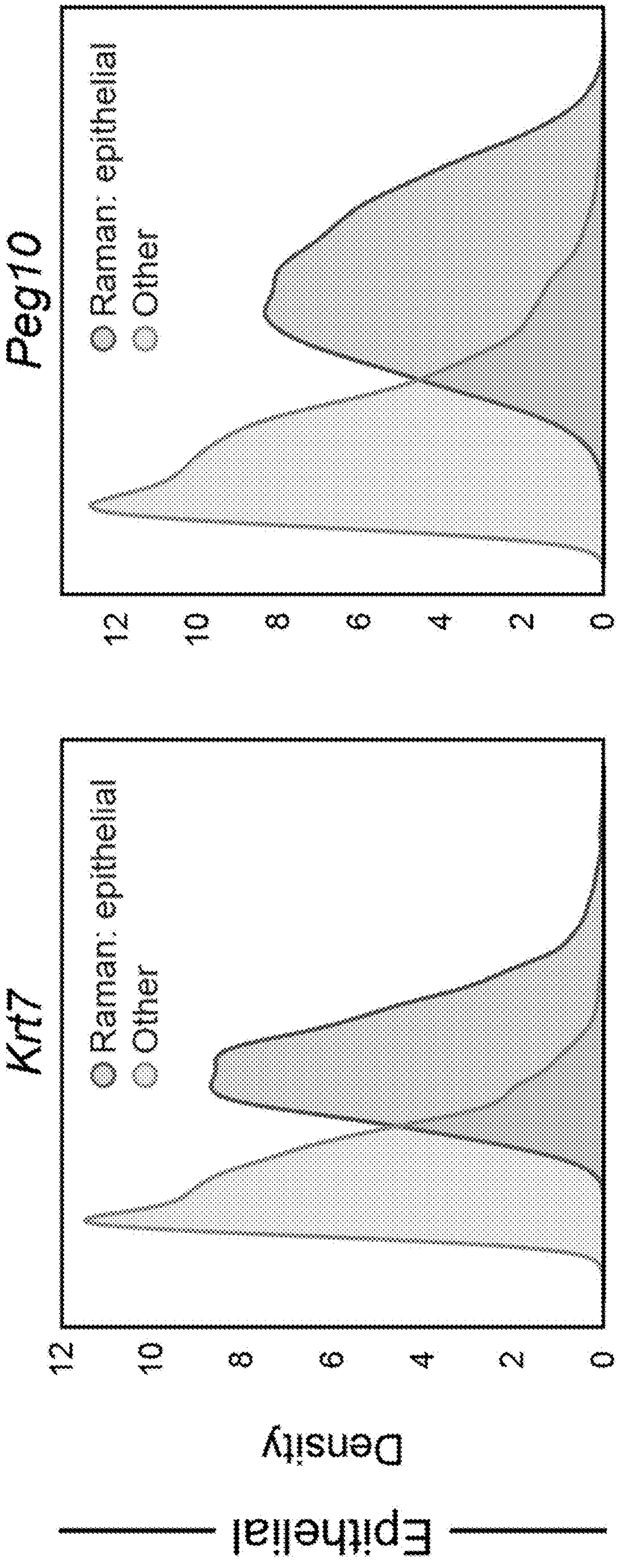
Figure 17:
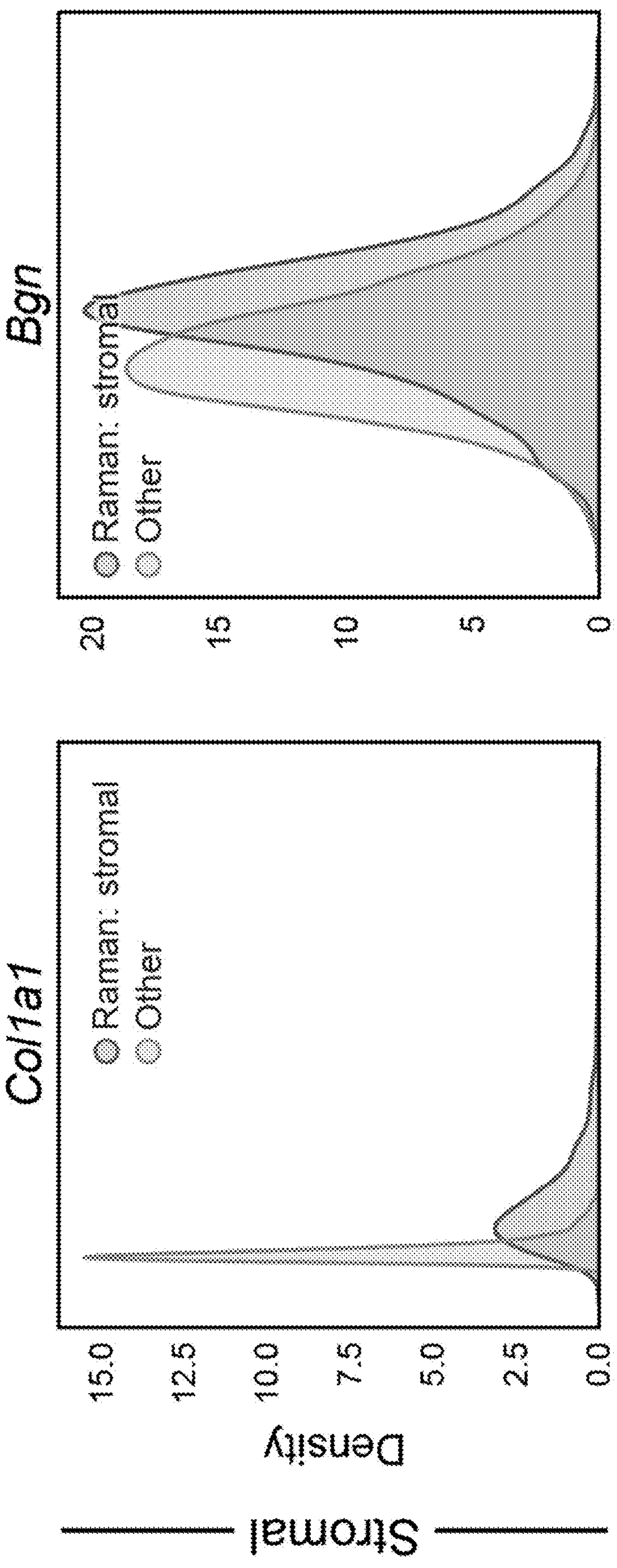

FIG. 17—Distributions of expression of marker genes based on R2R-predicted profiles. Distributions (density plots) of the predicted expression in Raman2RNA inferred profiles for each marker gene (panel) in its expected corresponding cell type (blue, based on the predicted expression profiles) and all other cells (orange).

Figure 18:
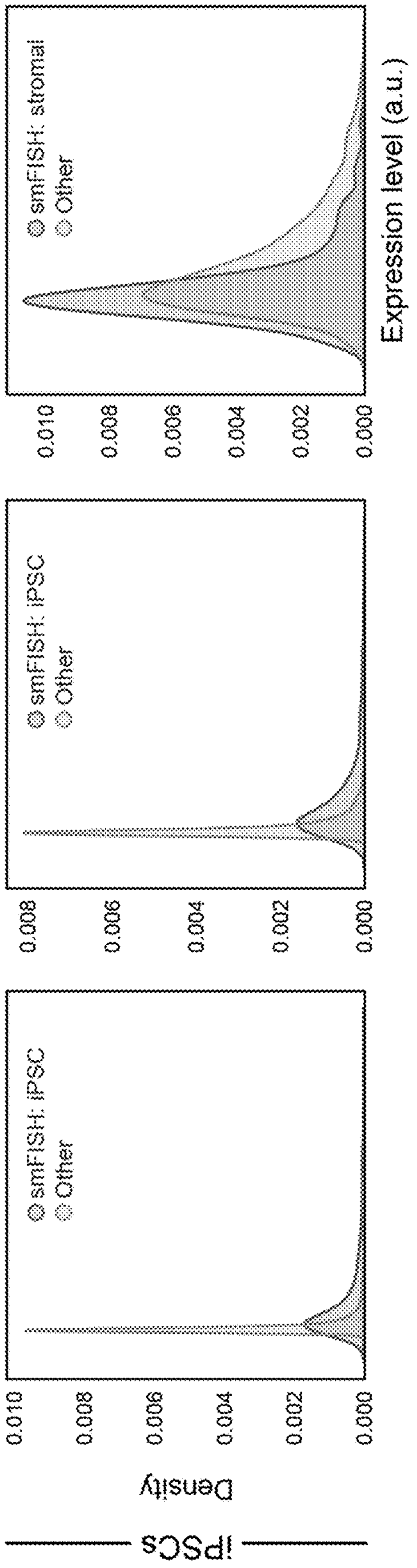
Figure 18:
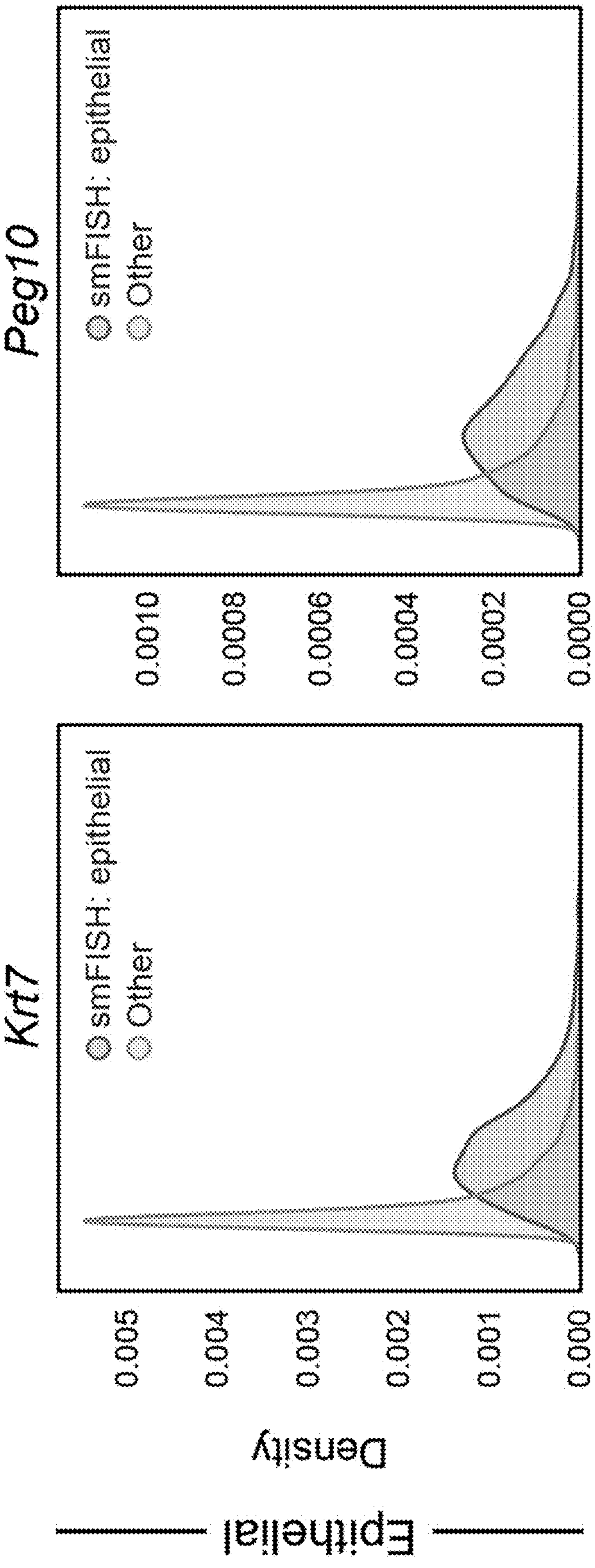
Figure 18:
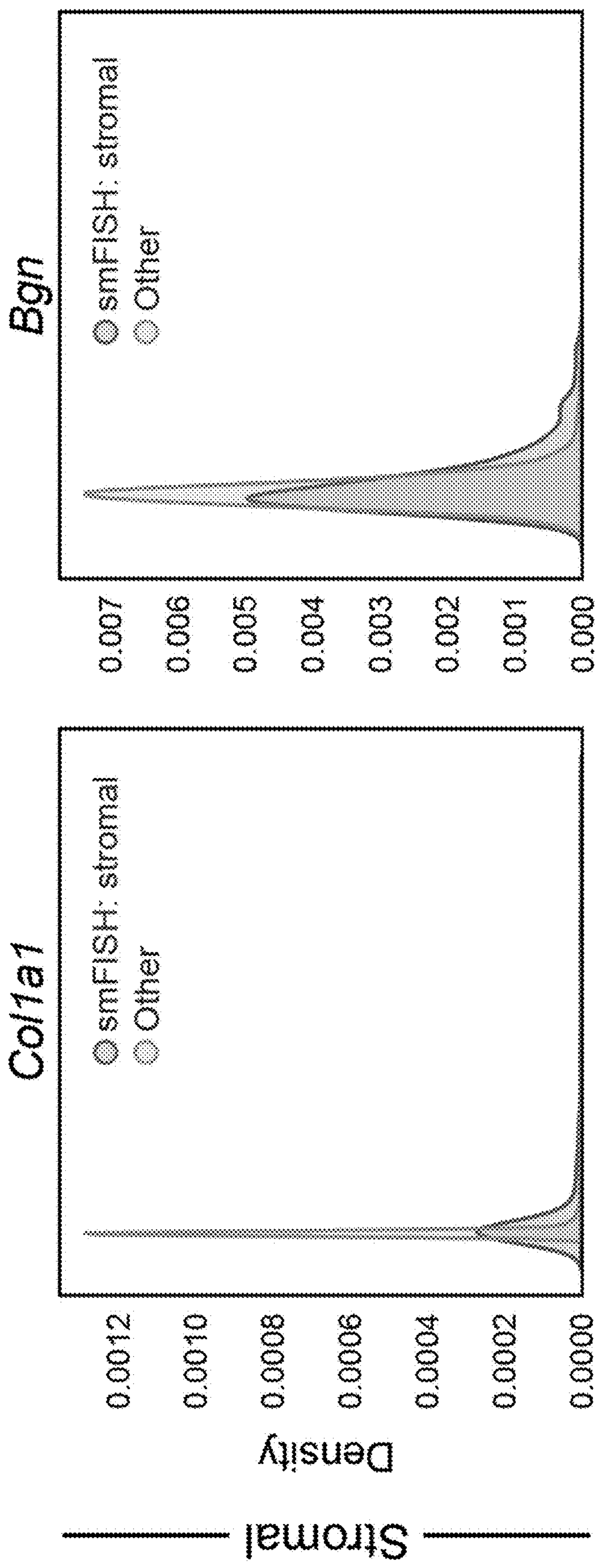
Figure 18:
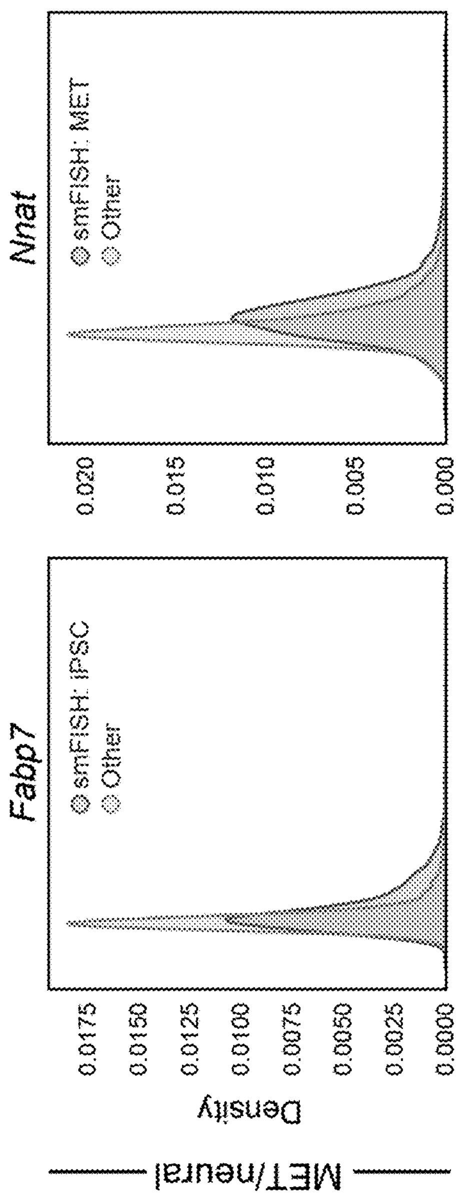

FIG. 18—Distributions of expression of marker genes based on real smFISH profiles. Distributions (density plots) of the real smFISH profiles for each marker gene (panel) in its expected corresponding cell type (blue, based on the R2R predicted expression profiles) and all other cells (orange).

Figure 19:
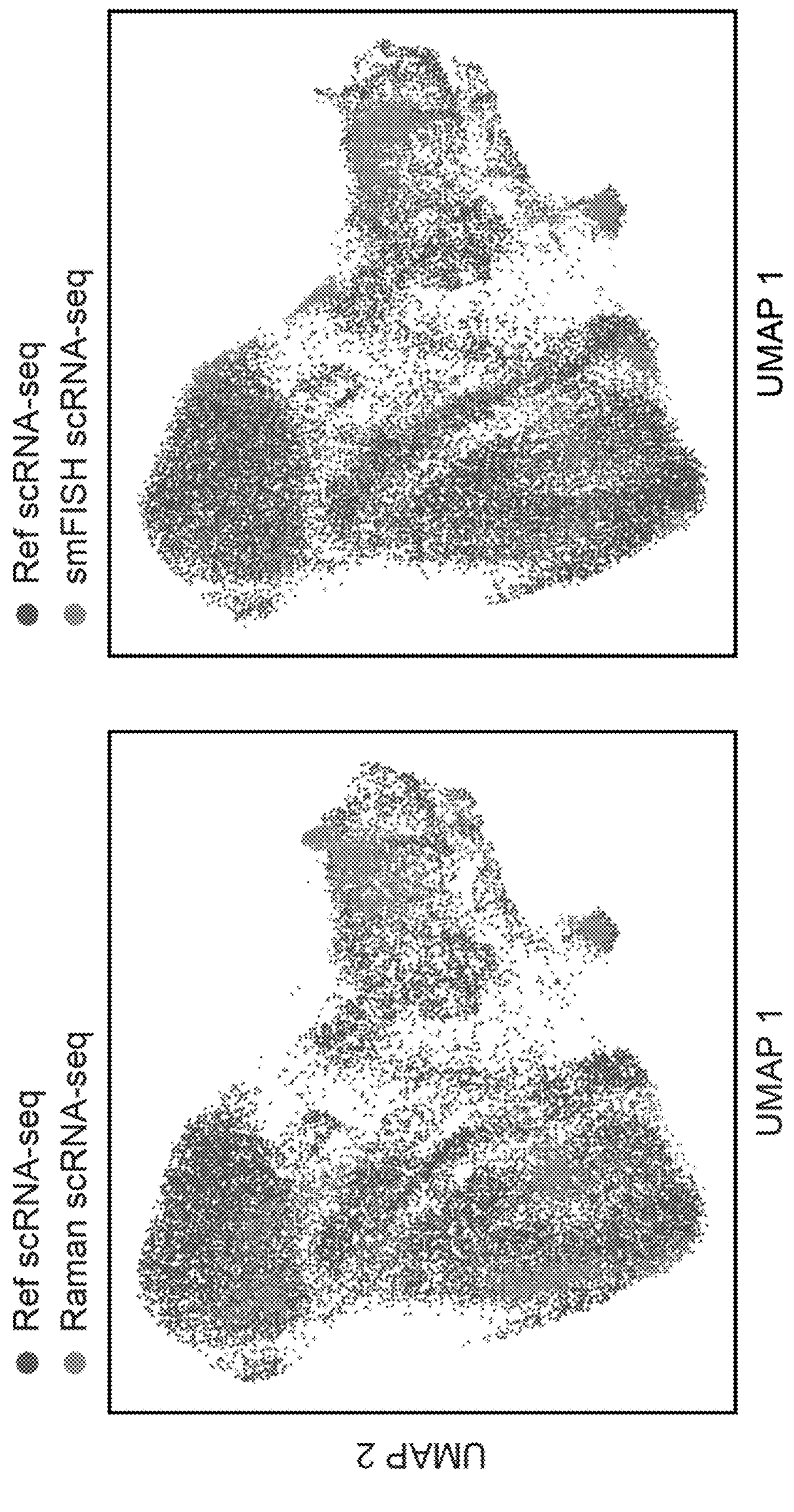

FIG. 19—RNA profiles predicted directly from 9 anchor smFISH measurements lead to reduced variance compared to scRNA-seq. UMAP co-embedding of cells from scRNA-seq (blue) and Raman (orange) experiments, with the latter based on either the Raman-predicted RNA profiles (left) or only smFISH-predicted RNA profiles (right).

Figure 20:
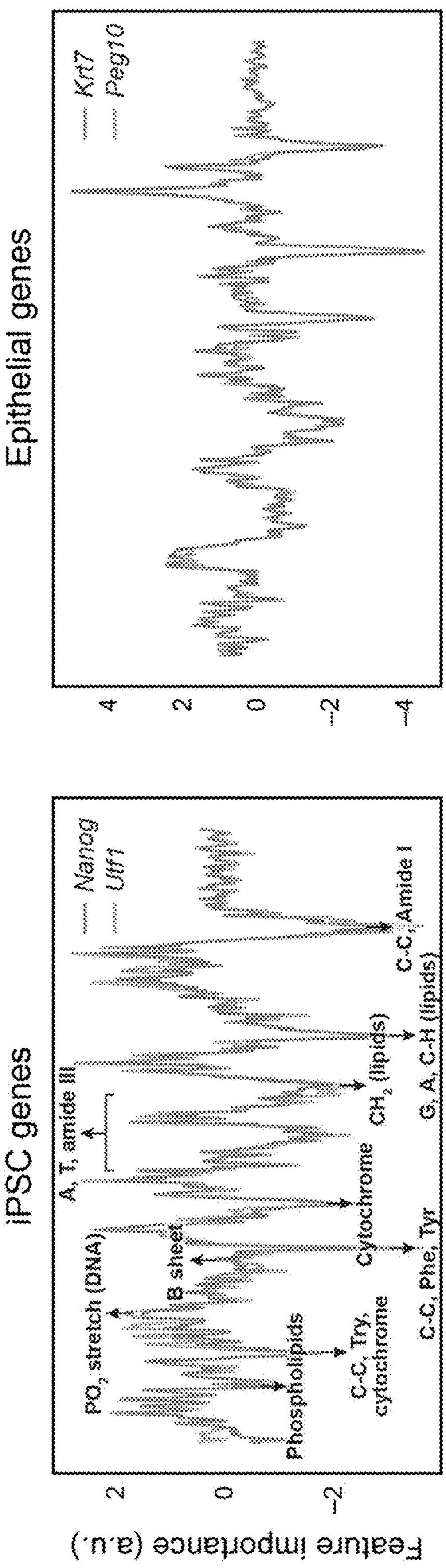
Figure 20:
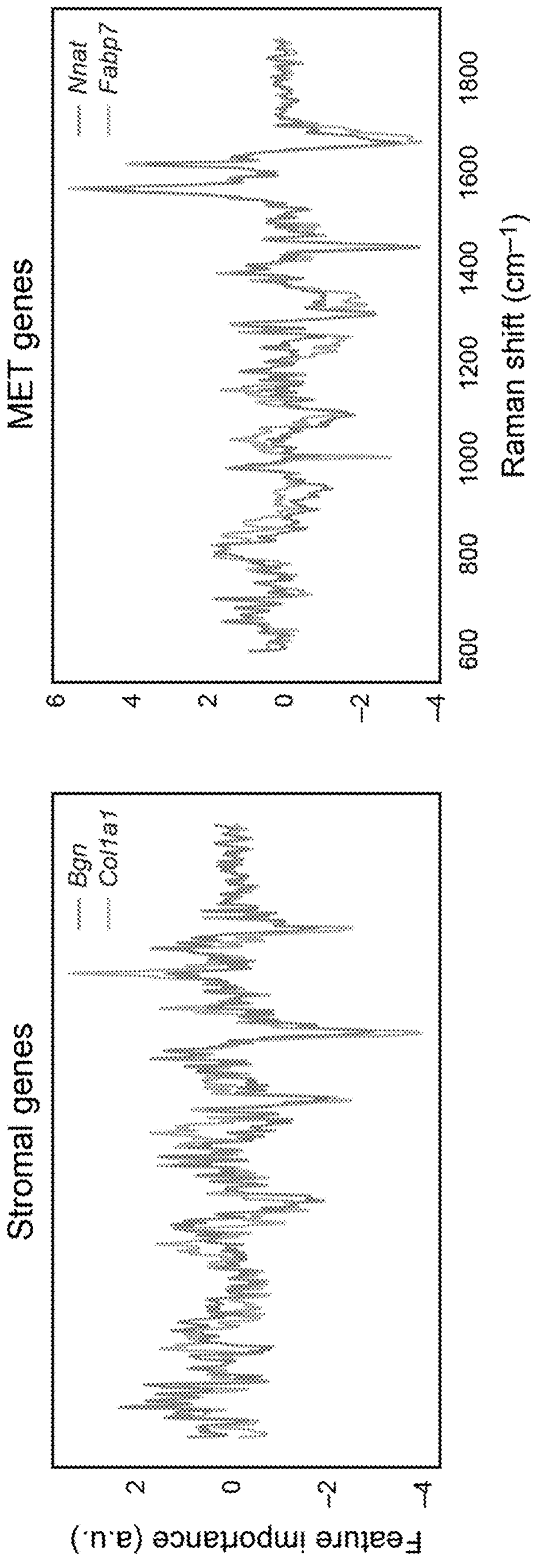
Figure 20:
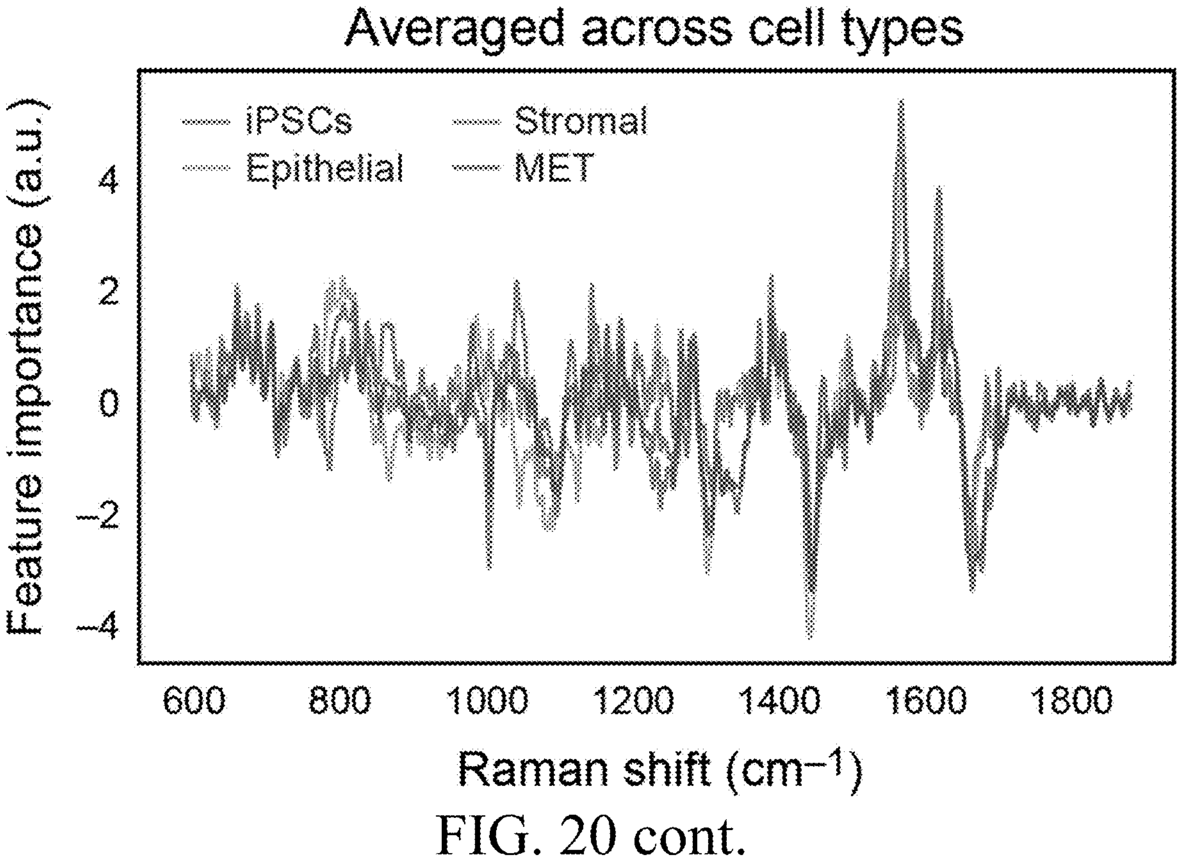

FIG. 20—Raman spectral feature importance scores for each smFISH anchor gene and its average across all genes for a cell type. Feature importance scores (y axis) for marker genes of each cell type (top two rows), and for all cell types (bottom row), along the Raman spectrum (x axis). Known signals[2] are annotated in the top left panel (identical to FIG. 6*k*).

Figure 21:
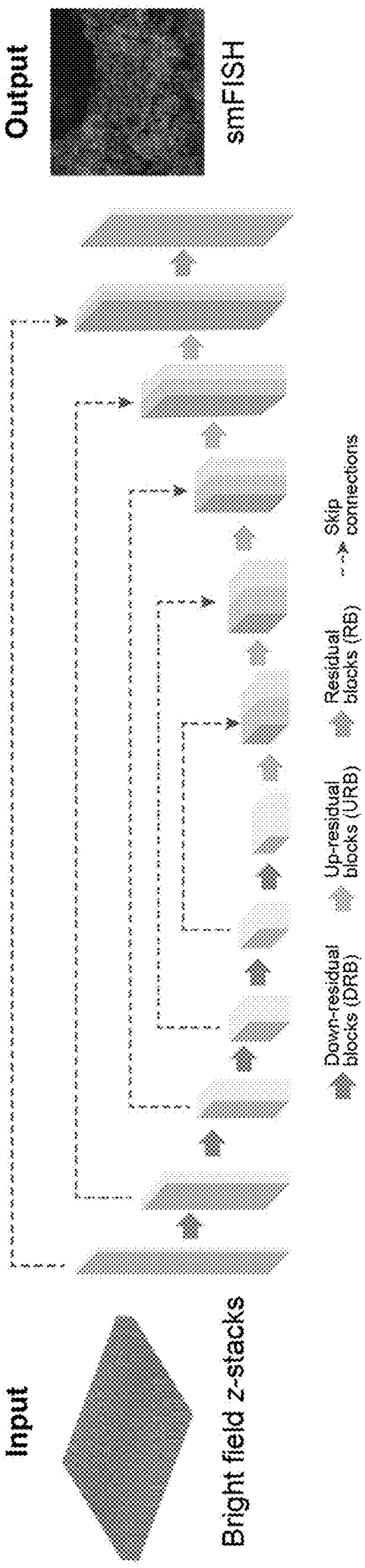
Figure 21:
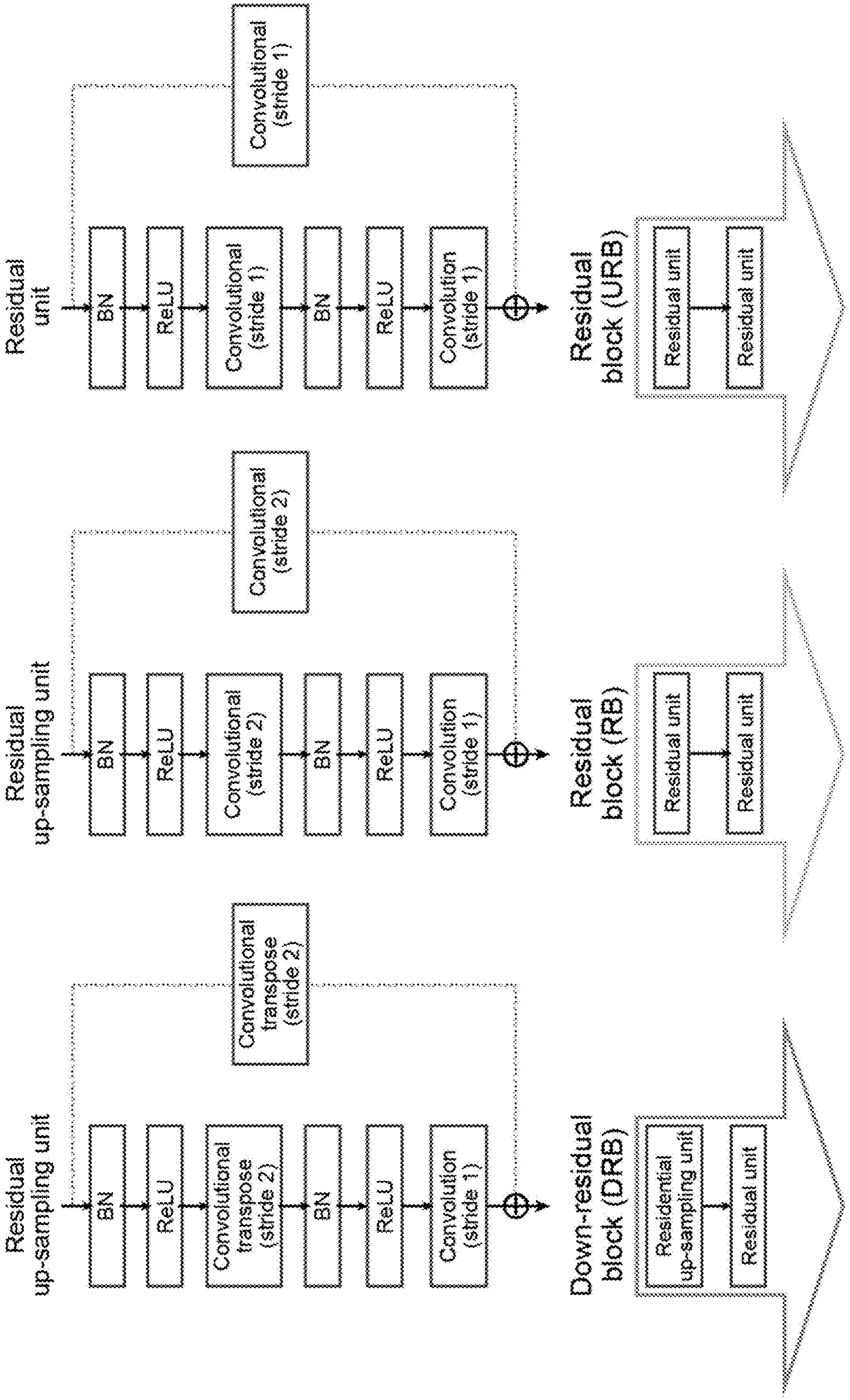

FIG. 21—Neural network-based prediction of smFISH using brightfield z-stacks.

Figure 22:
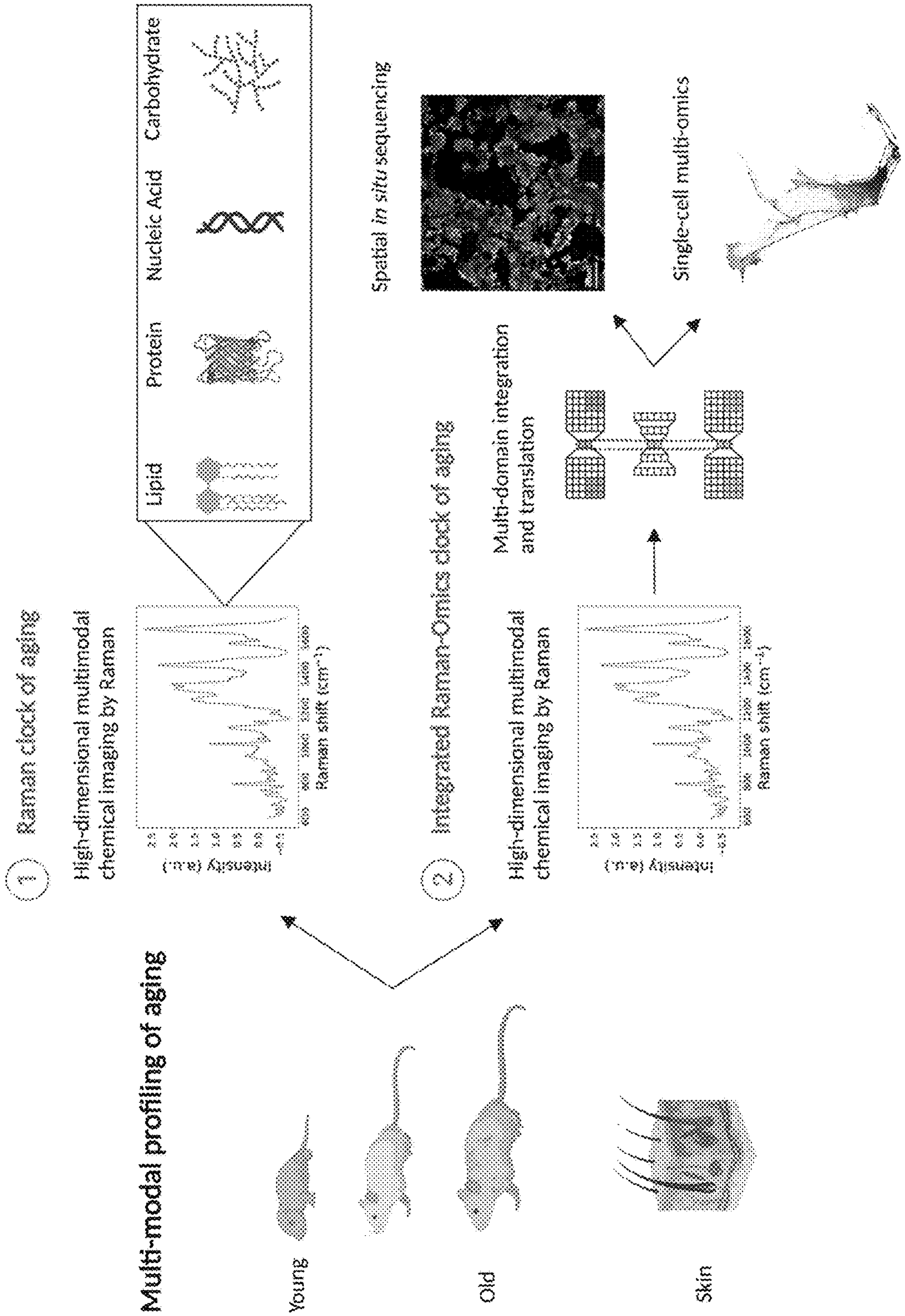

FIG. 22—Illustrative design of Raman clock of aging.

Figure 23:
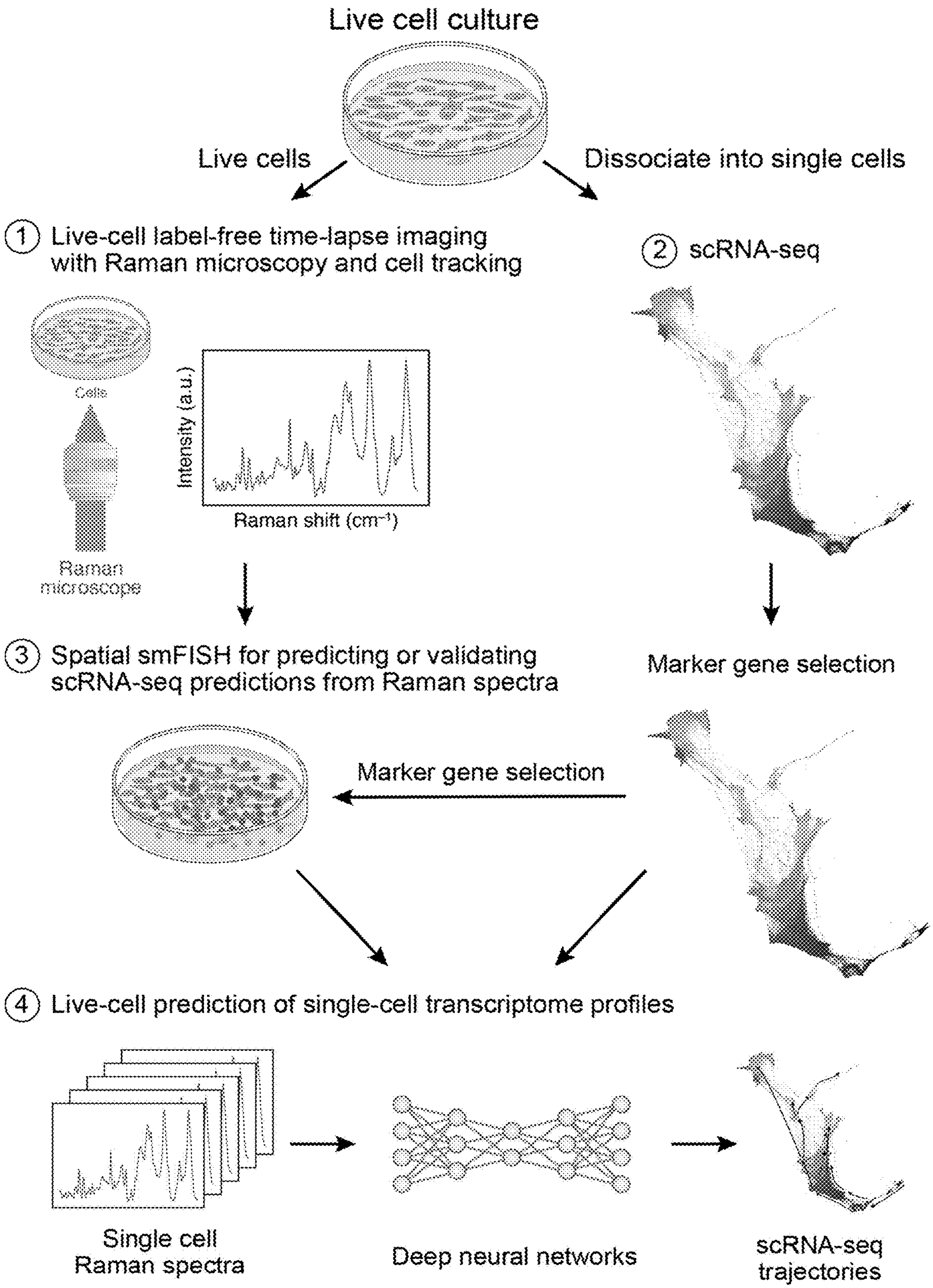

FIG. 23—Raman2RNA. Live cells are cultured on gelatin-coated quartz glass-bottom plates (top) and Raman spectra are then measured at each pixel (at sub-cellular spatial resolution) within an image frame, and after time-lapse imaging and cell tracking (1), smFISH imaging in the same area is carried out (3). From parallel plates, cells are dissociated into a single cell suspension and profiled by scRNA-seq (2). scRNA-seq profiles are used to select 9 marker genes for 5 major cell clusters for mouse iPSC reprogramming and 4 marker genes for 3 major cell lineages during mouse ESC differentiation, and those are measured with spatial smFISH (3). Lastly, we demonstrate both anchor (measured by smFISH) and anchor-free predictions of scRNA-seq profiles from Raman images (4) using fully connected neural networks and adversarial autoencoders. Marker gene profiles measured by smFISH are either used for training or validation.

Figure 24A:
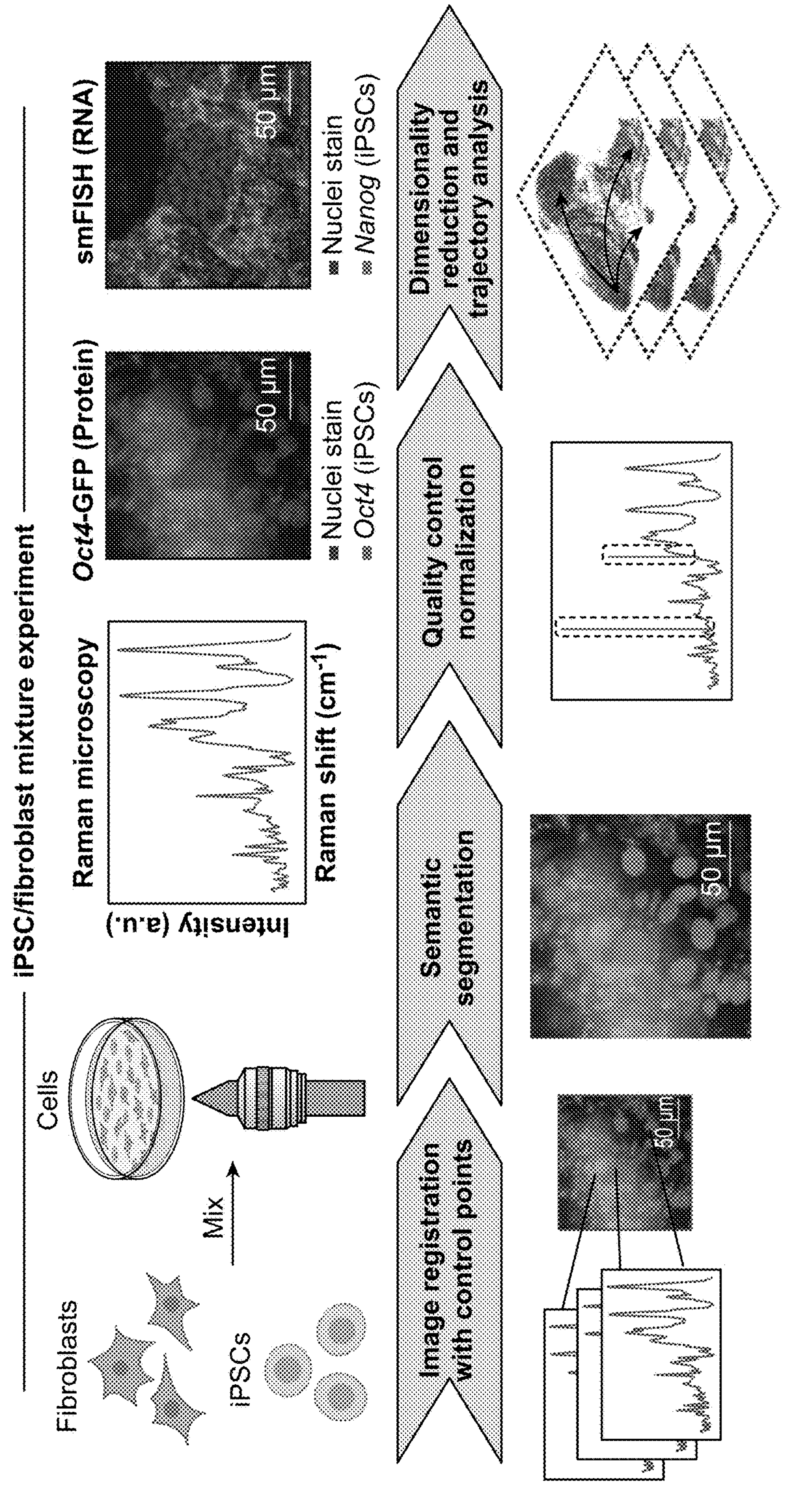
Figure 24B:
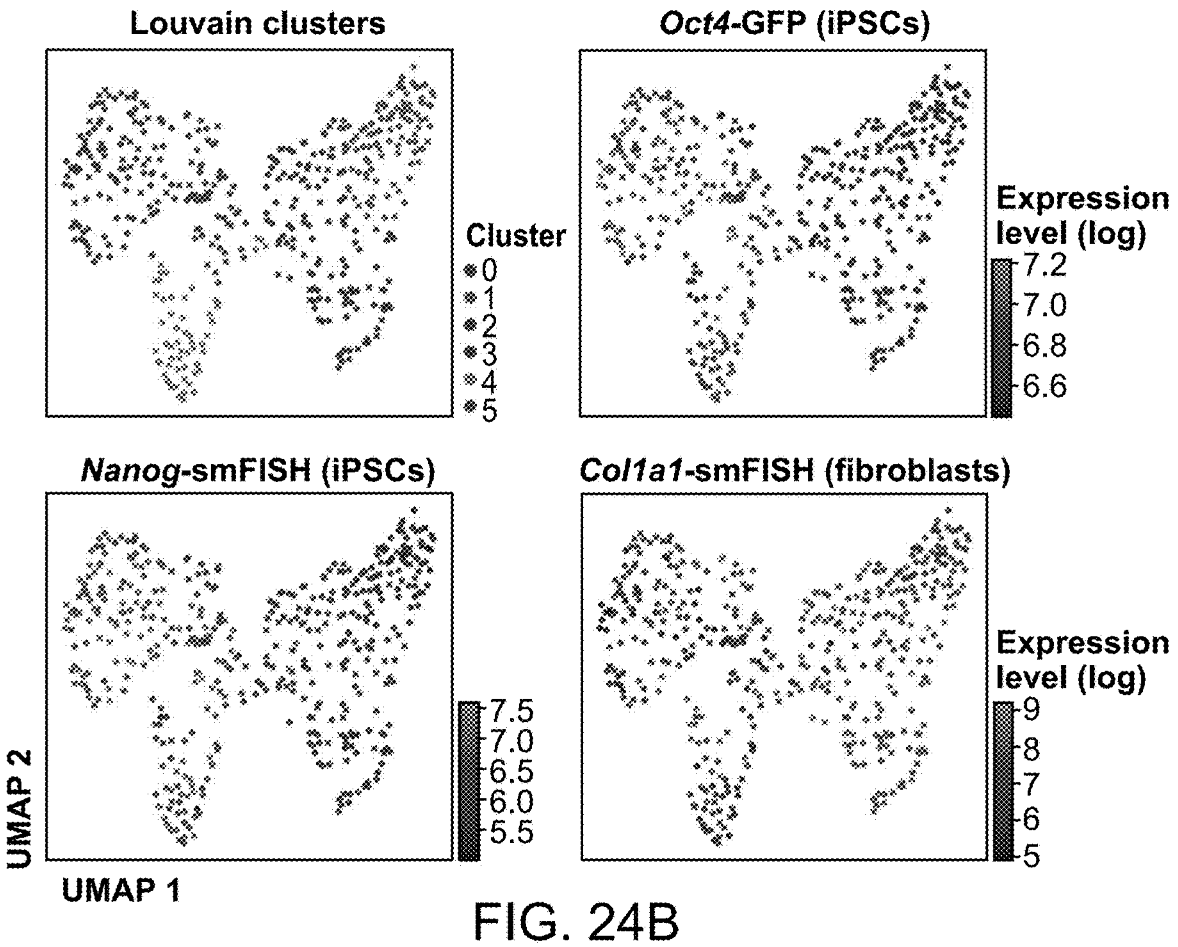
Figure 24C:
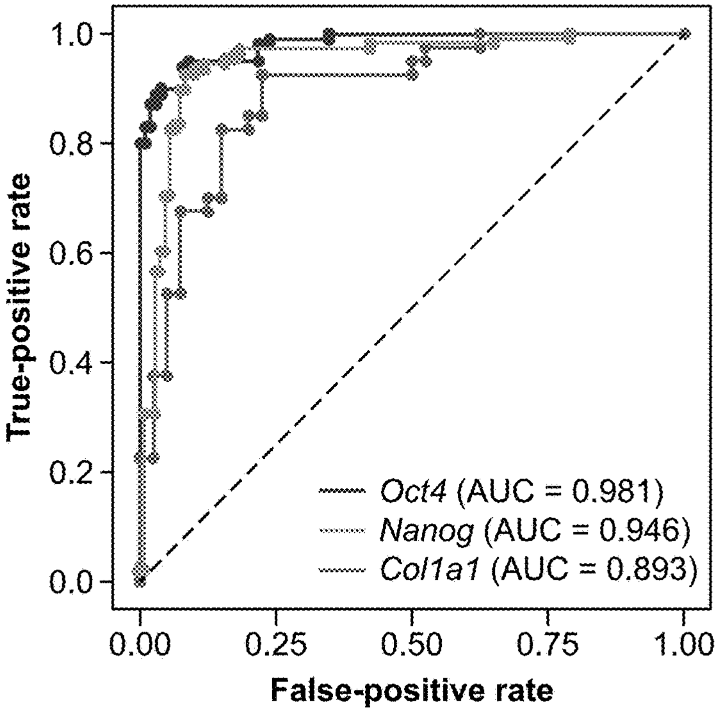

FIG. 24*a*-24*c*—Raman2RNA accurately distinguishes cell types and predicts binary expression of marker genes in a mixture of mouse fibroblasts and iPSCs. 24*a*. Overview. Top: Experimental procedures. Mouse fibroblasts and iPSCs were mixed 1:1 and plated on glass-bottom plates, followed by Raman imaging of live cells, nuclei staining and measurement of endogenous Oct4-GFP (iPSC marker) reporter by fluorescence imaging, and cell fixation and processing for smFISH with DAPI and probes for Nanog (iPSCs, magenta) and Col1a1 (fibroblasts). Bottom: Preprocessing and analysis. From left: Image registration with control points (Methods), was followed by semantic cell segmentation, outlier removal/normalization and dimensionality reduction/trajectory analysis. 24*b*. Raman2RNA distinguishes cell states from Raman spectra. 2D UMAP embedding of single-cell Raman spectra (dots) colored by Louvain clustering labels (top left) or smFISH measured expression of Oct4 (top right), Nanog (bottom left) and Col1a1 (bottom right). 24*c*. Raman2RNA accurately predicts binary (on/off) expression of marker genes. Receiver operating characteristic (ROC) plots and area under the curve (AUC) obtained by classifying the 'on' and 'off' states of Oct4 (blue), Nanog (orange) and Col1a1 (green).

FIG. 25*a*-25*m*—Raman2RNA predicts single-cell RNA profiles across cell types during reprogramming of mouse fibroblasts to iPSCs. 25*a*. Approach overview. From left: Mouse fibroblasts were reprogrammed into induced pluripotent stem cells (iPSCs) over the course of 14.5 days ('D'), and, at half-day intervals from days 8 to 14.5, spatial Raman spectra, smFISH for nine anchor genes, and nuclei stain by fluorescence imaging were measured for each plate. Machine learning and multi-modal data integration methods (fully connected neural network and Tangram) were used to predict single-cell RNA-seq profiles from Raman spectra using smFISH as anchor. 25*b,c*. Low dimensionality embedding of single-cell Raman spectra captures progress in reprogramming. Force-directed layout embedding (FLE) of Raman spectra (b, dots) or scRNA-seq (c, dots) colored by days of measurement (colorbar). 25*d*. Prediction of smFISH anchors from Raman spectra. Cosine similarity (y axis) between measured (smFISH) and Raman-predicted levels for each smFISH anchor (x axis) in leave-one-out cross-validation where 8 out of 9 smFISH anchor genes were used for training, and the left-out gene was predicted. Error bar represents standard error of 5 trials with different subset of cells used for training. 25*e.f*. Raman2RNA accurately predicts pseudo-bulk expression profiles of major cell types. e. scRNA-seq measured (y axis) and R2R-predicted (x axis) for each gene (dot) in pseudo-bulk RNA profiles averaged across iPSCs. The genes shown are the top 2000 highly variable genes (HVGs). 25*f*. Pair-wise correlation (color bar) between Raman-predicted and scRNA-seq measured pseudo-bulk profiles (top 2000 HVGs) in each cell types (rows, columns). 25*g-i*. Co-embedding highlights agreement between real and R2R inferred single cell profiles. Data points are all R2R projections of test cells (cells that were not used for training R2R). UMAP co-embedding of Raman predicted RNA profiles and measured scRNA-seq profiles (dots) colored by cell type annotations (25*g*) or by iPSC gene signature scores (calculated by averaging expression of genes Nanog and Utf1, and subtracting the average of a randomly selected set of reference genes; Methods) of Raman-predicted profiles (25*h*) or of real scRNA-seq (25*i*). 25*j*. Feature importance scores of Raman spectra in predicting expression profiles. Feature scores for iPSC related marker genes (y axis) along the Raman spectrum (x axis). Known Raman peaks2 were annotated. 25*k*. Overview of the generative adversarial network conducted on Raman spectra. 25*l*. Ground truth scRNA-seq measured (y axis) and anchor-free R2R-predicted (x axis) values for each gene (dot) in pseudo-bulk RNA profiles averaged across iPSCs. The genes shown are the top 2000 HVGs 25*m*. Pair-wise correlation (color bar) between anchor-free Raman-predicted and scRNA-seq measured pseudo-bulk profiles (top 2000 HVGs) in each cell types (rows, columns).

FIG. 26*a*-26*i*-Raman2RNA tracks and predicts gene expression dynamics during mouse embryonic stem cells (mESCs) during differentiation in single live cells. 26*a*. Overview of time-lapse imaging during mESC differentiation under RA treatment. Raman and brightfield images were obtained every 6 hours and 30 minutes, respectively. 26*b-f*. UMAP co-embedding of Raman predicted RNA profiles and measured scRNA-seq profiles (dots) colored by source of measurement (26*d*), by hours (26*e*), by cell types (26*f*), Raman predicted gene expression (26*e*), or by scRNA-seq measured gene expression (26*f*). 26*g*. Cell type transition visualized by direct time-lapse measurements. Trajectories are directly tracked by brightfield time-lapse images and cell tracking of nuclei segmentation. 26*h*. scRNA-seq measured (y axis) and R2R-predicted (x axis) for each gene (dot) in pseudo-bulk RNA profiles averaged across mESCs at day 0. 26*i*. Pair-wise correlation (color bar) between anchor-free Raman-predicted and scRNA-seq measured pseudo-bulk profiles in each cell types (rows, columns).

Figure 27:
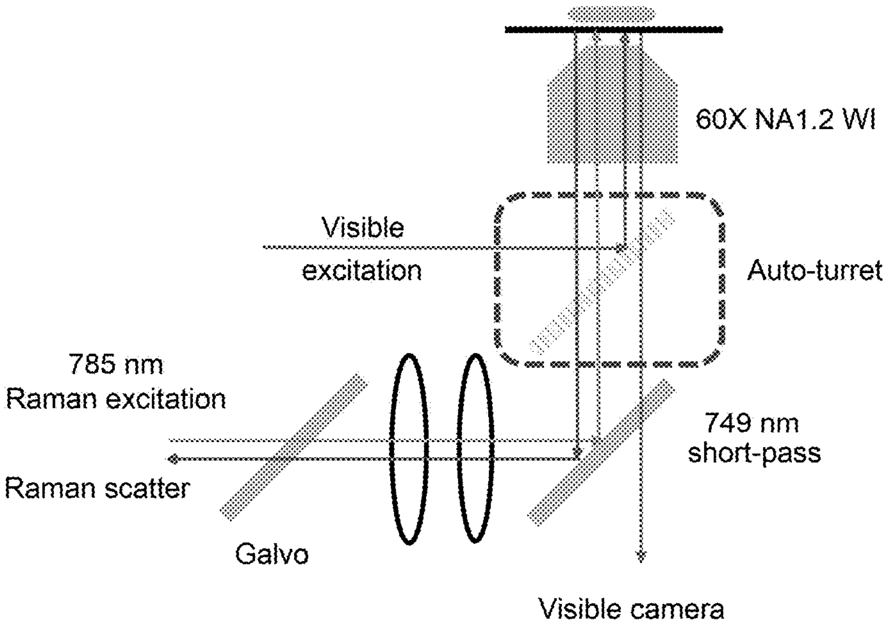

FIG. 27—A multi-modal Raman microscope capable of fluorescence imaging and Raman microscopy. Schematic of a Raman microscope integrated with a wide-field fluorescence microscope for simultaneous detection of nuclei staining, bright field, fluorescence channels, and Raman images.

Figure 28:
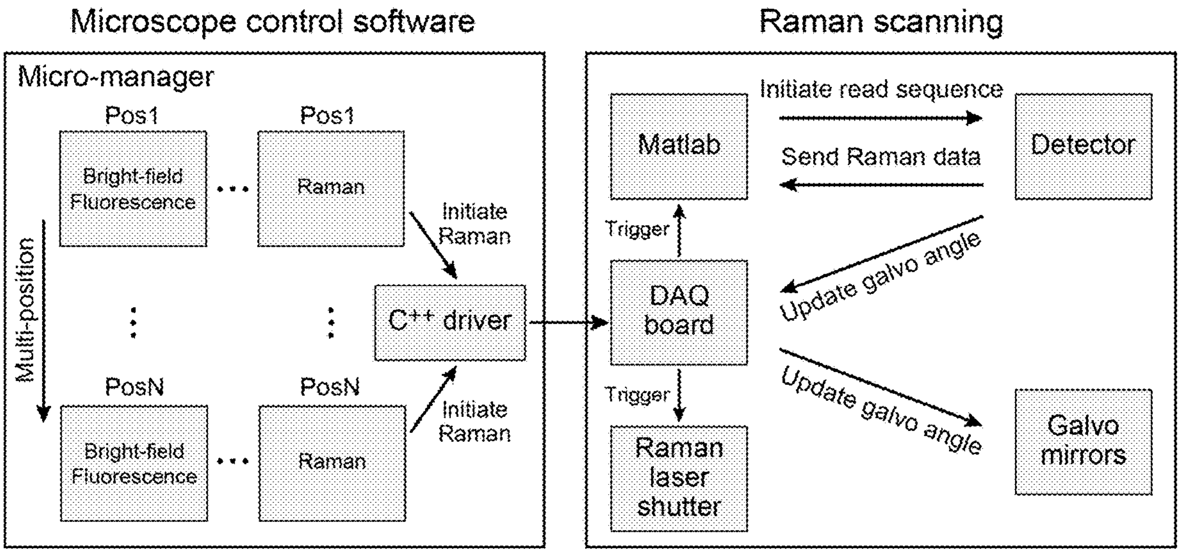

FIG. 28—Overview of high-throughput Raman imaging software used in the study. A general-purpose microscope control software Micro-manager and custom MATLAB script were combined to enable automated multi-modal measurements. Under Micro-manager, a Raman channel was registered as a 'dummy' channel along with brightfield and fluorescence channels. Micro-manager was responsible for changing the field of view (FOV) and imaging modality. During the Raman sequence, Micro-manager communicated with a digital acquisition (DAQ) board, through which a transistor-to-transistor logic (TTL) signal was generated to initiate the scanning sequence. Upon detection of the TTL signal, the MATLAB script controlled the Raman detector, laser shutter, and updated the galvo mirror angles through the DAQ board.

Figure 29:
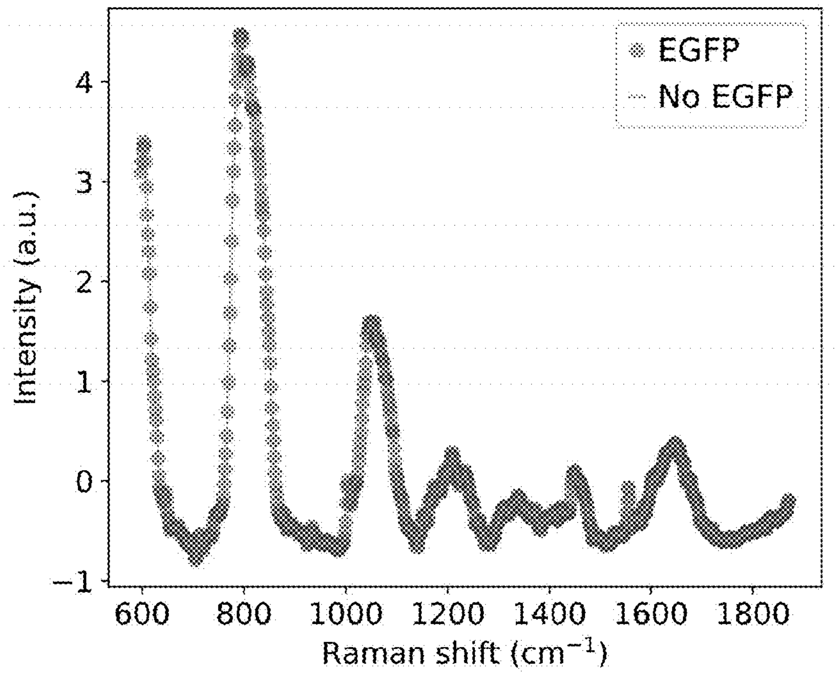

FIG. 29—GFP does not interfere in Raman spectra measurement. Raman spectra of culture media with (blue) and without (orange) GFP at physiological concentration.

Figure 30:

FIG. 30—Death rate induced from photo-toxicity measured by Live/Dead staining. Mouse fibroblast survival was assessed up to 3 h after exposure by Raman laser under conditions used in FIGS. 2 and 3 (typically 20 ms at 210 mW) and above. Survival was assayed with a live/dead stain. Statistics over 20 fields of view.

Figure 31:
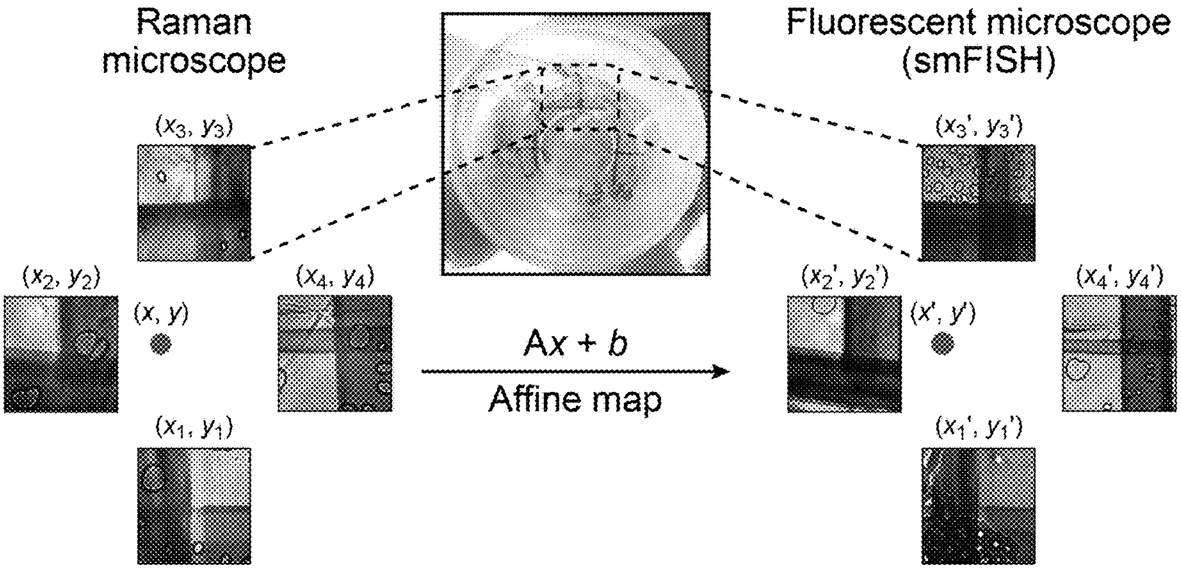

FIG. 31—Image registration between the Raman and smFISH microscope using control points. Control points were inscribed under petri dishes with permanent markers and the coordinates were measured prior to any data acquisition. After Raman measurement and smFISH processing, samples were placed back to the microscope and control point coordinates were remeasured. Then, affine mapping was used to update the FOV coordinates to locate the exact same cells.

Figure 32:
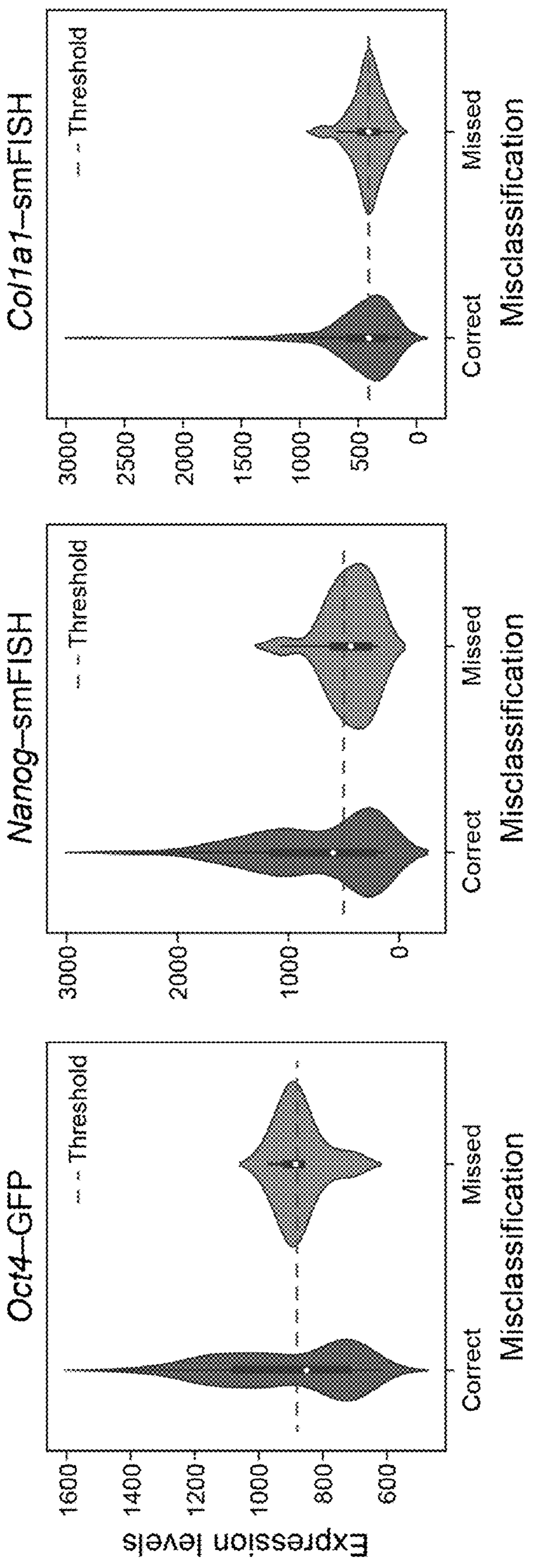

FIG. 32—Misclassification of genes in the cell mixture classification experiment occurs when the ground truth smFISH is near the expression threshold. Distribution of measured smFISH expression level (y axis) for cells correctly (blue) or incorrectly (orange) classified by their Raman spectra for the expression of that gene. Horizontal line: an example threshold used for the logistic regression classifier.

Figure 33:
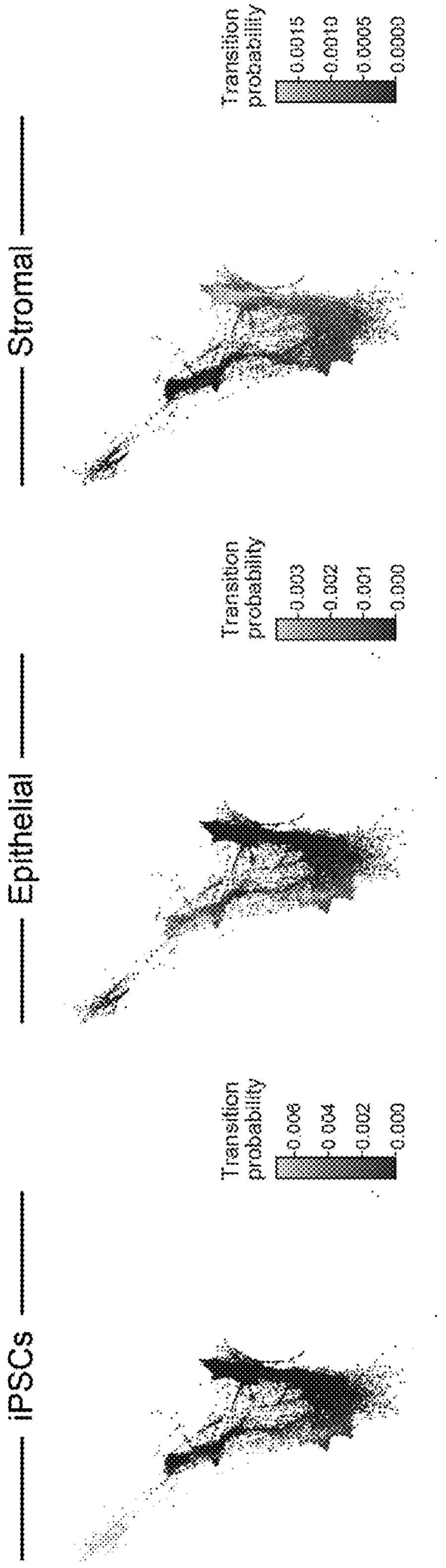

FIG. 33—Cell transition probabilities inferred by Waddignton-OT from scRNA-seq during reprogramming. Force-directed layout embedding (FLE) of scRNA-seq profiles (dots) from days 8 to 14.5 of reprogramming (dots) colored by the transition probability of each cell as inferred by Waddington-OT to be an ancestor of iPSCs (left), epithelial cells (middle) or stromal cells (right) at day 14.5.

Figure 34:
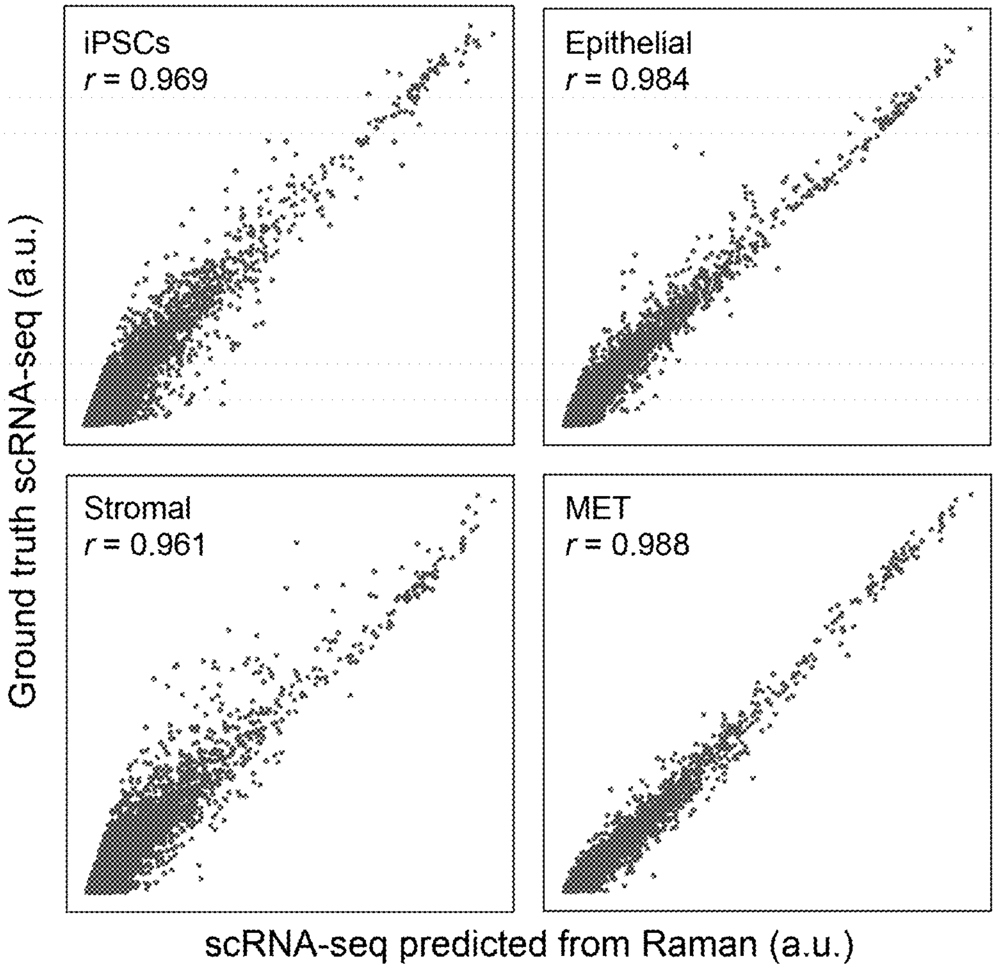

FIG. 34—Raman-predicted and scRNA-seq measured pseudo-bulk profiles are well correlated across cell types. scRNA-seq measured (y axis) and R2R-predicted (x axis) expression for each gene (dot) in pseudo-bulk RNA profiles averaged across cells labeled as iPSC (top left), epithelial (top right), stromal (bottom left) and MET (bottom right). Pearson's r is denoted at the top left corner.

Figure 35:
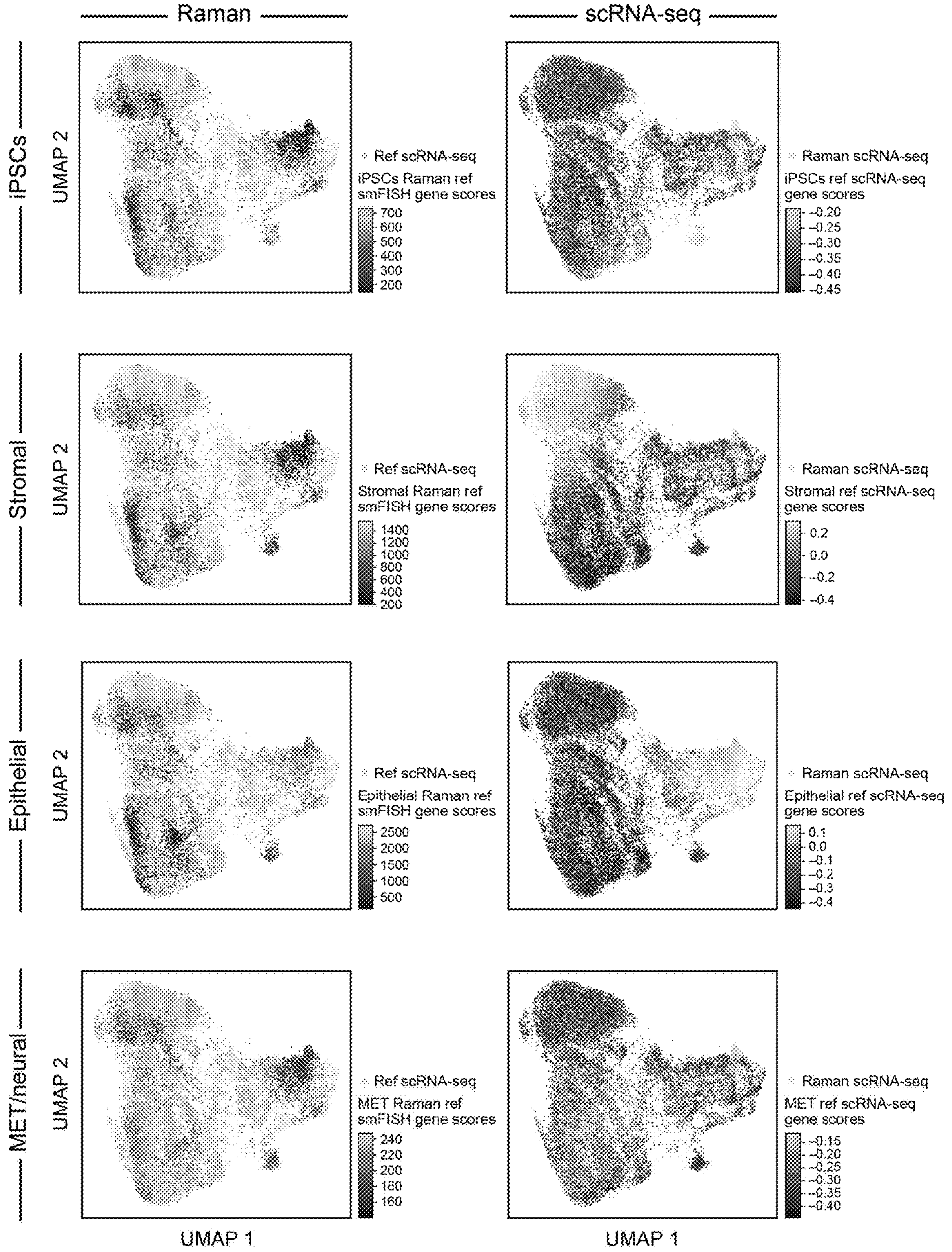

FIG. 35—Measured and Raman-predicted single cell profiles co-embed well as reflected by gene scores for each cell type. UMAP co-embedding of Raman predicted RNA profiles and measured scRNA-seq profiles (dots) colored by scores of marker gene for different cell types (rows) determined by smFISH measurements (left, for cells with Raman-predicted profiles) or real scRNA-seq measurements (right, for cells with scRNA-seq profiles).

Figure 36:
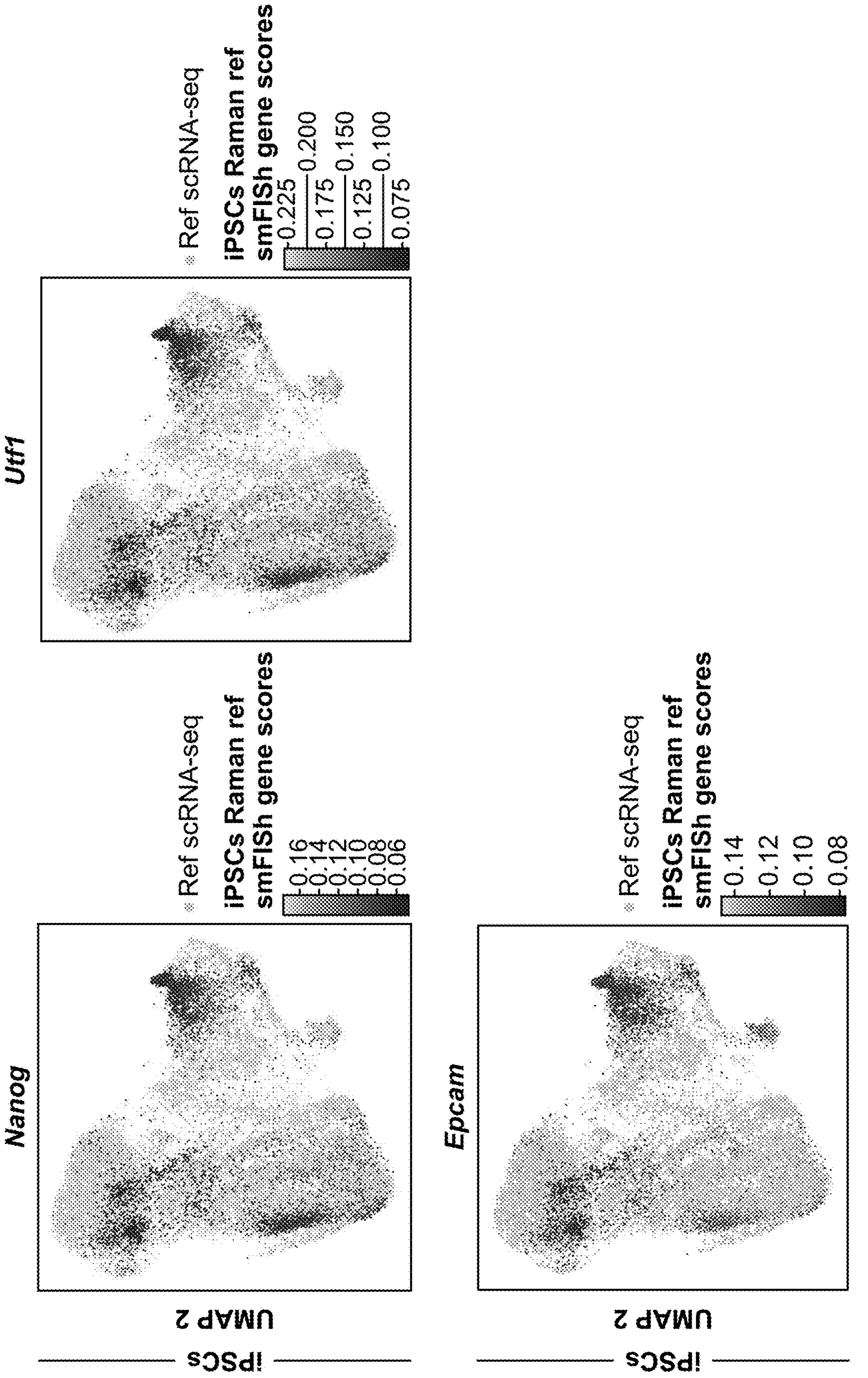

FIG. 36—Measured and Raman-predicted single cell profiles co-embed well as reflected by smFISH measurement of Raman cells. UMAP co-embedding of Raman predicted RNA profiles and measured scRNA-seq profiles (dots) where the Raman cells are colored by smFISH measurement of each of nine anchor genes.

Figure 37:
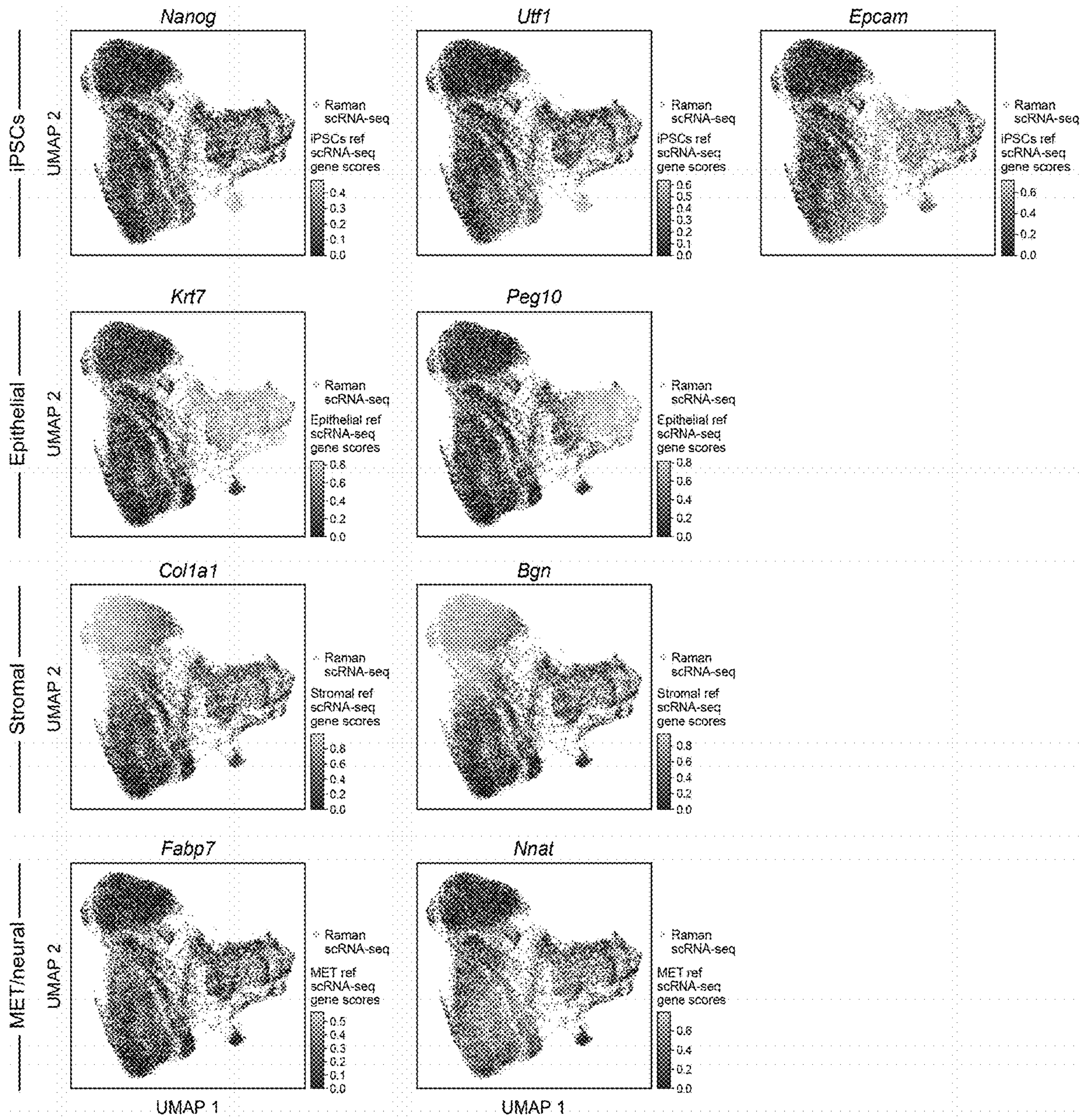

FIG. 37—Measured and Raman-predicted single cell profiles co-embed well as reflected by scRNA-seq based expression of nine anchor genes. UMAP co-embedding of Raman predicted RNA profiles and measured scRNA-Seq profiles (dots) where the scRNA-seq profiled cells are colored by scRNA-seq measured expression of each of nine anchor genes.

Figure 38:
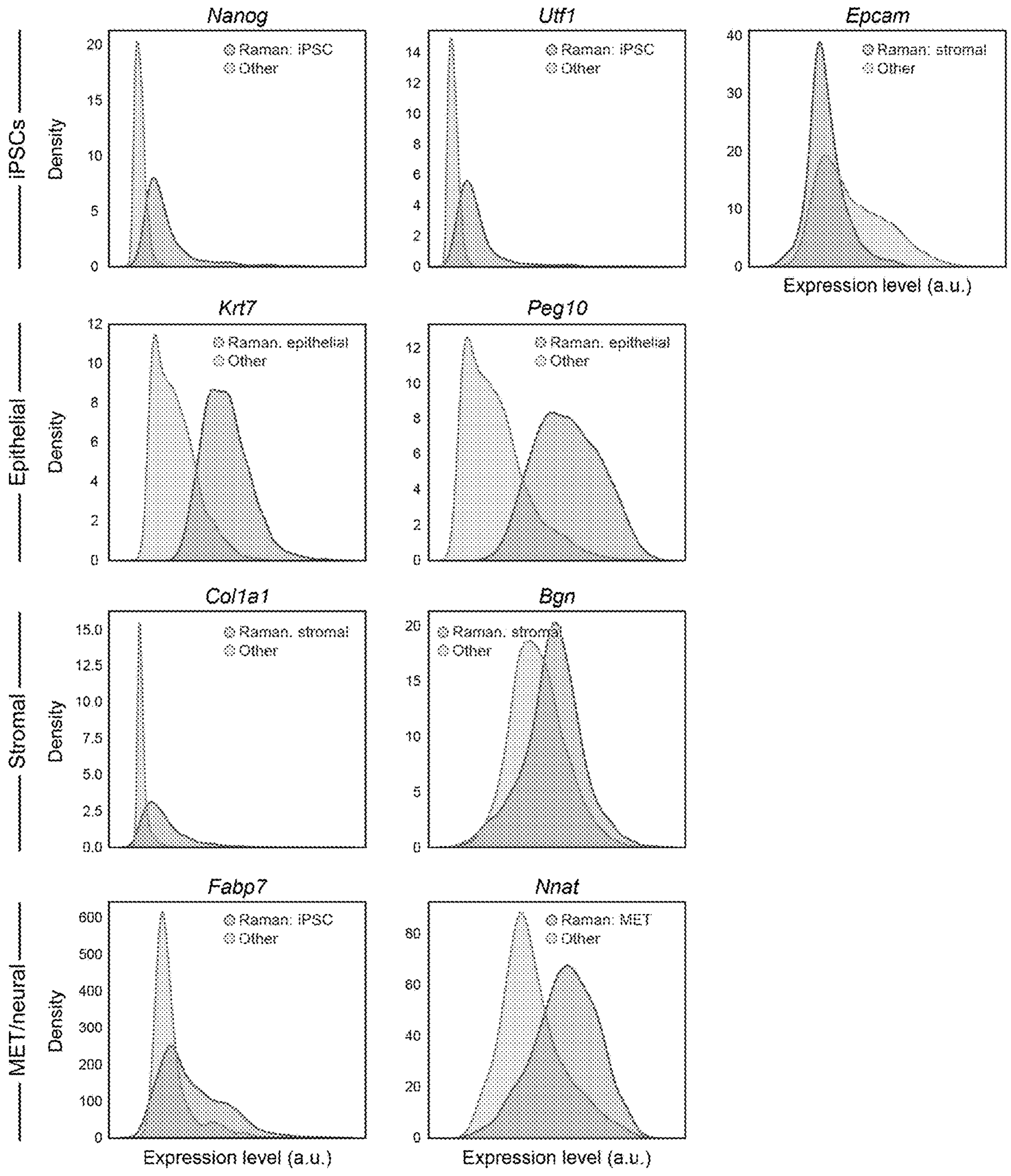

FIG. 38—Distributions of expression of marker genes based on R2R-predicted profiles. Distributions (density plots) of the predicted expression in Raman2RNA inferred profiles for each marker gene (panel) in its expected corresponding cell type (blue, based on the predicted expression profiles) and all other cells (orange).

Figure 39:
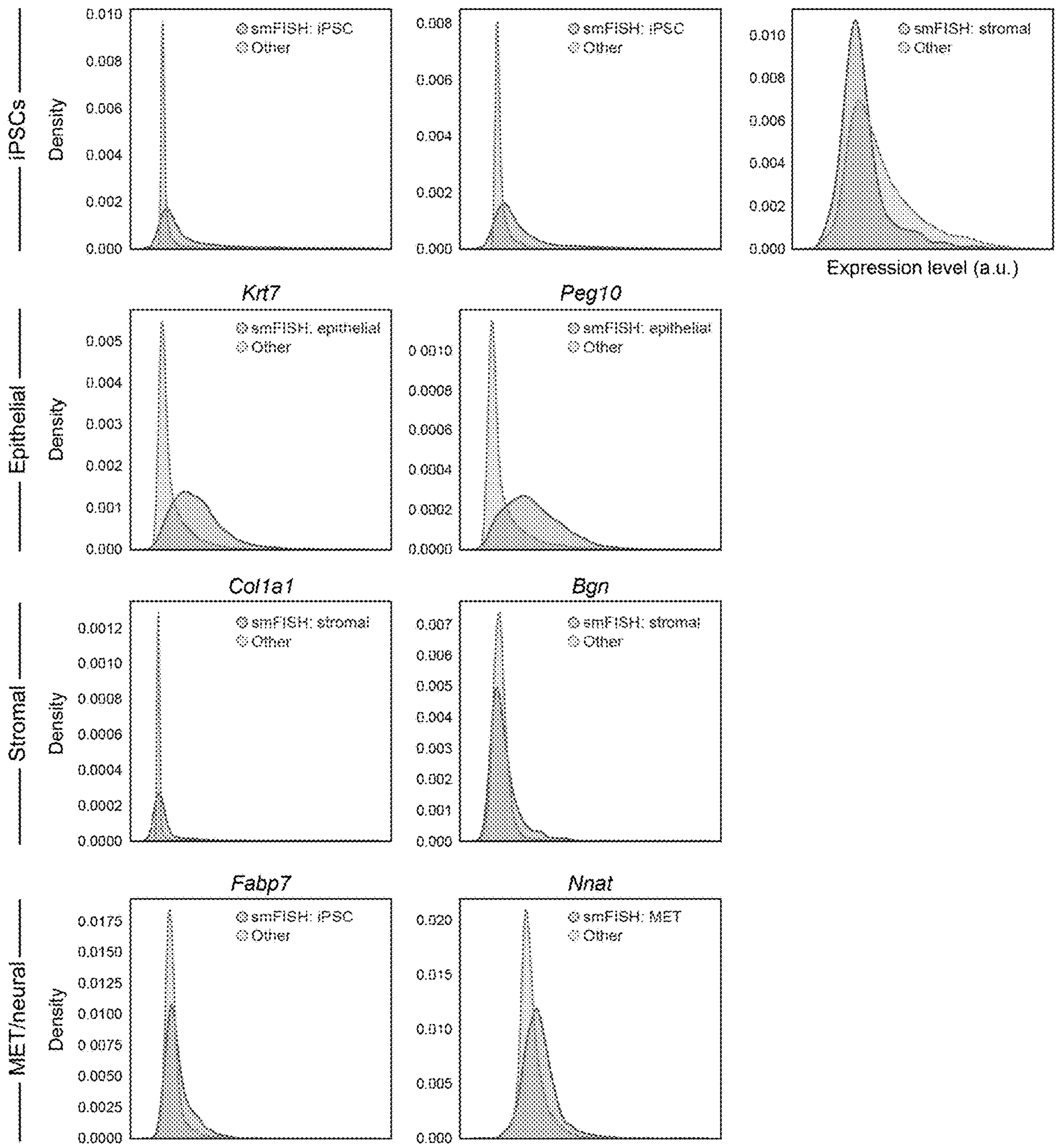

FIG. 39—Distributions of expression of marker genes based on real smFISH profiles. Distributions (density plots) of the real smFISH profiles for each marker gene (panel) in its expected corresponding cell type (blue, based on the R2R predicted expression profiles) and all other cells (orange).

Figure 40:
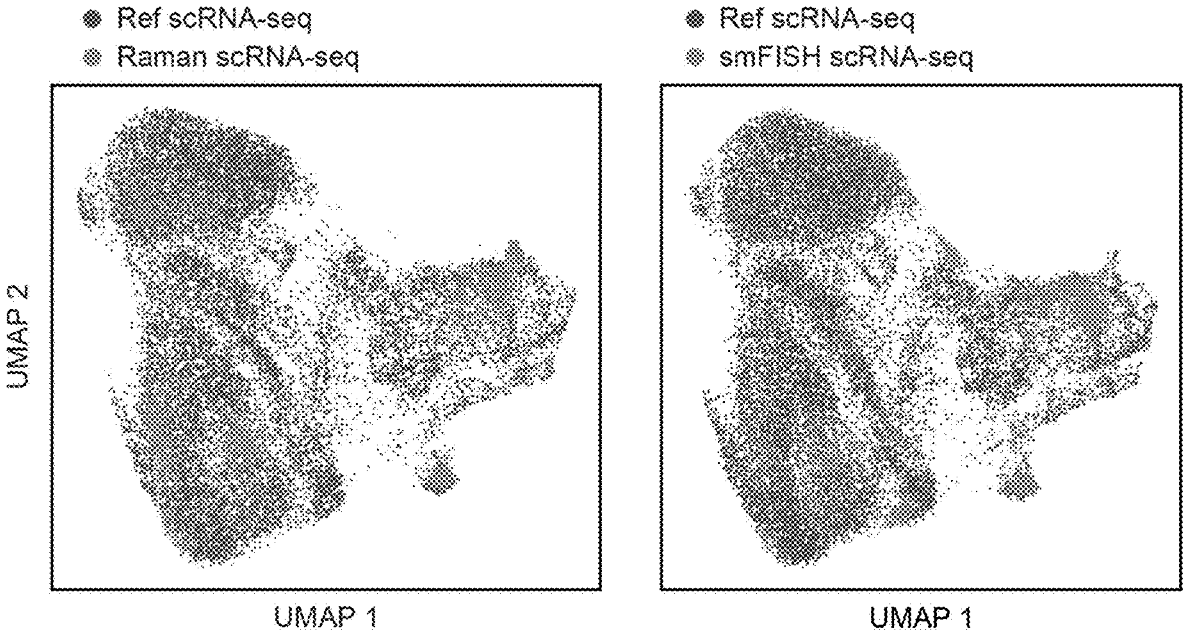

FIG. 40—RNA profiles predicted directly from 9 anchor smFISH measurements lead to reduced variance compared to scRNA-seq. UMAP co-embedding of cells from scRNA-seq (blue) and Raman (orange) experiments, with the latter based on either the Raman-predicted RNA profiles (left) or only smFISH-predicted RNA profiles (right).

Figure 41:
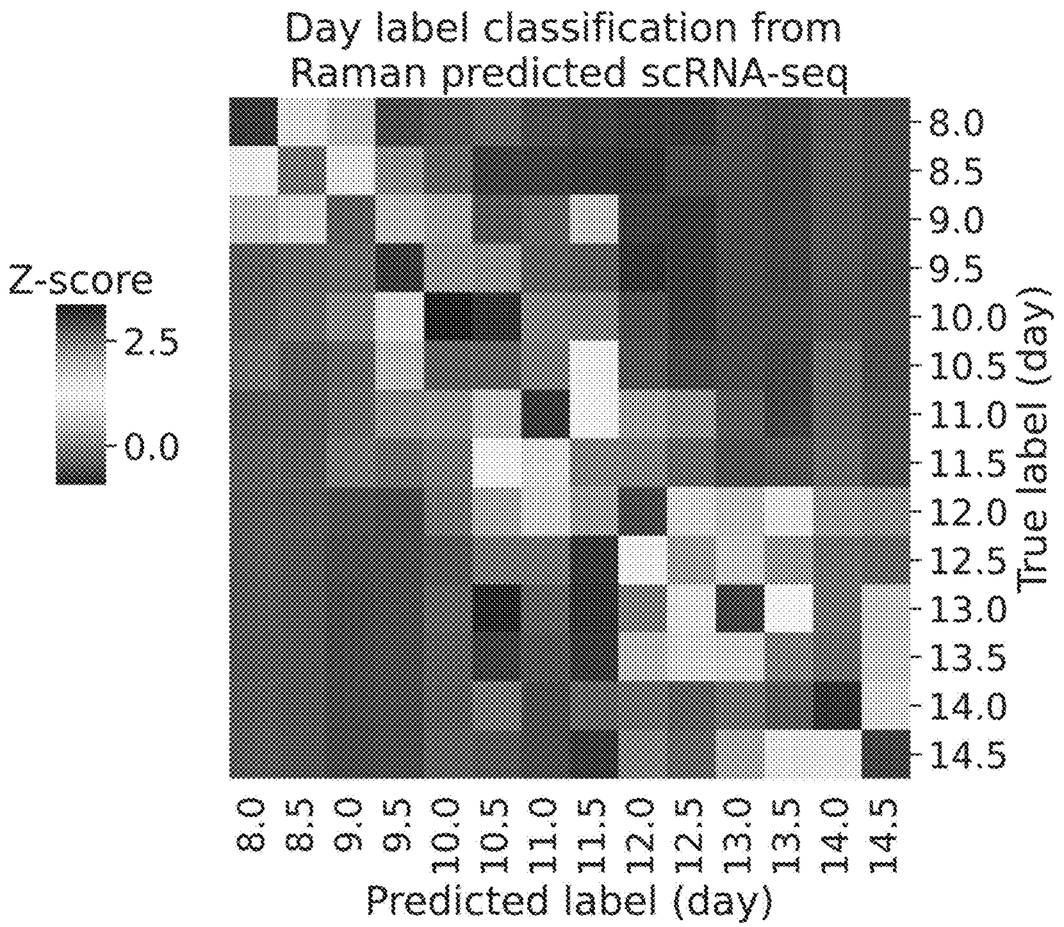

FIG. 41—Confusion matrix of day label classification in mouse reprogramming shows that Raman predicted scRNA-seq reflect temporal information at 0.5-day resolution. A Catboost classifier was trained with day labels as ground truth with 50/50 train/test split ratio. Shown is the confusion matrix where the x-axis is the predicted label and γ-axis is the true label. Color bar is the number of classifications.

Figure 42:
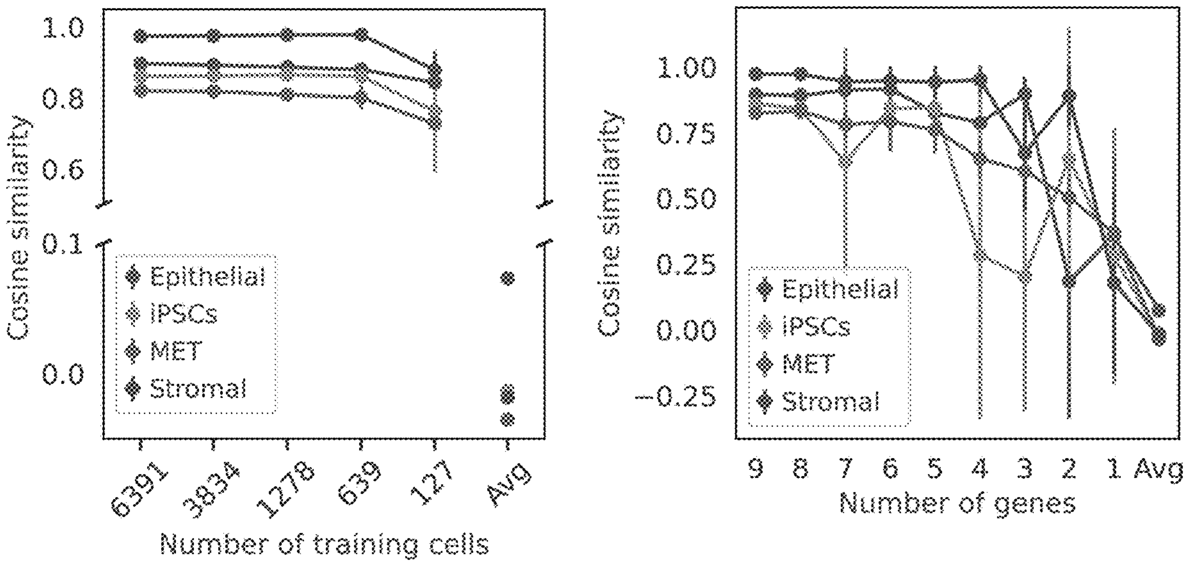

FIG. 42—Cosine similarities of Raman predicted profiles compared to real scRNA-seq profiles decrease monotonically as the number of cells or genes decreases. Average (Avg) is the profile where the average of gene expression profiles across all cells and cell types were calculated and used as baseline. Either the number of training cells (left) or number of randomly chosen genes used were decreased (right). Error bar is the standard deviation of 5 random trials.

Figure 43A:
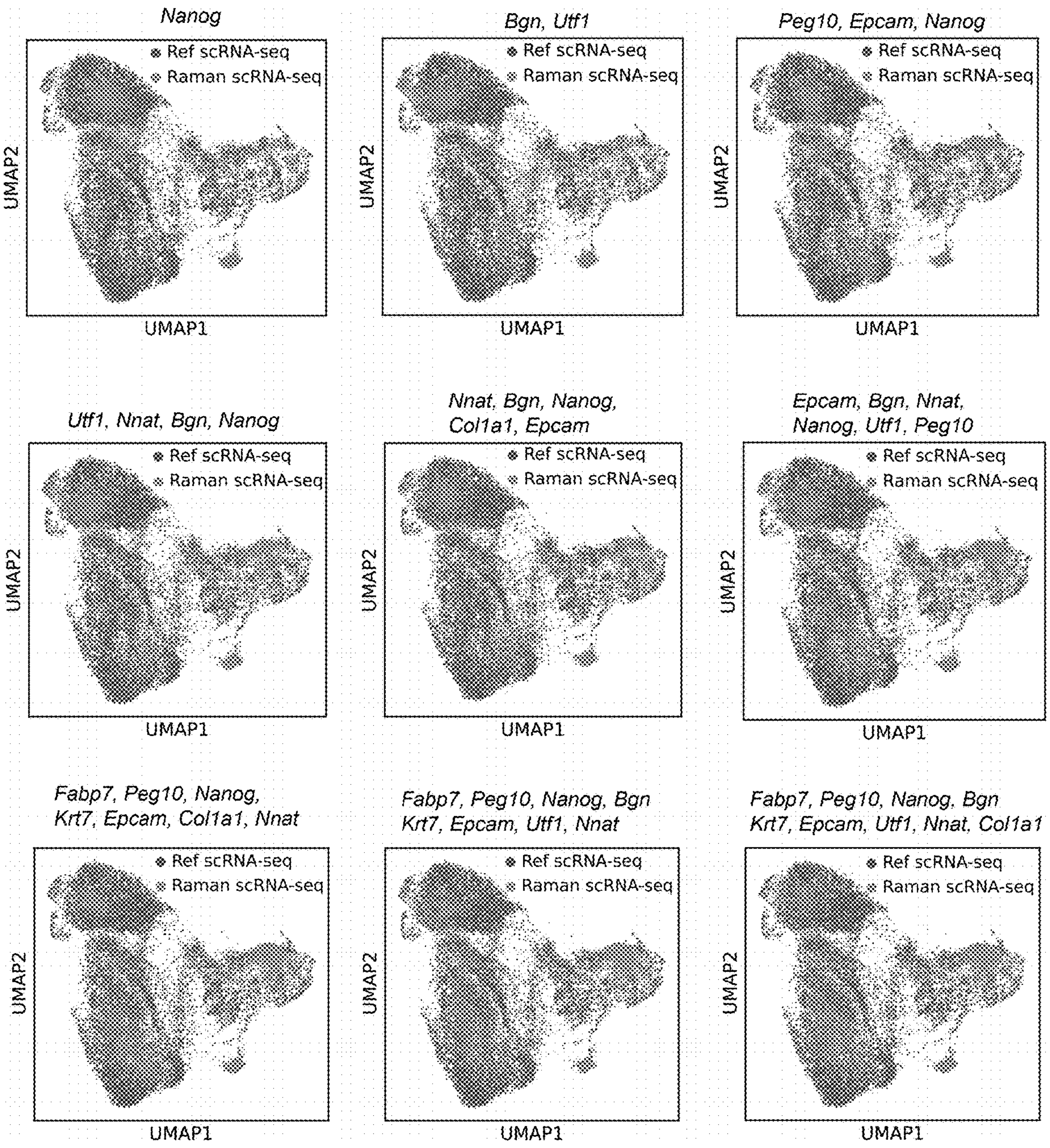
Figure 43B:
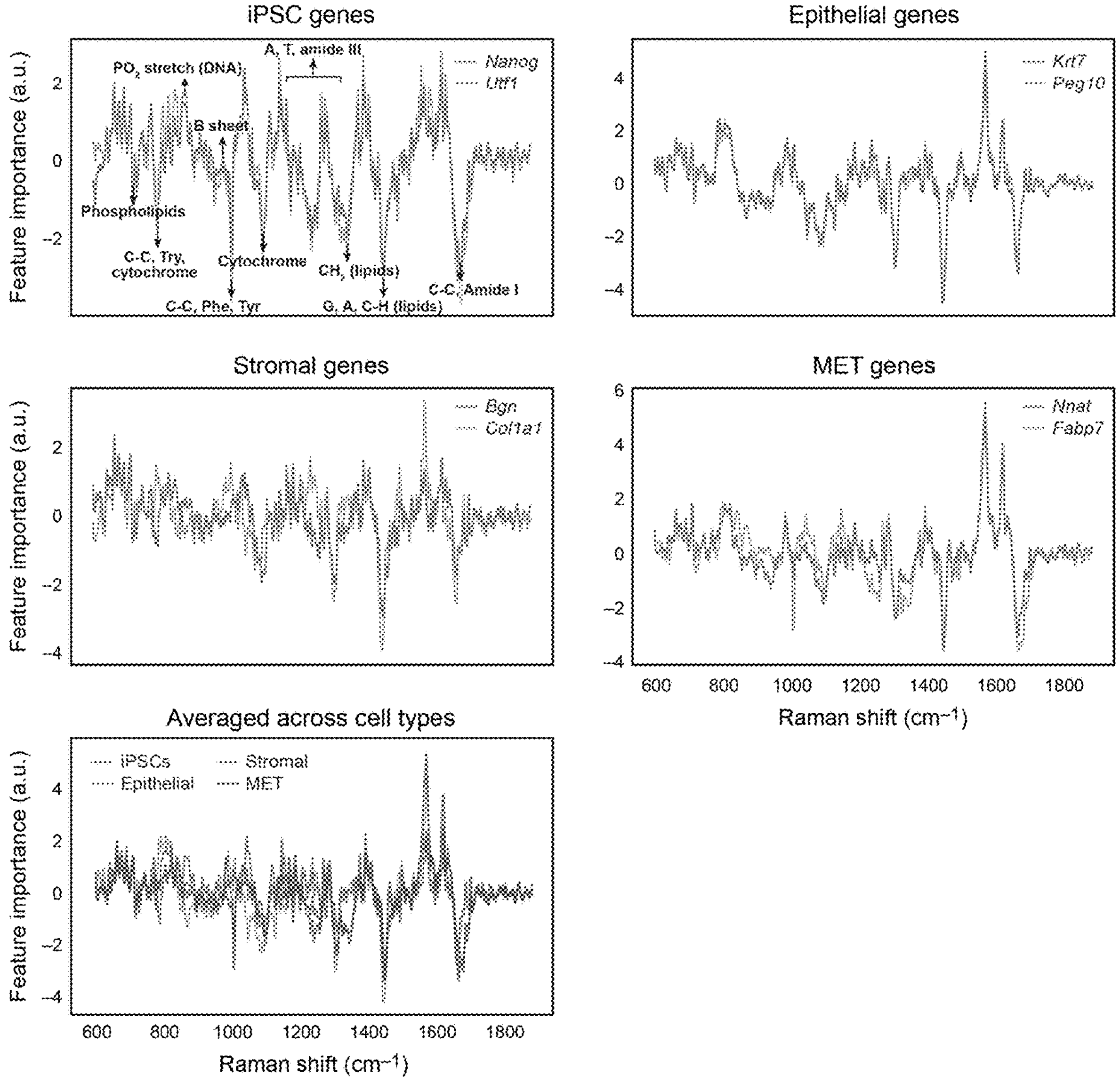

FIG. 43*a*-43*b*—43*a*. Example co-embeddings of Raman predicted scRNA-seq and real scRNA-seq profiles with varying numbers of anchor genes. 43*b*. Raman spectral feature importance scores for each smFISH anchor gene and its average across all genes for a cell type. Feature importance scores (y axis) for marker genes of each cell type (top two rows), and for all cell types (bottom row), along the Raman spectrum (x axis). Known signals2 are annotated in the top left panel (identical to FIG. 3*k*).

Figure 44:
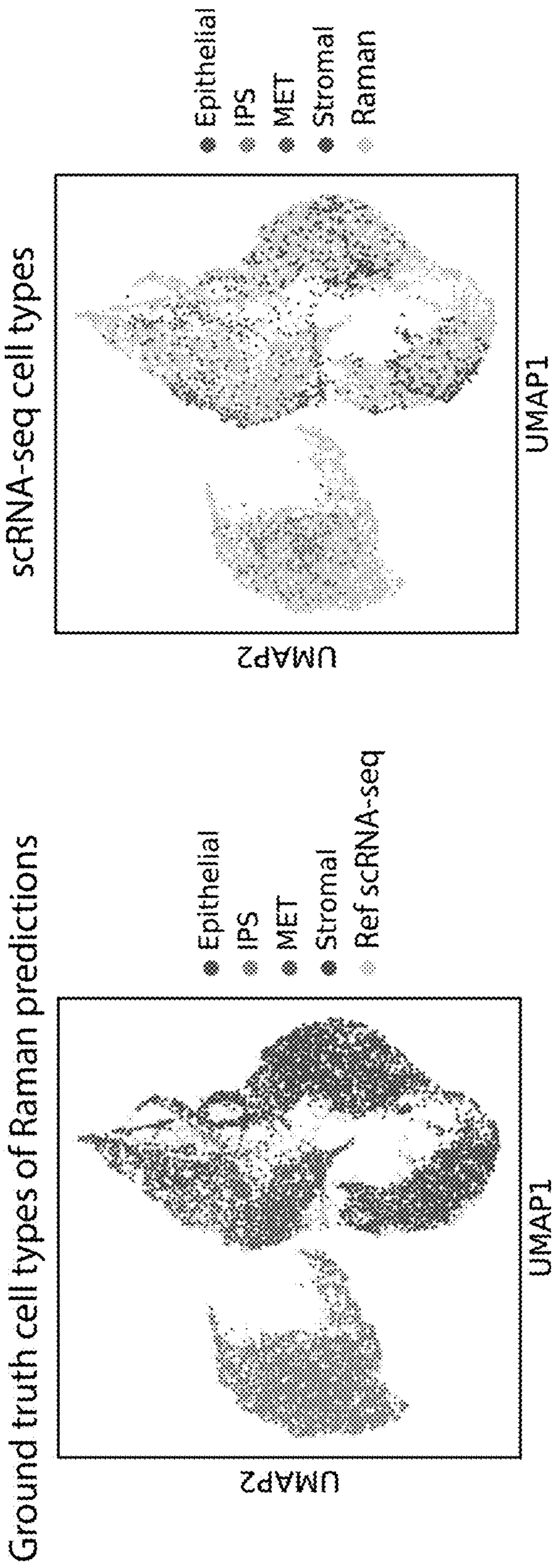

FIG. 44—Measured and anchor-free R2R-predicted single cell profiles co-embed well as reflected by ground truth cell type assignments. UMAP co-embedding of anchor-free Raman predicted RNA profiles and ground truth scRNA-seq profiles (dots) colored by cell types (rows) determined by Tangram label-transfer on smFISH measurements (left, for cells with Raman-predicted profiles) or ground truth scRNA-seq measurements (right, for cells with scRNA-seq profiles).

Figure 45:
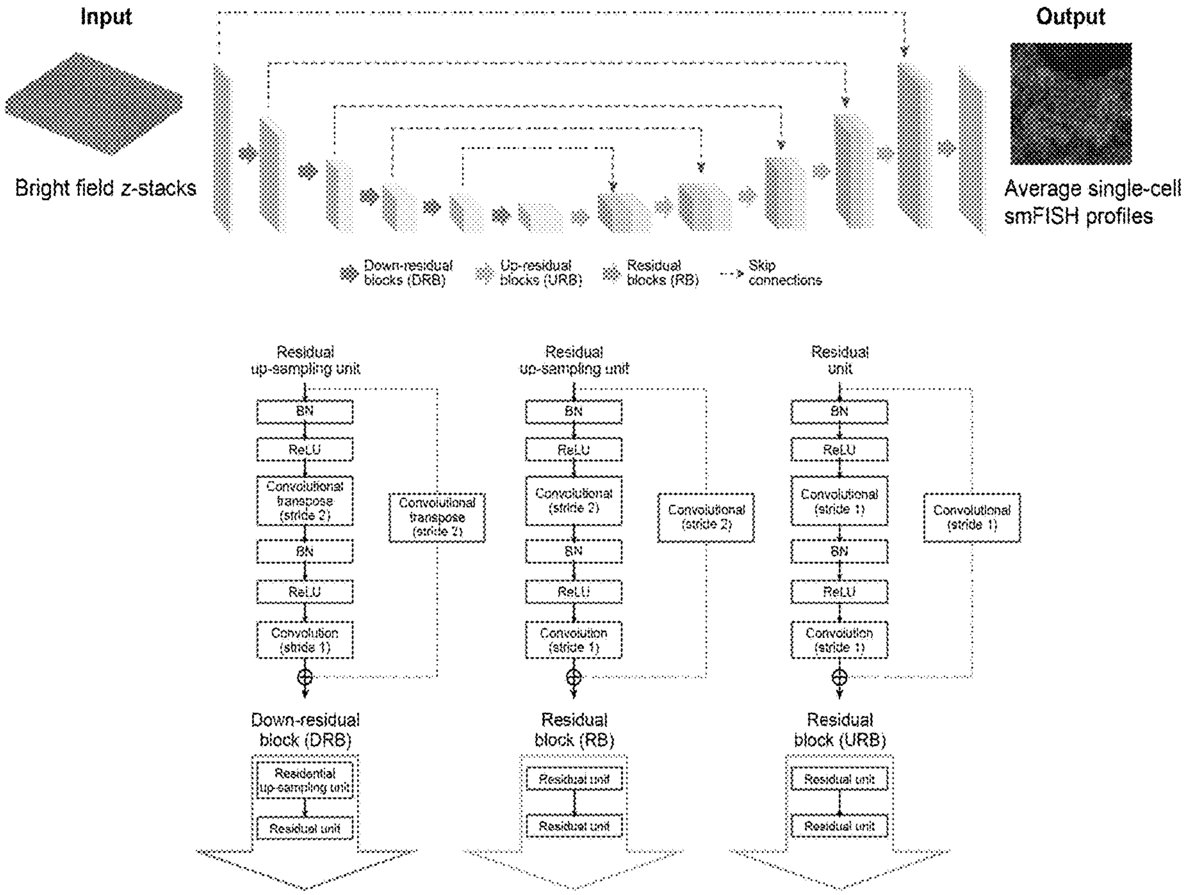

FIG. 45—U-net with residual connection for regression of mean single-cell smFISH profiles from brightfield z-stacks.

Figure 46:
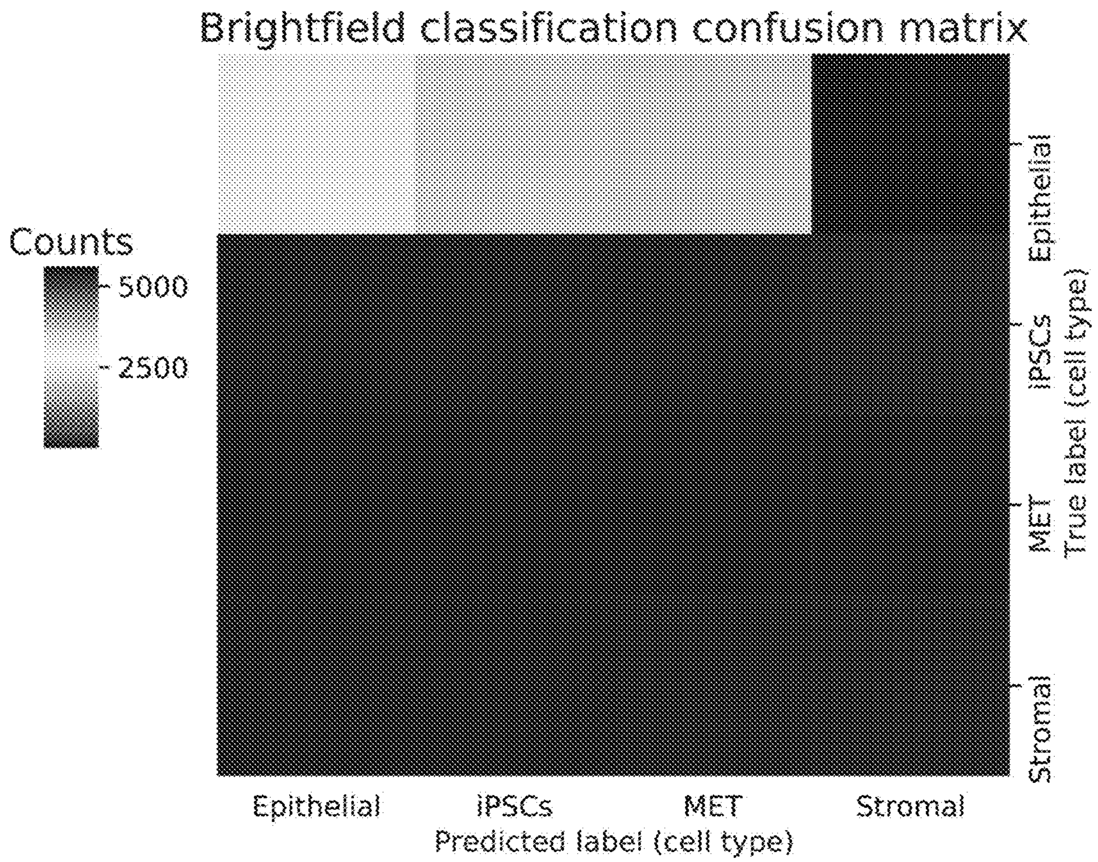

FIG. 46—Confusion matrix of convolutional neural network-based cell type classification of brightfield images show low accuracy in mouse iPSCs reprogramming.

Figure 47:
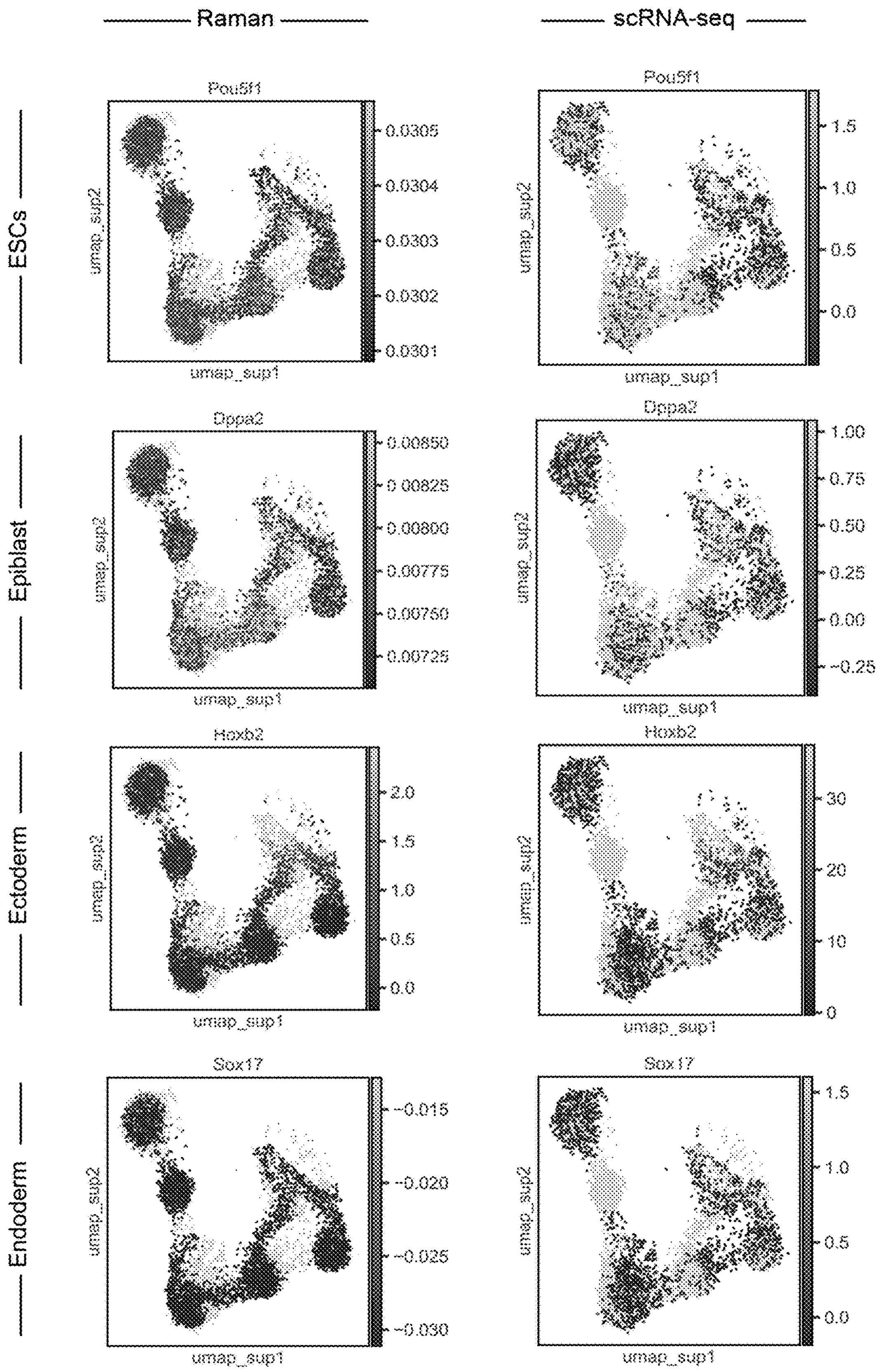

FIG. 47—Measured and Raman-predicted single cell profiles co-embed well as reflected by expression values. UMAP co-embedding of Raman predicted RNA profiles and measured scRNA-seq profiles (dots) colored by marker genes for different cell types (rows) determined by smFISH measurements (left, for cells with Raman-predicted profiles) or real scRNA-seq measurements (right, for cells with scRNA-seq profiles).

Figure 48:
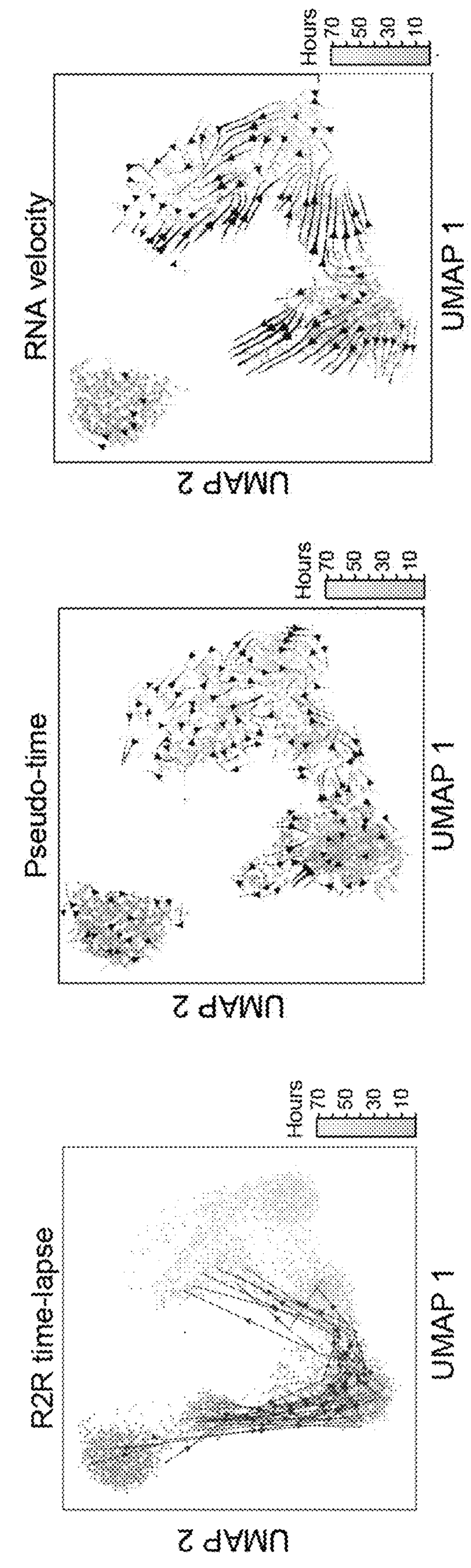

FIG. 48—Comparison of R2R with computational trajectory inference methods highlights importance of direct time-lapse imaging during mESCs differentation. Pseudo-time trajectory inference and generalized RNA velocity was conducted using CellRank2 with default parameters.

Figure 49:
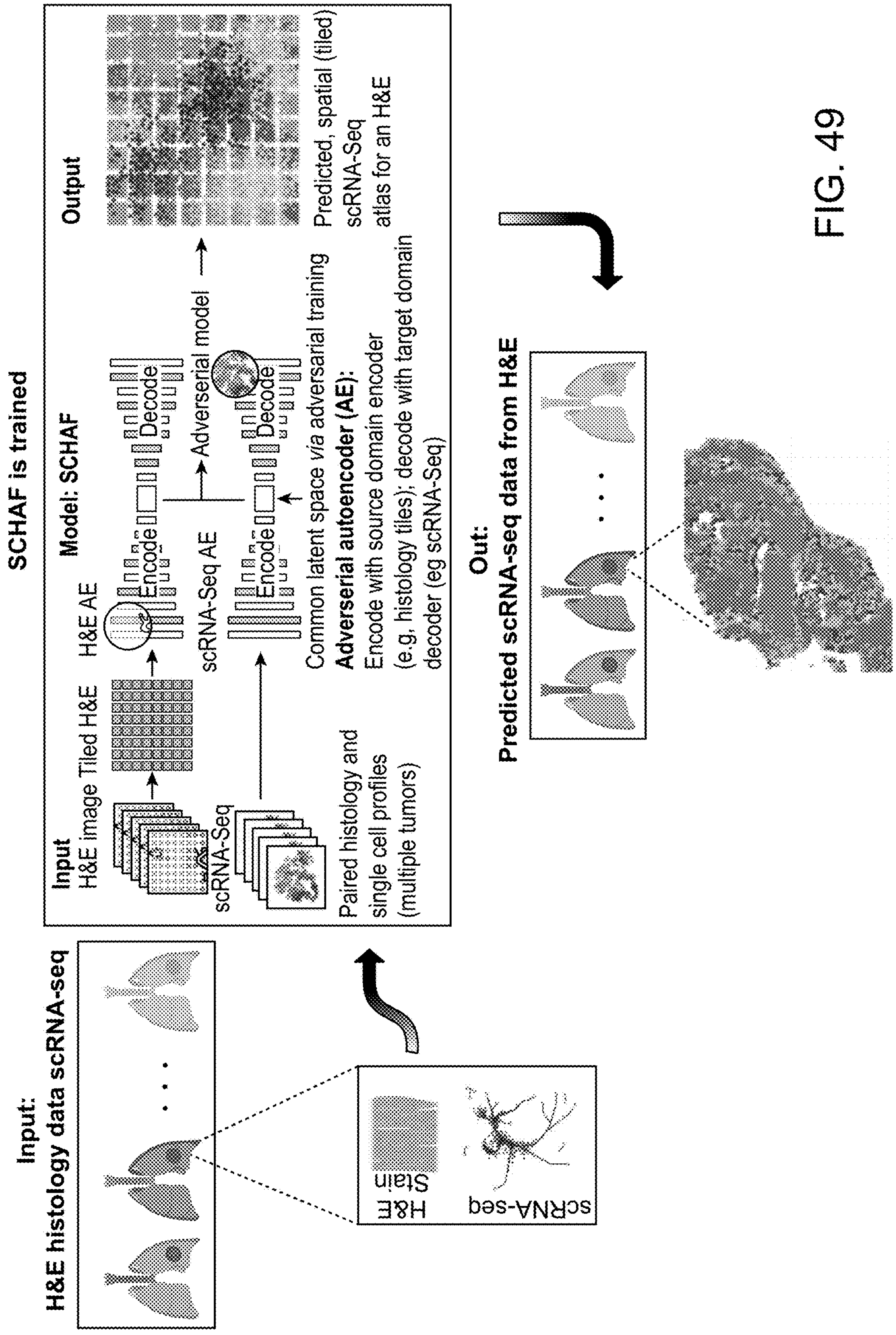

FIG. 49—SCHAF learns to predict a tissue's single-cell omics dataset from its histology image. Training overview. Schematic outlining training for SCHAF. A reconstructing autoencoder is trained on the gene-expression data. Histology images are normalized (if needed) and tiled, after which a histology-image-tile autoencoder is trained to reconstruct and encode to a latent space indistinguishable from that of the gene-expression encoder adversarially via training against a latent discriminator. Applicants demonstrate SCHAF on three tissue corpora: one of small cell lung cancer data with snRNA-seq transcriptomic data (sn-SCLC), one of metastatic breast cancer data with snRNA-seq transcriptomic data (sn-MBC), and one of metastatic breast cancer data with scRNA-seq transcriptomic data (sc-MBC). After training SCHAF, Applicants evaluate with a series of spatial and non-spatial criteria.

FIG. 50*a*-50*f*—SCHAF's inferences are initially validated on non-spatial criteria. 50*a*-50*c*. Bulk gene-expression proportions. 50*a*. Plotted bulk gene-expression proportions, with SCHAF (orange) and the original target (blue) being compared in each of the four evaluation samples (top), and the random baseline (orange) and the original target (blue) being compared in each of the four evaluation samples (bottom). 50*b*. Comparison of the correlation of the original target's proportions with SCHAF's inferences (orange) and the original target's proportions against those of the random baseline (blue) for each of the four evaluation samples, with all improvement of correlations from random baseline to SCHAF inferred having statistical significance with Fisher-Steiger improvement-of-correlation test p-values close to 0 for all samples. 50*c*. Comparison of the Jensen-Shannon divergence between the original target's proportions and SCHAF's inferences (orange) and the original target's proportions and the random baseline (blue) for each of the four evaluation samples. 50*d-e* Intergene correlations. 50*d*. Visualization of the portion of samples' correlation matrices consisting of the top 100 most highly-variable genes, with those of the original datasets (top), SCHAF inferred datasets (middle), and random-baseline datasets (bottom), all corresponding to the left-most colorbar. 50*e*. Comparison of the strength of the meta-correlations, the correlations between two correlation matrices' flattened entries corresponding to the 100 most highly-variable genes, between the same meta-correlation of the original target dataset and SCHAF's (orange) and of the original target dataset and the random-baseline for each sample, with significance of the improvement of correlation of SCHAF's inferences over the random baseline for each sample having Fisher-Steiger improvement-of-correlation test p-values close to 0. 50*f*. Gene count distributions. Histograms that, for each sample, overlay the distribution, over genes, of the Earth Mover Distances between each gene's count distributions in the original target dataset and SCHAF's inferences (orange) and those of each gene's count distributions in the original target dataset and the random baseline (blue), with a lower value implying more similarity between two probability distributions.

FIG. 51*a*-51*d*—Celltype label transfers validate SCHAF's preservation of well-formed celltype clusters. 51*a*. Celltype-labeled dataset UMAPs. For each of the four evaluation samples, Applicants have original target dataset UMAPs colored with their manually-annotated celltypes (top), SCHAF-inferred dataset UMAPs colored by their toy classifier-assigned celltypes (middle), and random-baseline datasets also colored by the celltypes assigned to them by the same toy classifiers used on the SCHAF-inferred datasets (bottom). Celltype-color legends can be found below the UMAPs corresponding to each sample. 51*b*. Silhouette coefficients of datasets' celltypes. For each of the four evaluation samples, box plots demonstrating the distributions of celltype silhouette coefficients for original target (left), SCHAF inferred (middle), and baseline random (right) datasets. Distribution medians are signified by the light-orange line. The statistical significance of SCHAF's silhouette coefficient distribution being greater than that of the random-baseline has p<<10-24 according to a Mann-Whitney U test for all evaluation samples. 51*c*. Datasets' celltype pseudobulk correlations. For each of the four evaluation samples, a histogram displaying, within each celltype, the correlation between the original data's pseudobulk measurements and the measurements of both the SCHAF inferred (orange) and random baseline (blue) datasets. 51*d*. Confidence in celltype assignment. Histograms that, for each sample, overlay the distribution, over cells, of the respective toy classifier's assigned probability that a cell is of a certain celltype for SCHAF's inferences (orange) and the random baseline (blue). Statistical significance of the distributions of SCHAF's probabilities being greater than those of the random-baseline has p<<10-100 according to a Mann-Whitney U test for all evaluation samples.

FIG. 52*a*-52*e*—SCHAF's gene-expression inferences are validated with respect to spatial accuracy with HTAPP corpora's spatial MERFISH validation data. 52*a*-52*c*. Individual genes' spatial correlations. 52*a*. Correlation between overlaid spatial tiles' SCHAF-inferred and MERFISH-validation expression values, for each of six genes (MYL6, TMSB10, JUN, CD63, HLA-B, and JUNB) for sample HTAPP-932 (left) and each of six genes (SOX4, CTCF, DCN, TMSB10, MYL6, and PABPC1) for sample HTAPP-6760 (right), with the number of tiles/points considered for each gene next to the gene's name in each graph, the mean-square-error-reducing line-of-best-fit for each gene dashed in black, and individual tiles' being represented by green-dots on the MERFISH-expression (x-axis) by SCHAF-inferred-expression (y-axis) planes. 52*b*. Comparative spatial-tile correlations. Histogram of the distribution over non-trivial genes of the strength of their spatial-tile correlation between the SCHAF-inferred expression and MERFISH-validation expression for samples HTAPP-932 (left) and HTAPP-6760 (right). 52*c*. Spatial correlations of all genes. For both samples HTAPP-932 (left) and HTAPP-6760 (right), for each gene visually considered in each sample, a histogram comparing the strength of the correlation between the SCHAF-inferred and MERFISH-validation expressions (orange), between the randomly-placed random-baseline and MERFISH-validation expressions (blue), and the randomly-placed original-dataset and MERFISH-validation expressions (green). 52*d-e*. Spatial celltype mappings. 52*d*. Spatial celltype mapping from SCHAF with toy celltype classifiers assistance for sample HTAPP-6760, a training sample with rich pathologist annotations. To the left of the mappings lie corresponding pathologist-annotated celltype functional regions (Fat, Vasculature, Tumor, Fibrosis, ImmuneCells). To the right lie the baseline of randomly-placed original-omics profiles (top) and SCHAF's mapping (bottom). 52*e*. Spatial celltype mapping from SCHAF with toy celltype classifiers assistance for sample HTAPP-932. On top of the mappings lie corresponding pathologist-annotated celltype functional regions (Tumor, Normal, BloodVessels, ImmuneCells). For both mappings, pathologist annotations appear in green atop of the original histology images themselves, while the SCHAF spatial-celltype mappings have colors corresponding to the right-most color legends. On the bottom lie the baseline of randomly-placed original-omics profiles (second to bottom) and SCHAF's mapping (bottom).

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M.J. MacPherson, B.D. Hames, and G. R. Taylor eds.): Antibodies, A Laboratory Manual (1988) (Harlow and Lane, eds.): Antibodies A Laboratory Manual, $2^{nd}$ edition 2013 (E.A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide a method, system, and computer program device for determining an omics profile of a cell using microscopy imaging data comprising first receiving microscopy imaging data of a cell or a population of cells, then determining a targeted spatial expression profile of a set of target genes from the microscopy imaging data using a first machine learning model, the target genes identifying a cell type or cell state of interest, finally determining a single-cell omics profile for the population of cells using a second machine learning algorithm model, wherein the targeted spatial expression profile previously mentioned, and a reference single-cell RNA-seq data set are used as inputs for the second machine learning model.

Ordinarily, the process of mapping an omics profile of a cell results in destruction of the cell under analysis. For example, most sequencing-based omics techniques require cell or tissue lysing. Even fluorescent dyes and reporters are limited in the number of targets they identify, resulting in an incomplete interpretation of a cell's operation. As a result, real time molecular dynamics of a cell as a function of its omics profile can only be loosely assumed. Described herein is a method that resolves the destructive and imperfect nature of previous methods of mapping cellular omics profiles by joining microscopy and machine learning.

As previously mentioned, imaging cells and tissues, a critical tool for studying cellular biology, inherently risks destroying the cell or tissue under analysis. High illumination and exposure time can, for example, photo bleach a cell or tissue. For that reason, a compromise is made between image quality and maintaining healthy cells. Typically, fluorescence microscopy is used since illumination intensity and exposure time are shortened. The necessity for optimal cell health ensures normal function is observed while on a microscopic stage and in the presence of fluorophores. There has been no previous all-purpose method of cell and tissue imaging. However, as described herein, the coupling of microscopy with machine learning provides a method for non-destructive determination of cellular function and omics. In example embodiments, microscopy image data of a cell is input into a machine learning module to determine an omics profile.

Single cell RNA-Seq (scRNA-seq) and other profiling assays have opened new windows into understanding the properties, regulation, dynamics, and function of cells at unprecedented resolution and scale. However, these assays are inherently destructive, precluding Applicants from tracking the temporal dynamics of live cells, in cell culture or whole organisms. Raman microscopy offers a unique opportunity to comprehensively report on the vibrational energy levels of molecules in a label-free and non-destructive manner at a subcellular spatial resolution, but it lacks in genetic and molecular interpretability. Here, Applicants developed Raman2RNA (R2R), an experimental and computational framework to infer single-cell expression profiles in live cells through label-free hyperspectral Raman microscopy images and multi-modal data integration and domain translation. Applicants used spatially resolved single-molecule RNA-FISH (smFISH) data as anchors to link scRNA-seq profiles to the paired spatial hyperspectral Raman images, and trained machine learning models to infer expression profiles from Raman spectra at the single-cell level. In reprogramming of mouse fibroblasts into induced pluripotent stem cells (iPSCs), R2R accurately (r>0.96) inferred from Raman images the expression profiles of various cell states and fates, including iPSCs, mesenchymal-epithelial transition (MET) cells, stromal cells, epithelial cells, and fibroblasts. R2R outperformed inference from brightfield images, showing the importance of spectroscopic content afforded by Raman microscopy. Raman2RNA lays a foundation for future investigations into exploring single-cell genome-wide molecular dynamics through imaging data, in vitro and in vivo.

Biodiversity of Methods and Systems

The methods and systems described herein can determine one or more omics profile or biomarker from a biological sample obtained from a subject. A subject may comprise a vertebrate or invertebrate. A subject may comprise one or more mammals, birds, reptiles, amphibians, fish, or any combination thereof. A subject may include, for example, mammals such as bovine, avian, canine, equine, feline, ovine, porcine, or primate animals (including humans and non-human primates). A subject may include, for example, carnivores such as cats and dogs; swine including pigs, hogs and wild boars; ruminants or ungulates such as cattle, oxen, sheep, giraffes, deer, goats, bison, camels or horses. Also included are birds, as well as fowl for example, domesticated fowl, i.e. poultry, such as turkeys and chickens, ducks, geese, guinea fowl. Also included are domesticated swine and horses. Also included are fish such as those found in freshwater, saltwater, or brackish water. In an example embodiment, any animal species connected to commercial activities, such as those connected to agriculture and aquaculture. In an example embodiment, an animal species connected to activities in which disease monitoring, diagnosis, and therapy selection are routine practice in husbandry for economic productivity and/or safety of the food chain.

A subject may comprise a plant. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. A subject may comprise a fungi. A fungal cell may be any type of eukaryotic cell within the kingdom of fungi, such as phyla of Ascomycota, Basidiomycota, Blastocladiomycota, Chytridiomycota, Glomeromycota, Microsporidia, and Neocallimastigomycota. Examples of fungi or fungal cells in include yeasts, molds, and filamentous fungi.

In addition, the subject may include prokaryotes. Prokaryotes may include bacteria and archaea. In one example embodiment, the prokaryotic cells are Gram-negative or Gram-positive. Various combinations of cells may form a set of prokaryotic cells. In one example embodiment, a set of prokaryotic cells includes one or more prokaryotic cell species, one or more strains of the same prokaryotic cell species, one or more phenotypes of the same prokaryotic cell species, one or more phenotypes of the same prokaryotic cell strain, or a combination thereof. In one example embodiment, a set of prokaryotic cells is a biological sample obtained from a subject. In another example embodiment, a set of prokaryotic cells is a biological sample comprising one or more uncharacterized organisms, an environmental microbiome, or an organismal microbiome.

In addition, the subject may comprise bacteria or a bacterium. A bacterium may comprise any of those belonging to spirochetes; spirilla; vibrios; gram-negative aerobic rods and cocci; enterics; pyogenic cocci; and endospore-forming bacteria; actinomycetes and related bacteria; rickettsias and chlamydiae; mycoplasmas, which are groups defined by some bacteriological criteria. A pathogenic bacteria may include: *Escherichia coli, Salmonella enterica, Salmonella typhi, Shigella dysenteriae, Yersina pestis, Pseudomonas aeruginosa, Vibrio cholerae, Bordetella pertussis, Haemophilus influenza, Helicobacter pylori, Campylobacter jejuni, Neisseria gonorrhoeae, Neisseria meningitidis, Brucella abortus, Bacteroides fragilis, Staphylococcus aureus, Streptococcus pyogenes, Streptococcus pneumoniae, Bacillus anthracis, Bacillus cereus, Clostridium tetani, Clostridium perfringens, Clostridium botulinum, Clostridium difficile, Corynebacterium diphtheriae, Listeria monocytogenes, Mycobacterium tuberculosis, Mycobacterium leprae, Chlamydia trachomatis, Chlamydia pneumoniae, Mycoplasma pneumoniae, Rickettisas, Treponema pallidum, Borrelia burgdorferi*, or a variant thereof. (Todar, K. Textbook of Bacteriology (2020) Online)

Example System Architectures

Turning now to the drawings, in which like numerals represent like (but not necessarily identical) elements throughout the figures, example embodiments are described in detail.

Figure 1:
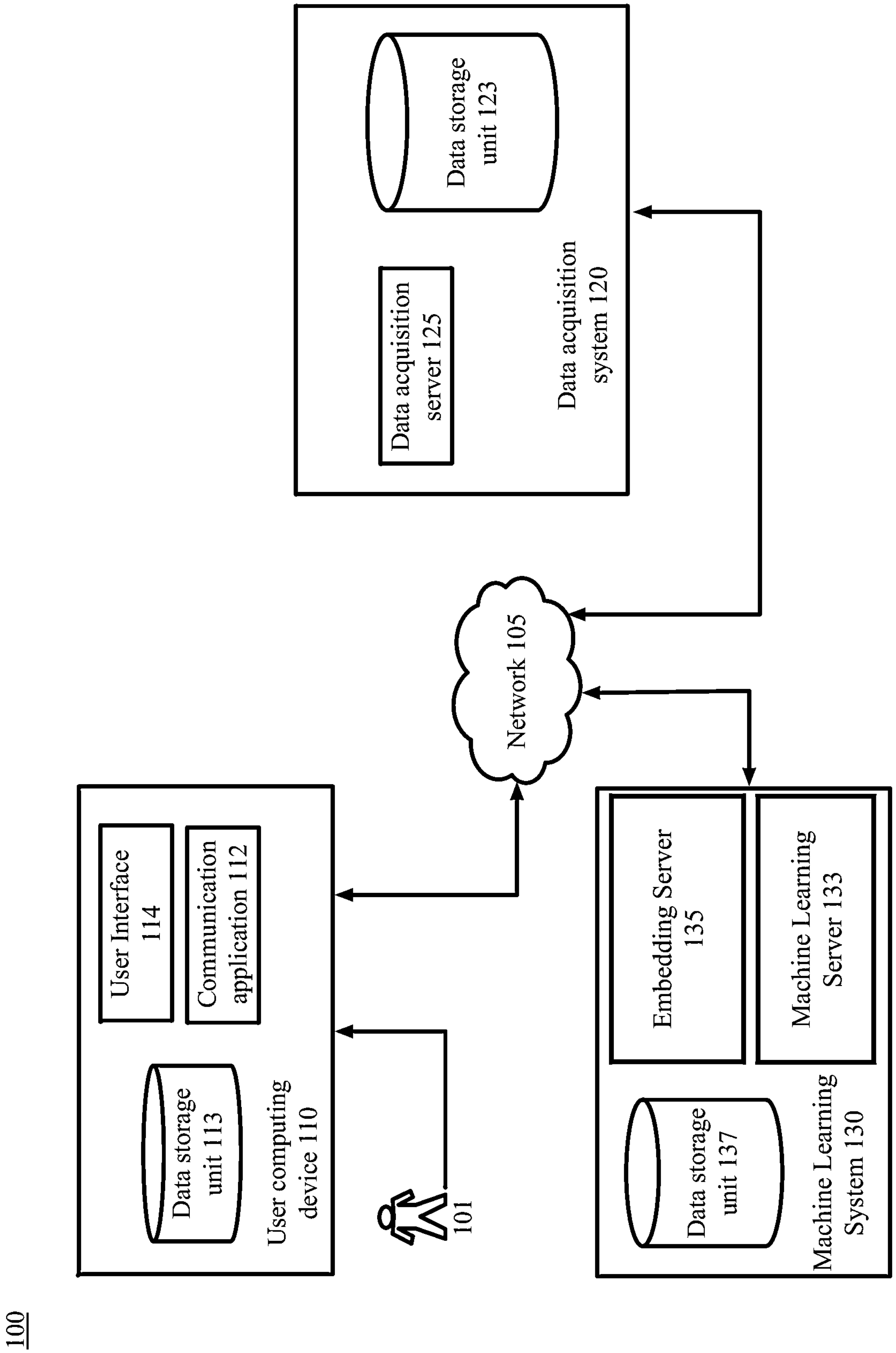
FIG. 1—A block diagram depicting a portion of a communications and processing architecture of a typical system to acquire microscopy imaging data from a database and perform machine learning, in accordance with certain examples of the technology disclosed herein.

FIG. 1 is a block diagram depicting a system 100 performing machine learning on microscopy imaging data to determine an omics profile of a cell. In one example embodiment, a user 101 associated with a user computing device 110 must install an application, and or make a feature selection to obtain the benefits of the techniques described herein.

As depicted in FIG. 1, the system 100 includes network computing devices/systems 110, 120, and 130 that are configured to communicate with one another via one or more networks 105 or via any suitable communication technology.

Each network 105 includes a wired or wireless telecommunication means by which network devices/systems (including devices 110, 120, and 130) can exchange data. For example, each network 105 can include a local area network ("LAN"), a wide area network ("WAN"), an intranet, an Internet, a mobile telephone network, storage area network ("SAN"), personal area network ("PAN"), a metropolitan area network ("MAN"), a wireless network ("WiFi;"), wireless access networks, a wireless local area network ("WLAN"), a virtual private network ("VPN"), a cellular or other mobile communication network, Bluetooth, near field communication ("NFC"), ultra-wideband, wired networks, telephone networks, optical networks, or any combination thereof or any other appropriate architecture or system that facilitates the communication of signals and data. Throughout the discussion of example embodiments, it should be understood the terms "data" and "information" are used interchangeably herein to refer to text, images, audio, video, or any other form of information that can exist in a computer-based environment. The communication technology utilized by the devices/systems 110, 120, and 130 may be similar networks to network 105 or an alternative communication technology.

Each network computing device/system 110, 120, and 130 includes a computing device having a communication module capable of transmitting and receiving data over the network 105 or a similar network. For example, each network device/system 110, 120, and 130 can include a server, desktop computer, laptop computer, tablet computer, a television with one or more processors embedded therein and/or coupled thereto, smartphone, handheld or wearable computer, personal digital assistant ("PDA"), wearable devices such as smartwatches or glasses, or any other wired or wireless, processor-driven device. In the example embodiment depicted in FIG. 1, the network devices/systems 110, 120, and 130 are operated by user 101, data acquisition system operators, and mapping system operators, respectively.

The user computing device 110 includes a user interface 114. The user interface 114 may be used to display a graphical user interface and other information to the user 101 to allow the user 101 to interact with the data acquisition system 120, the machine learning system 130, and others. The user interface 114 receives user input for data acquisition and/or machine learning and displays results to user 101. In another example embodiment, the user interface 114 may be provided with a graphical user interface by the data acquisition system 120 and or the machine learning system 130. The user interface 114 may be accessed by the processor of the user computing device 110. The user interface may display 114 may display a webpage associate with the data acquisition system 120 and/or the machine learning system 130. The user interface 114 may be used to provide input, configuration data, and other display direction by the webpage of the data acquisition system 120 and/or the machine learning system 130. In another example embodiment, the user interface 114 may be managed by the data acquisition system 120, the machine learning system 130, or others. In another example embodiment, the user interface 114 may be managed by the user computing device 110 and be prepared and displayed to the user 101 based on the operations of the user computing device 110.

The user 101 can use the communication application 112 on the user computing device 110, which may be, for example, a web browser application or a stand-alone application, to view, download, upload, or otherwise access documents or web pages through the user interface 114 via the network 105. The user computing device 110 can interact with the web servers or other computing devices connected to the network, including the data acquisition server 125 of the data acquisition system 120 and the embedding server 135 of the machine learning system 130. In another example embodiment, the user computing device 110 communicates with devices in the data acquisition system 120 and/or the machine learning system 130 via any suitable technology, including the example computing system described below.

The user computing device 110 also includes a data storage unit 113 accessible by the user interface 114, the communication application 112, or other applications. The example data storage unit 113 can include one or more tangible computer-readable storage devices. The data storage unit 113 can be stored on the user computing device 110 or can be logically coupled to the user computing device 110. For example, the data storage unit 113 can include on-board flash memory and/or one or more removable memory accounts or removable flash memory. In another example embodiments, the data storage unit 113 may reside in a cloud-based computing system.

An example data acquisition system 120 comprises a data storage unit 123 and an acquisition server 125. The data storage unit 123 can include any local or remote data storage structure accessible to the data acquisition system 120 suitable for storing information. The data storage unit 123 can include one or more tangible computer-readable storage devices, or the data storage unit 123 may be a separate system, such as a different physical or virtual machine or a cloud-based storage service.

In one aspect, the data acquisition server 125 communicates with the user computing device 110 and/or the machine learning system 130 to transmit requested data. The data may include microscopy imaging data, omics data, or sequencing data.

An example machine learning system 130 comprises, comprises an embedding system 133, a machine learning server 135, and a data storage unit 137. The embedding server 135 communicates with the user computing device 110 and/or the data acquisition system 120 to request and receive data. The data may comprise the data types previously described in reference to the data acquisition server 125.

The embedding system 133 receives an input of data from the machine learning server 135. The embedding system 133 can comprise one or more functions to implement any of the previously mentioned training method to learn an omics profile of a cell. In a preferred embodiment, the machine learning program may comprise decision tree or random forest module. In one example embodiment, the program may comprise embedding. In another example embodiment, the decision tree or random forest program may comprise embedding. Any suitable architecture may be applied to learn an omics profile of a cell.

The data storage unit 137 can include any local or remote data storage structure accessible to the machine learning system 130 suitable for storing information. The data storage unit 137 can include one or more tangible computer-readable storage devices, or the data storage unit 137 may be a separate system, such as a different physical or virtual machine or a cloud-based storage service.

In an alternate embodiment, the functions of either or both of the data acquisition system 120 and the machine system 130 may be performed by the user computing device 110.

It will be appreciated that the network connections shown are examples, and other means of establishing a communications link between the computers and devices can be used. Moreover, those having ordinary skill in the art having the benefit of the present disclosure will appreciate that the user computing device 110, data acquisition system 120, and the machine learning system 130 illustrated in FIG. 1 can have any of several other suitable computer system configurations. For example, a user computing device 110 embodied as a mobile phone or handheld computer may not include all the components described above.

Figure 3:
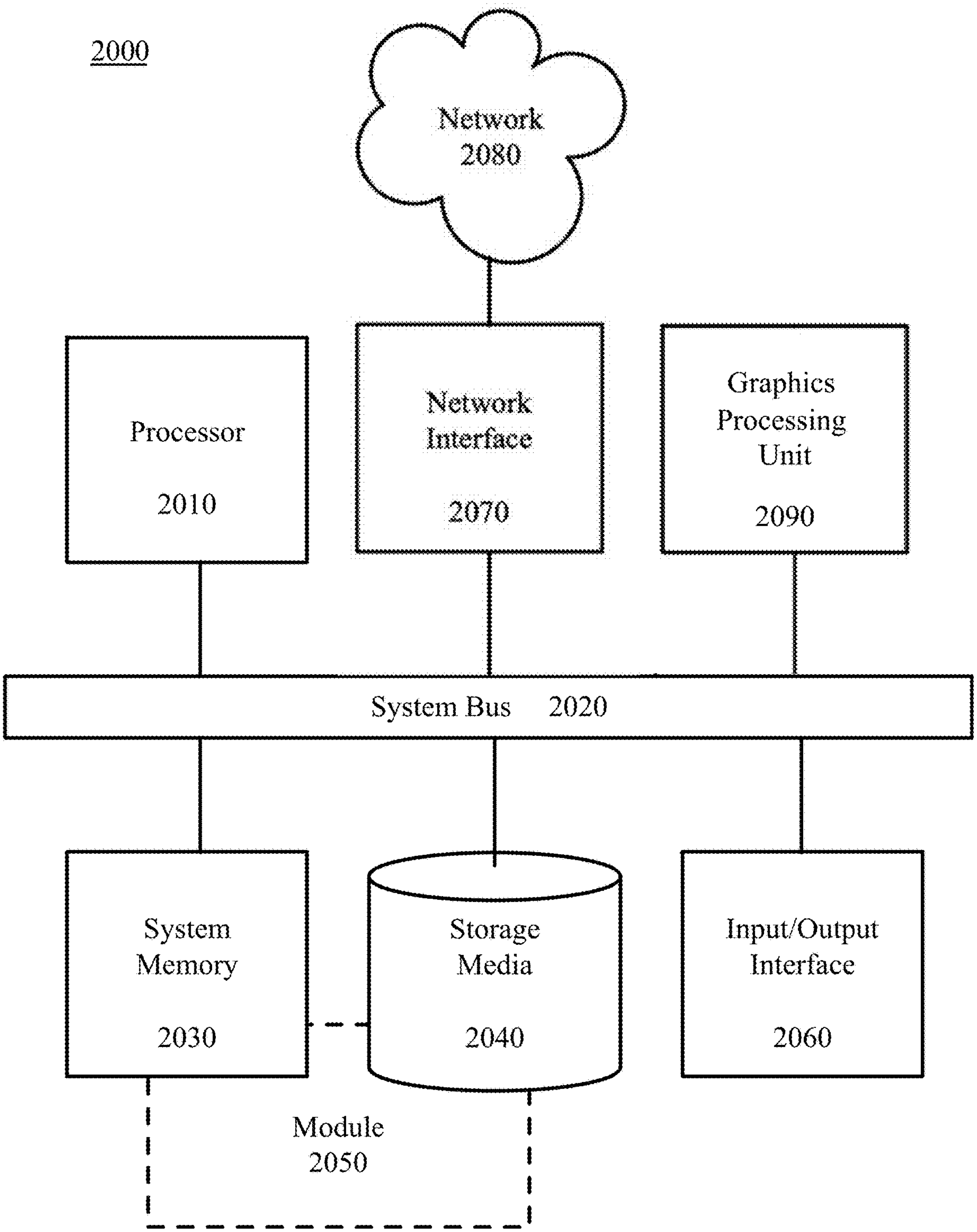
FIG. 3—A block diagram depicting a computing machine and modules, in accordance with certain examples of the technology disclosed herein.

In example embodiments, the network computing devices and any other computing machines associated with the technology presented herein may be any type of computing machine such as, but not limited to, those discussed in more detail with respect to FIG. 3. Furthermore, any modules associated with any of these computing machines, such as modules described herein or any other modules (scripts, web content, software, firmware, or hardware) associated with the technology presented herein may by any of the modules discussed in more detail with respect to FIG. 3. The computing machines discussed herein may communicate with one another as well as other computer machines or communication systems over one or more networks, such as network 105. The network 105 may include any type of data or communications network, including any of the network technology discussed with respect to FIG. 3.

Example Processes

Figure 2:
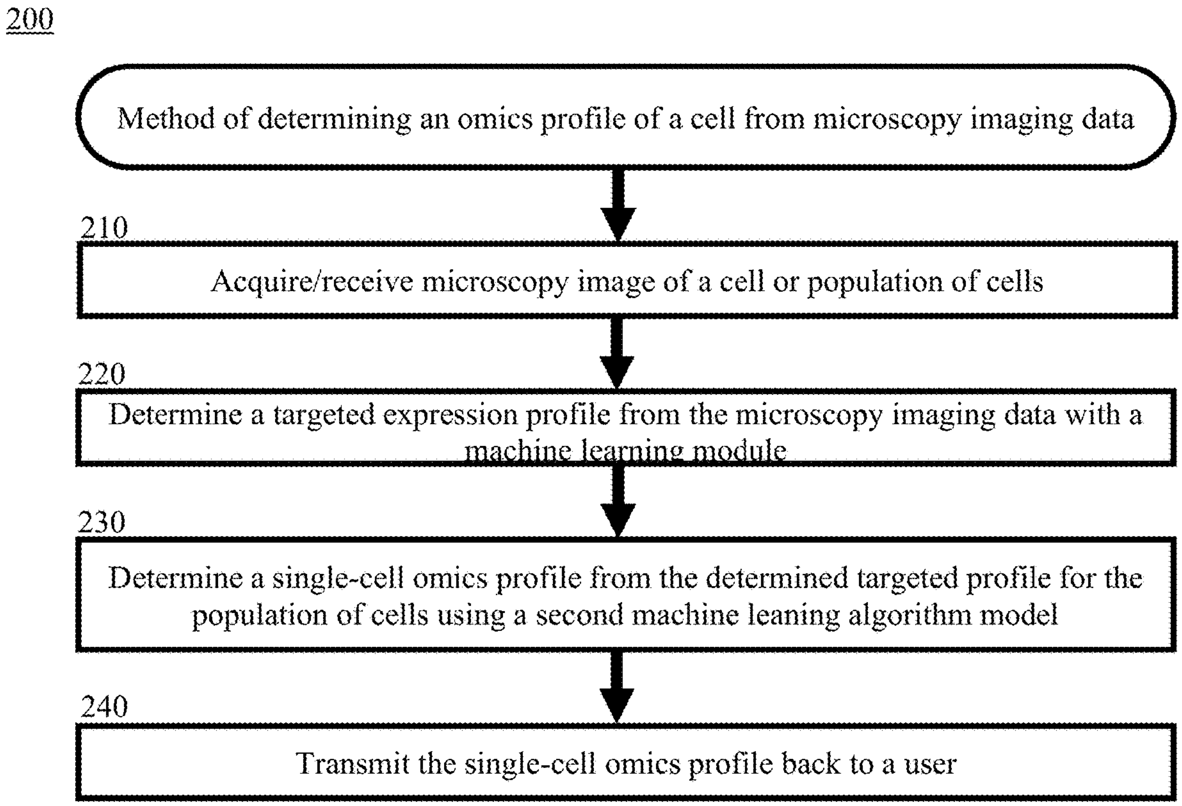
FIG. 2—A block flow diagram depicting methods to determining an omics profile of a cell from microscopy imaging data, in accordance with certain examples of the technology disclosed herein.

The example methods illustrated in FIG. 2 is described hereinafter with respect to the components of the example architecture 100. The example methods also can be performed with other systems and in other architectures including similar elements.

Referring to FIG. 2, and continuing to refer to FIG. 1 for context, a block flow diagram illustrates methods 200 to determine an omics profile of a cell from microscopy imaging data, in accordance with example examples of the technology disclosed herein.

In block 210, the machine learning system 130 receives an input of microscopy imaging data. The machine learning system 130 may receive the microscopy imaging data from the user computing device 110, the data acquisition system 120, or any other suitable source of imaging data via the network 105 to the machine learning system 130, discussed in more detail in other sections herein.

Raman Spectroscopy

In one aspect, the microscopy imaging data received in block 210 by the machine learning system 130 may comprise microscopy techniques that utilize vibrational modes offer a noninvasive method to observe a live cell. Raman spectroscopy applies a non-absorbable electromagnetic spectrum to a sample wherein the resting vibrational state of an object is exited to a higher energy state. The resulting inelastic scattering of photons characterizes the structure and composition of the sample. In example embodiments, Raman spectroscopy is implemented to capture microscopy image data of a cell.

Raman spectroscopy affords label-free imaging of a cell. In some cases of cellular imaging, labels are used to track cells or components of the cells. However, labels may cause photobleaching, blinking, and saturation thereby limiting the image quality. In addition, labels, such as dyes and fluorescent proteins, may interfere with cell function thereby compromising the results. Instead, a cell can be identified through its unique molecular fingerprint. The inelastic scattering from a cell provides a unique set of wavelengths or fingerprints, which are used to identify the composition of the cell. (See e.g. Kumamoto, Y.; et al. Label-Free Molecular Imaging and Analysis by Raman Spectroscopy. Acta Histochem. Cytochem 2018, 51 (3), 101-110) In example embodiments, label-free imaging is used.

In some instances, hyperspectral Raman spectroscopy may be implemented to observe structural and chemical information of a cell. Hyperspectral imaging is a method of collecting and processing information from a range of wavelengths within the electromagnetic spectrum. In Raman spectroscopy, hyperspectral imaging comprises measuring many (e.g. tens, hundreds, thousands, or more) vibrational spectra from multiple fields of view (i.e. creating a 3-dimensional representation). This method provides location and composition information of a cell in a sample such as distribution of cells in a population or the protein, nucleic acid, or fatty acid content of a cell. In example embodiments, hyperspectral Raman spectroscopy is implemented to capture microscopy image data of a cell.

Depending on the sensitivity, spatial resolution, or information required, different Raman methods may be preferred. Raman spectroscopy methods can be generalized into three groups: spontaneous (far-field) Raman spectroscopy, enhanced (near-field) Raman spectroscopy, or non-linear Raman spectroscopy. Spontaneous Raman spectroscopy measures the electromagnetic spectrum in a "far-field" wherein the radiation behaves normally. Raman techniques grouped under spontaneous Raman spectroscopy measure in the far-field but differ on, for example, excitation geometries, excitation wavelengths, optics, and/or combination with other techniques. Example spontaneous Raman spectroscopy techniques include: Resonance Raman, Angle-resolved Raman, Optical tweezer Raman, Spatially offset Raman, Transmission Raman, Micro-cavity Raman. Enhanced Raman spectroscopy measures the electromagnetic spectrum in a "near-field" wherein the radiation is interfered with.

Raman techniques grouped under enhanced Raman spectroscopy measure in the near-field, where radiation behaves atypical, but differ on, for example, the local electric-field effects. Example enhanced Raman spectroscopy techniques include: Surface-enhanced Raman, Surface-enhanced resonance Raman, Tip-enhanced Raman, Surface plasmon polariton enhanced Raman scattering. Non-linear Raman spectroscopy measures the electromagnetic spectrum through non-linear optical effects typically by mixing, spatially and/or temporally, two or more wavelengths. Raman techniques grouped under non-linear Raman spectroscopy typically differ in the mixing technique. Example non-linear Raman spectroscopy techniques include: Hyper Raman, Stimulated Raman, Inverse Raman, Coherent anti-stokes Raman. In example embodiments, spontaneous (far-field) Raman spectroscopy, enhanced (near-field) Raman spectroscopy, or non-linear Raman spectroscopy techniques are implemented to capture microscopy image data of a cell. In example embodiments, Resonance Raman, Angle-resolved Raman, Optical tweezer Raman, Spatially offset Raman, Transmission Raman, Micro-cavity Raman, Surface-enhanced Raman, Surface-enhanced resonance Raman, Tip-enhanced Raman, Surface plasmon polariton enhanced Raman scattering, Hyper Raman, Stimulated Raman, Inverse Raman, or Coherent anti-stokes Raman are implemented to capture microscopy image data of a cell.

In Vivo Imaging Techniques

In one aspect, the microscopy imaging data received in block 210 by the machine learning system 130 may comprise in vivo imaging techniques are used to obtain images of live cells or tissues. In vivo imaging techniques are non-invasive and can afford cellular information such as location, distribution, as well as activation and differentiation. There are many in vivo imaging modalities but differ on their capabilities. For example, and without limitation, Positron Emission Tomography (PET), Single Photon Emission Computed Tomography (SPECT), computed tomography (CT), bioluminescence imaging (BLI), fluorescent lifetime imaging (FLI), fluorescent reflectance imaging (FRI), fluorescence molecular tomography (FMT), optical coherence tomography (OCT), optical projection tomography (OPT), photoacoustic tomography (PAT), multispectral optoacoustic tomography (MSOT), raster-scan optoacoustic mesoscopy (RSOM), magnetic resonance imaging (MRI), ultrasound (US), photo-thermal microscopy, or a combination thereof. See e.g., Iafrate, M.; Fruhwirth, G. O. How Non-Invasive in Vivo Cell Tracking Supports the Development and Translation of Cancer Immunotherapies. Frontiers in Physiology, 2020, 11.

In one example embodiment, the in vivo imaging technique may use ionizing radiation, for example PET/SPECT or CT techniques (Y-ray and X-ray respectively). In an example embodiment, one or more PET or SPECT images of a cell or tissue are received by a machine learning model and result in single-cell omics profile of the cell. PET and SPECT techniques require trace amounts of contrast agents to obtain an image and are typically more sensitive than other in vivo imaging techniques. In an example embodiment, one or more CT images of a cell or tissue are received by a machine learning model and result in single-cell omics profile of the cell. CT uses X-rays to obtain stacks of two-dimensional radiographs. These stacks can be combined to form three-dimensional representations of a cell.

In one example embodiment, the in vivo imaging technique may use non-ionizing radiation, for example BLI, FLI, FRI, FMT, OCT, OPT, PAT, MSOT, RSOM, MRI, and US. In an example embodiment, one or more BLI images of a cell or tissue are received by a machine learning model and result in single-cell omics profile of the cell. BLI techniques require cells to express luciferase proteins and the resulting fluorescence is captured and cellular properties measured. In an example embodiment, one or more FLI or FRI images of a cell or tissue are received by a machine learning model and result in single-cell omics profile of the cell. FLI and FRI, similar to BLI, captures fluorescence to measure information about a cell. FLI measures the time and location of endogenous and/or exogenous fluorophores as a function of cellular features, see e.g. Fluorescence Lifetime Imaging Microscopy: Fundamentals and Advances in Instrumentation, Analysis, and Applications. Journal of Biomedical Optics, 2020, 25, 1. FRI techniques comprise exposing cells to external radiation wherein the resulting fluorescence is measured to obtain information about the cells, see e.g. Fantoni, F.; et al., Laser Line Scanning for Fluorescence Reflectance Imaging: A Phantom Study and In Vivo Validation of the Enhancement of Contrast and Resolution. Journal of Biomedical Optics, 2014, 19, 106003.

In an example embodiment, one or more FMT images of a cell or tissue are received by a machine learning model and result in single-cell omics profile of the cell. FMT uses photon tissue propagation theory with exogenous fluorophores to measure information about cells, see e.g. Li, M.; et al. In Vivo Diffuse Optical Tomography and Fluorescence Molecular Tomography. Journal of Healthcare Engineering, 2010, 1, 477-507. In an example embodiment, one or more OCT images of a cell or tissue are received by a machine learning model and result in single-cell omics profile of the cell. OCT techniques involve measuring the backscattering of near-infrared light from cells to capture cellular information, see e.g. Hariri, L. P.; et al. In Vivo Optical Coherence Tomography: The Role of the Pathologist. Archives of Pathology & Laboratory Medicine, 2012, 136, 1492-1501.

In an example embodiment, one or more OPT images of a cell or tissue are received by a machine learning model and result in single-cell omics profile of the cell. OPT, a non-ionizing equivalent of CT, measures absorption/scattering transmission or fluorescence emission from cells and reconstructs the image by transforming back-propagated photons, see e.g. Vallejo Ramirez, P. P.; et al. OptiJ: Open-Source Optical Projection Tomography of Large Organ Samples. Scientific Reports, 2019, 9. In an example embodiment, one or more PAT images of a cell or tissue are received by a machine learning model and result in single-cell omics profile of the cell. PAT techniques convert optical excitation to ultrasonic information by measuring pressure waves induced by irradiating cells thereby capturing cellular information, see e.g. Wang, L. V.; Hu, S. Photoacoustic Tomography: In Vivo Imaging from Organelles to Organs. Science, 2012, 335, 1458-1462.

In an example embodiment, one or more MSOT images of a cell or tissue are received by a machine learning model and result in single-cell omics profile of the cell. MSOT techniques, similar to PAT, use near-infrared radiation to generate broadband ultrasonic waves resulting in information of the cells, see e.g. Ai, X.; et al. Multispectral Optoacoustic Imaging of Dynamic Redox Correlation and Pathophysiological Progression Utilizing Upconversion Nanoprobes. Nature Communications, 2019, 10. In an example embodiment, one or more RSOM images of a cell or tissue are received by a machine learning model and result in single-cell omics profile of the cell. RSOM techniques comprise raster-scanning of a near-infrared radiation by an ultrasound detector to measure cellular information, see e.g. Schwarz, M.; et al. Motion Correction in Optoacoustic Mesoscopy. Scientific Reports, 2017, 7.

In an example embodiment, one or more MRI images of a cell or tissue are received by a machine learning model and result in single-cell omics profile of the cell. In an example embodiment, one or more US images of a cell or tissue are received by a machine learning model and result in single-cell omics profile of the cell.

In example embodiments, the microscopy method uses labels. In example embodiments, labeling techniques may comprise Cell Painting and Cell profiler (see e.g. Bray M A, Singh S, Han H, et al. Cell Painting, a high-content image-based assay for morphological profiling using multiplexed fluorescent dyes. *Nat Protoc.* 2016; 11(9):1757-1774. doi: 10.1038/nprot.2016.105 and Kamentsky L, Jones T R, Fraser A, et al. Improved structure, function and compatibility for CellProfiler: modular high-throughput image analysis software. *Bioinformatics.* 2011; 27(8):1179-1180. doi: 10.1093/bioinformatics/btr095).

In example embodiments, the microscopy method is photo-thermal microscopy. Photothermal detection generally operates by an object (e.g., a cell or component thereof) absorbing heat and then releasing the heat into the environment thereby producing a refractive index thermal gradient around the object. A probe beam produces an image as it is scattered by the thermal gradient. The photothermal image is the difference in probe intensity resulting from the absorption of the heat released by the object. See e.g., Adhikari, S.; et al. Photothermal Microscopy: Imaging the Optical Absorption of Single Nanoparticles and Single Molecules. ACS Nano, 2020, 14, 16414-16445.

Compressed Sensing

In example embodiments, the method further comprises compressed sensing. In instances when the imaging data is of low or insufficient quality as input for any of the machine learning methods described herein, then compresses sensing can be used to increase the quality of the image. See e.g., Brian Cleary, et al. bioRxiv 743039; doi.org/10.1101/

743039 and US Patent Publication No US20200152289 A1, both of which are incorporated herein by reference.

In block 220 of FIG. 2, the microscopy image data transferred over the network 150 from the user associated device 110 or the data acquisition system 120 is measured and transformed into spatial expression profile. In example embodiments, the microscopy data is first embedded. In example embodiments, a machine learning module is first developed to measure spatial expression profile from microscopy imaging data. In example embodiments, the machine learning module comprises a decision tree. In example embodiments, the machine learning module comprises random forest. In example embodiments, the machine learning module comprises a suitable machine learning module described herein.

Expression Profiles

In one aspect, the microscopy image data in FIG. 2, block 220 is transformed into an expression profile. The expression profile may comprise sequencing based omics data. The sequencing based omics data may comprise single-cell sequencing data. Single-cell sequencing techniques and methods are described further below.

In an example embodiment, the expression profile is a spatial expression profile. The resulting spatial expression profile resembles that of an actual spatial expression profile. Fluorescence labeling is a common technique to identify and measure biomolecules within a cell thereby creating a spatial expression profile. In general, a fluorescent label is bound to a biomolecule, such as a protein, peptide, antibody, or nucleic acid, and is excited with one- or two-photon fluorescence. In live-cell imaging, fluorescent measurements provide information regarding cell composition, growth, and transport mechanisms as well as the location and development of cellular components. In some situations, the composition of a cell is measured as a function of the genetics.

There are many well-known fluorescence labeling techniques known in the art and, for brevity, only a few will be mentioned herein. In example embodiments, the spatial expression profile results from Fluorescence microscopy techniques. Fluorescence microscopy uses broad spectrum sources and multiple fluorescent labels to determine cell physiology from identified cells and cellular components. Fluorescence microscopy further takes advantage of optical fibers to separate emitted light from excited light providing high specificity. (See e.g. Sanderson, M. J.; et al. Fluorescence Microscopy. Cold Spring Harbor Protocols 2014, 2014 (10), pdb.top071795-pdb.top071795) In example embodiments, the spatial expression profile results from flow cytometry. Flow cytometry measures a specific fluorescent marker that binds to the cell surface or inside the cell. Cells flow through a light beam detector and are identified, sorted, and quantified. (See e.g. Nolan, J. P.; Condello, D. Spectral Flow Cytometry. Current Protocols in Cytometry 2013, 63 (1). doi.org/10.1002/0471142956.cy0127s63.) In example embodiments, the spatial expression profile results from Fluorescence correlation spectroscopy (FCS). FCS measures the temporal changes in fluorescent intensity. The change in fluorescent intensity is achieved by fluorochromes due to the dependence of their fluorescence intensity on physical, chemical, or biological interactions. Therefore, the interaction between cells or molecules within cells can be measured. (See e.g. Tian, Y.; et al. Fluorescence Correlation Spectroscopy: A Review of Biochemical and Microfluidic Applications. Appl Spectrosc 2011, 65 (4), 115-124.)

FISH Methods

In one aspect, the spatial expression profile results from Fluorescence in situ hybridization (FISH) techniques to train a machine learning module and determine single-cell sequencing data. FISH is a macromolecule measurement technique wherein fluorophore-coupled nucleotides are used to probe complementary sequences in tissue and cells. FISH techniques measure the location and quantity of target sequences. In short, the common method to perform FISH comprises denaturing the sample and probe, annealing the sample and probe, measure the fluorescence of the resulting hybridization. The last step, however, is dependent on the probe type employed. In general, FISH comprises two labeling techniques: direct labeling or indirect labeling. Direct labeling comprises of a nucleotide probe containing a fluorophore wherein the fluorescence measurement is taken during and/or after hybridization. Indirect labeling comprises a modified nucleotide probe, which first hybridizes with a target sequence, then a fluorophore specific for the modified nucleotide probe is introduced, allowed to bind or bond, and finally the fluorescence is measured.

The general FISH method has branched into many techniques and is well known in the art, accordingly, each one will not be individually mentioned herein but is contemplated to function within an embodiment. (See e.g. Volpi, E. V.; Bridger, J. M. FISH Glossary: An Overview of the Fluorescence in Situ Hybridization Technique. BioTechniques 2008, 45 (4), 385-409.; Cui, C.; et al. Fluorescence In Situ Hybridization: Cell-Based Genetic Diagnostic and Research Applications. Front. Cell Dev. Biol. 2016, 4.—herein incorporated by reference).

smFISH

In one example embodiment, single molecule FISH is (smFISH) is used to produce spatial expression profile. smFISH is a variation of FISH to detect individual RNA molecules in single cells. In general, the technique uses many short fluorescent-conjugated DNA probes complementary to target RNA. The multiplicity creates an ensemble signal improving robustness and signal-to-noise ratio of the measurement. smFISH may produce spatial expression profile associated with gene expression such as transcription elongation, splicing, transcriptional bursting, intracellular allelic expression, and RNA localization. (See e.g. Chen, J.; et al. Single Molecule Fluorescence In Situ Hybridization (SmFISH) Analysis in Budding Yeast Vegetative Growth and Meiosis. JoVE 2018, No. 135.)

seq FISH

In one example embodiment, sequential FISH (seqFISH) is used to produce spatial expression profile. seqFISH is a variation of FISH wherein multiple transcripts in a single cell can be measured. In general, the technique requires an iterative cycle of hybridization, imaging, and denaturing. For each cycle a different fluorophore attached to unique nucleic acid is used and creates a color-coded sequential barcode of transcripts within a cell. seqFISH may produce a spatial expression profile associated with inter- and intracellular signaling and transcript location within one or more cells. (See e.g. Lubeck, E.; et al. Single-Cell in Situ RNA Profiling by Sequential Hybridization. Nat Methods 2014, 11 (4), 360-361.

merFISH

In one example embodiment, multiplexed error-robust FISH (merFISH) is used to produce spatial expression profile. merFISH is a variation of FISH wherein cellular RNAs are labelled with a set of encoding probes. The probes comprise of an RNA targeting sequence and two flanking readout sequences. The readout sequences are assigned to each RNA species based on a modified Hamming distance code word of the RNA. The readout sequences are then identified with complementary FISH probes (the readout probes) via multiple rounds of hybridization and imaging. Each round of hybridization and imagining uses a unique readout probe. (See e.g. Wang, X.; et al. Three-Dimensional Intact-Tissue Sequencing of Single-Cell Transcriptional States. Science 2018, 361 (6400), eaat5691)

Other Methods

In example embodiments, spatially-resolved transcript amplicon readout mapping (STARmap) is used to produce spatial expression profile. STARmap integrates in-situ DNA sequencing and hydrogel-tissue chemistry to achieve non-destructive, single-cell measurements of thousands of genes. Essentially, DNA probes hybridize with cellular RNA and then enzymatically amplified to produce an amplicon (i.e. a DNA nanoball). The amplicon is then anchored to a hydrogel and is decoded in multicolor fluorescence. STARmap may produce a spatial expression profile associated with the genetic expression. (See e.g. Wang, X.; et al. Three-Dimensional Intact-Tissue Sequencing of Single-Cell Transcriptional States. Science 2018, 361 (6400), eaat5691.

In example embodiments, expansion sequencing (ExSeq) is used to produce spatial expression profile. ExSEQ comprises the steps of (a) linking target nucleic acids present in the biological sample with a small molecule linker or a nucleic acid adaptor capable of linking to a target nucleic acid and to a swellable material; (b) embedding the biological sample comprising the target nucleic acids and attached small molecule linker or nucleic acid adaptor in a swellable material wherein the small molecule linker or the nucleic acid adaptor is linked to the target nucleic acids present in the sample and to the swellable material; (c) digesting proteins present in the biological sample; (d) swelling the swellable material to form a first enlarged biological sample that is enlarged as compared to the biological sample; (e) re-embedding the first enlarged sample in a non-swellable material; (f) modifying the target nucleic acids or the nucleic acid adaptor to form a nucleic acid adaptor useful for sequencing; and (g) sequencing the nucleic acids present in the first enlarged sample. (See e.g. U.S. Pat. No. 10,059,990; Chen F. et al. Science 347, 543-548 (2015); Lee J. H. et al. Science 343, 1360-1363 (2014))

In example embodiments, the imaging bases omics data comprise hematoxylin and eosin H&E stains. H&S stains are well known and one skilled in the art would readily be able to carry out H&E staining of a cell or population of cells to produce H&E staining images for methods and systems described herein, see e.g., Li, Y., et al. Hematoxylin and eosin staining of intact tissues via delipidation and ultrasound. Sci Rep 8, 12259 (2018).

In block 230, the same machine learning system 130 or a different machine learning system 130 receives input of the spatial expression profile from the first machine learning module 133 or over the network 150 from the user associated device 110 or the data acquisition system 120 and passes the spatial expression profile to the same machine learning server 133 or a different machine learning server 133. The same or different machine learning system 130 measures and transforms the spatial expression profile into a single-cell omics profile. In example embodiments, the second machine learning module comprises a neural network. In example embodiments, the second machine learning module comprises a deep learning neural network. The spatial expression profile may comprise any type described herein. In example embodiments, the spatial expression profile may comprise FISH image data. In example embodiments, the spatial expression profile may comprise smFISH, seqFISH, merFISH, STARmap, ExSeq, or a combination thereof.

Omics Profile

In an example embodiment, a second machine learning module is developed and employed in block 230 of FIG. 2. The second machine learning module predicts a single cell omics profile from a spatial expression profile of a cell. Omics is the measure and quantification of biological molecules in a tissue or cell such as proteins, RNA, gene expression, chromatin accessibility, chromatin structures and modifications (e.g. loop formations, epigenetic modifications such as DNA methylation, and histone protein modifications) metabolites, lipids, carbohydrates, or combinations thereof. (See e.g. Micheel C M, et al. editors. Evolution of Translational Omics: Lessons Learned and the Path Forward. Washington (DC): National Academies Press (US); 2012 Mar. 23. 2, Omics-Based Clinical Discovery: Science, Technology, and Applications.) In one example embodiment, single-cell proteomics measurements may be determined by mass spectrometry, mass cytometry, micro-engraving, single-cell western blotting, droplet-based microfluidic approaches for single-cell analysis, single cell barcode chip (SCBC), microbeads-based techniques, DNA barcoding methods (e.g., antibodies tagged with a DNA barcode), and cyclic immunofluorescence (see, e.g., Yang L, George J, Wang J. Deep Profiling of Cellular Heterogeneity by Emerging Single-Cell Proteomic Technologies. Proteomics. 2020; 20(13):e1900226. doi:10.1002/pmic.201900226; and Kelly R T. Single-cell Proteomics: Progress and Prospects. Mol Cell Proteomics. 2020; 19(11): 1739-1748. doi: 10.1074/mcp.R120.002234) and provided as inputs to the second machine learning module In one example embodiment, chromatin accessibility may be analyzed using single-cell ATAC-seq (Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4; Buenrostro J D, Corces M R, Lareau C A, et al. Integrated Single-Cell Analysis Maps the Continuous Regulatory Landscape of Human Hematopoietic Differentiation. Cell. 2018; 173(6):1535-1548.e16. doi: 10.1016/j.cell.2018.03.074; and Lal A, Chiang Z D, Yakovenko N, Duarte F M, Israeli J, Buenrostro J D. Deep learning-based enhancement of epigenomics data with AtacWorks. Nat Commun. 2021; 12(1):1507. Published 2021 Mar. 8. doi: 10.1038/s41467-021-21765-5) and provided as inputs. In one example embodiment, chromatin structure measurements may be detected using Hi-C(See e.g., U.S. Pat. No. 9,708,648, and U.S. Patent App. Pub. No. 2017/0362649) and provided as inputs to the second machine learning module. In one example embodiment, DNA methylation status may be determined, such as, by using bi-sulfite sequencing or any other methylation detection method (see, e.g., Farlik M, Sheffield N C, Nuzzo A, et al. Single-cell DNA methylome sequencing and bioinformatic inference of epigenomic cell-state dynamics. Cell Rep. 2015; 10(8): 1386-1397. doi: 10.1016/j.celrep.2015.02.001; Ahn J, Heo S, Lee J, Bang D. Introduction to Single-Cell DNA Methylation Profiling Methods. Biomolecules. 2021; 11(7):1013. Published 2021 Jul. 10. doi: 10.3390/biom11071013; Mulqueen R M, Pokholok D, Norberg S J, et al. Highly scalable generation of DNA methylation profiles in single cells. Nat Biotechnol. 2018; 36(5):428-431. doi: 10.1038/nbt.4112; Karemaker I D, Vermeulen M. Single-Cell DNA Methylation Profiling: Technologies and Biological Applications. Trends Biotechnol. 2018; 36(9):952-965. doi: 10.1016/ j.tibtech.2018.04.002; and Clark S J, Smallwood S A, Lee H J, Krueger F, Reik W, Kelsey G. Genome-wide base-resolution mapping of DNA methylation in single cells using single-cell bisulfite sequencing (scBS-seq). Nat Protoc. 2017; 12(3):534-547) and used as inputs to the second machine learning module. Multiple such measurements may be made to obtain multi-omic measurements (see, e.g., Lee J, Hyeon D Y, Hwang D. Single-cell multiomics: technologies and data analysis methods. Exp Mol Med. 2020; 52(9):1428-1442. doi: 10.1038/s12276-020-0420-2). Other example multi-omic approaches include SHARE-seq for measuring chromatin accessibility and gene expression (See, Ma et al. *Chromatin Potential Identified by Shared Single-Cell Profiling of RNA and Chromatin* 183 Cell, 1103-1116 (2020) and U.S. Patent App. Pub. No. 2020/0248255). In certain example embodiments, spatial transcriptomic and/or combined transcriptomic and proteomic methods may be used to provide spatial expression inputs to the second learning module. (See e.g, WO 2020/160044, Vickovic et al. *SM-Omics: An automated platform for high-throughput spatial multi-omics*. bioRxiv (Oct. 15, 2020) https://doi.org/10.1101/2020.10.14338418).

A machine learning module may be trained to determine single cell sequencing data from spatial expression profile. In example embodiments, transcriptomic data of RNA transcripts is used to train a machine learning module and to determine single cell sequencing. Transcription RNA may comprise information regarding the quantity, structure, composition, and/or location of ribosomal RNA (rRNA), messenger RNA (mRNA), transfer RNA (tRNA), micro RNA (miRNA), and other non-coding RNA (ncRNA).

In example embodiments, proteomic data of protein expression is used to train a machine learning module and to determine single cell sequencing. Proteomic data may comprise posttranslational modifications, spatial configurations, intracellular localizations, interactions between proteins, and interactions between proteins and other molecules. In example embodiments, epigenomic data of chemically modified DNA or histones that bind DNA is used to train a machine learning module and to determine single cell sequencing. Epigenomic data may comprise methylation of DNA cytosine residues and/or modifications of histone proteins.

In example embodiments, metabolomic data of metabolites is used to train a machine learning module and to determine single cell sequencing. Metabolomic data may comprise information regarding the quantity, structure, composition, and/or location of carbohydrates, lipids, amino acids, nucleic acids, hormones, signaling molecules, as well as drugs and their metabolites. In example embodiments, lipidomic data of cellular lipids is used to train a machine learning module and to determine single cell sequencing. Lipidomic data may comprise information regarding the quantity, structure, composition, and/or location of fatty acids, glycerolipids, glycerophospholipids, sphingolipids, sterols, prenols, saccharolipids, and polyketides.

In example embodiments, genomic data is used to train a machine learning module and to determine single cell sequencing. Genomic data may comprise information regarding the expression, quantity, structure, composition, and/or location of genetic material within the cellular nucleus or other organelles such as the mitochondria.

In block 240, the single cell-omics profile is transferred to a user via the network 105. In example embodiments, the single cell-omics profile may be permanently or temporarily stored on the data storage 137 or on the data storage unit 123. The single-omics profile may be subsequently accessed by the user associated device 100 or machine learning system 130. The single cell-omics profile may be immediately or subsequently transferred to a user.

Single Cell Sequencing

In example embodiments, the machine learning module is trained with and determines single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In example embodiments, the machine learning module is trained with and determines plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In example embodiments, the machine learning module is trained with and determines high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12 (1): 44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14 (3): 302-308, 2017; Cao, et al., Comprehensive single-cell transcriptional profiling of a multicellular organism. Science, 357 (6352): 661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi:

doi.org/10.1101/689273, all the contents and disclosure of each of which are herein incorporated by reference in their entirety.

In example embodiments, the machine learning module is trained with and determines single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14 (10): 955-958; International Patent Application No. PCT/US2016/059239, published as WO2017164936 on Sep. 28, 2017; International Patent Application No. PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In example embodiments, the machine learning module is trained with and determines Assay for Transposase Accessible Chromatin using sequencing (ATAC-seq). (see, e.g., Buenrostro, et al., Transposition of native chromatin for fast and sensitive epigenomic profiling of open chromatin, DNA-binding proteins and nucleosome position. Nature methods 2013; 10(12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1). In example embodiments, the machine learning module is trained with dual RNA+ATAC-seq. (see e.g. Li, R.; et al. Simple and Robust Method for Simultaneous Dual-Omics Profiling with Limited Numbers of Cells. Cell Reports Methods, 2021, 1, 100041; Hendrickson, D. G.; et al. Simultaneous Profiling of DNA Accessibility and Gene Expression Dynamics with ATAC-Seq and RNA-Seq. Methods in Molecular Biology, 2018, 317-333.; Reyes, M.; et al. Simultaneous Profiling of Gene Expression and Chromatin Accessibility in Single Cells. Advanced Biosystems, 2019, 3, 1900065.)

In example embodiments, the machine learning module is trained with and determines single cell epigenetic data which may comprise epigenetic marks on chromatin in single cells. The epigenetic marks can indicate genomic loci that are in active or silent chromatin states (see, e.g., Epigenetics, Second Edition, 2015, Edited by C. David Allis; Marie-Laure Caparros; Thomas Jenuwein; Danny Reinberg; Associate Editor Monika Lachlan). In example embodiments, the machine learning module is trained with and determines single cell ChIP-seq, which can be used to determine chromatin states in single cells (see, e.g., Rotem, et al., Single-cell ChIP-seq reveals cell subpopulations defined by chromatin state. Nat Biotechnol. 2015 November; 33 (11): 1165-1172). In example embodiments, epigenetic features can be chromatin contact domains, chromatin loops, superloops, or chromatin architecture data, such as obtained by single cell HiC (see, e.g., Rao et al., Cell. 2014 Dec. 18; 159(7):1665-80; and Ramani, et al., Sci-Hi-C: A single-cell Hi-C method for mapping 3D genome organization in large number of single cells Methods. 2020 Jan. 1; 170:61-68).

In example embodiments, the machine learning module is trained with and determines spatially resolved single cell data. The spatial data used in the present invention can be any spatial data. Methods of generating spatial data of varying resolution are known in the art, for example, ISS (Ke, R. et al. In situ sequencing for RNA analysis in preserved tissue and cells. *Nat. Methods* 10, 857-860 (2013)), MERFISH (Chen, K. H., Boettiger, A. N., Moffitt, J. R., Wang, S. & Zhuang, X. Spatially resolved, highly multiplexed RNA profiling in single cells. Science 348, (2015)), smFISH (Codeluppi, S. et al. *Spatial organization of the somatosensory cortex revealed by cyclic smFISH.* biorxiv.org/lookup/doi/10.1101/276097 (2018) doi: 10.1101/276097), osmFISH (Codeluppi, S. et al. Spatial organization of the somatosensory cortex revealed by osmFISH. *Nat. Methods* 15, 932-935 (2018)), STARMap (Wang, X. et al. Three-dimensional intact-tissue sequencing of single-cell transcriptional states. *Science* 361, eaat5691 (2018)), Targeted ExSeq (Alon, S. et al. *Expansion Sequencing: Spatially Precise* In Situ *Transcriptomics in Intact Biological Systems.* biorxiv.org/lookup/doi/10.1101/2020.05.13.094268 (2020) doi: 10.1101/2020.05.13.094268), seqFISH+ (Eng, C.-H. L. et al. Transcriptome-scale super-resolved imaging in tissues by RNA seqFISH+. *Nature* (2019) doi: 10.1038/s41586-019-1049-y.), Spatial Transcriptomics methods (e.g., Spatial Transcriptomics (ST)) (see, e.g., Ståhl, P. L. et al. Visualization and analysis of gene expression in tissue sections by spatial transcriptomics. *Science* 353, 78-82 (2016)) (now available commercially as Visium); Visium Spatial Capture Technology, 10× Genomics, Pleasanton, CA; WO2020047007A2; WO2020123317A2; WO2020047005A1; WO2020176788A1; and WO2020190509A9), Slide-seq (Rodriques, S. G. et al. Slide-seq: A scalable technology for measuring genome-wide expression at high spatial resolution. *Science* 363, 1463-1467 (2019)), or High Definition Spatial Transcriptomics (Vickovic, S. et al. High-definition spatial transcriptomics for in situ tissue profiling. *Nat. Methods* 16, 987-990 (2019)). In example embodiments, proteomics and spatial patterning using antenna networks is used to spatially map a tissue specimen and this data can be further used to align single cell data to a larger tissue specimen (see, e.g., US20190285644A1). In example embodiments, the spatial data can be immunohistochemistry data or immunofluorescence data.

In example embodiments, the machine learning module is trained with and determines single cell proteomics data. In example embodiments, single cell proteomics can be used to generate the single cell data. In example embodiments, the single cell proteomics data is combined with single cell transcriptome data. Non-limiting examples include multiplex analysis of single cell constituents (US20180340939A), single-cell proteomic assay using aptamers (US20180320224A1), and methods of identifying multiple epitopes in cells (US20170321251A1). In example embodiments, the machine learning module is trained with and determines single cell multimodal data. In example embodiments, SHARE-Seq (Ma, S. et al. Chromatin potential identified by shared single cell profiling of RNA and chromatin. *bioRxiv* 2020.06.17.156943 (2020) doi: 10.1101/2020.06.17.156943) is used to generate single cell RNA-seq and chromatin accessibility data. In example embodiments, CITE-seq (Stoeckius, M. et al. Simultaneous epitope and transcriptome measurement in single cells. *Nat. Methods* 14, 865-868 (2017)) (cellular proteins) is used to generate single cell RNA-seq and proteomics data. In example embodiments, Patch-seq (Cadwell, C. R. et al. Electrophysiological, transcriptomic and morphologic profiling of single neurons using Patch-seq. Nat. Biotechnol. 34, 199-203 (2016)) is used to generate single cell RNA-seq and patch-clamping electrophysiological recording and morphological analysis of single neurons data (e.g., for the brain or enteric nervous system (ENS)) (see, e.g., van den Hurk, et al., Patch-Seq Protocol to Analyze the Electrophysiology, Morphology and Transcriptome of Whole Single Neurons Derived From Human Pluripotent Stem Cells, Front Mol Neurosci. 2018; 11:261).

The ladder diagrams, scenarios, flowcharts and block diagrams in the figures and discussed herein illustrate architecture, functionality, and operation of example embodiments and various aspects of systems, methods, and computer program products of the present invention. Each block in the flowchart or block diagrams can represent the processing of information and/or transmission of information corresponding to circuitry that can be configured to execute the logical functions of the present techniques. Each block in the flowchart or block diagrams can represent a module, segment, or portion of one or more computer executable instructions for implementing the specified operation or step. In example embodiments, the functions/acts in a block can occur out of the order shown in the figures and nothing requires that the operations be performed in the order illustrated. For example, two blocks shown in succession can executed concurrently or essentially concurrently. In another example, blocks can be executed in the reverse order. Furthermore, variations, modifications, substitutions, additions, or reduction in blocks and/or functions may be used with any of the ladder diagrams, scenarios, flow charts and block diagrams discussed herein, all of which are explicitly contemplated herein.

The ladder diagrams, scenarios, flow charts and block diagrams may be combined with one another, in part or in whole. Coordination will depend upon the required functionality. Each block of the block diagrams and/or flowchart illustration as well as combinations of blocks in the block diagrams and/or flowchart illustrations can be implemented by special purpose hardware-based systems that perform the aforementioned functions/acts or carry out combinations of special purpose hardware and computer instructions. Moreover, a block may represent one or more information transmissions and may correspond to information transmissions among software and/or hardware modules in the same physical device and/or hardware modules in different physical devices.

The present techniques can be implemented as a system, a method, a computer program product, digital electronic circuitry, and/or in computer hardware, firmware, software, or in combinations of them. The computer program product can include a program tangibly embodied in an information carrier (e.g., computer readable storage medium or media) having computer readable program instructions thereon for execution by, or to control the operation of, data processing apparatus (e.g., a processor) to carry out aspects of one or more embodiments of the present invention. It will be understood that each block of the flowchart illustrations and/or block diagrams, and combinations of blocks in the flowchart illustrations and/or block diagrams, can be implemented by computer readable program instructions.

The computer readable program instructions can be performed on general purpose computing device, special purpose computing device, or other programmable data processing apparatus to produce a machine, such that the instructions, which execute via, at least partially, by one or more processors that are temporarily configured (e.g., by software) or permanently configured to perform the functions/acts specified in the flowchart and/or block diagram block or blocks. The processors, either: temporarily or permanently; or partially configured, may comprise processor-implemented modules. The present techniques referred to herein may, in example embodiments, comprise processor-implemented modules. Functions/acts of the processor-implemented modules may be distributed among the one or more processors. Moreover, the functions/acts of the processor-implements modules may be deployed across a number of machines, where the machines may be located in a single geographical location or distributed across a number of geographical locations.

The computer readable program instructions can also be stored in a computer readable storage medium that can direct one or more computer devices, programmable data processing apparatuses, and/or other devices to carry out the function/acts of the processor-implemented modules. The computer readable storage medium containing all or partial processor-implemented modules stored therein, comprises an article of manufacture including instructions which implement aspects, operations, or steps to be performed of the function/act specified in the flowchart and/or block diagram block or blocks.

Computer readable program instructions described herein can be downloaded to a computer readable storage medium within a respective computing/processing devices from a computer readable storage medium. Optionally, the computer readable program instructions can be downloaded to an external computer device or external storage device via a network. A network adapter card or network interface in each computing/processing device can receive computer readable program instructions from the network and forward the computer readable program instructions for permanent or temporary storage in a computer readable storage medium within the respective computing/processing device.

Computer readable program instructions described herein can be assembler instructions, instruction-set-architecture (ISA) instructions, machine instructions, machine dependent instructions, microcode, firmware instructions, state-setting data, or either source code or object code. The computer readable program instructions can be written in any programming language such as compiled or interpreted languages. In addition, the programming language can be object-oriented programming language (e.g. "C++") or conventional procedural programming languages (e.g. "C") or any combination thereof may be used to as computer readable program instructions. The computer readable program instructions can be distributed in any form, for example as a stand-alone program, module, subroutine, or other unit suitable for use in a computing environment. The computer readable program instructions can execute entirely on one computer or on multiple computers at one site or across multiple sites connected by a communication network, for example on user's computer, partly on the user's computer, as a stand-alone software package, partly on the user's computer and partly on a remote computer or entirely on a remote computer or server. If the computer readable program instructions are executed entirely remote, then the remote computer can be connected to the user's computer through any type of network or the connection can be made to an external computer. In examples embodiments, electronic circuitry including, but not limited to, programmable logic circuitry, field-programmable gate arrays (FPGA), or programmable logic arrays (PLA) can execute the computer readable program instructions. Electronic circuitry can utilize state information of the computer readable program instructions to personalize the electronic circuitry, to execute functions/acts of one or more embodiments of the present invention.

Example embodiments described herein include logic or a number of components, modules, or mechanisms. Modules may comprise either software modules or hardware-implemented modules. A software module may be code embodied on a non-transitory machine-readable medium or in a transmission signal. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In example embodiments, a hardware-implemented module may be implemented mechanically or electronically. In example embodiments, hardware-implemented modules may comprise permanently configured dedicated circuitry or logic to execute certain functions/acts such as a special-purpose processor or logic circuitry (e.g., a field programmable gate array (FPGA) or an application-specific integrated circuit (ASIC)). In example embodiments, hardware-implemented modules may comprise temporary programmable logic or circuitry to perform certain functions/acts. For example, a general-purpose processor or other programmable processor.

The term "hardware-implemented module" encompasses a tangible entity. A tangible entity may be physically constructed, permanently configured, or temporarily or transitorily configured to operate in a certain manner and/or to perform certain functions/acts described herein. Hardware-implemented modules that are temporarily configured need not be configured or instantiated at any one time. For example, if the hardware-implemented modules comprise a general-purpose processor configured using software, then the general-purpose processor may be configured as different hardware-implemented modules at different times.

Hardware-implemented modules can provide, receive, and/or exchange information from/with other hardware-implemented modules. The hardware-implemented modules herein may be communicatively coupled. Multiple hardware-implemented modules operating concurrently, may communicate through signal transmission, for instance appropriate circuits and buses that connect the hardware-implemented modules. Multiple hardware-implemented modules configured or instantiated at different times may communicate through temporarily or permanently archived information, for instance the storage and retrieval of information in memory structures to which the multiple hardware-implemented modules have access. For example, one hardware-implemented module may perform an operation, and store the output of that operation in a memory device to which it is communicatively coupled. Consequently, another hardware-implemented module may, at some time later, access the memory device to retrieve and process the stored information. Hardware-implemented modules may also initiate communications with input or output devices, and can operate on information from the input or output devices.

In example embodiments, the present techniques can be at least partially implemented in a cloud or virtual machine environment.

Machine Learning

In one aspect, microscopy imaging data or expression profile data of a cell from any of the techniques described herein are used as input data to train a machine learning module and determine omics profile of a cell with the trained machine learning module. Machine learning is a field of study within artificial intelligence that allows computers to learn functional relationships between inputs and outputs without being explicitly programmed. Machine learning involves a module comprising algorithms that may learn from existing data by analyzing, categorizing, or identifying the data. Such machine-learning algorithms operate by first constructing a model from training data to make predictions or decisions expressed as outputs. In example embodiments, the training data includes data for one or more identified features and one or more outcomes, for example microscopy imaging data or expression profile data of a cell and its corresponding omics profile. Although example embodiments are presented with respect to a few machine-learning algorithms, the principles presented herein may be applied to other machine-learning algorithms.

Data supplied to a machine learning algorithm can be considered a feature, which can be described as an individual measurable property of a phenomenon being observed. The concept of feature is related to that of an independent variable used in statistical techniques such as those used in linear regression. The performance of a machine learning algorithm in pattern recognition, classification and regression is highly dependent on choosing informative, discriminating, and independent features. Features may comprise numerical data, categorical data, time-series data, strings, graphs, or images. Features of the invention may further comprise microscopy imaging data or expression profile data of a cell. The microscopy imaging data or expression profile data of a cell may include Raman microscopy imaging data or H&E staining of a cell, respectively. In an example embodiment, the microscopy imaging data or expression profile data of a cell comprise the features supplied to a machine learning algorithm.

In general, there are two categories of machine learning problems: classification problems and regression problems. Classification problems, also referred to as categorization problems, aim at classifying items into discrete category values. Training data teaches the classifying algorithm how to classify. In example embodiments, features to be categorized may include microscopy imaging data or expression profile data of a cell, which can be provided to the classifying machine learning algorithm and then placed into categories of, for example, omics profiles. Regression algorithms aim at quantifying and correlating one or more features. Training data teaches the regression algorithm how to correlate the one or more features into a quantifiable value. In example embodiments, features such as microscopy imaging data or expression profile data of a cell can be provided to the regression machine learning algorithm resulting in one or more continuous values, for example characteristics of omics profiles.

Multimodal Translation

In an example embodiment, the machine learning module comprises multimodal translation (MT), also known as multimodal machine translation or multimodal neural machine translation. MT comprises of a machine learning module capable of receiving multiple (e.g. two or more) modalities. Typically, the multiple modalities comprise of information connected to each other. In example embodiments, the machine learning module receives one or more microscopy imaging data or expression profile data comprising information on one or more biological materials (e.g. proteins, peptides, carbohydrates, lipids, vesicles, RNAs, DNAs, and/or variations/modifications thereof). The machine learning module then determines one or more omics profiles (or one or more biomarkers) corresponding to the microscopy imaging data or expression profile data of the biological material.

In example embodiments, the MT may comprise of a machine learning method further described herein. In an example embodiment, the MT comprises a neural network, deep neural network, convolutional neural network, convolutional autoencoder, recurrent neural network, or an LSTM. For example, one or more microscopy imaging data or expression profile data comprising multiple modalities from a subject is embedded as further described herein. The embedded data is then received by the machine learning module. The machine learning module processes the embedded data (e.g. encoding and decoding) through the multiple layers of architecture then determines the omics profile or biomarkers corresponding the modalities comprising the input. The machine learning methods further described herein may be engineered for MT wherein the inputs described herein comprise of multiple modalities of biological material. See e.g. Sulubacak, U., Caglayan, O., Grönroos, S A. et al. Multimodal machine translation through visuals and speech. Machine Translation 34, 97-147 (2020) and Huang, Xun, et al. "Multimodal unsupervised image-to-image translation." Proceedings of the European conference on computer vision (ECCV). 2018.

Embedding

A machine learning module may use embedding to provide a lower dimensional representation, such as a vector, of features to organize them based off respective similarities. In some situations, these vectors can become massive. In the case of massive vectors, particular values may become very sparse among a large number of values (e.g., a single instance of a value among 50,000 values). Because such vectors are difficult to work with, reducing the size of the vectors, in some instances, is necessary. A machine learning module can learn the embeddings along with the model parameters. In example embodiments, features such as microscopy imaging data or expression profile data can be mapped to vectors implemented in embedding methods. In example embodiments, embedded semantic meanings are utilized. Embedded semantic meanings are values of respective similarity. For example, the distance between two vectors, in vector space, may imply two values located elsewhere with the same distance are categorically similar. Embedded semantic meanings can be used with similarity analysis to rapidly return similar values. In example embodiments, microscopy imaging data or expression profile data of a cell is embedded. The microscopy imaging data or expression profile data, for example, may comprise Raman imaging data of a cell. The Raman imaging data be processed into, for example, vector space organized by intensity at a particular frequency and/or fingerprint region. The Raman imaging data may also be embedded into vector space organized by frequency and gene expression. In example embodiments, the methods herein are developed to identify meaningful portions of the vector and extract semantic meanings between that space.

Training Methods

In example embodiments, the machine learning module can be trained using techniques such as unsupervised, supervised, semi-supervised, reinforcement learning, transfer learning, incremental learning, curriculum learning techniques, and/or learning to learn. Training typically occurs after selection and development of a machine learning module and before the machine learning module is operably in use. In one aspect, the training data used to teach the machine learning module can comprise input data such as microscopy imaging data or expression profile data of a cell and the respective target output data such as an omics profile. In an example embodiment, a first machine learning module is trained with a first training data set comprising input data such microscopy imaging data or expression profile data of a cell to estimate spatial omics. Next, a second machine learning module is trained with a second training data set comprising spatial omics to estimate omics profiles. The first and second machine learning module can be used together as one machine learning module to estimate omics profiles from microscopy imaging data or expression profile data. The first and second may be the same type of machine learning algorithm or may be different types of machine learning algorithms.

In an example embodiment, unsupervised learning is implemented. Unsupervised learning can involve providing all or a portion of unlabeled training data to a machine learning module. The machine learning module can then determine one or more outputs implicitly based on the provided unlabeled training data. In an example embodiment, supervised learning is implemented. Supervised learning can involve providing all or a portion of labeled training data to a machine learning module, with the machine learning module determining one or more outputs based on the provided labeled training data, and the outputs are either accepted or corrected depending on the agreement to the actual outcome of the training data. In some examples, supervised learning of machine learning system(s) can be governed by a set of rules and/or a set of labels for the training input, and the set of rules and/or set of labels may be used to correct inferences of a machine learning module.

In one example embodiment, semi-supervised learning is implemented. Semi-supervised learning can involve providing all or a portion of training data that is partially labeled to a machine learning module. During semi-supervised learning, supervised learning is used for a portion of labeled training data, and unsupervised learning is used for a portion of unlabeled training data. In one example embodiment, reinforcement learning is implemented. Reinforcement learning can involve first providing all or a portion of the training data to a machine learning module and as the machine learning module produces an output, the machine learning module receives a "reward" signal in response to a correct output. Typically, the reward signal is a numerical value and the machine learning module is developed to maximize the numerical value of the reward signal. In addition, reinforcement learning can adopt a value function that provides a numerical value representing an expected total of the numerical values provided by the reward signal over time.

In one example embodiment, transfer learning is implemented. Transfer learning techniques can involve providing all or a portion of a first training data to a machine learning module, then, after training on the first training data, providing all or a portion of a second training data. In example embodiments, a first machine learning module can be pre-trained on data from one or more computing devices. The first trained machine learning module is then provided to a computing device, where the computing device is intended to execute the first trained machine learning model to produce an output. Then, during the second training phase, the first trained machine learning model can be additionally trained using additional training data, where the training data can be derived from kernel and non-kernel data of one or more computing devices. This second training of the machine learning module and/or the first trained machine learning model using the training data can be performed using either supervised, unsupervised, or semi-supervised learning. In addition, it is understood transfer learning techniques can involve one, two, three, or more training attempts. Once the machine learning module has been trained on at least the training data, the training phase can be completed. The resulting trained machine learning model can be utilized as at least one of trained machine learning module.

In one example embodiment, incremental learning is implemented. Incremental learning techniques can involve providing a trained machine learning module with input data that is used to continuously extend the knowledge of the trained machine learning module. Another machine learning training technique is curriculum learning, which can involve training the machine learning module with training data arranged in a particular order, such as providing relatively easy training examples first, then proceeding with progressively more difficult training examples. As the name suggests, difficulty of training data is analogous to a curriculum or course of study at a school.

In one example embodiment, learning to learn is implemented. Learning to learn, or meta-learning, comprises, in general, two levels of learning: quick learning of a single task and slower learning across many tasks. For example, a machine learning module is first trained and comprises of a first set of parameters or weights. During or after operation of the first trained machine learning module, the parameters or weights are adjusted by the machine learning module. This process occurs iteratively on the success of the machine learning module. In another example, an optimizer, or another machine learning module, is used wherein the output of a first trained machine learning module is fed to an optimizer that constantly learns and returns the final results. Other techniques for training the machine learning module and/or trained machine learning module are possible as well.

In example embodiment, contrastive learning is implemented. Contrastive learning is a self-supervised model of learning in which training data is unlabeled is considered as a form of learning in-between supervised and unsupervised learning. This method learns by contrastive loss, which separates unrelated (i.e., negative) data pairs and connects related (i.e., positive) data pairs. For example, to create positive and negative data pairs, more than one view of a datapoint, such as rotating an image or using a different time-point of a video, is used as input. Positive and negative pairs are learned by solving dictionary look-up problem. The two views are separated into query and key of a dictionary. A query has a positive match to a key and negative match to all other keys. The machine learning module then learns by connecting queries to their keys and separating queries from their non-keys. A loss function, such as those described herein, is used to minimize the distance between positive data pairs (e.g., a query to its key) while maximizing the distance between negative data points. See e.g., Tian, Yonglong, et al. "What makes for good views for contrastive learning?." Advances in Neural Information Processing Systems 33 (2020): 6827-6839.

In example embodiments, the machine learning module is pre-trained. A pre-trained machine learning model is a model that has been previously trained to solve a similar problem. The pre-trained machine learning model is generally pre-trained with similar input data to that of the new problem. A pre-trained machine learning model further trained to solve a new problem is generally referred to as transfer learning, which is described herein. In some instances, a pre-trained machine learning model is trained on a large dataset of related information. The pre-trained model is then further trained and tuned for the new problem. Using a pre-trained machine learning module provides the advantage of building a new machine learning module with input neurons/nodes that are already familiar with the input data and are more readily refined to a particular problem. For example, a machine learning module previously trained using microscopy imaging data or expression profile data, an expression profile, or any combination thereof may be further trained to estimate an omics profile. See e.g., Diamant N, et al. Patient contrastive learning: A performant, expressive, and practical approach to electrocardiogram modeling. PLOS Comput Biol. 2022 Feb. 14; 18(2): e1009862.

In some examples, after the training phase has been completed but before producing predictions expressed as outputs, a trained machine learning module can be provided to a computing device where a trained machine learning module is not already resident, in other words, after training phase has been completed, the trained machine learning module can be downloaded to a computing device. For example, a first computing device storing a trained machine learning module can provide the trained machine learning module to a second computing device. Providing a trained machine learning module to the second computing device may comprise one or more of communicating a copy of trained machine learning module to the second computing device, making a copy of trained machine learning module for the second computing device, providing access to trained machine learning module to the second computing device, and/or otherwise providing the trained machine learning system to the second computing device. In example embodiments, a trained machine learning module can be used by the second computing device immediately after being provided by the first computing device. In some examples, after a trained machine learning module is provided to the second computing device, the trained machine learning module can be installed and/or otherwise prepared for use before the trained machine learning module can be used by the second computing device.

After a machine learning model has been trained it can be used to output, estimate, infer, predict, or determine, for simplicity these terms will collectively be referred to as results. A trained machine learning module can receive input data and operably generate results. As such, the input data can be used as an input to the trained machine learning module for providing corresponding results to kernel components and non-kernel components. For example, a trained machine learning module can generate results in response to requests. In example embodiments, a trained machine learning module can be executed by a portion of other software. For example, a trained machine learning module can be executed by a result daemon to be readily available to provide results upon request.

In example embodiments, a machine learning module and/or trained machine learning module can be executed and/or accelerated using one or more computer processors and/or on-device co-processors. Such on-device co-processors can speed up training of a machine learning module and/or generation of results. In some examples, trained machine learning module can be trained, reside, and execute to provide results on a particular computing device, and/or otherwise can make results for the particular computing device.

Input data can include data from a computing device executing a trained machine learning module and/or input data from one or more computing devices. In example embodiments, a trained machine learning module can use results as input feedback. A trained machine learning module can also rely on past results as inputs for generating new results. In example embodiments, input data can comprise microscopy imaging data or expression profile data of a cell and, when provided to a trained machine learning module, results in output data such as an omics profile.

Algorithms

Different machine-learning algorithms have been contemplated to carry out the embodiments discussed herein. For example, linear regression (LiR), logistic regression (LoR), Bayesian networks (for example, naive-bayes), random forest (RF) (including decision trees), neural networks (NN) (also known as artificial neural networks), matrix factorization, a hidden Markov model (HMM), support vector machines (SVM), K-means clustering (KMC), K-nearest neighbor (KNN), a suitable statistical machine learning algorithm, and/or a heuristic machine learning system for classifying or evaluating microscopy imaging data or expression profile data of a cell into an omics profile.

Linear Regression (LiR)

In one example embodiment, linear regression machine learning is implemented. LiR is typically used in machine learning to predict a result through the mathematical relationship between an independent and dependent variable, such as microscopy imaging data or expression profile data of a cell and an omics profile, respectively. A simple linear regression model would have one independent variable (x) and one dependent variable (y). A representation of an example mathematical relationship of a simple linear regression model would be $y=mx+b$. In this example, the machine learning algorithm tries variations of the tuning variables m and b to optimize a line that includes all the given training data.

The tuning variables can be optimized, for example, with a cost function. A cost function takes advantage of the minimization problem to identify the optimal tuning variables. The minimization problem preposes the optimal tuning variable will minimize the error between the predicted outcome and the actual outcome. An example cost function may comprise summing all the square differences between the predicted and actual output values and dividing them by the total number of input values and results in the average square error.

To select new tuning variables to reduce the cost function, the machine learning module may use, for example, gradient descent methods. An example gradient descent method comprises evaluating the partial derivative of the cost function with respect to the tuning variables. The sign and magnitude of the partial derivatives indicate whether the choice of a new tuning variable value will reduce the cost function, thereby optimizing the linear regression algorithm. A new tuning variable value is selected depending on a set threshold. Depending on the machine learning module, a steep or gradual negative slope is selected. Both the cost function and gradient descent can be used with other algorithms and modules mentioned throughout. For the sake of brevity, both the cost function and gradient descent are well known in the art and are applicable to other machine learning algorithms and may not be mentioned with the same detail.

LiR models may have many levels of complexity comprising one or more independent variables. Furthermore, in an LiR function with more than one independent variable, each independent variable may have the same one or more tuning variables or each, separately, may have their own one or more tuning variables. The number of independent variables and tuning variables will be understood to one skilled in the art for the problem being solved. In example embodiments, microscopy imaging data or expression profile data of a cell are used as the independent variables to train a LiR machine learning module, which, after training, is used to estimate, for example, an omics profile.

Logistic Regression (LoR)

In one example embodiment, logestic regression machine learning is implemented. Logistic Regression, often considered a LiR type model, is typically used in machine learning to classify information, such as microscopy imaging data or expression profile data of a cell into categories such as omics profiles. LoR takes advantage of probability to predict an outcome from input data. However, what makes LoR different from a LiR is that LoR uses a more complex logistic function, for example a sigmoid function. In addition, the cost function can be a sigmoid function limited to a result between 0 and 1. For example, the sigmoid function can be of the form $f(x)=1/(1+e^{-x})$, where x represents some linear representation of input features and tuning variables. Similar to LiR, the tuning variable(s) of the cost function are optimized (typically by taking the log of some variation of the cost function) such that the result of the cost function, given variable representations of the input features, is a number between 0 and 1, preferably falling on either side of 0.5. As described in LiR, gradient descent may also be used in LoR cost function optimization and is an example of the process. In example embodiments, microscopy imaging data or expression profile data of a cell are used as the independent variables to train a LoR machine learning module, which, after training, is used to estimate, for example, omics profiles.

Bayesian Network

In one example embodiment, a Bayesian Network is implemented. BNs are used in machine learning to make predictions through Bayesian inference from probabilistic graphical models. In BNs, input features are mapped onto a directed acyclic graph forming the nodes of the graph. The edges connecting the nodes contain the conditional dependencies between nodes to form a predicative model. For each connected node the probability of the input features resulting in the connected node is learned and forms the predictive mechanism. The nodes may comprise the same, similar, or different probability functions to determine movement from one node to another. The nodes of a Bayesian network are conditionally independent of its non-descendants given its parents thus satisfying a local Markov property. This property affords reduced computations in larger networks by simplifying the joint distribution.

There are multiple methods to evaluate the inference, or predictability, in a Bayesian network but only two are mentioned for demonstrative purposes. The first method involves computing the joint probability of a particular assignment of values for each variable. The joint probability can be considered the product of each conditional probability and, in some instances, comprises the logarithm of that product. The second method is Markov chain Monte Carlo (MCMC), which can be implemented when the sample size is large. MCMC is a well-known class of sample distribution algorithms and will not be discussed in detail herein.

The assumption of conditional independence of variables forms the basis for Naïve Bayes classifiers. This assumption implies there is no correlation between different input features. As a result, the number of computed probabilities is significantly reduced as well as the computation of the probability normalization. While independence between features is rarely true, this assumption exchanges reduced computations for less accurate predictions, however the predictions are reasonably accurate. In example embodiments, microscopy imaging data or expression profile data of a cell are mapped to the BN graph to train the BN machine learning module, which, after training, is used to estimate an omics profile.

Random Forest

In one example embodiment, random forest is implemented. RF consists of an ensemble of decision trees producing individual class predictions. The prevailing prediction from the ensemble of decision trees becomes the RF prediction. Decision trees are branching flowchart-like graphs comprising of the root, nodes, edges/branches, and leaves. The root is the first decision node from which feature information is assessed and from it extends the first set of edges/branches. The edges/branches contain the information of the outcome of a node and pass the information to the next node. The leaf nodes are the terminal nodes that output the prediction. Decision trees can be used for both classification as well as regression and is typically trained using supervised learning methods. Training of a decision tree is sensitive to the training data set. An individual decision tree may become over or under-fit to the training data and result in a poor predictive model. Random forest compensates by using multiple decision trees trained on different data sets. In example embodiments, microscopy imaging data or expression profile data of a cell are used to train the nodes of the decision trees of a RF machine learning module, which, after training, is used to estimate an omics profile. In preferred embodiments, microscopy imaging data or expression profile data of a cell are used to train the nodes of a decision tree, which, after training, is used to estimate an omics profile Gradient Boosting In an example embodiment, gradient boosting is implemented. Gradient boosting is a method of strengthening the evaluation capability of a decision tree node. In general, a tree is fit on a modified version of an original data set. For example, a decision tree is first trained with equal weights across its nodes. The decision tree is allowed to evaluate data to identify nodes that are less accurate. Another tree is added to the model and the weights of the corresponding underperforming nodes are then modified in the new tree to improve their accuracy. This process is performed iteratively until the accuracy of the model has reached a defined threshold or a defined limit of trees has been reached. Less accurate nodes are identified by the gradient of a loss function. Loss functions must be differentiable such as a linear or logarithmic functions. The modified node weights in the new tree are selected to minimize the gradient of the loss function. In an example embodiment, a decision tree is implemented to determine an omics profile from microscopy imaging data or expression profile data of a cell and gradient boosting is applied to the tree to improve its ability to accurately determine the omics profile of a cell.

Neural Networks

In one example embodiment, Neural Networks are implemented. NNs are a family of statistical learning models influenced by biological neural networks of the brain. NNs can be trained on a relatively-large dataset (e.g., 50,000 or more) and used to estimate, approximate, or predict an output that depends on a large number of inputs/features. NNs can be envisioned as so-called "neuromorphic" systems of interconnected processor elements, or "neurons", and exchange electronic signals, or "messages". Similar to the so-called "plasticity" of synaptic neurotransmitter connections that carry messages between biological neurons, the connections in NNs that carry electronic "messages" between "neurons" are provided with numeric weights that correspond to the strength or weakness of a given connection. The weights can be tuned based on experience, making NNs adaptive to inputs and capable of learning. For example, an NN for estimating local fat depots is defined by a set of input neurons that can be given input data such as representations of a subject's body. The input neuron weighs and transforms the input data and passes the result to other neurons, often referred to as "hidden" neurons. This is repeated until an output neuron is activated. The activated output neuron makes a prediction. In example embodiments, microscopy imaging data or expression profile data of a cell are used to train the neurons in a NN machine learning module, which, after training, is used to estimate an omics profile.

Deep Learning

In example embodiments, deep learning is implemented. Deep learning expands the neural network by including more layers of neurons. A deep learning module is characterized as having three "macro" layers: (1) an input layer which takes in the input features, and fetches embeddings for the input, (2) one or more intermediate (or hidden) layers which introduces nonlinear neural net transformations to the inputs, and (3) a response layer which transforms the final results of the intermediate layers to the prediction. In example embodiments, microscopy imaging data or expression profile data of a cell are used to train the neurons of a deep learning module, which, after training, is used to estimate an omics profile.

Convolutional Neural Network (CNN)

In an example embodiment, a convolutional neural network is implemented. CNNs is a class of NNs further attempting to replicate the biological neural networks, but of the animal visual cortex. CNNs process data with a grid pattern to learn spatial hierarchies of features. A typical CNN comprises of three layers: convolution, pooling, and fully connected. The convolution and pooling layers extract features, such as those described herein. The convolutional layer comprises of multiple mathematical operations such as of linear operations, a specialized type being a convolution. The fully connected layer combines the extracted features into an output, for example an omics profile or one or more biomarkers. The input data, such as microscopy imaging data or expression profile data, may be represented in a grid, i.e., an array of numbers. A grid of parameters, called a kernel, operates as an optimizable feature extractor and is applied to each position in the grid. Extracted features may become hierarchically more complex as one layer feeds its output into the next layer. See Yamashita, R., et al Convolutional neural networks: an overview and application in radiology. Insights Imaging 9, 611-629 (2018).

In an example embodiment, a convolutional neural network is implemented. CNNs is a class of NNs further attempting to replicate the biological neural networks, but of the animal visual cortex. CNNs process data with a grid pattern to learn spatial hierarchies of features. Wherein NNs are highly connected, sometimes fully connected, CNNs are connected such that neurons corresponding to neighboring data (e.g., pixels) are connected. This significantly reduces the number of weights and calculations each neuron must perform.

In general, input data, such microscopy imaging data or expression profile data or expression profile data, comprises of a multidimensional vector. A CNN, typically, comprises of three layers: convolution, pooling, and fully connected. The convolution and pooling layers extract features and the fully connected layer combines the extracted features into an output, such as omics profile or one or more biomarkers.

In particular, the convolutional layer comprises of multiple mathematical operations such as of linear operations, a specialized type being a convolution. The convolutional layer calculates the scalar product between the weights and the region connected to the input volume of the neurons. These computations are performed on kernels, which are reduced dimensions of the input vector. The kernels span the entirety of the input. The rectified linear unit (i.e., ReLu) applies an elementwise activation function (e.g., sigmoid function) on the kernels.

CNNs can optimized with hyperparameters. In general, there three hyperparameters are used: depth, stride, and zero-padding. Depth controls the number of neurons within a layer. Reducing the depth may increase the speed of the CNN but may also reduce the accuracy of the CNN. Stride determines the overlap of the neurons. Zero-padding controls the border padding in the input.

The pooling layer down-samples along the spatial dimensionality of the given input (i.e., convolutional layer output), reducing the number of parameters within that activation. As an example, kernels are reduced to dimensionalities of 2×2 with a stride of 2, which scales the activation map down to 25%. The fully connected layer uses inter-layer-connected neurons (i.e., neurons are only connected to neurons in other layers) to score the activations for classification and/or regression. Extracted features may become hierarchically more complex as one layer feeds its output into the next layer. See O'Shea, K.; Nash, R. An Introduction to Convolutional Neural Networks. arXiv 2015 and Yamashita, R., et al Convolutional neural networks: an overview and application in radiology. Insights Imaging 9, 611-629 (2018).

Convolutional Autoencoder

In example embodiments, convolutional autoencoder (CAE) is implemented. A CAE is a type of neural network and comprises, in general, two main components. First, the convolutional operator that filters an input signal to extract features of the signal. Second, an autoencoder that learns a set of signals from an input and reconstructs the signal into an output. By combining these two components, the CAE learns the optimal filters that minimize reconstruction error resulting an improved output. CAEs are trained to only learn filters capable of feature extraction that can be used to reconstruct the input. Generally, convolutional autoencoders implement unsupervised learning. In example embodiments, the convolutional autoencoder is a variational convolutional autoencoder. In example embodiments, features from microscopy imaging data or expression profile data are used as an input signal into a CAE which reconstructs that signal into an output such as an omics profile or one or more biomarkers.

Recurrent Neural Network (RNN)

In an example embodiment, a recurrent neural network is implemented. RNNs are class of NNs further attempting to replicate the biological neural networks of the brain. RNNs comprise of delay differential equations on sequential data or time series data to replicate the processes and interactions of the human brain. RNNs have "memory" wherein the RNN can take information from prior inputs to influence the current output. RNNs can process variable length sequences of inputs by using their "memory" or internal state information. Where NNs may assume inputs are independent from the outputs, the outputs of RNNs may be dependent on prior elements with the input sequence. For example, input such as microscopy imaging data or expression profile data is received by a RNN, which determines an omics profile or one or more biomarkers with the "memory" of additional inputs. See Sherstinsky, Alex. "Fundamentals of recurrent neural network (RNN) and long short-term memory (LSTM) network." Physica D: Nonlinear Phenomena 404 (2020): 132306.

Long Short-Term Memory (LSTM)

In an example embodiment, a Long Short-term Memory is implemented. LSTM are a class of RNNs designed to overcome vanishing and exploding gradients. In RNNs, long term dependencies become more difficult to capture because the parameters or weights either do not change with training or fluctuate rapidly. This occurs when the RNN gradient exponentially decreases to zero, resulting in no change to the weights or parameters, or exponentially increases to infinity, resulting in large changes in the weights or parameters. This exponential effect is dependent on the number of layers and multiplicative gradient. LSTM overcomes the vanishing/exploding gradients by implementing "cells" within the hidden layers of the NN. The "cells" comprise three gates: an input gate, an output gate, and a forget gate. The input gate reduces error by controlling relevant inputs to update the current cell state. The output gate reduces error by controlling relevant memory content in the present hidden state. The forget gate reduces error by controlling whether prior cell states are put in "memory" or forgotten. The gates use activation functions to determine whether the data can pass through the gates. While one skilled in the art would recognize the use of any relevant activation function, example activation functions are sigmoid, tanh, and RELU. See Zhu, Xiaodan, et al. "Long short-term memory over recursive structures." International Conference on Machine Learning. PMLR, 2015.

Matrix Factorization

In example embodiments, Matrix Factorization is implemented. Matrix factorization machine learning exploits inherent relationships between two entities drawn out when multiplied together. Generally, the input features are mapped to a matrix F which is multiplied with a matrix R containing the relationship between the features and a predicted outcome. The resulting dot product provides the prediction. The matrix R is constructed by assigning random values throughout the matrix. In this example, two training matrices are assembled. The first matrix X contains training input features and the second matrix Z contains the known output of the training input features. First the dot product of R and X are computed and the square mean error, as one example method, of the result is estimated. The values in R are modulated and the process is repeated in a gradient descent style approach until the error is appropriately minimized. The trained matrix R is then used in the machine learning model. In example embodiments, microscopy imaging data or expression profile data of a cell are used to train the relationship matrix R in a matrix factorization machine learning module. After training, the relationship matrix R and input matrix F, which comprises vector representations of microscopy imaging data or expression profile data of a cell, results in the prediction matrix P comprising an omics profile. In example embodiments, spatial expression profile are used to train the relationship matrix R in a matrix factorization machine learning module. After training, the relationship matrix R and input matrix F, which comprises vector representations of microscopy imaging data or expression profile data of a cell, results in the prediction matrix P comprising an omics profile.

Hidden Markov Model

In example embodiments, a hidden Markov model is implemented. A HMM takes advantage of the statistical Markov model to predict an outcome. A Markov model assumes a Markov process, wherein the probability of an outcome is solely dependent on the previous event. In the case of HMM, it is assumed an unknown or "hidden" state is dependent on some observable event. A HMM comprises a network of connected nodes. Traversing the network is dependent on three model parameters: start probability; state transition probabilities; and observation probability. The start probability is a variable that governs, from the input node, the most plausible consecutive state. From there each node i has a state transition probability to node j. Typically the state transition probabilities are stored in a matrix $M_{ij}$ wherein the sum of the rows, representing the probability of state i transitioning to state j, equals 1. The observation probability is a variable containing the probability of output o occurring. These too are typically stored in a matrix $N_{oj}$ wherein the probability of output o is dependent on state j. To build the model parameters and train the HMM, the state and output probabilities are computed. This can be accomplished with, for example, an inductive algorithm. Next, the state sequences are ranked on probability, which can be accomplished, for example, with the Viterbi algorithm. Finally, the model parameters are modulated to maximize the probability of a certain sequence of observations. This is typically accomplished with an iterative process wherein the neighborhood of states are explored, the probabilities of the state sequences are measured, and model parameters updated to increase the probabilities of the state sequences. In example embodiments, microscopy imaging data or expression profile data of a cell are used to train the nodes/states of the HMM machine learning module, which, after training, is used to estimate an omics profile.

Support Vector Machine

In example embodiments, support vector machines are implemented. SVMs separate data into classes defined by n-dimensional hyperplanes (n-hyperplane) and are used in both regression and classification problems. Hyperplanes are decision boundaries developed during the training process of a SVM. The dimensionality of a hyperplane depends on the number of input features. For example, a SVM with two input features will have a linear (1-dimensional) hyperplane while a SVM with three input features will have a planer (2-dimensional) hyperplane. A hyperplane is optimized to have the largest margin or spatial distance from the nearest data point for each data type. In the case of simple linear regression and classification a linear equation is used to develop the hyperplane. However, when the features are more complex a kernel is used to describe the hyperplane. A kernel is a function that transforms the input features into higher dimensional space. Kernel functions can be linear, polynomial, a radial distribution function (or gaussian radial distribution function), or sigmoidal. In example embodiments, microscopy imaging data or expression profile data of a cell are used to train the linear equation or kernel function of the SVM machine learning module, which, after training, is used to estimate an omics profile.

K-Means Clustering

In one example embodiment, K-means clustering is implemented. KMC assumes data points have implicit shared characteristics and "clusters" data within a centroid or "mean" of the clustered data points. During training, KMC adds a number of k centroids and optimizes its position around clusters. This process is iterative, where each centroid, initially positioned at random, is re-positioned towards the average point of a cluster. This process concludes when the centroids have reached an optimal position within a cluster. Training of a KMC module is typically unsupervised. In example embodiments, microscopy imaging data or expression profile data of a cell are used to train the centroids of a KMC machine learning module, which, after training, is used to estimate an omics profile.

K-Nearest Neighbor

In one example embodiment, K-nearest neighbor is implemented. On a general level, KNN shares similar characteristics to KMC. For example, KNN assumes data points near each other share similar characteristics and computes the distance between data points to identify those similar characteristics but instead of k centroids, KNN uses k number of neighbors. The k in KNN represents how many neighbors will assign a data point to a class, for classification, or object property value, for regression. Selection of an appropriate number of k is integral to the accuracy of KNN. For example, a large k may reduce random error associated with variance in the data but increase error by ignoring small but significant differences in the data. Therefore, a careful choice of k is selected to balance overfitting and underfitting. Concluding whether some data point belongs to some class or property value k, the distance between neighbors is computed. Common methods to compute this distance are Euclidean, Manhattan or Hamming to name a few. In some embodiments, neighbors are given weights depending on the neighbor distance to scale the similarity between neighbors to reduce the error of edge neighbors of one class "out-voting" near neighbors of another class. In one example embodiment, k is 1 and a Markov model approach is utilized. In example embodiments, microscopy imaging data or expression profile data of a cell are used to train a KNN machine learning module, which, after training, is used to estimate an omics profile.

To perform one or more of its functionalities, the machine learning module may communicate with one or more other systems. For example, an integration system may integrate the machine learning module with one or more email servers, web servers, one or more databases, or other servers, systems, or repositories. In addition, one or more functionalities may require communication between a user and the machine learning module.

Any one or more of the module described herein may be implemented using hardware (e.g., one or more processors of a computer/machine) or a combination of hardware and software. For example, any module described herein may configure a hardware processor (e.g., among one or more hardware processors of a machine) to perform the operations described herein for that module. In some example embodiments, any one or more of the modules described herein may comprise one or more hardware processors and may be configured to perform the operations described herein. In example embodiments, one or more hardware processors are configured to include any one or more of the modules described herein.

Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices. The multiple machines, databases, or devices are communicatively coupled to enable communications between the multiple machines, databases, or devices. The modules themselves are communicatively coupled (e.g., via appropriate interfaces) to each other and to various data sources, to allow information to be passed between the applications to allow the applications to share and access common data.

Additional Applications

Methods and systems described herein can be further expanded to cover applications beyond the scope single cell omics profile. The combination of Raman and machine learning offers the opportunity to non-destructively identify biomarkers associated with diseases and/or aging. In addition, this combination offers the opportunity to non-destructively perform perturbative analysis.

Biomarkers

In example embodiments, methods and systems described herein may determine a biomarker for disease or age. A biomarker may be any measure or measurable characteristic associated with a biological system or process or pathogenic system or process and their potential outcome, for example chemical, physical, or biological. Biomarkers may not only identify incidence or outcome of disease or aging but also environmental exposure. For example, a biomarker may be from a subject's gene expression, the influence of environmental factors, the interactions between the two, epigenetic modifications, or any combination thereof. In example embodiments, microscopy imaging data or expression profile data of the body, its part(s), and/or product(s) encompassing molecules, structures, or processes, is used by a machine learning module/network to determine one or more biomarkers and may further determine an advantageous response to that biomarker. An advantageous response may comprise a known treatment corresponding to the disease or determined age associated with the biomarker. An advantageous response may comprise a diagnosis, prognosis, theranosis, or determining the stage or progression of the disease or stage or progression of the age of the subject. An advantageous response may further comprise identifying appropriate treatments or treatment efficacy for specific diseases, conditions, disease or age stages and condition stages, analysis of disease or age progression, particularly disease recurrence, metastatic spread or disease relapse. See e.g. Strimbu K, Tavel J A. What are biomarkers? Curr Opin HIV AIDS. 2010; 5(6):463-466. doi: 10.1097/COH.0b013e32833ed177.

In an example embodiment, the methods and systems described herein identify biomarkers of disease or age. The methods and systems described herein may use microscopy imaging data or expression profile data and machine learning modules/networks to determine these biomarkers. The microscopy imaging data or expression profile data may comprise of microscopy imaging data or expression profile data of biological material comprising necessary information to determine the biomarkers of disease such as tissue, blood, plasma, serum, breast milk, ascites, bronchoalveolar lavage fluid, urine, and cerebrospinal fluid for example. Microscopy imaging data or expression profile data of biological materials may comprise information regarding proteins, peptides, carbohydrates, lipids, vesicles, RNAs, DNAs, and/or variations/modifications thereof further describing one or more biomarkers. For example, a biomarker may be characterized (e.g. identified or learned) by obtaining a biological sample (e.g. biological material) from a subject, such as microscopy imaging data or expression profile data of the biological sample, and analyzing it with a machine learning module/network. The analysis of the biomarkers and their corresponding information may comprise a subclinical manifestation, stage of a disorder, a surrogate manifestation of the disease or age. See e.g. Mayeux R. Biomarkers: potential uses and limitations. NeuroRx. 2004; 1(2):182-188. doi: 10.1602/neurorx.1.2.182.

In example embodiments, one or more biomarkers linked to an endotype (e.g., a low risk endotype or high risk endotype) by using a machine learning module/network (e.g. trained machine learning module/network) on microscopy imaging data or expression profile data. In example embodiments, endotype data includes any data that defines a distinct functional or pathobiological mechanism, such as biomarkers that contribute to a disease. In example embodiments, samples having different levels for the endotype can be distributed into categorical variables (e.g., samples having different numbers of biomarkers). In preferred embodiments, the endotype can be characterized by a machine learning module/network from Raman microscopy imaging data. In order to learn one or more biomarkers of an endotype a dataset that comprises both endotype and molecular profile data (including microscopy imaging data) for individual samples is required. The dataset can be an existing dataset or can be generated de novo. In example embodiments, the dataset includes data from bulk tissue samples. The tissue samples are preferably derived from tissues associated with the disease of interest. In example embodiments, the dataset comprises endotype data and single cell data. The single cell data is preferably from single cells associated with the disease of interest.

In example embodiments, the dataset comprises genotype data and includes genetic variants. The genetic variants can be in the nuclear genome. The genetic variants may also be present in the mitochondrial genome. In an example embodiment, one or more biomarker is determined for a population of subjects having a disease (e.g., using a database described herein: UK Biobank, MGB Biobank, TOPMed, and All of Us). The specific variants that make up the one or more biomarkers can then be evaluated in a dataset comprising genotype data and molecular profiles (e.g., Genotype-Tissue Expression (GTEx) project), including microscopy imaging data. The specific variants that make up the one or more biomarkers can then be evaluated in samples without sequencing the whole genome of each sample. The samples can then be evaluated for a molecular profile either simultaneously or after determining one or more biomarkers. The samples can be tissue samples obtained from a plurality of subjects. The samples can be cells that have the one or more biomarkers and are modified to have different one or more biomarkers. The cells having different biomarkers can then be evaluated for a molecular profile.

In example embodiments, the dataset can be a cell atlas or single cell atlas. As used herein "atlas" refers to a collection of data from any tissue sample of interest having a phenotype of interest (see, e.g., Rozenblatt-Rosen O, Stubbington M J T, Regev A, Teichmann S A., The Human Cell Atlas: from vision to reality., Nature. 2017 Oct. 18; 550(7677):451-453; and Regev, A. et al. The Human Cell Atlas Preprint available at bioRxiv at dx.doi.org/10.1101/121202 (2017)). The atlas can include biological information, including medical records, histology, single cell profiles, and genetic information.

Molecular Profile Data

In example embodiments, the molecular profiles in the dataset comprise a transcriptomic profile, a proteomic profile, a metabolomic profile, a cell-imaging based profile, a spatial transcriptomic profile, a spatial proteomics profile, a spatial metabolomics profile, an epigenomic profile, a clinical imaging profile, a lipodomic profile, or a combination thereof.

In example embodiments, the molecular profiles are obtained from single cell data. The single cell data is preferably from single cells associated with the disease of interest (e.g., originating from a tissue associated with the disease or specific cell types). In example embodiments, an endotype is linked to a molecular profile in single cell types associated with the disease. In example embodiments, the molecular profile that is linked to an endotype is a molecular profile from a single cell type that has the highest correlation with the endotype. For example, a molecular profile from a plurality of single cells is compared to an endotype score and a molecular profile in a single cell type that most closely correlates with the endotype score is selected.

Transcriptomic Profiles

In example embodiments, the molecular profile comprises transcriptome data (e.g., gene expression). As used herein the term "transcriptome" refers to the set of transcript molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In example embodiments, transcriptome data comprises bulk RNA sequencing (e.g., RNA-seq). In example embodiments, transcriptome data comprises single cell RNA sequencing (e.g., scRNA-seq). In example embodiments, an endotype is linked to one or more biomarkers in single cell types associated with the disease. In example embodiments, the one or more biomarkers that are linked to an endotype is one or more biomarkers from a single cell type that the machine learning module/network connects with the endotype. For example, a transcriptome from a plurality of single cells are compared to an endotype and a gene signature in a single cell type with a machine learning module/network that determines the one or more biomarkers.

In certain embodiments, the invention involves single cell RNA sequencing (see, e.g., Qi Z, Barrett T, Parikh A S, Tirosh I, Puram S V. Single-cell sequencing and its applications in head and neck cancer. Oral Oncol. 2019; 99:104441; Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12 (1): 44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14 (3): 302-308, 2017; Cao, et al., Comprehensive single-cell transcriptional profiling of a multicellular organism. Science, 357 (6352): 661-667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14 (10): 955-958; International Patent Application No. PCT/US2016/059239, published as WO2017164936 on Sep. 28, 2017; International Patent Application No. PCT/

US2018/060860, published as WO/2019/094984 on May 16, 2019; International Patent Application No. PCT/US2019/055894, published as WO/2020/077236 on Apr. 16, 2020; Drokhlyansky, et al., "The enteric nervous system of the human and mouse colon at a single-cell resolution," bioRxiv 746743; doi: doi.org/10.1101/746743; and Drokhlyansky E, Smillie C S, Van Wittenberghe N, et al. The Human and Mouse Enteric Nervous System at Single-Cell Resolution. Cell. 2020; 182(6):1606-1622.e23, which are herein incorporated by reference in their entirety.

Proteomic Profiles

In example embodiments, the molecular profile comprises proteome data. Proteome data may include mass spectrometry. A variety of configurations of mass spectrometers can be used to detect one or more biomarkers. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS) n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab') 2 fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

Single cells can be analyzed by mass cytometry (CyTOF) and tissue samples can be analyzed by Multiplexed Ion Beam Imaging (MIBI) (see, e.g., Hartmann F J, Bendall S C. Immune monitoring using mass cytometry and related high-dimensional imaging approaches. Nat Rev Rheumatol. 2020; 16(2):87-99). Non-limiting examples include multiplex analysis of single cell constituents (US20180340939A), single-cell proteomic assay using aptamers (US20180320224A1), and methods of identifying multiple epitopes in cells (US20170321251A1). In example embodiments, CITE-seq (cellular proteins) is used to generate single cell RNA-seq and proteomics data (see, e.g., Stoeckius, M. et al. Simultaneous epitope and transcriptome measurement in single cells. Nat. Methods 14, 865-868 (2017)).

Epigenomic Profiles

In example embodiments, the molecular profile comprises epigenomic profiles. Epigenomic profiles have been described and are obtainable in databases (see, e.g., NIH Roadmap Epigenomics Mapping Consortium, ENCODE, Cistrome, and ChIP Atlas; ENCODE Project Consortium, Moore J E, Purcaro M J, et al. Expanded encyclopedias of DNA elements in the human and mouse genomes. Nature. 2020; 583(7818):699-710; Li S, Wan C, Zheng R, et al. Cistrome-GO: a web server for functional enrichment analysis of transcription factor ChIP-seq peaks. Nucleic Acids Res. 2019; 47(W1):W206-W211; and Shinya Oki, Tazro Ohta, et al. ChIP-Atlas: a data-mining suite powered by full integration of public ChIP-seq data. EMBO Rep. (2018) e46255). The epigenomic profile can be a chromatin accessibility profile (e.g. ATAC-seq), a chromatin modification profile (e.g., ChIP-seq), a chromatin binding profile (e.g., ChIP-seq), a DNA methylation profile (e.g, Bisulfite-Seq), a DNase hypersensitivity profile (e.g., DNase-seq), or a DNA-DNA contact profile (e.g., Hi-C).

In example embodiments, epigenomic profiles are single cell profiles. In example embodiments, the invention involves the Assay for Transposase Accessible Chromatin using sequencing (ATAC-seq) (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. Nature 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1). In example embodiments, genome wide chromatin immunoprecipitation is used (ChIP) (see, e.g., Rotem, et al., Single-cell ChIP-seq reveals cell subpopulations defined by chromatin state, Nat Biotechnol 33, 1165-1172 (2015)). In example embodiments, epigenetic features can be chromatin contact domains, chromatin loops, superloops, or chromatin architecture data, such as obtained by single cell Hi-C (see, e.g., Rao et al., Cell. 2014 Dec. 18; 159(7):1665-80; and Ramani, et al., Sci-Hi-C: A single-cell Hi-C method for mapping 3D genome organization in large number of single cells Methods. 2020 Jan. 1; 170:61-68). In example embodiments, SHARE-Seq is used to generate single cell RNA-seq and chromatin accessibility data (see, e.g., Ma, S. et al. Chromatin potential identified by shared single cell profiling of RNA and chromatin. bioRxiv 2020.06.17.156943 (2020) doi: 10.1101/2020.06.17.156943).

Spatial Detection Profiles

In example embodiments, the molecular profile comprises spatial detection data. In example embodiments, spatially resolved molecular profiles are anchored to an endotype. For example, microscopy imaging data can be linked to gene or protein expression in specific cells located at the sites of disease or the location where the disease manifests. An example spatial detection platform includes the digital spatial profiler (DSP), GeoMx DSP, which is built on Nanostring's digital molecular barcoding core technology and is further extended by linking the target complementary sequence probe to a unique DSP barcode through a UV cleavable linker (see, e.g., Li X, Wang C Y. From bulk, single-cell to spatial RNA sequencing. Int J Oral Sci. 2021; 13(1):36). A pool of such barcode-labeled probes is hybridized to mRNA targets that are released from fresh or FFPE tissue sections mounted on a glass slide. The slide is also stained using fluorescent markers (i.e., fluorescently conjugated antibodies) and imaged to establish tissue "geography" using the GeoMx DSP instrument. After the regions-of-interest (ROIs) are selected, the DSP barcodes are released via UV exposure and collected from the ROIs on the tissue. These barcodes are sequenced through standard NGS procedures. The identity and number of sequenced barcodes can be translated into specific mRNA molecules and their abundance, respectively, and then mapped to the tissue section based on their geographic location. The DSP barcode can also be linked to antibodies to detect proteins. An example spatial detection platform includes the CosMx Spatial Molecular Imager (Nanostring) platform, which enables high-plex (~1,000 genes) spatial transcriptomics and proteomics at single cell and subcellular resolution (see, e.g., He, et al., High-plex Multiomic Analysis in FFPE at Subcellular Level by Spatial Molecular Imaging, bioRxiv 2021.11.03.467020). Other spatial detection methods or platform applicable to the present invention have been described (see, e.g., Li X, Wang C Y. From bulk, single-cell to spatial RNA sequencing. Int J Oral Sci. 2021; 13(1):36. Published 2021 Nov. 15. doi: 10.1038/s41368-021-00146-0). Additional non-limiting methods of generating spatial data of varying resolution are known in the art, for example, multiplexed ion beam imaging (MIBI) (see, e.g., Angelo et al., Nat Med. 2014 April; 20(4): 436-442), NanoString (DSP, digital spatial profiling) (see e.g., Li X, Wang C Y. From bulk, single-cell to spatial RNA sequencing. Int J Oral Sci. 2021; 13(1):36; and Geiss G K, et al., Direct multiplexed measurement of gene expression with color-coded probe pairs. Nat Biotechnol. 2008 March;26 (3): 317-25), ISS (Ke, R. et al. In situ sequencing for RNA analysis in preserved tissue and cells. Nat. Methods 10, 857-860 (2013)), MERFISH (Chen, K. H., Boettiger, A. N., Moffitt, J. R., Wang, S. & Zhuang, X. Spatially resolved, highly multiplexed RNA profiling in single cells. *Science* 348, (2015)), smFISH (Codeluppi, S. et al. *Spatial organization of the somatosensory cortex revealed by cyclic smFISH*. biorxiv.org/lookup/doi/10.1101/276097 (2018) doi: 10.1101/276097), osmFISH (Codeluppi, S. et al. Spatial organization of the somatosensory cortex revealed by osmFISH. *Nat. Methods* 15, 932-935 (2018)), STARMap (Wang, X. et al. Three-dimensional intact-tissue sequencing of single-cell transcriptional states. Science 361, eaat5691 (2018)), Targeted ExSeq (Alon, S. et al. Expansion Sequencing: *Spatially Precise In Situ Transcriptomics in Intact Biological Systems*. biorxiv.org/lookup/doi/10.1101/2020.05.13.094268 (2020) doi: 10.1101/2020.05.13.094268), seqFISH+ (Eng, C.-H. L. et al. Transcriptome-scale super-resolved imaging in tissues by RNA seqFISH+. Nature (2019) doi: 10.1038/s41586-019-1049-y.), Spatial Transcriptomics methods (e.g., Spatial Transcriptomics (ST)) (see, e.g., Ståhl, P. L. et al. Visualization and analysis of gene expression in tissue sections by spatial transcriptomics. *Science* 353, 78-82 (2016)) (commercially as Visium); Visium Spatial Capture Technology, 10× Genomics, Pleasanton, CA; WO2020047007A2; WO2020123317A2; WO2020047005A1; WO2020176788A1; and WO2020190509A9), Slide-seq (Rodriques, S. G. et al. Slide-seq: A scalable technology for measuring genome-wide expression at high spatial resolution. Science 363, 1463-1467 (2019)), or High Definition Spatial Transcriptomics (Vickovic, S. et al. High-definition spatial transcriptomics for in situ tissue profiling. *Nat. Methods* 16, 987-990 (2019)). In certain embodiments, proteomics and spatial patterning using antenna networks is used to spatially map a tissue specimen and this data can be further used to align single cell data to a larger tissue specimen (see, e.g., US20190285644A1). In certain embodiments, the spatial data can be immunohistochemistry data or immunofluorescence data.

Metabolic Profiles

In example embodiments, the dataset includes cellular metabolic states obtained from analyzing tissue samples or single cells. In example embodiments, metabolites are detected (see, e.g., Rappez L, Stadler M, Triana S, et al. SpaceM reveals metabolic states of single cells. Nat Methods. 2021; 18(7):799-805. doi: 10.1038/s41592-021-01198-0). In example embodiments, the dataset includes cellular metabolic states based on RNA-seq or single-cell RNA sequencing (see, e.g., Wagner A, Wang C, Fessler J, et al. Metabolic modeling of single Th17 cells reveals regulators of autoimmunity. Cell. 2021; 184(16):4168-4185.e21).

Cell-Imaging Based Profiles

In example embodiments, the dataset comprises morphological data obtained from differentiating stem cells for a plurality of subjects. The morphological data can be used to generate one or more biomarkers for the subjects (e.g., by quantitating the number and intensity of features) or can be the molecular profile for the subjects. Morphological features can be identified by cell painting (see, e.g., Bray M A, Singh S, Han H, et al. Cell Painting, a high-content image-based assay for morphological profiling using multiplexed fluorescent dyes. Nat Protoc. 2016; 11(9):1757-1774); and Laber, et al., Discovering cellular programs of intrinsic and extrinsic drivers of metabolic traits using LipocyteProfiler, bioRxiv 2021.07.17.452050).

In example embodiments, the molecular profile comprises histology data. Histology, also known as microscopic anatomy or microanatomy, is the branch of biology which studies the microscopic anatomy of biological tissues. Histology is the microscopic counterpart to gross anatomy, which looks at larger structures visible without a microscope. Although one may divide microscopic anatomy into organology, the study of organs, histology, the study of tissues, and cytology, the study of cells, modern usage places these topics under the field of histology. In medicine, histopathology is the branch of histology that includes the microscopic identification and study of diseased tissue. Biological tissue has little inherent contrast in either the light or electron microscope. Staining is employed to give both contrast to the tissue as well as highlighting particular features of interest. When the stain is used to target a specific chemical component of the tissue (and not the general structure), the term histochemistry is used. Antibodies can be used to specifically visualize proteins, carbohydrates, and lipids. This process is called immunohistochemistry, or when the stain is a fluorescent molecule, immunofluorescence. This technique has greatly increased the ability to identify categories of cells under a microscope. Other advanced techniques, such as nonradioactive in situ hybridization (ISH), can be combined with immunochemistry to identify specific DNA or RNA molecules with fluorescent probes or tags that can be used for immunofluorescence and enzyme-linked fluorescence amplification.

Lipidomic Profiles

In an example embodiment, the molecular profile comprises lipidomic data. As used herein the term "lipidomic(s)" refers to the study of pathways and/or networks of cellular lipids, which may comprise the structure and function of lipids. In example embodiments, lipidomics comprises of the complete set of lipids (i.e. lipidome) in a given cell. In an example embodiment, a lipid may comprise triacylglycerols (i.e. triglycerides), phospholipids, sterols, or any combination thereof. In example embodiments, the lipidomic data comprises Mass Spectrometry (MS) imaging data. See e.g. Yang K, Han X. Lipidomics: Techniques, Applications, and Outcomes Related to Biomedical Sciences. Trends Biochem Sci. 2016; 41(11):954-969.

A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Lipid biomarkers and biomarker values can be detected and measured by any of the following: electrospray ionization mass spectrometry (ESI-MS), ESI-MS/MS, ESI-MS/(MS) n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab') 2 fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

Linking Endotypes to Molecular Signatures

The one or more biomarkers may encompass any gene or genes, protein or proteins, epigenetic element(s), clinical features, or morphological features whose expression profile or whose occurrence is correlated with a specific endotype (e.g., determined by a machine learning module/network). For example, a specific endotype may be correlated with genes, proteins, epigenetic element(s), clinical features or morphological features. Further, therapeutic agents can have similar signatures of genes, proteins, epigenetic element(s), clinical features, or morphological features and can be identified (e.g., using perturbation studies). The one or more biomarkers of the present invention may be microenvironment specific, such as their expression in a particular spatio-temporal context. The one or more biomarkers according to certain embodiments of the present invention may comprise or consist of one or more genes, proteins, epigenetic elements, and/or features, such as for instance 1, 2, 3, 4, 5, 6, 7, 8, 9, 10, 25, 50, 100, 500, 1000 or more. In certain embodiments, the one or more biomarkers may comprise or consist of two or more genes, proteins and/or epigenetic elements, such as for instance 2, 3, 4, 5, 6, 7, 8, 9, 10, 25, 50, 100, 500, 1000 or more. It is to be understood that biomarkers according to the invention may for instance also include genes or proteins as well as epigenetic elements combined. In this context, one or more biomarkers consists of one or more differentially expressed genes/proteins or differential epigenetic elements or features when comparing different cells or cell (sub) populations. It is to be understood that "differentially expressed" genes/proteins include genes/proteins which are up-or down-regulated as well as genes/proteins which are turned on or off. When referring to up-or down-regulation, in certain embodiments, such up-or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art. As discussed herein, differentially expressed genes/proteins, or differential epigenetic elements may be differentially expressed on a single cell level or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells).

One or more biomarkers may be functionally validated as being uniquely associated with a particular phenotype. Induction or suppression of a particular signature may consequentially be associated with or causally drive a particular phenotype. Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere. Particular advantageous uses include methods for identifying agents capable of inducing or suppressing particular pathways based on the gene signatures, protein signature, and/or other genetic or epigenetic signature as defined herein.

Biomarker of Disease

Biomarkers are useful in methods and systems of diagnosing, prognosing and/or staging an immune response in a subject by detecting a first level of expression, activity and/or function of one or more biomarker and comparing the detected level to a control of level wherein a difference in the detected level and the control level indicates that the presence of an immune response in the subject.

In an example embodiment, the machine learning module determines a biomarker of a disease from microscopy imaging data of a biological sample as described above. The disease may comprise cancer, neurodegenerative/neurological disorders, cardiovascular disease, pain disorders, digestive system abnormalities, endocrine disorders, diseases and disorders of the skin, urological disorders, hepatic disease/injury, kidney disease/injury, endometriosis, osteoporosis, pancreatitis, asthma, allergies, prion-related diseases, viral infections, sepsis, organ rejection/transplantation, differentiating conditions (e.g. adenoma versus hyperplastic polyp), pregnancy related physiological states, conditions, or affiliated diseases.

The disease may also comprise one or more pathogens, such as a virus, bacterium, or a protozoan. A virus may contain RNA or DNA surrounded by a virus-coded protein coat. The DNA or RNA may be single- or double-stranded and linear or circular. The virus structure may be helical or icosahedral. In example embodiments, the virus has an out envelope. See e.g. Gelderblom H R. Structure and Classification of Viruses. In: Baron S, editor. Medical Microbiology. 4th edition. Galveston (TX): University of Texas Medical Branch at Galveston; 1996. Chapter 41. A bacterium may comprise any of those belonging to the spherical (cocci), rod (bacilli), spiral (spirilla), comma (vibrios), corkscrew (spirochaetes) groups, or any of those described herein. A protozoa may comprise any unicellular eukaryotes of the Kingdom Protista. See e.g. Yaeger R G. Protozoa: Structure, Classification, Growth, and Development. In: Baron S, editor. Medical Microbiology. 4th edition. Galveston (TX): University of Texas Medical Branch at Galveston; 1996. Chapter 77.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The biomarkers of the present invention are useful in methods and systems of identifying patient populations at risk or suffering from a disease based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments.

The term "monitoring" generally refers to the follow-up of a disease or a condition in a subject for any changes which may occur over time.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Suitably, an altered quantity or phenotype of the immune cells in the subject compared to a control subject having normal immune status or not having a disease comprising an immune component indicates that the subject has an impaired immune status or has a disease comprising an immune component or would benefit from an immune therapy.

Hence, the methods may rely on comparing the quantity of immune cell populations, biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterised by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

Biomarker of Age

Biomarkers are useful in determining, monitoring, treating, and reversing age. A human or organism has two types of age: "chronological", which is the calendar time a human or organism has been alive and "biological/physiological" which pertains to the physiological health and biomarkers thereof. Example metrics of biological age are organ and regulatory system health, general homeostasis, and the decline of general functionality associated with chronological age. Biomarkers associated with age, for example, include genetic variation, telomere length, intracellular and extracellular aggregates, racemization of the amino acids. Genetic variation for determining age may comprise genetic instability, gene expression, and DNA methylation. Furthermore, protein-protein interactions, optionally in combination with gene expression, may also be used as a biomarker for aging. In some instances, a two or more biomarkers are used to determine age. In an example embodiment, microscopy imaging data of a subject (e.g. human or organism) is received by a machine learning module/network, which determines biomarkers of the subject resulting in further determination of the biological age of the subject.

The methods and systems described herein allow for measuring various biological samples (e.g. proteins, peptides, carbohydrates, lipids, vesicles, RNAs, DNAs, and/or variations/modifications thereof) which may produce various omic profiles (e.g. epigenomic transcriptomic, proteomic, etc.) wherein the omics profiles comprise of age-related biomarkers.

For example, epigenetic changes including reduced global heterochromatin, formation of distinct heterochromatin foci, remodeling and loss of nucleosomes, changes in the abundance of histone variants, altered histone marks, global hypomethylation of DNA with distinct areas of hypermethylation, changes in ncRNA abundance, and re-localization of chromatin-modifying factors may be determined by a machine learning module/network from microscopy imaging data. These epigenetic changes may further result in increased genomic instability, changes in gene expression (e.g. loss of silencing), increased translation, increased expression of retrotransposons, cellular senescence and mitochondrial dysfunction, which may also be captured by microscopy imaging data and determined by machine learning modules described herein. See e.g. Kane A E, Sinclair D A. Epigenetic changes during aging and their reprogramming potential. Crit Rev Biochem Mol Biol. 2019; 54(1): 61-83.

Example transcriptomic biomarkers include many age-related phenotypes. For example, cell senescence is the state of cell with respect to the senescence of its tissue or organism. Therefore, the change in cell senescence may become a biomarker of age. Additional age-related transcriptomic biomarkers may include up- and down-regulated pathways and proteins. In particular, transcriptomic biomarkers may include blood RNA profiles, skin fibroblast, or muscle tissue. See e.g. olzscheck, N., Falckenhayn, C., Söhle, J. et al. Modeling transcriptomic age using knowledge-primed artificial neural networks. npj Aging Mech Dis 7, 15 (2021). Example proteomic biomarkers of age include circulating proteins including plasma proteins (e.g. GDF15 and NPPB). See e.g. Tanaka T, et al., Plasma proteomic signature of age in healthy humans. Aging Cell. 2018 October; 17(5):e12799. The methods and systems described herein may determine omics profiles and/or biomarkers from microscopy imaging data pertaining to metabolomics. For example microscopy imaging data of the levels of nicotinamide adenine dinucleotide [NAD+], reduced nicotinamide dinucleotide phosphate [NADPH], a-ketoglutarate [αKG], and β-hydroxybutyrate [BHB] metabolome within a cell or tissue may be received by a machine learning module/network to determine an omics profile and/or biomarker of age. See e.g. Sharma R, Ramanathan A. The Aging Metabolome-Biomarkers to Hub Metabolites. Proteomics. 2020; 20(5-6):e1800407.

After an omics profile or biomarker of aging has been determined by the machine learning module from microscopy imaging data, a treatment for aging (e.g. slowing or reversing) can be determined. For example, a determination from the resulting omics profile or biomarker may include dietary intervention, pharmacological intervention, or genetic modification. Dietary intervention may include, but is not limited to, calorie restriction thereby modulating AMPK, IGF-1/Insulin, mechanistic target of rapamycin (mTOR) and the sirtuins pathways, for example. Additional, age-related benefits of dietary intervention include increased retrotransposon expression, changes in DNA methylation, histone post-translational modifications and the loss of heterochromatin.

Pharmacological interventions may include compounds that mimic the of calorie restriction, such as sirtuin-activating compounds (STACs) and rapamycin. For example, SIRT activation with STACs suppresses genomic instability and reduces the effect of RCM on aging while rapamycin treatment can also prevent age-related epigenetic changes, in part by increasing the occupancy at targets of Rsc9, a subunit of the RSC chromatin remodeling complex. Additional age-related compounds include chromatin modifying enzymes (e.g. Remodelin), histone acetylation (e.g. spermidine, sodium butyrate, and suberoylanilide hydroxamic acid (SAHA)). Genetic modifications may include methods further described herein. Example transcription factors for genetic modification include Oct3/4, Sox2, Klf4 and c-Myc, for example.

Perturbative Analysis

The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature really was the proxy for a phenotype of interest, it could be used to find small molecules that effect that phenotype without knowledge of a validated drug target. The methods and systems described herein may be used to screen for drugs that reduce the signature in cells having a specific endotype as described herein. In an example embodiment, the invention comprises identifying one or more key regulatory features by matching microscopy imaging data with one or more perturbation molecular signatures from a perturbation analysis. In an example embodiment, a machine learning model/network learns phenotype perturbation from microscopy imaging data and phenotype analysis. In an example embodiment, microscopy imaging data is received by at least one computing device, a machine learning network determines one or more phenotype perturbation, and determines whether a small molecule or genetic modifying agents is related to the phenotypic perturbation. In example embodiments, the result of the phenotypic perturbation resolves a diagnosis, prognosis, or theranosis of a disease or age.

In example embodiments, the perturbation analysis can be generated by perturbation of cells (e.g., cell lines, or primary cells) or complex cell populations (e.g., multicellular systems, such as, organoid, tissue explant, or organ on a chip). The perturbation analysis can include signatures for therapeutic agents, such as drugs, small molecules, or antibodies. More generally, any compound screen with a molecular read-out as described herein (e.g., a read-out, such as Raman microscopy, differential gene expression, proteomic, metabolic, spatial, epigenetic, image-based profiling of morphology and cellular markers, or lipodomics, used to construct the microscopy imaging data) can be used to nominate compounds by similarity or connectivity with the methods and systems described herein. The perturbation datasets can include signatures for gene knockdown, gene knockout, gene overexpression, gene repression or gene activation. In an example embodiment, regulatory proteins, such as transcription factors are perturbed (e.g., by overexpression or knockdown). In an example embodiment, perturbation is by deletion of regulatory elements.

In example embodiments, the perturbation analysis include pooled perturbation assays. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; Feldman et al., Lentiviral co-packaging mitigates the effects of intermolecular recombination and multiple integrations in pooled genetic screens, bioRxiv 262121, doi: doi.org/10.1101/262121; Datlinger, et al., 2017, Pooled CRISPR screening with single-cell transcriptome readout. Nature Methods. Vol. 14 No. 3 DOI: 10.1038/nmeth.4177; Hill et al., On the design of CRISPR-based single cell molecular screens, Nat Methods. 2018 April; 15 (4): 271-274; Replogle, et al., "Combinatorial single-cell CRISPR screens by direct guide RNA capture and targeted sequencing" Nat Biotechnol (2020). doi.org/10.1038/s41587-020-0470-y; Schraivogel D, Gschwind A R, Milbank J H, et al. "Targeted Perturb-seq enables genome-scale genetic screens in single cells". Nat Methods. 2020; 17(6):629-635; Frangieh C J, Melms J C, Thakore P I, et al. Multimodal pooled Perturb-CITE-seq screens in patient models define mechanisms of cancer immune evasion. Nat Genet. 2021; 53(3):332-341; US patent application publication number US20200283843A1; and US Patent number U.S. Pat. No. 11,214,797B2).

In example embodiments, the methods and systems described herein are compared to signatures obtained in prior perturbation assays. For example, the Connectivity Map (cmap) is a comprehensive catalog of cellular signatures representing systematic perturbation with genetic (thus reflecting protein function) and pharmacologic (thus reflecting small-molecule function) perturbagens. The methods and systems described herein can learn the functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). As of 2022, CMap has generated a library containing over 1.5M gene expression profiles from ~5,000 small-molecule compounds, and ~3,000 genetic reagents, tested in multiple cell types. Cmap can be used to learn matching signatures in silico. In another example, the JUMP-Cell Painting Consortium is a data-driven approach to drug discovery based on cellular imaging, image analysis, and high dimensional data analytics (see, e.g., jump-cellpainting.broadinstitute.org). The consortium will create a massive cell-imaging dataset, displaying more than 1 billion cells responding to over 140,000 small molecules and genetic perturbations. JUMP-Target provides lists and 384-well plate maps of 306 compounds and corresponding genetic perturbations, designed to assess connectivity in profiling assays. JUMP-MOA provides a list and a 384-well plate map of 90 compounds in quadruplicate (corresponding to 47 mechanism-of-action classes), designed to assess connectivity in profiling assays.

In one embodiment, CRISPR systems may be used to perturb protein-coding genes or non-protein-coding DNA. CRISPR systems may be used to knockout protein-coding genes by frameshifts, point mutations, inserts, or deletions. In example embodiments, a CRISPR system is used to create an INDEL. CRISPRa/i/x technology may be used in perturbation assays (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353 (6305); Yang et al., 2016, Engineering and optimising deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035).

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

In one embodiment, perturbation is performed using small molecules. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

Epigenetic proteins can regulate many cellular pathways. In example embodiments, a perturbation signature identified using epigenetic protein targeting drugs are matched to microscopy imaging data. Small molecules targeting epigenetic proteins are currently being developed and/or used in the clinic to treat disease (see, e.g., Qi et al., HEDD: the human epigenetic drug database. Database, 2016, 1-10; and Ackloo et al., Chemical probes targeting epigenetic proteins: Applications beyond oncology. Epigenetics 2017, VOL. 12, NO. 5, 378-400). In certain embodiments, the one or more agents comprise a histone acetylation inhibitor, histone deacetylase (HDAC) inhibitor, histone lysine methylation inhibitor, histone lysine demethylation inhibitor, DNA methyltransferase (DNMT) inhibitor, inhibitor of acetylated histone binding proteins, inhibitor of methylated histone binding proteins, sirtuin inhibitor, protein arginine methyltransferase inhibitor or kinase inhibitor. In certain embodiments, any small molecule exhibiting the functional activity described above may be used in the present invention. In certain embodiments, the DNA methyltransferase (DNMT) inhibitor is selected from the group consisting of azacitidine (5-azacytidine), decitabine (5-aza-2'-deoxycytidine), EGCG (epigallocatechin-3-gallate), zebularine, hydralazine, and procainamide. In certain embodiments, the histone acetylation inhibitor is C646. In certain embodiments, the histone deacetylase (HDAC) inhibitor is selected from the group consisting of vorinostat, givinostat, panobinostat, belinostat, entinostat, CG-1521, romidepsin, ITF-A, ITF-B, valproic acid, OSU-HDAC-44, HC-toxin, magnesium valproate, plitidepsin, tasquinimod, sodium butyrate, mocetinostat, carbamazepine, SB939, CHR-2845, CHR-3996, JNJ-26481585, sodium phenylbutyrate, pivanex, abexinostat, resminostat, dacinostat, droxinostat, and trichostatin A (TSA). In certain embodiments, the histone lysine demethylation inhibitor is selected from the group consisting of pargyline, clorgyline, bizine, GSK2879552, GSK-J4, KDM5-C70, JIB-04, and tranylcypromine. In certain embodiments, the histone lysine methylation inhibitor is selected from the group consisting of EPZ-6438, GSK126, CPI-360, CPI-1205, CPI-0209, DZNep, GSK343, EI1, BIX-01294, UNC0638, EPZ004777, GSK343, UNC1999 and UNC0224. In certain embodiments, the inhibitor of acetylated histone binding proteins is selected from the group consisting of AZD5153 (see e.g., Rhyasen et al., AZD5153: A Novel Bivalent BET Bromodomain Inhibitor Highly Active against Hematologic Malignancies, Mol Cancer Ther. 2016 November; 15 (11): 2563-2574. Epub 2016 Aug. 29), PFI-1, CPI-203, CPI-0610, RVX-208, OTX015, I-BET151, I-BET762, I-BET-726, dBET1, ARV-771, ARV-825, BETd-260/ZBC260 and MZ1. In certain embodiments, the inhibitor of methylated histone binding proteins is selected from the group consisting of UNC669 and UNC1215. In certain embodiments, the sirtuin inhibitor comprises nicotinamide.

Selecting Therapeutic Agents

In example embodiments, a therapeutic agent is selected if the therapeutic agent has a signature in a perturbation screen determined from microscopy imaging data by methods and systems described herein (e.g., positively or negatively correlates with microscopy imaging data for a high or low risk endotype, such as a pPS). In example embodiments, the therapeutic agent generates a signature in the correct direction for treating a subject having the disease and the endotype. For example, reducing a high risk endotype signature or increasing a low risk endotype signature. In example embodiments, a therapeutic agent is selected if the therapeutic agent targets a gene or pathway identified in a perturbation screen. For example, if perturbation of a gene or pathway provides a signature that correlates (negatively or positively) with microscopy imaging data determined by methods and/or systems described herein, then any therapeutic agent targeting the gene or pathway could be used as a therapeutic agent. In example embodiments, the one or more agents comprises a small molecule inhibitor, small molecule degrader (e.g., ATTEC, AUTAC, LYTAC, or PROTAC), genetic modifying agent, antisense oligonucleotides (ASO), antibody, antibody fragment, antibody-like protein scaffold, aptamer, protein, or any combination thereof.

Small Molecules

One type of small molecule applicable to the present invention is a degrader molecule (see, e.g., Ding, et al., Emerging New Concepts of Degrader Technologies, Trends Pharmacol Sci. 2020 July; 41(7):464-474). The terms "degrader" and "degrader molecule" refer to all compounds capable of specifically targeting a protein for degradation (e.g., ATTEC, AUTAC, LYTAC, or PROTAC, reviewed in Ding, et al. 2020). Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57:107-123; and Lai et al., Modular PROTAC Design for the Degradation of Oncogenic BCR-ABL Angew Chem Int Ed Engl. 2016 January 11; 55(2): 807-810). In certain embodiments, LYTACs are particularly advantageous for cell surface proteins.

Genetic Modifying Agents

In example embodiments, a genetic modifying agent, such as a programmable nuclease, may be used to alter expression of a target gene, such as a regulator protein for a genetically-anchored molecular signature. Gene editing using programmable nucleases may utilize two different cell repair pathways, non-homologous end joining (NHEJ) and homology directed repair. Example programmable nucleases for use in this manner include zinc finger nucleases (ZFN), TALE nucleases (TALENS), meganucleases, and CRISPR-Cas systems.

CRISPR-Cas

In one example embodiment, the gene editing system is a CRISPR-Cas system. The CRISPR-Cas system comprises a Cas polypeptide and a guide sequence, wherein the guide sequence is capable of forming a CRISPR-Cas complex with the Cas polypeptide and directing site-specific binding of the CRISPR-Cas sequence to a target sequence. The Cas polypeptide may induce a double- or single-stranded break at a designated site in the target sequence. The site of CRISPR-Cas cleavage, for most CRISPR-Cas systems, is dictated by distance from a protospacer-adjacent motif (PAM), discussed in further detail below. Accordingly, a guide sequence may be selected to direct the CRISPR-Cas system to induce cleavage at a desired target site at or near the one or more variants.

NHEJ-Based Editing

In one example embodiment, the CRISPR-Cas system is used to introduce one or more insertions or deletions in a target gene. More than one guide sequence may be selected to insert multiple insertion, deletions, or combination thereof. Likewise, more than one Cas protein type may be used, for example, to maximize targets sites adjacent to different PAMs. In one example embodiment, a guide sequence is selected that directs the CRISPR-Cas system to make one or more insertions or deletions within an enhancer region in a target gene.

HDR Template Based Editing

In one example embodiment, a donor template is provided to replace a genomic sequence in a target gene. A donor template may comprise an insertion sequence flanked by two homology regions. The insertion sequence comprises an edited sequence to be inserted in place of the target sequence (e.g. a portion of genomic DNA comprising the one or more variants). The homology regions comprise sequences that are homologous to the genomic DNA strands at the site of the CRISPR-Cas induced double-strand break. Cellular HDR mechanisms then facilitate insertion of the insertion sequence at the site of the DSB. The donor template may include a sequence which results in a change in sequence of 1, 2, 3, 4, 5, 6, 7, 8, 9, 10, 11, 12 or more nucleotides of the target sequence.

A donor template may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

The homology regions of the donor template may be complementary to a portion of a polynucleotide comprising the target sequence. When optimally aligned, a donor template might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The donor template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

Homology arms of the donor template may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In one example embodiment, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

The donor template may further comprise a marker. Such a marker may make it easy to screen for targeted integrations. Examples of suitable markers include restriction sites, fluorescent proteins, or selectable markers. The donor template of the disclosure can be constructed using recombinant techniques (see, for example, Sambrook et al., 2001 and Ausubel et al., 1996).

In one example embodiment, a donor template is a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Class 1 Systems

The CRISPR-Cas therapeutic methods disclosed herein may be designed for use with Class 1 CRISPR-Cas systems. In certain example embodiments, the Class 1 system may be Type I, Type III or Type IV CRISPR-Cas as described in Makarova et al. "Evolutionary classification of CRISPR-Cas systems: a burst of class 2 and derived variants" Nature Reviews Microbiology, 18:67-81 (February 2020)., incorporated in its entirety herein by reference, and particularly as described in FIG. 1, p. 326. The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g. Cas1, Cas2, RNA nuclease), and/or one or more accessory proteins (e.g. Cas 4, DNA nuclease), CRISPR associated Rossman fold (CARF) domain containing proteins, and/or RNA transcriptase. Although Class 1 systems have limited sequence similarity, Class 1 system proteins can be identified by their similar architectures, including one or more Repeat Associated Mysterious Protein (RAMP) family subunits, e.g. Cas 5, Cas6, Cas7. RAMP proteins are characterized by having one or more RNA recognition motif domains. Large subunits (for example cas8 or cas10) and small subunits (for example, cas11) are also typical of Class 1 systems. See, e.g., FIGS. 1 and 2. Koonin E V, Makarova K S. 2019 Origins and evolution of CRISPR-Cas systems. Phil. Trans. R. Soc. B 374:20180087, DOI: 10.1098/rstb.2018.0087. In one aspect, Class 1 systems are characterized by the signature protein Cas3. The Cascade in particular Class1 proteins can comprise a dedicated complex of multiple Cas proteins that binds pre-crRNA and recruits an additional Cas protein, for example Cas6 or Cas5, which is the nuclease directly responsible for processing pre-crRNA. In one aspect, the Type I CRISPR protein comprises an effector complex comprises one or more Cas5 subunits and two or more Cas7 subunits. Class 1 subtypes include Type I-A, I-B, I-C, I-U, I-D, I-E, and I-F, Type IV-A and IV-B, and Type III-A, III-D, III-C, and III-B. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas. 1709035114; see also, Makarova et al, the CRISPR Journal, v. 1, n5, FIG. 5.

Class 2 Systems

The CRISPR-Cas therapeutic methods disclosed herein may be designed for use with. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1 (V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside a split Ruv-C like nuclease domain sequence. The Type V systems (e.g., Cas12) only contain a RuvC-like nuclease domain that cleaves both strands. Some Type V systems have also been found to possess this collateral activity with two single-stranded DNA in in vitro contexts.

In one example embodiment, the Class 2 system is a Type II system. In one example embodiment, the Type II CRISPR-Cas system is a II-A CRISPR-Cas system. In one example embodiment, the Type II CRISPR-Cas system is a II-B CRISPR-Cas system. In one example embodiment, the Type II CRISPR-Cas system is a II-C1 CRISPR-Cas system. In one example embodiment, the Type II CRISPR-Cas system is a II-C2 CRISPR-Cas system. In sone example embodiments, the Type II system is a Cas9 system. In some embodiments, the Type II system includes a Cas9.

In one example embodiment, the Class 2 system is a Type V system. In one example embodiment, the Type V CRISPR-Cas system is a V-A CRISPR-Cas system. In one example embodiment, the Type V CRISPR-Cas system is a V-B1 CRISPR-Cas system. In one example embodiment, the Type V CRISPR-Cas system is a V-B2 CRISPR-Cas system. In one example embodiment, the Type V CRISPR-Cas system is a V-C CRISPR-Cas system. In one example embodiment, the Type V CRISPR-Cas system is a V-D CRISPR-Cas system. In one example embodiment, the Type V CRISPR-Cas system is a V-E CRISPR-Cas system. In one example embodiment, the Type V CRISPR-Cas system is a V-F1 CRISPR-Cas system. In one example embodiment, the Type V CRISPR-Cas system is a V-F1 (V-U3) CRISPR-Cas system. In one example embodiment, the Type V CRISPR-Cas system is a V-F2 CRISPR-Cas system. In one example embodiment, the Type V CRISPR-Cas system is a V-F3 CRISPR-Cas system. In one example embodiment, the Type V CRISPR-Cas system is a V-G CRISPR-Cas system. In one example embodiment, the Type V CRISPR-Cas system is a V-H CRISPR-Cas system. In one example embodiment, the Type V CRISPR-Cas system is a V-I CRISPR-Cas system. In one example embodiment, the Type V CRISPR-Cas system is a V-K (V-U5) CRISPR-Cas system. In one example embodiment, the Type V CRISPR-Cas system is a V-U1 CRISPR-Cas system. In one example embodiment, the Type V CRISPR-Cas system is a V-U2 CRISPR-Cas system. In one example embodiment, the Type V CRISPR-Cas system is a V-U4 CRISPR-Cas system. In one example embodiment, the Type V CRISPR-Cas is a Cas12a (Cpf1), Cas12b (C2c1), Cas12c (C2c3), Cas12d (CasY), Cas12e (CasX), Cas14, and/or CasΦ.

Guide Molecules

The following include general design principles that may be applied to the guide molecule. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36 (4) 702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A.R. Gruber et al., 2008, Cell 106 (1): 23-24; and PA Carr and GM Church, 2009, Nature Biotechnology 27 (12): 1151-62).

In one example embodiment, a guide RNA or crRNA may comprise, consist essentially of, or consist of a direct repeat (DR) sequence and a guide sequence or spacer sequence. In another example embodiment, the guide RNA or crRNA may comprise, consist essentially of, or consist of a direct repeat sequence fused or linked to a guide sequence or spacer sequence. In another example embodiment, the direct repeat sequence may be located upstream (i.e., 5') from the guide sequence or spacer sequence. In other embodiments, the direct repeat sequence may be located downstream (i.e., 3') from the guide sequence or spacer sequence.

In one example embodiment, the crRNA comprises a stem loop, preferably a single stem loop. In one example embodiment, the direct repeat sequence forms a stem loop, preferably a single stem loop.

In one example embodiment, the spacer length of the guide RNA is from 15 to 35 nt. In another example embodiment, the spacer length of the guide RNA is at least 15 nucleotides. In another example embodiment, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All of (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT US2019/045582, specifically paragraphs [0178]-[0333], which is incorporated herein by reference.

Target Sequences, PAMs, and PFSs

In the context of formation of a CRISPR complex, "target sequence" refers to a sequence to which a guide sequence is designed to have complementarity, where hybridization between a target sequence and a guide sequence promotes the formation of a CRISPR complex. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

PAM elements are sequences that can be recognized and bound by Cas proteins. Cas proteins/effector complexes can then unwind the dsDNA at a position adjacent to the PAM element. It will be appreciated that Cas proteins and systems target RNA do not require PAM sequences (Marraffini et al. 2010. Nature. 463:568-571). Instead, many rely on PFSs, which are discussed elsewhere herein. In one example embodiment, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16 (4): 504-517. Table A (from Gleditzsch et al. 2019) below shows several Cas polypeptides and the PAM sequence they recognize.

TABLE A

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |
| Cas1 | 5'-CTT-3' |
| Cas8e | 5'-ATG-3' |
| Type I-A | 5'-CCN-3' |
| Type I-B | TTC, ACT, TAA, TAT, TAG, and CAC |
| Type I-C | NTTC |
| Type I-E | 5'-AAG-3' |
| TypeI-F | GG |

In a preferred embodiment, the CRISPR effector protein may recognize a 3' PAM. In one example embodiment, the CRISPR effector protein may recognize a 3' PAM which is 5'H, wherein His A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23;523 (7561): 481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155 (Pt. 3): 733-740; Atschul et al. 1990. J. Mol. Biol. 215:403-410; Biswass et al. 2013 RNA Biol. 10:817-827; and Grissa et al. 2007. Nucleic Acid Res. 35: W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016.Mol. Cell. 16:253), and negative screening (Zetsche et al. 2015. Cell. 163:759-771).

As previously mentioned, CRISPR-Cas systems that target RNA do not typically rely on PAM sequences. Instead, such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16 (4): 504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16 (4): 504-517.

Overall Type VI CRISPR-Cas systems appear to have less restrictive rules for substrate (e.g., target sequence) recognition than those that target DNA (e.g., Type V and type II).

Sequences Related to Nucleus Targeting and Transportation

In some embodiments, one or more components (e.g., the Cas protein) in the composition for engineering cells may comprise one or more sequences related to nucleus targeting and transportation. Such sequences may facilitate the one or more components in the composition for targeting a sequence within a cell. In order to improve targeting of the CRISPR-Cas protein used in the methods of the present disclosure to the nucleus, it may be advantageous to provide one or both of these components with one or more nuclear localization sequences (NLSs).

In one example embodiment, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO:1) or PKKKRKVEAS (SEQ ID NO:2); the NLS from nucleoplasmin (e.g., the nucleoplasmin bipartite NLS with the sequence KRPAATKKAGQAKKKK (SEQ ID NO:3)); the c-myc NLS having the amino acid sequence PAAKRVKLD (SEQ ID NO:4) or RQRRNELKRSP (SEQ ID NO:5); the hRNPA1 M9 NLS having the sequence NQSSNFGPMKGGNFGGRSSGPYGGGGQYFAKPRNQGGY (SEQ ID NO:6); the sequence RMRIZFKNKGKDTAELRRRRVEVSVELRKAKKDEQILKRRNV (SEQ ID NO:7) of the IBB domain from importin-alpha; the sequences VSRKRPRP (SEQ ID NO:8) and PPKKARED (SEQ ID NO: 9) of the myoma T protein; the sequence PQPKKKPL (SEQ ID NO: 10) of human p53; the sequence SALIKKKKKMAP (SEQ ID NO:11) of mouse c-abl IV; the sequences DRLRR (SEQ ID NO: 12) and PKQKKRK (SEQ ID NO:13) of the influenza virus NS1; the sequence RKLKKKIKKL (SEQ ID NO:14) of the Hepatitis virus delta antigen; the sequence REKKKFLKRR (SEQ ID NO:15) of the mouse Mx1 protein; the sequence KRKGDEVDGVDEVAKKKSKK (SEQ ID NO:16) of the human poly (ADP-ribose) polymerase; and the sequence RKCLQAGMNLEARKTKK (SEQ ID NO: 17) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the Cas protein, or exposed to a Cas protein lacking the one or more NLSs.

The Cas proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the Cas proteins, an NLS attached to the C-terminal of the protein.

Zinc Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

Zinc Finger proteins can comprise a functional domain (e.g., activator domain). The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALENS

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ Of $_{34}$ or $_{35})$ z, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011). each of which is incorporated herein by reference in its entirety.

The polypeptides used in methods of the invention can be isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in one example embodiment, the TALE polypeptides described herein further comprise an N-terminal capping region and/or a C-terminal capping region.

An exemplary amino acid sequence of a N-terminal capping region is:

```
                                        (SEQ ID NO: 18)
MDPIRSRTPSPARELLSGPQPDGVQPTADRGVSPPAGGP

LDGLPARRTMSRTRLPSPPAPSPAFSADSFSDLLRQFDPSLFNTS

LFDSLPPFGAHHTEAATGEWDEVQSGLRAADAPPPTMRVAVTA

ARPPRAKPAPRRRAAQPSDASPAAQVDLRTLGYSQQQQEKIKP

KVRSTVAQHHEALVGHGFTHAHIVALSQHPAALGTVAVKYQD

MIAALPEATHEAIVGVGKQWSGARALEALLTVAGELRGPPLQL

DTGQLLKIAKRGGVTAVEAVHAWRNALTGAPLN
```

An exemplary amino acid sequence of a C-terminal capping region is:

```
                                        (SEQ ID NO: 19)
RPALESIVAQLSRPDPALAALTNDHLVALACLGGRPAL

DAVKKGLPHAPALIKRTNRRIPERTSHRVADHAQVVRVLGFFQ

CHSHPAQAFDDAMTQFGMSRHGLLQLFRRVGVTELEARSGTLP

PASQRWDRILQASGMKRAKPSPTSTQTPDQASLHAFADSLERD

LDAPSPMHEGDQTRAS
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in one example embodiment, fragments of the N-terminal and/or C-terminal capping regions are included in the TALE polypeptides described herein.

In one example embodiment, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In another example embodiment, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In one example embodiment, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In one example embodiment, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4× domain or a Krüppel-associated box (KRAB) or fragments of the KRAB domain. In some embodiments, the effector domain is an enhancer of transcription (i.e., an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021, 867, 8,119,361, 8,119,381, 8,124,369, and 8,129,134, which are specifically incorporated herein by reference.

Engineered Transcriptional Activators (CRISPRa)

In one example embodiment, a programmable nuclease system is used to recruit an activator protein to a target gene in order to enhance expression. In one example embodiment, the activator protein is recruited to the enhancer region of the target gene. For example, a catalytically inactive Cas protein ("dCas") fused to an activator can be used to recruit that activator protein to the target sequence. Accordingly, a guide sequence is designed to direct binding of the dCas-activator fusion such that the activator can interact with the target genomic region and induce target gene expression. The Cas protein used may be any of the Cas proteins disclosed above. In one example protein, the Cas protein is a dCas9.

In one embodiment, the programmable nuclease system is a CRISPRa system (see, e.g., US20180057810A1; and Konermann et al. "Genome-scale transcriptional activation by an engineered CRISPR-Cas9 complex" Nature. 2014 Dec. 10. doi: 10.1038/nature14136). Numerous genetic variants associated with disease phenotypes are found to be in non-coding region of the genome, and frequently coincide with transcription factor (TF) binding sites and non-coding RNA genes. In one embodiment, a CRISPR system may be used to activate gene transcription. A nuclease-dead RNA-guided DNA binding domain, dCas9, tethered to transcriptional activator domains that promote gene activation (e.g., p65) may be used for "CRISPRa" that activates transcription. In one example embodiment, for use of dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, one or more activator domains are recruited. In one example embodiment, the activation domain is linked to the CRISPR enzyme. In another example embodiment, the guide sequence includes aptamer sequences that bind to adaptor proteins fused to an activation domain. In general, the positioning of the one or more activator domains on the inactivated CRISPR enzyme or CRISPR complex is one which allows for correct spatial orientation for the activator domain to affect the target with the attributed functional effect. For example, the transcription activator is placed in a spatial orientation which allows it to affect the transcription of the target. This may include positions other than the N-/C-terminus of the CRISPR enzyme.

In another example embodiment, a zinc finger system is used to recruit an activation domain to the target gene. In one example embodiment, the activation domain is linked to the zinc finger system. In general, the positioning of the one or more activator domains on the zinc finger system is one which allows for correct spatial orientation for the activator domain to affect the target with the attributed functional effect.

In another example embodiment, a TALE system is used to recruit an activation domain to the target gene. In one example embodiment, the activation domain is linked to the TALE system. In general, the positioning of the one or more activator domains on the TALE system is one which allows for correct spatial orientation for the activator domain to affect the target with the attributed functional effect. For example, the transcription activator is placed in a spatial orientation which allows it to affect the transcription of the target.

In another example embodiment, a meganuclease system is used to recruit an activation domain to the target gene. In one example embodiment, the activation domain is linked to the meganuclease system. In general, the positioning of the one or more activator domains on the inactivated meganuclease system is one which allows for correct spatial orientation for the activator domain to affect the target with the attributed functional effect. For example, the transcription activator is placed in a spatial orientation which allows it to affect the transcription of the target.

Base Editing

In one example embodiment, a method of treating subjects comprises administering a base editing system that is directed to a target gene (e.g., a regulator). A base-editing system may comprise a Cas polypeptide linked to a nucleobase deaminase ("base editing system") and a guide molecule capable of forming a complex with the Cas polypeptide and directing sequence-specific binding of the base editing system at a target sequence. In one example embodiment, the Cas polypeptide is catalytically inactive. In another example embodiment, the Cas polypeptide is a nickase. The Cas polypeptide may be any of the Cas polypeptides disclosed above. In one example embodiment, the Cas polypeptide is a Type II Cas polypeptide. In one example embodiment, the Cas polypeptide is a Cas9 polypeptide. In another example embodiment, the Cas polypeptide is a Type V Cas polypeptide. In one example embodiment, the Cas polypeptide is a Cas12a or Cas12b polypeptide. The nucleobase deaminase may be cytosine base editor (CBE) or adenosine base editors (ABEs). CBEs convert C·G base pairs into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Example base editing systems are disclosed in Rees and Liu. 2018. Nat. Rev. Genet. 19 (12): 770-788, particularly at FIGS. 1*b*, 2*a*-2*c*, 3*a*-3*f*, and Table 1, which is specifically incorporated herein by reference. In certain example embodiments, the base editing system may further comprise a DNA glycosylase inhibitor.

The editing window of a base editing system may range over a 5-8 nucleotide window, depending on the base editing system used. Id. Accordingly, given the base editing system used, a guide sequence may be selected to direct the base editing system to convert a base or base pair of one or more target genes.

ARCUS Based Editing

In one example embodiment, a method of treating subjects comprises administering an ARCUS base editing system. Exemplary methods for using ARCUS can be found in U.S. Pat. No. 10,851,358, US Publication No. 2020-0239544, and WIPO Publication No. 2020/206231 which are incorporated herein by reference Prime Editing In one example embodiment, a method of treating subjects comprises administering a prime editing system directed to a target gene. In one example embodiment, a prime editing system comprises a Cas polypeptide having nickase activity, a reverse transcriptase, and a prime editing guide RNA (pegRNA). Cas polypeptide, and/or reverse transcriptase can be coupled together or otherwise associate with each other to form a prime editing complex and edit a target sequence. The Cas polypeptide may be any of the Cas polypeptides disclosed above. In one example embodiment, the Cas polypeptide is a Type II Cas polypeptide. In another example embodiment, the Cas polypeptide is a Cas9 nickase. In one example embodiment, the Cas polypeptide is a Type V Cas polypeptide. In another example embodiment, the Cas polypeptide is a Cas12a or Cas12b.

The prime editing guide molecule (pegRNA) comprises a primer binding site (PBS) configured to hybridize with a portion of a nicked strand on a target polynucleotide (e.g. genomic DNA) a reverse transcriptase (RT) template comprising the edit to be inserted in the genomic DNA and a spacer sequence designed to hybridize to a target sequence at the site of the desired edit. The nicking site is dependent on the Cas polypeptide used and standard cutting preference for that Cas polypeptide relative to the PAM. Thus, based on the Cas polypeptide used, a pegRNA can be designed to direct the prime editing system to introduce a nick where the desired edit should take place.

The pegRNA can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576:149-157, particularly at pg. 3, FIG. 2*a*-2b, and Extended Data FIGS. 5*a-c*.

CRISPR Associated Transposases (CAST)

In one example embodiment, a method of treating a subject comprises administering a CAST system that replaces a genomic region in a target gene. In one example embodiment, a CAST system is used to replace all or a portion of an enhancer controlling target gene expression.

CAST systems comprise a Cas polypeptide, a guide sequence, a transposase, and a donor construct. The transposase is linked to or otherwise capable of forming a complex with the Cas polypeptide. The donor construct comprises a donor sequence to be inserted into a target polynucleotide and one or more transposase recognition elements. The transposase is capable of binding the donor construct and excising the donor template and directing insertion of the donor template into a target site on a target polynucleotide (e.g. genomic DNA). The guide molecule is capable of forming a CRISPR-Cas complex with the Cas polypeptide, and can be programmed to direct the entire CAST complex such that the transposase is positioned to insert the donor sequence at the target site on the target polynucleotide. For multimeric transposase, only those transposases needed for recognition of the donor construct and transposition of the donor sequence into the target polypeptide may be required. The Cas may be naturally catalytically inactive or engineered to be catalytically inactive.

In one example embodiment, the CAST system is a Tn7-like CAST system, wherein the transposase comprises one or more polypeptides from a Tn7 or Tn7-like transposase. The Cas polypeptide of the Tn7-like transposase may be a Class 1 (multimeric effector complex) or Class 2 (single protein effector) Cas polypeptide.

In one example embodiments, the Cas polypeptide is a Class 1 Type-If Cas polypeptide. In one example embodiment, the Cas polypeptide may comprise a cas6, a cas7, and a cas8-cas5 fusion. In one example embodiments, the Tn7 transposase may comprise TnsB, TnsC, and TniQ. In another example embodiment, the Tn7 transposase may comprise TnsB, TnsC, and TnsD. In certain example embodiments, the Tn7 transposase may comprise TnsD, TnsE, or both. As used herein, the terms "TnsAB", "TnsAC", "TnsBC", or "TnsABC" refer to a transponson complex comprising TnsA and TnsB, TnsA and TnsC, TnsB and TnsC, TnsA and TnsB and TnsC, respectively. In these combinations, the transposases (TnsA, TnsB, TnsC) may form complexes or fusion proteins with each other. Similarly, the term TnsABC-TniQ refer to a transposon comprising TnsA, TnsB, TnsC, and TniQ, in a form of complex or fusion protein. An example Type 1f-Tn7 CAST system is described in Klompe et al. Nature, 2019, 571:219-224 and Vo et al. bioRxiv, 2021, doi.org/10.1101/2021.02.11.430876, which are incorporated herein by reference.

In one example embodiment, the Cas polypeptide is a Class 1 Type-1b Cas polypeptide. In one example embodiment, the Cas polypeptide may comprise a cas6, a cas7, and a cas8b (e.g. a ca8b3). In one example embodiments, the Tn7 transposase may comprise TnsB, TnsC, and TniQ. In another example embodiment, the Tn7 transposase may comprise TnsB, TnsC, and TnsD. In certain example embodiments, the Tn7 transposase may comprise TnsD, TnsE, or both. As used herein, the terms "TnsAB", "TnsAC", "TnsBC", or "TnsABC" refer to a transponson complex comprising TnsA and TnsB, TnsA and TnsC, TnsB and TnsC, TnsA and TnsB and InsC, respectively. In these combinations, the transposases (TnsA, TnsB, TnsC) may form complexes or fusion proteins with each other. Similarly, the term TnsABC-TniQ refer to a transposon comprising TnsA, TnsB, TnsC, and TniQ, in a form of complex or fusion protein.

In one example embodiment, the Cas polypeptide is Class 2, Type V Cas polypeptide. In one example embodiment, the Type V Cas polypeptide is a Cas12k. In one example embodiments, the Tn7 transposase may comprise TnsB, TnsC, and TniQ. In another example embodiment, the Tn7 transposase may comprise TnsB, TnsC, and TnsD. In certain example embodiments, the Tn7 transposase may comprise TnsD, TnsE, or both. As used herein, the terms "TnsAB", "TnsAC", "TnsBC", or "TnsABC" refer to a transponson complex comprising TnsA and TnsB, TnsA and TnsC, TnsB and TnsC, TnsA and TnsB and TnsC, respectively. In these combinations, the transposases (TnsA, TnsB, TnsC) may form complexes or fusion proteins with each other. Similarly, the term TnsABC-TniQ refer to a transposon comprising TnsA, TnsB, TnsC, and TniQ, in a form of complex or fusion protein. An example Cas12k-Tn7 CAST system is described in Strecker et al. Science, 2019 365:48-53, which is incorporated herein by reference.

In one example embodiment, the CAST system is a Mu CAST system, wherein the transposase comprises one or more polypeptides of a Mu transposase. An example Mu CAST system is disclosed in WO/2021/041922 which is incorporated herein by reference.

In one example embodiment, the CAST comprise a catalytically inactive Type II Cas polypeptide (e.g. dCas9) fused to one or more polypeptides of a Tn5 transposase. In another example embodiment, the CAST system comprises a catalytically inactive Type II Cas polypeptide (e.g. dCas9) fused to a piggyback transposase.

Epigenetic Editing

In example embodiments, the one or more agents is an epigenetic modification polypeptide comprising a DNA binding domain linked to or otherwise capable of associating with an epigenetic modification domain such that binding of the DNA binding domain at target sequence on genomic DNA (e.g., chromatin) results in one or more epigenetic modifications by the epigenetic modification domain that increases or decreases expression of the one or more polypeptides. As used herein, "linked to or otherwise capable of associating with" refers to a fusion protein or a recruitment domain or an adaptor protein, such as an aptamer (e.g., MS2) or an epitope tag. The recruitment domain or the adaptor protein can be linked to an epigenetic modification domain or the DNA binding domain (e.g., an adaptor for an aptamer). The epigenetic modification domain can be linked to an antibody specific for an epitope tag fused to the DNA binding domain. An aptamer can be linked to a guide sequence.

In example embodiments, the DNA binding domain is a programmable DNA binding protein linked to or otherwise capable of associating with an epigenetic modification domain. Programmable DNA binding proteins for modifying the epigenome include, but are not limited to CRISPR systems, transcription activator-like effectors (TALEs), Zn finger proteins and meganucleases (see, e.g., Thakore P I, Black J B, Hilton I B, Gersbach C A. Editing the epigenome: technologies for programmable transcription and epigenetic modulation. Nat Methods. 2016; 13 (2): 127-137; and described further herein). In example embodiments, the DNA binding domain is a nuclease-deficient RNA-guided DNA endonuclease enzyme or a nuclease-deficient endonuclease enzyme. In example embodiments, a CRISPR system having an inactivated nuclease activity (e.g., dCas) is used as the DNA binding domain.

In example embodiments, the epigenetic modification domain is a functional domain and includes, but is not limited to a histone methyltransferase (HMT) domain, histone demethylase domain, histone acetyltransferase (HAT) domain, histone deacetylation (HDAC) domain, DNA methyltransferase domain, DNA demethylation domain, histone phosphorylation domain (e.g., serine and threonine, or tyrosine), histone ubiquitylation domain, histone sumoylation domain, histone ADP ribosylation domain, histone proline isomerization domain, histone biotinylation domain, histone citrullination domain (see, e.g., Epigenetics, Second Edition, 2015, Edited by C. David Allis; Marie-Laure Caparros; Thomas Jenuwein; Danny Reinberg; Associate Editor Monika Lachlan; Dawson M A, Kouzarides T. Cancer epigenetics: from mechanism to therapy. Cell. 2012; 150 (1): 12-27; Syding L A, Nickl P, Kasparek P, Sedlacek R. CRISPR/Cas9 Epigenome Editing Potential for Rare Imprinting Diseases: A Review. Cells. 2020; 9 (4): 993; and Zhang Y. Transcriptional regulation by histone ubiquitination and deubiquitination. Genes Dev. 2003; 17 (22): 2733-2740). Example epigenetic modification domains can be obtained from, but are not limited to chromatin modifying enzymes, such as, DNA methyltransferases (e.g., DNMT1, DNMT3a and DNMT3b), TET1, TET2, thymine-DNA glycosylase (TDG), GCN5-related N-acetyltransferases family (GNAT), MYST family proteins (e.g., MOZ and MORF), and CBP/p300 family proteins (e.g., CBP, p300), Class I HDACs (e.g., HDAC 1-3 and HDAC8), Class II HDACs (e.g., HDAC 4-7 and HDAC 9-10), Class III HDACs (e.g., sirtuins), HDAC11, SET domain containing methyltransferases (e.g., SET7/9 (KMT7, NCBI Entrez Gene: 80854), KMT5A (SET8), MMSET, EZH2, and MLL family members), DOTIL, LSD1, Jumonji demethylases (e.g., KDM5A (JARIDIA), KDM5C (JARIDIC), and KDM6A (UTX)), kinases (e.g., Haspin, VRK1, PKCa, PKCB, PIM1, IKKα, Rsk2, PKB/Akt, Aurora B, MSK1/2, JNK1, MLTKα, PRK1, Chk1, DIk/ZIP, PKCδ, MST1, AMPK, JAK2, Abl, BMK1, CaMK, S6K1, SIK1), Ubp8, ubiquitin C-terminal hydrolases (UCH), the ubiquitin-specific processing proteases (UBP), and poly(ADP-ribose) polymerase 1 (PARP-1). See, also, US Patent U.S. Pat. No. 11,001,829B2 for additional domains.

In example embodiments, histone acetylation is targeted to a target sequence using a CRISPR system (see, e.g., Hilton I B, et al. Epigenome editing by a CRISPR-Cas9-based acetyltransferase activates genes from promoters and enhancers. Nat Biotechnol. 2015). In example embodiments, histone deacetylation is targeted to a target sequence (see, e.g., Cong et al., 2012; and Konermann S, et al. Optical control of mammalian endogenous transcription and epigenetic states. Nature. 2013; 500:472-476). In example embodiments, histone methylation is targeted to a target sequence (see, e.g., Snowden A W, Gregory P D, Case C C, Pabo C O. Gene-specific targeting of H3K9 methylation is sufficient for initiating repression in vivo. Curr Biol. 2002; 12:2159-2166; and Cano-Rodriguez D, Gjaltema R A, Jilderda L J, et al. Writing of H3K4Me3 overcomes epigenetic silencing in a sustained but context-dependent manner. Nat Commun. 2016; 7:12284). In example embodiments, histone demethylation is targeted to a target sequence (see, e.g., Kearns N A, Pham H, Tabak B, et al. Functional annotation of native enhancers with a Cas9-histone demethylase fusion. Nat Methods. 2015; 12 (5): 401-403). In example embodiments, histone phosphorylation is targeted to a target sequence (see, e.g., Li J, Mahata B, Escobar M, et al. Programmable human histone phosphorylation and gene activation using a CRISPR/Cas9-based chromatin kinase. Nat Commun. 2021; 12 (1): 896). In example embodiments, DNA methylation is targeted to a target sequence (see, e.g., Rivenbark A G, et al. Epigenetic reprogramming of cancer cells via targeted DNA methylation. Epigenetics. 2012; 7:350-360; Siddique A N, et al. Targeted methylation and gene silencing of VEGF-A in human cells by using a designed Dnmt3a-Dnmt3L single-chain fusion protein with increased DNA methylation activity. J Mol Biol. 2013; 425:479-491; Bernstein D L, Le Lay J E, Ruano E G, Kaestner K H. TALE-mediated epigenetic suppression of CDKN2A increases replication in human fibroblasts. J Clin Invest. 2015; 125:1998-2006; Liu X S, Wu H, Ji X, et al. Editing DNA Methylation in the Mammalian Genome. Cell. 2016; 167 (1): 233-247.e17; Stepper P, Kungulovski G, Jurkowska R Z, et al. Efficient targeted DNA methylation with chimeric dCas9-Dnmt3a-Dnmt3L methyltransferase. Nucleic Acids Res. 2017; 45 (4): 1703-1713; and Pflueger C., Tan D., Swain T., Nguyen T., Pflueger J., Nefzger C., Polo J.M., Ford E., Lister R. A modular dCas9-SunTag DNMT3A epigenome editing system overcomes pervasive off-target activity of direct fusion dCas9-DNMT3A constructs. Genome Res. 2018; 28:1193-1206). In example embodiments, DNA demethylation is targeted to a target sequence using a CRISPR system (see, e.g., TET1, see Xu et al, Cell Discov. 2016 May 3; 2:16009; Choudhury et al, Oncotarget. 2016 Jul. 19;7 (29): 46545-46556; and Kang J G, Park J S, Ko J H, Kim Y S. Regulation of gene expression by altered promoter methylation using a CRISPR/Cas9-mediated epigenetic editing system. Sci Rep. 2019; 9 (1): 11960). In example embodiments, DNA demethylation is targeted to a target sequence (see, e.g., TDG, see, Gregory D J, Zhang Y, Kobzik L, Fedulov A V. Specific transcriptional enhancement of inducible nitric oxide synthase by targeted promoter demethylation. Epigenetics. 2013; 8:1205-1212).

Example epigenetic modification domains can be obtained from, but are not limited to transcription activators, such as, VP64 (see, e.g., Ji Q, et al. Engineered zinc-finger transcription factors activate OCT4 (POU5F1), SOX2, KLF4, c-MYC (MYC) and miR302/367. Nucleic Acids Res. 2014; 42:6158-6167; Perez-Pinera P, et al. Synergistic and tunable human gene activation by combinations of synthetic transcription factors. Nat Methods. 2013; 10:239-242; Farzadfard F, Perli S D, Lu T K. Tunable and multifunctional eukaryotic transcription factors based on CRISPR/Cas. ACS Synth Biol. 2013; 2:604-613; Black J B, Adler A F, Wang H G, et al. Targeted Epigenetic Remodeling of Endogenous Loci by CRISPR/Cas9-Based Transcriptional Activators Directly Converts Fibroblasts to Neuronal Cells. Cell Stem Cell. 2016; 19 (3): 406-414; and Maeder M L, Linder S J, Cascio V M, Fu Y, Ho Q H, Joung J K. CRISPR RNA-guided activation of endogenous human genes. Nat Methods. 2013; 10 (10): 977-979), p65 (see, e.g., Liu P Q, et al. Regulation of an endogenous locus using a panel of designed zinc finger proteins targeted to accessible chromatin regions. Activation of vascular endothelial growth factor A. J Biol Chem. 2001; 276:11323-11334; and Konermann S, et al. Genome-scale transcriptional activation by an engineered CRISPR-Cas9 complex. Nature. 2015; 517:583-588), HSF1, and RTA (see, e.g., Chavez A, et al. Highly efficient Cas9-mediated transcriptional programming. Nat Methods. 2015; 12:326-328). Example epigenetic modification domains can be obtained from, but are not limited to transcription repressors, such as, KRAB (see, e.g., Beerli R R, Segal D J, Dreier B, Barbas C F., 3rd Toward controlling gene expression at will: specific regulation of the erbB-2/HER-2 promoter by using polydactyl zinc finger proteins constructed from modular building blocks. Proc Natl Acad Sci USA. 1998; 95:14628-14633; Cong L, Zhou R, Kuo Y C, Cunniff M, Zhang F. Comprehensive interrogation of natural TALE DNA-binding modules and transcriptional repressor domains. Nat Commun. 2012; 3:968; Gilbert L A, et al. CRISPR-mediated modular RNA-guided regulation of transcription in eukaryotes. Cell. 2013; 154:442-451; and Yeo N C, Chavez A, Lance-Byrne A, et al. An enhanced CRISPR repressor for targeted mammalian gene regulation. Nat Methods. 2018; 15 (8): 611-616).

In example embodiments, the epigenetic modification domain linked to a DNA binding domain recruits an epigenetic modification protein to a target sequence. In example embodiments, a transcriptional activator recruits an epigenetic modification protein to a target sequence. For example, VP64 can recruit DNA demethylation, increased H3K27ac and H3K4me. In example embodiments, a transcriptional repressor protein recruits an epigenetic modification protein to a target sequence. For example, KRAB can recruit increased H3K9me3 (see, e.g., Thakore P I, D'Ippolito A M, Song L, et al. Highly specific epigenome editing by CRISPR-Cas9 repressors for silencing of distal regulatory elements. Nat Methods. 2015; 12 (12): 1143-1149). In an example embodiment, methyl-binding proteins linked to a DNA binding domain, such as MBD1, MBD2, MBD3, and MeCP2 recruits an epigenetic modification protein to a target sequence. In an example embodiment, Mi2/NuRD, Sin3A, or Co-REST recruit HDACs to a target sequence.

In example embodiments, the epigenetic modification domain can be a eukaryotic or prokaryotic (e.g., bacteria or Archaea) protein. In example embodiments, the eukaryotic protein can be a mammalian, insect, plant, or yeast protein and is not limited to human proteins (e.g., a yeast, insect, plant chromatin modifying protein, such as yeast HATs, HDACs, methyltransferases, etc.

In one aspect of the invention, is provided a fusion protein (epigenetic modification polypeptide) comprising from N-terminus to C-terminus, an epigenetic modification domain, an XTEN linker, and a nuclease-deficient RNA-guided DNA endonuclease enzyme or a nuclease-deficient endonuclease enzyme.

In aspects, the epigenetic modification polypeptide further comprises a transcriptional activator. In aspects, the transcriptional activator is VP64, p65, RTA, or a combination of two or more thereof. In another aspect, the epigenetic modification polypeptide further comprises one or more nuclear localization sequences. In embodiments, the epigenetic modification polypeptide comprises the nuclease-deficient RNA-guided DNA endonuclease enzyme. In embodiments, the fusion protein comprises the nuclease-deficient DNA endonuclease enzyme.

In some embodiments, the functional domains associated with the adaptor protein or the CRISPR enzyme is a transcriptional activation domain comprising VP64, p65, MyoD1, HSF1, RTA or SET7/9. Other references herein to activation (or activator) domains in respect of those associated with the adaptor protein(s) include any known transcriptional activation domain and specifically VP64, p65, MyoD1, HSF1, RTA or SET7/9 (see, e.g., US Patent, U.S. Pat. No. 11,001,829B2).

In certain embodiments, the present invention provides a fusion protein comprising from N-terminus to C-terminus, an RNA-binding sequence, an XTEN linker, and a transcriptional activator. In aspects, the transcriptional activator is VP64, p65, RTA, or a combination of two or more thereof. In aspects, the fusion protein further comprises a demethylation domain, a nuclease-deficient RNA-guided DNA endonuclease enzyme or a nuclease-deficient endonuclease enzyme, a nuclear localization sequence, or a combination of two or more thereof. In embodiments, the fusion protein comprises the nuclease-deficient RNA-guided DNA endonuclease enzyme. In embodiments, the fusion protein comprises the nuclease-deficient DNA endonuclease enzyme.

In certain embodiments, the present invention provides a method of activating a target nucleic acid sequence in a cell, the method comprising: (i) delivering a first polynucleotide encoding a epigenetic modification polypeptide described herein including embodiments thereof to a cell containing the silenced target nucleic acid; and (ii) delivering to the cell a second polynucleotide comprising: (a) a sgRNA or (b) a cr:tracrRNA; thereby reactivating the silenced target nucleic acid sequence in the cell. In aspects, the sgRNA comprises at least one MS2 stem loop. In aspects, the second polynucleotide comprises a transcriptional activator. In aspects, the second polynucleotide comprises two or more sgRNA.

Donor Polynucleotides

The system may further comprise one or more donor polynucleotides (e.g., for insertion into the target polynucleotide). A donor polynucleotide may be an equivalent of a transposable element that can be inserted or integrated to a target site. The donor polynucleotide may be or comprise one or more components of a transposon. A donor polynucleotide may be any type of polynucleotides, including, but not limited to, a gene, a gene fragment, a non-coding polynucleotide, a regulatory polynucleotide, a synthetic polynucleotide, etc. The donor polynucleotide may include a transposon left end (LE) and transposon right end (RE). The LE and RE sequences may be endogenous sequences for the CAST used or may be heterologous sequences recognizable by the CAST used, or the LE or RE may be synthetic sequences that comprise a sequence or structure feature recognized by the CAST and sufficient to allow insertion of the donor polynucleotide into the target polynucleotides. In certain example embodiments, the LE and RE sequences are truncated. In certain example embodiments may be between 100-200 bps, between 100-190 base pairs, 100-180 base pairs, 100-170 base pairs, 100-160 base pairs, 100-150 base pairs, 100-140 base pairs, 100-130 base pairs, 100-120 base pairs, 100-110 base pairs, 20-100 base pairgs, 20-90 base pairs, 20-80 base pairs, 20-70 base pairs, 20-60 base pairs, 20-50 base pairs, 20-40 base paris, 20-30 base pairs, 50 to 100 base pairs, 60-100 base pairs, 70-100 base pairs, 80-100 base pairs, or 90-100 base pairs in length.

The donor polynucleotide may be inserted at a position upstream or downstream of a PAM on a target polynucleotide. In some embodiments, a donor polynucleotide comprises a PAM sequence. Examples of PAM sequences include TTTN, ATTN, NGTN, RGTR, VGTD, or VGTR.

The donor polynucleotide may be inserted at a position between 10 bases and 200 bases, e.g., between 20 bases and 150 bases, between 30 bases and 100 bases, between 45 bases and 70 bases, between 45 bases and 60 bases, between 55 bases and 70 bases, between 49 bases and 56 bases or between 60 bases and 66 bases, from a PAM sequence on the target polynucleotide. In some cases, the insertion is at a position upstream of the PAM sequence. In some cases, the insertion is at a position downstream of the PAM sequence. In some cases, the insertion is at a position from 49 to 56 bases or base pairs downstream from a PAM sequence. In some cases, the insertion is at a position from 60 to 66 bases or base pairs downstream from a PAM sequence.

The donor polynucleotide may be used for editing the target polynucleotide. In some cases, the donor polynucleotide comprises one or more mutations to be introduced into the target polynucleotide. Examples of such mutations include substitutions, deletions, insertions, or a combination thereof. The mutations may cause a shift in an open reading frame on the target polynucleotide. In some cases, the donor polynucleotide alters a stop codon in the target polynucleotide. For example, the donor polynucleotide may correct a premature stop codon. The correction may be achieved by deleting the stop codon or introduces one or more mutations to the stop codon. In other example embodiments, the donor polynucleotide addresses loss of function mutations, deletions, or translocations that may occur, for example, in certain disease contexts by inserting or restoring a functional copy of a gene, or functional fragment thereof, or a functional regulatory sequence or functional fragment of a regulatory sequence. A functional fragment refers to less than the entire copy of a gene by providing sufficient nucleotide sequence to restore the functionality of a wild type gene or non-coding regulatory sequence (e.g. sequences encoding long non-coding RNA). In certain example embodiments, the systems disclosed herein may be used to replace a single allele of a defective gene or defective fragment thereof. In another example embodiment, the systems disclosed herein may be used to replace both alleles of a defective gene or defective gene fragment. A "defective gene" or "defective gene fragment" is a gene or portion of a gene that when expressed fails to generate a functioning protein or non-coding RNA with functionality of a corresponding wild-type gene. In certain example embodiments, these defective genes may be associated with one or more disease phenotypes. In certain example embodiments, the defective gene or gene fragment is not replaced but the systems described herein are used to insert donor polynucleotides that encode gene or gene fragments that compensate for or override defective gene expression such that cell phenotypes associated with defective gene expression are eliminated or changed to a different or desired cellular phenotype.

In certain embodiments of the invention, the donor may include, but not be limited to, genes or gene fragments, encoding proteins or RNA transcripts to be expressed, regulatory elements, repair templates, and the like. According to the invention, the donor polynucleotides may comprise left end and right end sequence elements that function with transposition components that mediate insertion.

In certain cases, the donor polynucleotide manipulates a splicing site on the target polynucleotide. In some examples, the donor polynucleotide disrupts a splicing site. The disruption may be achieved by inserting the polynucleotide to a splicing site and/or introducing one or more mutations to the splicing site. In certain examples, the donor polynucleotide may restore a splicing site. For example, the polynucleotide may comprise a splicing site sequence.

The donor polynucleotide to be inserted may have a size from 10 bases to 50 kb in length, e.g., from 50 to 40 kb, from 100 to 30 kb, from 100 bases to 300 bases, from 200 bases to 400 bases, from 300 bases to 500 bases, from 400 bases to 600 bases, from 500 bases to 700 bases, from 600 bases to 800 bases, from 700 bases to 900 bases, from 800 bases to 1000 bases, from 900 bases to from 1100 bases, from 1000 bases to 1200 bases, from 1100 bases to 1300 bases, from 1200 bases to 1400 bases, from 1300 bases to 1500 bases, from 1400 bases to 1600 bases, from 1500 bases to 1700 bases, from 600 bases to 1800 bases, from 1700 bases to 1900 bases, from 1800 bases to 2000 bases, from 1900 bases to 2100 bases, from 2000 bases to 2200 bases, from 2100 bases to 2300 bases, from 2200 bases to 2400 bases, from 2300 bases to 2500 bases, from 2400 bases to 2600 bases, from 2500 bases to 2700 bases, from 2600 bases to 2800 bases, from 2700 bases to 2900 bases, or from 2800 bases to 3000 bases in length.

The components in the systems herein may comprise one or more mutations that alter their (e.g., the transposase(s)) binding affinity to the donor polynucleotide. In some examples, the mutations increase the binding affinity between the transposase(s) and the donor polynucleotide. In certain examples, the mutations decrease the binding affinity between the transposase(s) and the donor polynucleotide. The mutations may alter the activity of the Cas and/or transposase(s).

In certain embodiments, the systems disclosed herein are capable of unidirectional insertion, that is the system inserts the donor polynucleotide in only one orientation.

Delivery mechanisms for CAST systems includes those discussed above for CRISPR-Cas systems.

Example Selection Criteria

In an example embodiment, the perturbation analysis comprises a measurable deviation between the perturbed system and a control. A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made. For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population). In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR-), Youden index, or similar.

Example Computing Device

FIG. 3 depicts a block diagram of a computing machine 2000 and a module 2050 in accordance with certain examples. The computing machine 2000 may comprise, but are not limited to, remote devices, work stations, servers, computers, general purpose computers, Internet/web appliances, hand-held devices, wireless devices, portable devices, wearable computers, cellular or mobile phones, personal digital assistants (PDAs), smart phones, smart watches, tablets, ultrabooks, netbooks, laptops, desktops, multi-processor systems, microprocessor-based or programmable consumer electronics, game consoles, set-top boxes, network PCs, mini-computers, and any machine capable of executing the instructions. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a router or other network node, a vehicular information system, one or more processors associated with a television, a customized machine, any other hardware platform, or any combination or multiplicity thereof. The computing machine 2000 may be a distributed system configured to function using multiple computing machines interconnected via a data network or bus system.

The one or more processors 2010 may be configured to execute code or instructions to perform the operations and functionality described herein, manage request flow and address mappings, and to perform calculations and generate commands. Such code or instructions could include, but is not limited to, firmware, resident software, microcode, and the like. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), tensor processing units (TPUs), a graphics processing unit ("GPU"), a field programmable gate array ("FPGA"), a programmable logic device ("PLD"), a radio-frequency integrated circuit (RFIC), a controller, a state machine, gated logic, discrete hardware components, any other processing unit, or any combination or multiplicity thereof. In example embodiments, each processor 2010 can include a reduced instruction set computer (RISC) microprocessor. The processor 2010 may be a single processing unit, multiple processing units, a single processing core, multiple processing cores, special purpose processing cores, co-processors, or any combination thereof. According to certain examples, the processor 2010 along with other components of the computing machine 2000 may be a virtualized computing machine executing within one or more other computing machines. Processors 2010 are coupled to system memory and various other components via a system bus 2020.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random-access memory ("RAM"), static random-access memory ("SRAM"), dynamic random-access memory ("DRAM"), and synchronous dynamic random-access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 is coupled to system bus 2020 and can include a basic input/output system (BIOS), which controls certain basic functions of the processor 2010 and/or operate in conjunction with, a non-volatile storage device such as the storage media 2040.

In example embodiments, the computing device 2000 includes a graphics processing unit (GPU) 2090. Graphics processing unit 2090 is a specialized electronic circuit designed to manipulate and alter memory to accelerate the creation of images in a frame buffer intended for output to a display. In general, a graphics processing unit 2090 is very efficient at manipulating computer graphics and image processing and has a highly parallel structure that makes it more effective than general-purpose CPUs for algorithms where processing of large blocks of data is done in parallel.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any electromagnetic storage device, any semiconductor storage device, any physical-based storage device, any removable and non-removable media, any other data storage device, or any combination or multiplicity thereof. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The module 2050 may comprise one or more hardware or software elements, as well as an operating system, configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. Each of the operating system, one or more application programs, other program modules, and program data or some combination thereof, may include an implementation of a networking environment. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for coupling in operation the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including cursor control devices, touch-screens, scanners, electronic digitizers, sensors, receivers, touchpads, trackballs, cameras, microphones, alphanumeric input devices, any other pointing devices, or any combinations thereof. The I/O interface 2060 may couple the computing machine 2000 to various output devices including video displays (The computing device 2000 may further include a graphics display, for example, a plasma display panel (PDP), a light emitting diode (LED) display, a liquid crystal display (LCD), a projector, a cathode ray tube (CRT), or any other display capable of displaying graphics or video), audio generation device, printers, projectors, tactile feedback devices, automation control, robotic components, actuators, motors, fans, solenoids, valves, pumps, transmitters, signal emitters, lights, and so forth. The I/O interface 2060 may couple the computing device 2000 to various devices capable of input and out, such as a storage unit. The devices can be interconnected to the system bus 2020 via a user interface adapter, which can include, for example, a Super I/O chip integrating multiple device adapters into a single integrated circuit.

The computing machine 2000 may operate in a networked environment using logical connections through the network interface 2070 to one or more other systems or computing machines across the network 2080. The network 2080 may include a local area network ("LAN"), a wide area network ("WAN"), an intranet, an Internet, a mobile telephone network, storage area network ("SAN"), personal area network ("PAN"), a metropolitan area network ("MAN"), a wireless network ("WiFi;"), wireless access networks, a wireless local area network ("WLAN"), a virtual private network ("VPN"), a cellular or other mobile communication network, Bluetooth, near field communication ("NFC"), ultra-wideband, wired networks, telephone networks, optical networks, copper transmission cables, or combinations thereof or any other appropriate architecture or system that facilitates the communication of signals and data. The network 2080 may be packet switched, circuit switched, of any topology, and may use any communication protocol. The network 2080 may comprise routers, firewalls, switches, gateway computers and/or edge servers. Communication links within the network 2080 may involve various digital or analog communication media such as fiber optic cables, free-space optics, waveguides, electrical conductors, wireless links, antennas, radio-frequency communications, and so forth.

Information for facilitating reliable communications can be provided, for example, as packet/message sequencing information, encapsulation headers and/or footers, size/time information, and transmission verification information such as cyclic redundancy check (CRC) and/or parity check values. Communications can be made encoded/encrypted, or otherwise made secure, and/or decrypted/decoded using one or more cryptographic protocols and/or algorithms, such as, but not limited to, Data Encryption Standard (DES), Advanced Encryption Standard (AES), a Rivest-Shamir-Adelman (RSA) algorithm, a Diffie-Hellman algorithm, a secure sockets protocol such as Secure Sockets Layer (SSL) or Transport Layer Security (TLS), and/or Digital Signature Algorithm (DSA). Other cryptographic protocols and/or algorithms can be used as well or in addition to those listed herein to secure and then decrypt/decode communications.

The processor 2010 may be connected to the other elements of the computing machine 2000 or the various peripherals discussed herein through the system bus 2020. The system bus 2020 represents one or more of any of several types of bus structures, including a memory bus or memory controller, a peripheral bus, an accelerated graphics port, and a processor or local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus. It should be appreciated that the system bus 2020 may be within the processor 2010, outside the processor 2010, or both. According to certain examples, any of the processor 2010, the other elements of the computing machine 2000, or the various peripherals discussed herein may be integrated into a single device such as a system on chip ("SOC"), system on package ("SOP"), or ASIC device.

Examples may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing examples in computer programming, and the examples should not be construed as limited to any one set of computer program instructions. Further, a skilled programmer would be able to write such a computer program to implement an example of the disclosed examples based on the appended flow charts and associated description in the application text. Therefore, disclosure of a particular set of program code instructions is not considered necessary for an adequate understanding of how to make and use examples. Further, those ordinarily skilled in the art will appreciate that one or more aspects of examples described herein may be performed by hardware, software, or a combination thereof, as may be embodied in one or more computing systems. Moreover, any reference to an act being performed by a computer should not be construed as being performed by a single computer as more than one computer may perform the act.

The examples described herein can be used with computer hardware and software that perform the methods and processing functions described herein. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

A "server" may comprise a physical data processing system (for example, the computing device 2000 as shown in FIG. 3) running a server program. A physical server may or may not include a display and keyboard. A physical server may be connected, for example by a network, to other computing devices. Servers connected via a network may operate in the capacity of a server machine or a client machine in a server-client network environment, or as a peer machine in a distributed (e.g., peer-to-peer) network environment. The computing device 2000 can include clients' servers. For example, a client and server can be remote from each other and interact through a network. The relationship of client and server arises by virtue of computer programs in communication with each other, running on the respective computers.

Methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as the processors described for 2010 and 2090 in FIG. 3. Further, a computer program product can include a computer-readable storage medium with code adapted to be implemented to carry out one or more method steps described herein, including the provision of the system with the distinct software modules.

The example systems, methods, and acts described in the examples and described in the figures presented previously are illustrative, not intended to be exhaustive, and not meant to be limiting. In alternative examples, certain acts can be performed in a different order, in parallel with one another, omitted entirely, and/or combined between different examples, and/or certain additional acts can be performed, without departing from the scope and spirit of various examples. Plural instances may implement components, operations, or structures described as a single instance. Structures and functionality that may appear as separate in example embodiments may be implemented as a combined structure or component. Similarly, structures and functionality that may appear as a single component may be implemented as separate components. Accordingly, such alternative examples are included in the scope of the following claims, which are to be accorded the broadest interpretation to encompass such alternate examples. The terminology used herein was chosen to best explain the principles of the embodiments, the practical application or technical improvement over technologies found in the marketplace, or to enable others of ordinary skill in the art to understand the embodiments disclosed herein.

Further embodiments are illustrated in the following Examples which are given for illustrative purposes only and are not intended to limit the scope of the invention.

EXAMPLES

Figure 4:
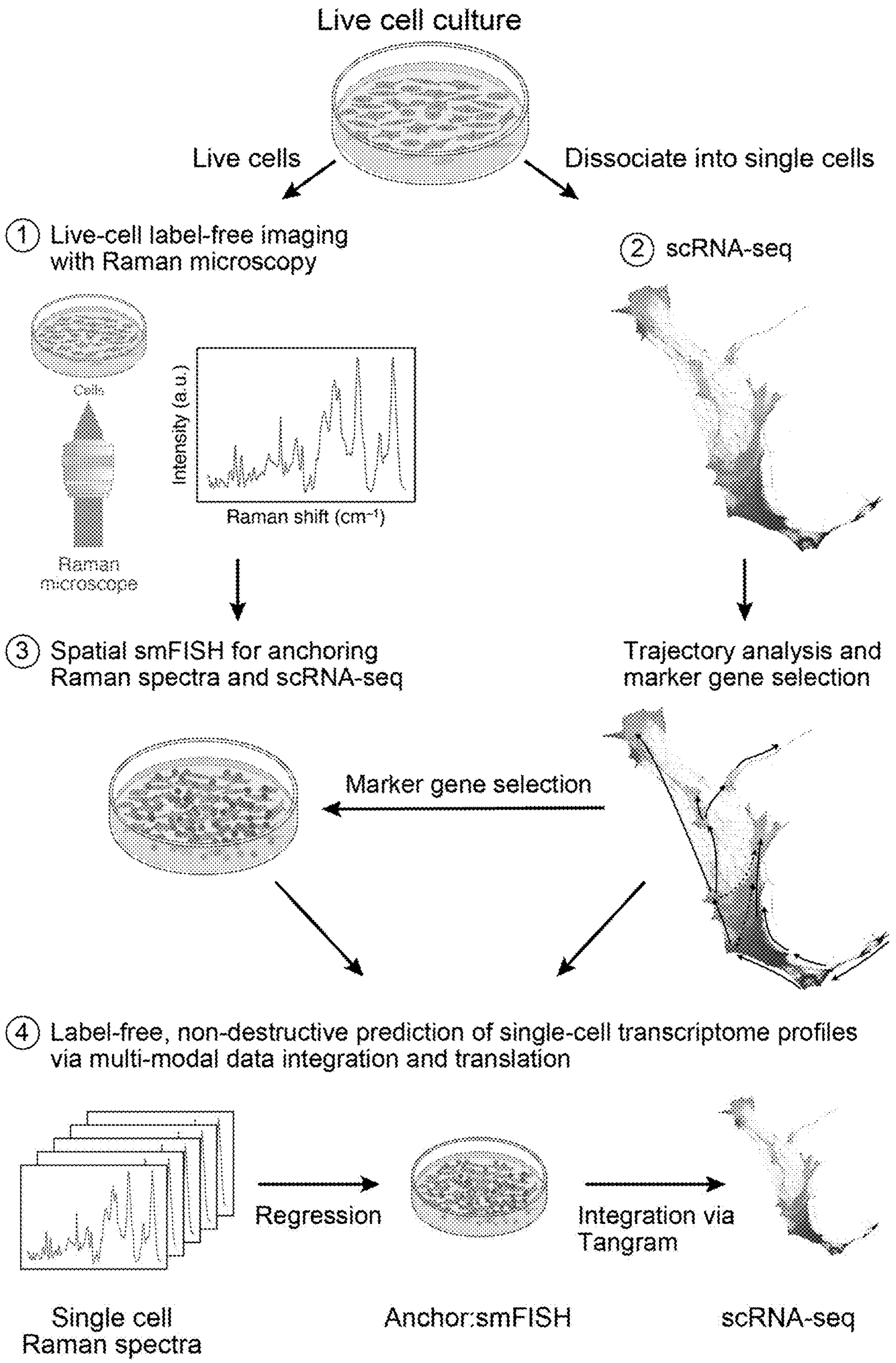
FIG. 4—Overview of Raman2RNA. Live cells are cultured on gelatin-coated quartz glass-bottom plates (top) and Raman spectra are then measured at each pixel (at spatial sub-cellular resolution) within an image frame (1), followed by smFISH imaging in the same area (3). From parallel plates, cells are dissociated into a single cell suspension and profiled by scRNA-seq (2). scRNA-seq profiles are used to select 9 marker genes for 5 major cell clusters, and those are measured with spatial smFISH (3). Lastly, a regression model is trained (4) to predict anchor smFISH profiles from Raman spectra, followed by integration via Tangram[31] to predict whole single-cell transcriptome profiles from smFISH profiles.

Example 1—Raman2RNA: Live-Cell Label-Free Prediction of Single-Cell RNA Expression Profiles by Raman Microscopy To address this challenge and leverage the complementary strengths of Raman microscopy and scRNA-Seq, Applicants developed Raman2RNA (R2R), an experimental and computational framework for inferring single-cell RNA expression profiles from label-free non-destructive Raman hyperspectral images (FIG. 4). R2R takes as input spatially resolved hyperspectral Raman images from live cells, smFISH data of selected markers from the same cells, and scRNA-seq from the same biological system. R2R then uses the smFISH data as an anchor to learn a model that links spatially resolved hyperspectral Raman images to scRNA-seq. Finally, from this model, R2R then computationally infers the anchor smFISH measurements from hyperspectral Raman images and then the single-cell expression profiles. The result is a label-free live-cell inference of single-cell expression profiles.

To facilitate data acquisition, Applicants developed a high-throughput multi-modal spontaneous Raman microscope that enables automated acquisition of Raman spectra, brightfield, and fluorescent images. In particular, Applicants integrated Raman microscopy optics to a fluorescence microscope, where high-speed galvo mirrors and motorized stages were combined to achieve a large field of view (FOV) scanning, and where dedicated electronics automate measurements across multiple modalities (FIG. 7-8, Methods).

Figure 5A:
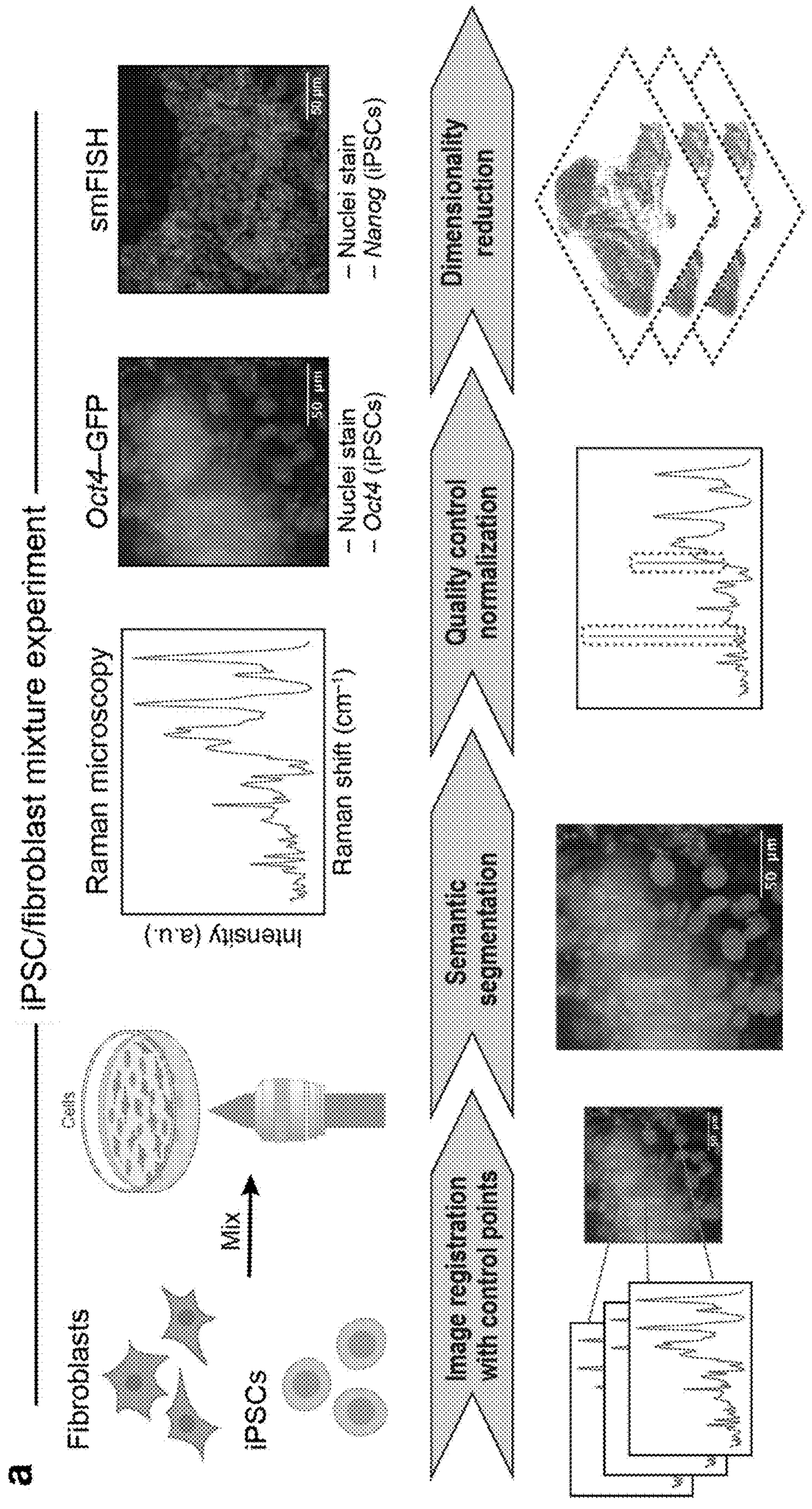
FIG. 5*a*-5*c*—Raman2RNA accurately distinguishes cell types and predicts binary expression of marker genes in a mixture of mouse fibroblasts and iPSCs. 5*a*) Overview. Top: Experimental procedures. Mouse fibroblasts and iPSCs were mixed 1:1 and plated on glass-bottom plates, followed by Raman imaging of live cells, nuclei staining and measurement of endogenous Oct4-GFP (iPSC marker) reporter) by fluorescence imaging, and cell fixation and processing for smFISH with DAPI and probes for Nanog (iPSCs, magenta) and Col1a1 (fibroblasts). Bottom: Preprocessing and analysis. From left: Image registration with control points (Methods), was followed by semantic cell segmentation, outlier removal/normalization and dimensionality reduction. 5*b*) Raman2RNA distinguishes cell states from Raman spectra. 2D UMAP embedding of single-cell Raman spectra (dots) colored by Louvain clustering labels (top left) or smFISH measured expression of Oct4 (top right), Nanog (bottom left) and Col1a1 (bottom right). 5*c*) Raman2RNA accurately predicts binary (on/off) expression of marker genes. Receiver operating characteristic (ROC) plots and area under the curve (AUC) obtained by classifying the 'on' and 'off' states of Oct4 (blue), Nanog (orange) and Col1a1 (green).

Applicants first demonstrated that R2R can infer profiles of two distinct cell types: mouse induced pluripotent stem cells (iPSCs) expressing an endogenous Oct4-GFP reporter and mouse fibroblasts[12]. To this end, Applicants mixed the cells in equal proportions, plated them in a gelatin-coated quartz glass-bottom Petri dish, and performed live-cell Raman imaging, along with fluorescent imaging of live-cell nucleus staining dye (Hoechst 33342) for cell segmentation and image registration, and an iPSC marker gene, Oct4-GFP (FIG. 5*a*). The excitation wavelength for the Raman microscope (785 nm) was distant enough from the GFP Stokes shift emission, such that there was no interference with the cellular Raman spectra (FIG. 9). Furthermore, there was no notable photo-toxicity induced in the cells. After Raman and fluorescence imaging, Applicants fixed and permeabilized the cells and performed smFISH (with hybridization chain reaction (HCR[13]), Methods) of marker genes for mouse iPSCs (Nanog) and fibroblasts (Col1a1). Applicants registered the nuclei stains, GFP images, HCR images, and Raman images through either polystyrene control bead images or reference points marked under the glass bottom dishes (FIG. 10, Methods).

Figure 5B:
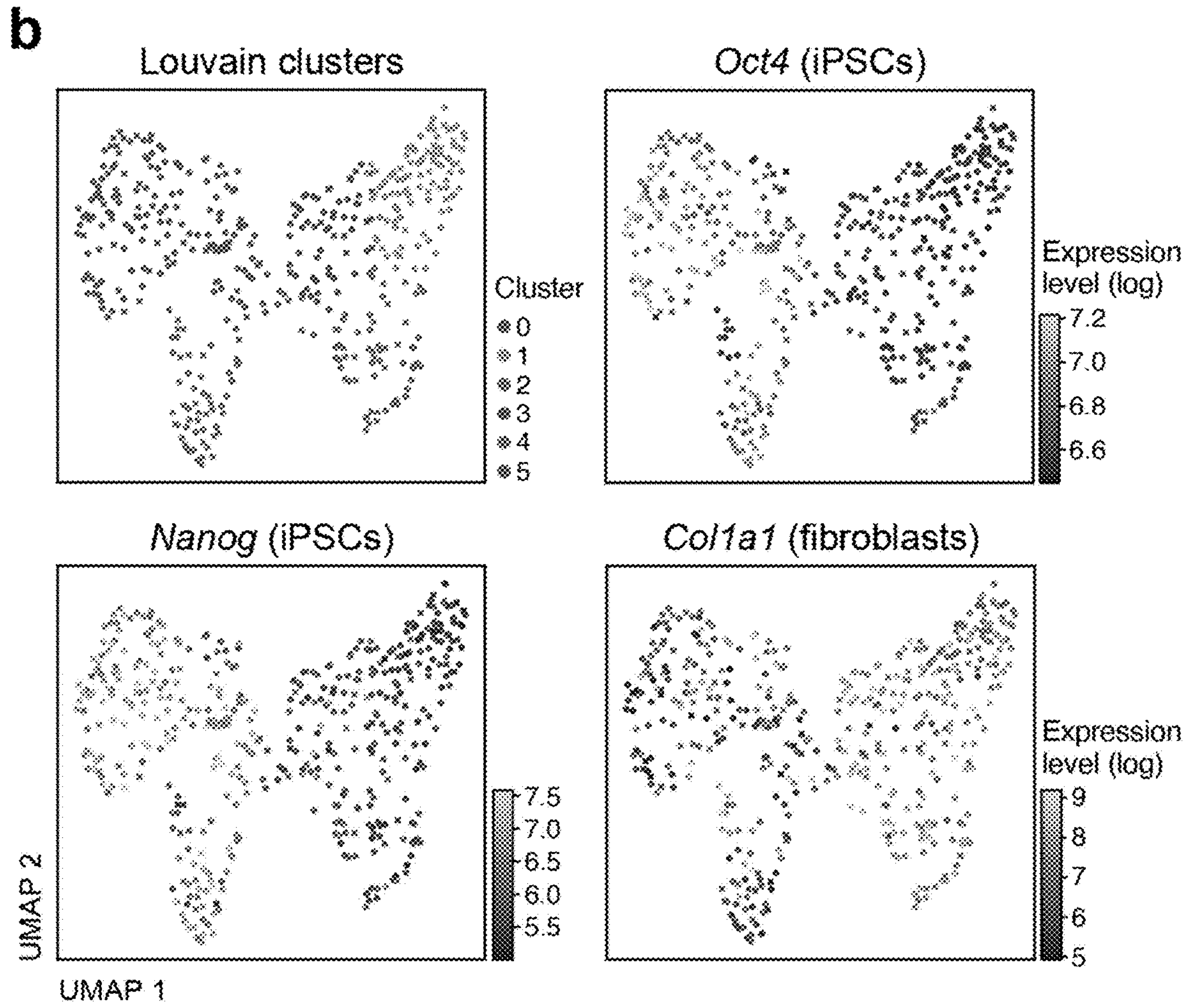

The Raman spectra distinguished the two cell populations in a manner congruent with the expression of their respective reporter (measured live or by smFISH in the same cells), as reflected by a low-dimensional embedding of hyperspectral Raman data (FIG. 5*b*). Specifically, Applicants focused on the fingerprint region of Raman spectra (600-1800 $cm^{-1}$, 930 of the 1,340 features in a Raman spectrum), where most of the signatures from various key biomolecules, such as proteins, nucleic acids, and metabolites, lie[8]. After basic preprocessing, including cosmic-ray and background removal and normalization, Applicants aggregated Raman spectra that are confined to the nuclei, obtaining a 930-dimensional Raman spectroscopic representation for each cell's nucleus. Applicants then visualized these Raman profiles in an embedding in two dimensions using Uniform Manifold Approximation and Projection (UMAP)[14] and labeled cells with the gene expression levels that were concurrently measured by either an Oct4-GFP reporter or smFISH (FIG. 5*b*). The cells separated clearly in their Raman profiles in a manner consistent with their gene expression characteristics, forming two main subsets in the embedding, one with cells with high Oct4 and Nanog expression (iPSCs markers) and another with cells with relatively high Col1a1 expression (fibroblasts marker), indicating that Raman spectra reflect cell-intrinsic expression differences (FIG. 5*b*).

Figure 5C:
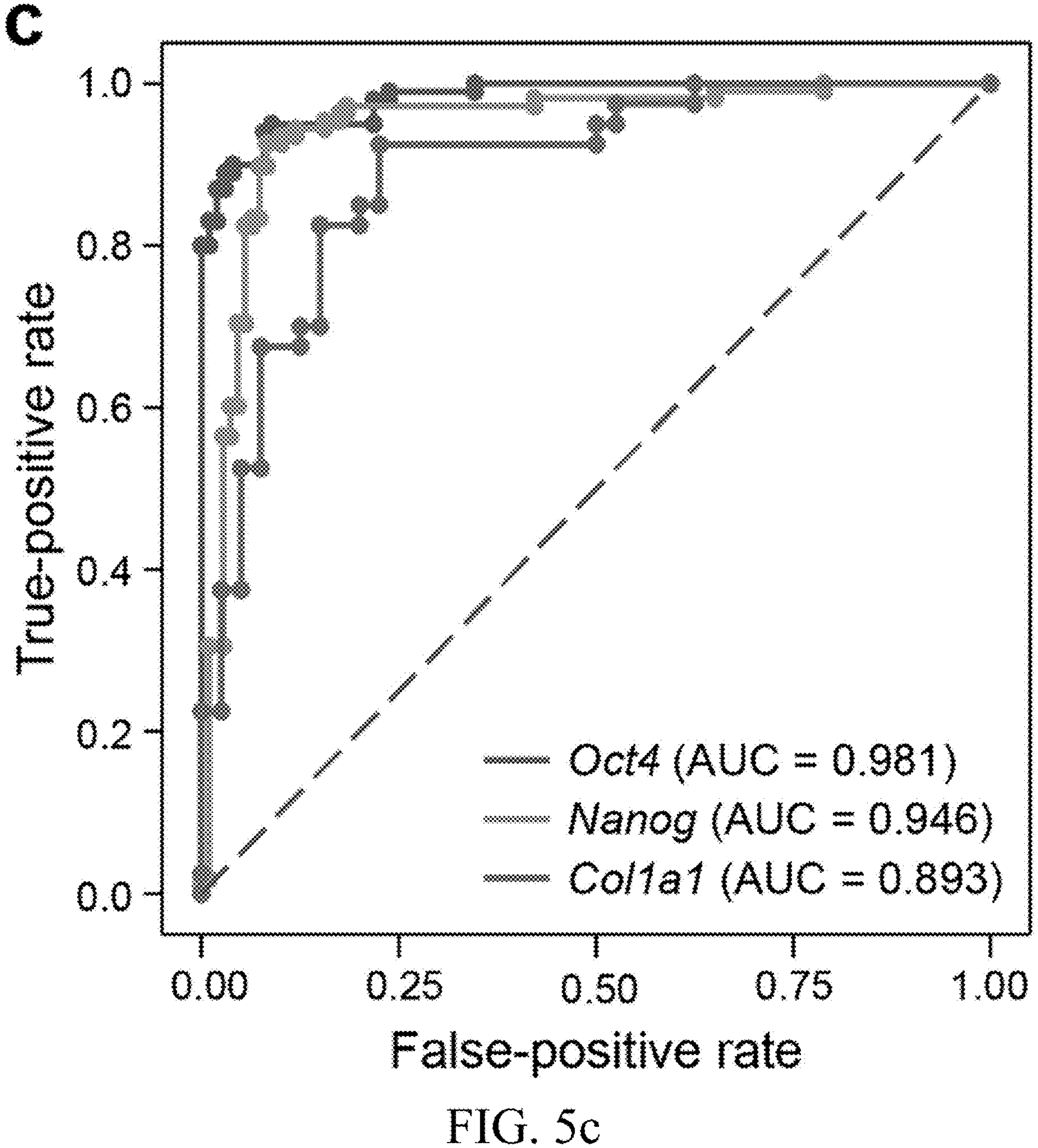

Applicants further successfully trained a classifier to classify the 'on' or 'off' expression states of Oct4, Nanog and Col1a1 in each cell based on its Raman profile (Methods). Applicants trained a logistic regression classifier with 50% of the data and held out 50% for testing. Applicants predicted Oct4 and Nanog expression states with high accuracy on the held-out test data (area under the receiver operating characteristic curve (AUROC)=0.98 and 0.95, respectively; FIG. 5*c*), indicating that expression of iPSC markers can be predicted confidently from Raman spectra of live, label-free cells. Applicants also successfully classified the expression state of the fibroblast marker Col1a1 (AUROC=0.87; FIG. 5*c*), albeit with lower confidence, which is consistent with the lower contrast in Col1a1 expression (FIG. 5*b*) between iPSC (Oct4+or Nanog+ cells) vs. non-iPSCs, compared to Oct4 or Nanog. Most misclassifications occurred when the ground truth expression levels were near the threshold of the classifier, showing that misclassifications were likely due to the uncertainty in the ground truth expression level (FIG. 11).

Figure 6A:
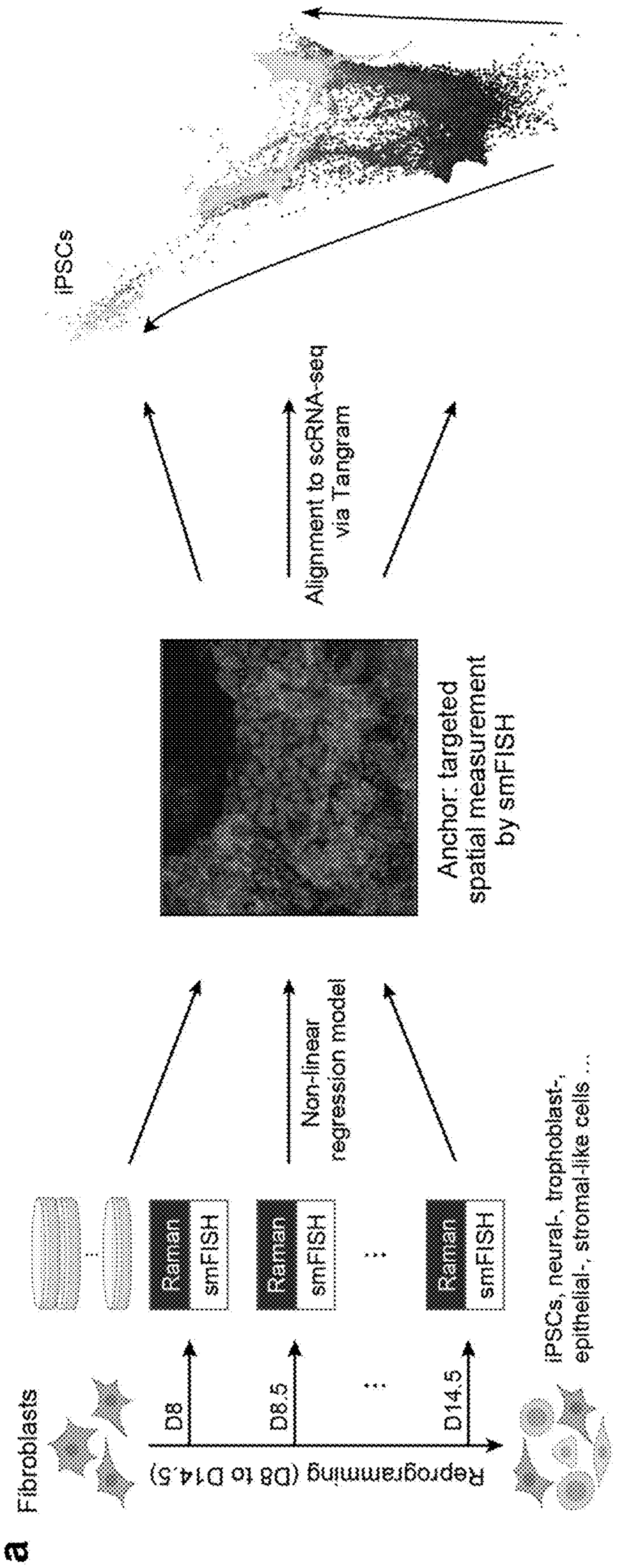
Figure 6H:
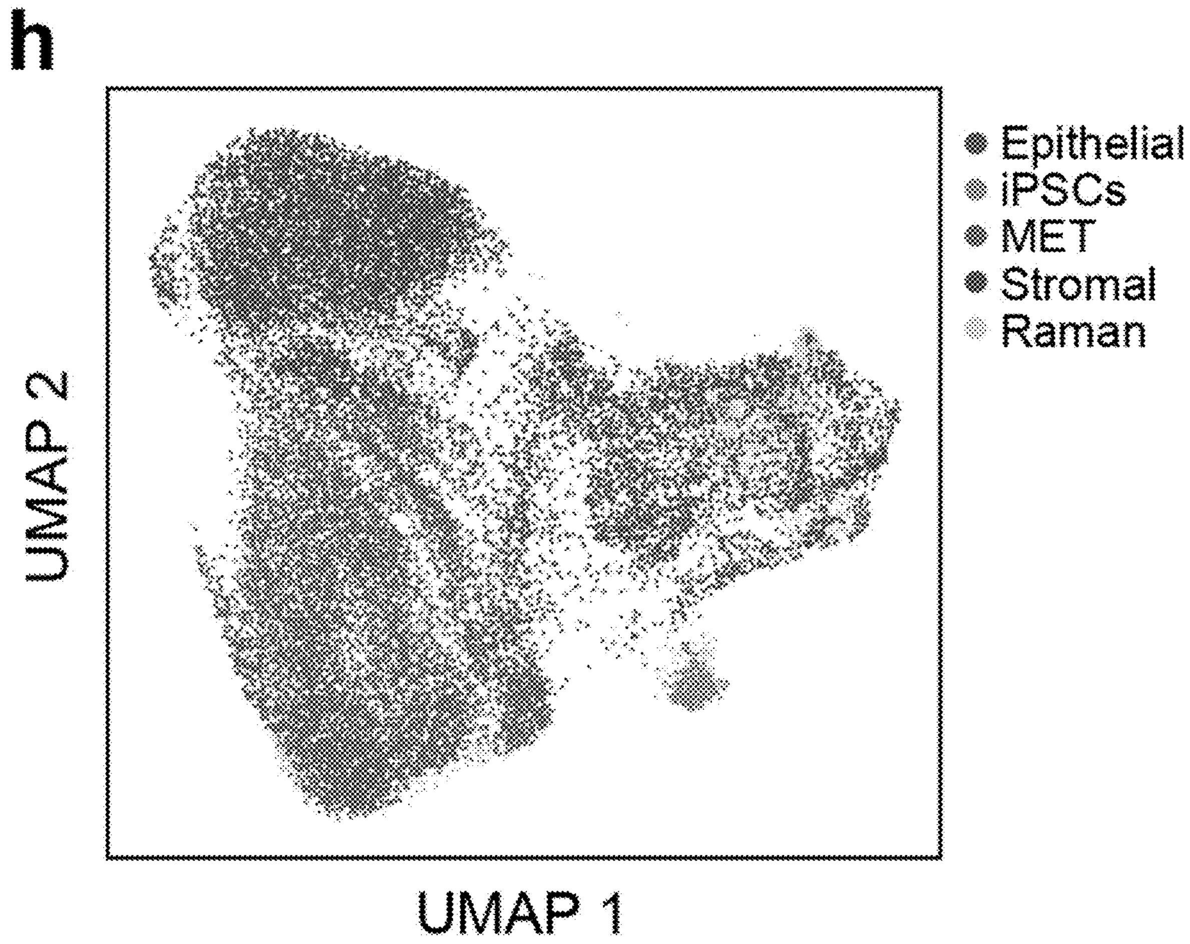

Next, Applicants asked if the Raman images could predict entire expression profiles non-destructively at single-cell resolution. To this end, Applicants aimed to reconstruct scRNA-seq profiles from Raman images by multi-modal data integration and translation, using multiplex smFISH data to anchor between the Raman images and scRNA-seq profiles (FIG. 6*a*). As a test case, Applicants focused on the mouse iPSC reprogramming model system, where Applicants have previously generated ~250,000 scRNA-seq profiles at 1/2 day intervals throughout an 18 day, 36 time point time course of reprogramming[3] (Methods). Applicants used Waddington-OT[3] (WOT) to select from the scRNA-seq profiles nine anchor genes that represent diverse cell types that emerge during reprogramming (iPSCs: Nanog, Utf1 and Epcam; MET and neural: Nnat and Fabp7; epithelial: Krt7 and Peg10; stromal: Bgn and Col1a1; Methods). Applicants performed live-cell Raman imaging from day 8 of reprogramming, in which distinct cell types begin to emerge[3], up to day 14.5, at half-day intervals, totaling 14 time points (Methods). Applicants imaged ~500 cells per plate at 1 μm spatial resolution. Finally, Applicants fixed cells immediately after each Raman imaging time point followed by smFISH on the 9 anchor genes (Methods).

Strikingly, a low dimensional representation of the Raman profiles showed that they encoded similar temporal dynamics to those observed with scRNA-seq during reprogramming (FIG. 6*b,c*, FIG. 12), indicating that they may qualitatively mirror scRNA-seq. Integrating Raman and scRNA-seq profiles (Methods), R2R then learned a model that can infer an scRNA-seq profile for each Raman imaged cell, by first predicting smFISH anchors from the Raman profiles using Catboost[15] (Methods) and then using the Tangram[16] method to map from the anchors to full scRNA-seq profiles (FIG. 4, FIG. 6*d-f*). In the first step, Applicants averaged the smFISH signal within a nucleus to represent a single nucleus's expression level. As Applicants conducted smFISH of 9 genes, the result was a 9-dimensional smFISH profile for each single nucleus. Then, Raman profiles were translated to these 9-dimensional profiles with Catboost[15], a non-linear regression model, using 50% of the Raman and smFISH profiles as training data.

In the second step, Applicants mapped these anchor smFISH profiles to full scRNA-seq profiles using Tangram, yielding well-predicted single cell RNA profiles, as supported by several lines of evidence. First, Applicants performed leave-one-out cross-validation (LOOCV) analysis, in which Applicants used eight out of the nine anchor genes to integrate Raman with scRNA-seq, and compared the predicted expression of the remaining genes to its smFISH measurements. The predicted left-out genes based on scRNA-seq showed a significant correlation with the measured smFISH expression for any left-out gene (Pearson r~0.7, p-value$<10^{-100}$, FIG. 6*d*). Notably, when Applicants analogously applied a modified U-net[18] to infer smFISH profiles from brightfield (FIG. 21, Methods), Applicants observed a poor, near-random prediction of expression profiles for all 9 genes in leave-one-out cross-validation (r<0.15), indicating that, unlike Raman spectra, brightfield z-stack images either do not have the necessary information to infer expression profiles, or require more data. Second, Applicants compared the real (scRNA-seq measured) and R2R predicted expression profiles averaged across cells of the same cell type ("pseudobulk" for each of iPSCs, epithelial cells, stromal cells, and MET). Here, Applicants obtained the "ground truth" cell types of the R2R profiles by transferring scRNA-seq annotations to the matching smFISH profiles using Tangram's label transfer function. Then, based on the labels, Applicants averaged R2R's predicted profiles across the cells of a single cell type. The two profiles (R2R-inferred and scRNA-seq pseudo-bulk per cell type) showed high correlations (Pearson's r>0.96) (FIG. 6*e,f*, FIG. 13), demonstrating the accuracy of R2R at the cell type level. Furthermore, projecting the R2R predicted profiles of each cell onto an embedding learned from the real scRNA-seq shows that the predicted profiles span the key cell types as captured in real profiles (FIG. 6*g-j*, FIG. 14-18). Applicants note that the predicted profiles had lower variance compared to real scRNA-seq. As this is observed even when co-embedding only smFISH and scRNA-seq measurements (with no Raman data or projection, FIG. 19), Applicants believe it mostly reflects the limited number and domain maladaptation of the smFISH anchor genes used for integration. Given the similarity of the separate embeddings of Raman and scRNA-seq profiles, future studies without anchors could address this.

Figure 6K:
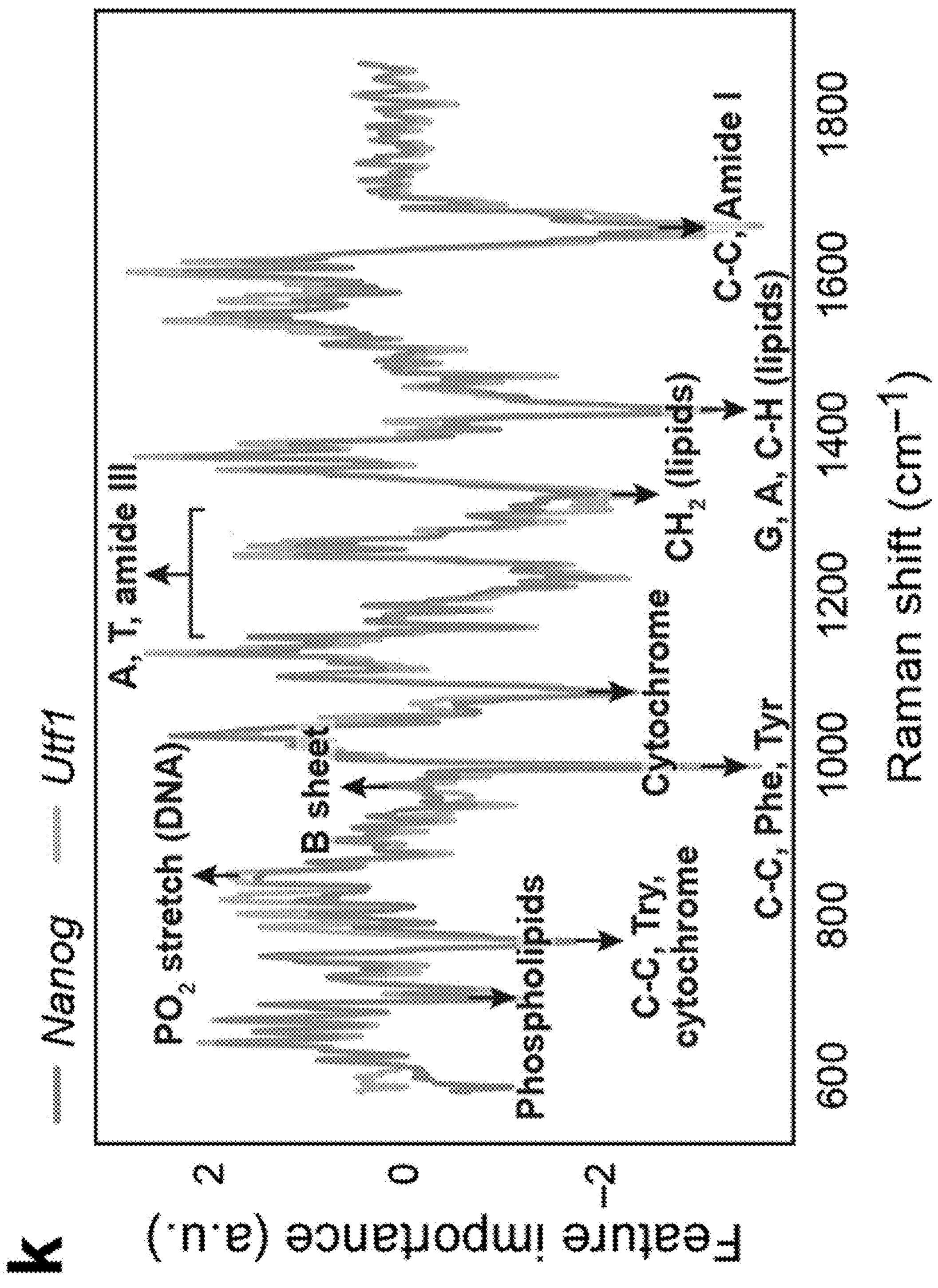

Lastly, Applicants calculated feature importance scores in R2R predictions (Methods) and identified Raman spectral features correlated with expression levels (FIG. 6*k*, FIG. 20). For example, Raman bands at approximately 752 $cm^{-1}$ (C—C, Try, cytochrome), 1004 $cm^{-1}$ (CC, Phe, Tyr), and 1445 $cm^{-1}$ ($CH_2$, lipids) contributed to predicting iPSCs-related expression profiles, which is consistent with previous research that employed single cell Raman spectra to identify mouse embryonic stem cells (ESCs)[17] (FIG. 6*k*). The contributions of these bands were either suppressed or increased for other cell types, such as stromal or epithelial cells (FIG. 20).

In conclusion, Applicants reported R2R, a label-free non-destructive framework for inferring expression profiles at single-cell resolution from Raman spectra of live cells, by integrating Raman hyperspectral images with scRNA-seq data through paired smFISH measurements and multi-modal data integration and translation. Applicants inferred single-cell expression profiles with high accuracy, based on both averages within cell types and co-embeddings of individual profiles. Applicants further showed that predictions using brightfield z-stacks had poor performance, indicating the importance of Raman microscopy for predicting expression profiles.

R2R can be further developed in several ways. First, the throughput of single-cell Raman microscopy is still limited. In this pilot study, Applicants profiled ~6,000 cells in total. By using emerging vibrational spectroscopy techniques, such as Stimulated Raman Scattering microscopy[19] or photo-thermal microscopy[20,21], Applicants envision increasing throughput by several orders of magnitude, to match the throughput of massively parallel single cell genomics. Second, because molecular circuits and gene regulation are structured, with strong co-variation in gene expression profiles across cells, Applicants can leverage the advances in computational microscopy to infer high-resolution data from low-resolution data, such as by using compressed sensing, to further increase throughput[22]. Third, increasing the number of anchor genes (e.g., by seqFISH[23], merFISH[24], STARmap[25], or ExSeq[26]) can increase the prediction accuracy and capture more single-cell variance. Additionally, with single-cell multi-omics, Applicants can project other modalities, such as scATAC-seq from Raman spectra. Finally, given the similarity in the overall independent embedding of Raman and scRNA-seq profiles, Applicants expect computational methods such as multi-domain translation[27] to allow mapping between Raman spectra and molecular profiles without measuring any anchors in situ. Overall, with further advances in single-cell genomics, imaging, and machine learning, Raman2RNA could allow Applicants to non-destructively infer omics profiles at scale in vitro, and possibly in vivo in living organisms.

Example 2—Materials and Methods

Mouse Fibroblast Reprogramming

OKSM secondary mouse embryonic fibroblasts (MEFs) were derived from E13.5 female embryos with a mixed B6; 129 background. The cell line used in this study was homozygous for ROSA26-M2rtTA, homozygous for a polycistronic cassette carrying Oct4, Klf4, Sox2, and Myc at the Col1a1 3' end, and homozygous for an EGFP reporter under the control of the Oct4 promoter. Briefly, MEFs were isolated from E13.5 embryos from timed-matings by removing the head, limbs, and internal organs under a dissecting microscope. The remaining tissue was finely minced using scalpels and dissociated by incubation at 37 °C for 10 minutes in trypsin-EDTA (ThermoFisher Scientific). Dissociated cells were then plated in MEF medium containing DMEM (ThermoFisher Scientific), supplemented with 10% fetal bovine serum (GE Healthcare Life Sciences), non-essential amino acids (ThermoFisher Scientific), and GlutaMAX (ThermoFisher Scientific). MEFs were cultured at 37 °C and 4% $CO_2$ and passaged until confluent. All procedures, including maintenance of animals, were performed according to a mouse protocol (2006N000104) approved by the MGH Subcommittee on Research Animal Care[3].

For the reprogramming assay, 50,000 low passage MEFs (no greater than 3-4 passages from isolation) were seeded in 14 3.5 cm quartz glass-bottom Petri dishes (Waken B Tech) coated with gelatin. These cells were cultured at 37 °C and 5% $CO_2$ in reprogramming medium containing KnockOut DMEM (GIBCO), 10% knockout serum replacement (KSR, GIBCO), 10% fetal bovine serum (FBS, GIBCO), 1% GlutaMAX (Invitrogen), 1% nonessential amino acids (NEAA, Invitrogen), 0.055 mM 2-mercaptoethanol (Sigma), 1% penicillin-streptomycin (Invitrogen) and 1,000 U/ml leukemia inhibitory factor (LIF, Millipore). Day 0 medium was supplemented with 2 mg/mL doxycycline Phase-1 (Dox) to induce the polycistronic OKSM expression cassette. The medium was refreshed every other day. On day 8, doxycycline was withdrawn. Fresh medium was added every other day until the final time point on day 14. One plate was taken every 0.5 days after day 8 (D8-D14.5) for Raman imaging and fixed with 4% formaldehyde immediately after for HCR.

High-Throughput Multi-Modal Raman Microscope

Due to the lack of commercial systems, Applicants developed an automated high-throughput multi-modal microscope capable of multi-position and multi-timepoint fluorescence imaging and point scanning Raman microscopy (FIG. 7). A 749 nm short-pass filter was placed to separate brightfield and fluorescence from Raman scattering signal, and the fluorescence and Raman imaging modes were switched by swapping dichroic filters with auto-turrets. To realize a high-throughput Raman measurement, galvo mirror-based point scanning and stage scanning was combined to acquire each FOV and multiple different FOVs, respectively.

To realize this in an automated fashion, a MATLAB (2020b) script that communicates with Micro-manager[28], a digital acquisition (DAQ) board, and Raman scattering detector (Princeton Instruments, PIXIS 100BR eXcelon) was written (FIG. 8). A 2D point scan Raman imaging sequence was regarded as a dummy image acquisition in Micro-manager, during which the script communicated via the DAQ board with 1. the detector to read out a spectrum, 2. the mirror to update the mirror angles, and 3. shutters to control laser exposure. All communications were realized using transistor-transistor logic (TTL) signaling. Updating of the galvo mirror angles was conducted during the readout of the detector. While the script ran in the background, Micro-manager initiated a multi-dimensional acquisition consisting of brightfield, DAPI, GFP, and dummy Raman channel at multiple positions and z-stacks.

An Olympus IX83 fluorescence microscope body was integrated with a 785 nm Raman excitation laser coupled to the backport, where the short-pass filter deflected the excitation to the sample through an Olympus UPLSAPO 60×NA 1.2 water immersion objective. The backscattered light was collimated through the same objective and collected with a 50 μm core multi-mode fiber, which was then sent to the spectrograph (Holospec f/1.8i 785 nm model) and detector. The fluorescence and brightfield channels were imaged by the Orca Flash 4.0 v2 sCMOS camera from Hamamatsu Photonics. The exposure time for each point in the Raman measurement was 20 msec, and laser power at the sample plane was 212 mW. Each FOV was $100\times10^0$ pixels, with each pixel corresponding to about 1 μm. The laser source was a 785 nm Ti-Sapphire laser cavity coupled to a 532 nm pump laser operating at 4.7 W.

The time to acquire Raman hyperspectral images was roughly 8 minutes per FOV. With 8 minutes, it is unrealistic to image an entire glass-bottom plate. Therefore, Applicants visually chose representative FOVs that cover all representative cell types including iPSC-like, epithelial-like, stromal-like and MET cells. 20 FOVs were chosen for each plate, where roughly 15 FOVs were from the boundaries of colonies, five from non-colonies, and one from non-cells to use for background correction.

Due to the extended Raman imaging time, evaporation of the immersion water was no longer negligible. Therefore, Applicants developed an automated water immersion feeder using syringe pumps and syringe needles glued to the tip of the objective lens. Here, water was supplied at a flow rate of 1 μL/min.

iPSC and MEF Mixture Experiment

Low passage iPSCs were first cultured in N2B27 2i media containing 3 mM CHIR99021, 1 mM PD0325901, and LIF. On the day of the experiment, 750,000 iPSCs and 750,000 MEFs were plated on the same gelatin-coated 3.5 cm quartz glass-bottom Petri dish. Cells were plated in the same reprogramming medium as previously described (with Dox) with the exception of utilizing DMEM without phenol red (Gibco) instead of KnockOut DMEM. 6 hours after plating, the quartz dishes were taken for Raman imaging and fixed with 4% formaldehyde immediately after for HCR.

Anchor Gene Selection by Waddington-OT

To select anchor genes for connecting spatial information to the full transcriptome data, Waddington-OT (WOT)[3], a probabilistic time-lapse algorithm that can reconstruct developmental trajectories, was used. Applicants applied WOT to mouse fibroblast reprogramming scRNA-seq data collected at matching time-points and culture condition (day 8-14.5 at ½ day intervals) 3. For each cell fate, Applicants calculated the transition probabilities of each cell and selected the top 10 percentile cells per time point (FIG. 12). Based on this, Applicants ran the FindMarker function in Seurat[29] to find genes differentially expressed in these cell subsets per time point. Through this approach, Applicants chose two genes per cell type that are both found by Seurat and commonly used for these cell types (iPSCs: Nanog, Utf1; epithelial: Krt7, Peg10; stromal: Bgn, Col1a1; MET and neural: Fabp7, Nnat), along with one gene that is an early marker of iPSCs, Epcam.

smRNA-FISH by Hybridization Chain Reaction (HCR)

Fixed samples were prepared for imaging using the HCR v3.0 protocol for mammalian cells on a chambered slide, incubating at the amplification step for 45 minutes in the dark at room temperature. Three probes with amplifiers conjugated to fluorophores Alexa Fluor 488, Alexa Fluor 546, and Alexa Fluor 647 were used. Samples were stained with DAPI prior to imaging. After imaging, probes were stripped from samples by washing samples once for 5 minutes in 80% formamide at room temperature and then incubating three times for 30 minutes in 80% formamide at 37 °C. Samples were washed once more with 80% formamide, then once with PBS, and reprobed with another panel of probes for subsequent imaging.

Image Registration of Raman Hyperspectral Images and Fluorescence/smFISH Images

Brightfield and fluorescence channels including DAPI and GFP, along with corresponding Raman images, were registered by using 5 μm polystyrene beads deposited on quartz glass-bottom Petri dishes (SF-S-D12, Waken B Tech) for calibration. The brightfield and fluorescence images of the beads were then registered by the scale-invariant template matching algorithm of the OpenCV (github.com/opencv/opencv) matchTemplate function followed by manual correction.

For the registration of smFISH and Raman images, four marks inscribed under the glass-bottom Petri dishes were used as reference points (FIG. 10). As the Petri dishes are temporarily removed from the Raman microscope after imaging to do smFISH measurements, the dishes cannot be placed back at the same exact location on the microscope. Therefore, the coordinates of these reference points were measured along with the different FOVs. When the dishes were placed again after smFISH measurements, the reference mark coordinates were measured, and an affine mapping was constructed to calculate the new FOV coordinates. Lastly, as smFISH consisted of 3 rounds of hybridization and imaging, the following steps were performed to register images across different rounds with a custom MATLAB script:

1. Maximum intensity projection of nuclei stain and RNA images
2. Automatic registration of round 1 images to rounds 2 and 3 based on nuclei stain images and MATLAB function imregtform. First, initial registration transformation functions were obtained with a similarity transformation model passing the 'multimodal' configuration. Then, those transformations were used as the initial conditions for an affine model-based registration with the imregtform function. Finally, this affine mapping transformation was applied to all the smFISH (RNA) images.
3. Use the protocol in (2) to register nuclei stain images obtained from the multimodal Raman microscope and the 1$^{st}$ round of images used for smFISH. Then, apply the transformation to the remaining 2$^{nd}$ and 3$^{rd}$ rounds.
4. Manually remove registration outliers in (3).

Fibroblast cells were mobile during the 2-class mixture experiment so that by the time Raman imaging finished, cells had moved far enough from their original position that the above semi-automated strategy could not be applied. Thus, Applicants manually identified cells present in both nuclei stain images before and after the Raman imaging.

Hyperspectral Raman Image Processing

Each raw Raman spectrum has 1,340 channels. Of those channels, Applicants extracted the fingerprint region (600-1800 cm$^{-1}$), which resulted in a total of 930 channels per spectrum. Thus, each FOV is a 100×100×930 hyperspectral image. The hyperspectral images were then preprocessed by a python script as follows:

1. Cosmic ray removal. Cosmic rays were detected by subtracting the median filtered spectra from the raw spectra, and any feature above 5 was classified as an outlier and replaced with the median value. The kernel window size for the median filter was 7.
2. Autofluorescence removal. The baseline function in rampy (github.com/charlesll/rampy), a python package for Raman spectral preprocessing, was used with the alternating least squares algorithm 'als'.
3. Savitzky-Golay smoothing. The scipy.signal.savgol filter function was used with window size 5 and polynomial order 3.
4. Averaging spectra at the single-cell level. Nuclei stain images were segmented using NucleAlzer (github.com/spreka/biomagdsb) and averaged pixel-level spectra that fall within each nucleus.
5. Spectra standardization. Spectra were standardized to a mean of 0 and a standard deviation of 1.

Inferring Anchor smFISH from Raman Spectra or Brightfield z-Stacks

For the two-class mixture and reprogramming experiment, Applicants trained a decision tree-based non-linear regression, Catboost[15], to predict the 'on' or 'off' expression states for each anchor gene from Raman spectra. Applicants used 80% of the data as training and the remaining 20% as test data. The early stopping parameter was set to 5.

For the brightfield z-stack to smFISH inference, Applicants applied deep learning to the whole image level. Applicants trained a modified U-net with skip connections and residual blocks to estimate the corresponding smFISH image[18]. Due to the small size of the available training dataset, Applicants augmented the data by rotation and flipping. Furthermore, a subsample of each brightfield image was taken due to memory constraints (50×50 pixel region).

Training was carried out on an NVIDIA Tesla P100 GPU, the number of epochs was 100, the learning rate was 0.01, and the batch size was 400. For each smFISH prediction, Applicants chose the epoch that gave the best validation score.

Inferring Expression Profiles from Raman Images

To infer expression profiles from Raman images, Applicants used Tangram[16]. Tangram enables the alignment of spatial measurements of a small number of genes to scRNA-seq measurements. After using Catboost to infer anchor expression levels from Raman profiles, Applicants aligned the inferred expression levels to scRNA-seq profiles using the map_cells_to_space function (learning_rate=0.1, num_epochs=1000) on an Nvidia Tesla P100 GPU, followed by the project genes function in Tangram.

When comparing different pseudo-bulk transcriptome predictions with the real scRNA-seq data, Applicants first transferred labels of annotated scRNA-seq profiles to the ground truth smFISH profiles using Tangram's label transfer function project_cell_annotations. Then, the average expression profiles across cells of a cell type were calculated by referring to the transferred labels and compared with those from the real scRNA-seq data[3].

Dimensionality Reduction, Embedding and Projection

For dimension reduction and visualization of Raman and scRNA-seq profiles, Applicants performed forced layout embedding (FLE) using the Pegasus pipeline (github.com/klarman-cell-observatory/pegasus). First, Applicants performed principal component analysis on both Raman and scRNA-seq profiles independently, calculated diffusion maps on the top 100 principal components, and performed an approximated FLE graph using Deep Learning by pegasus.net_fle with default parameters.

To project Raman profiles to a scRNA-seq embedding, Applicants calculated a k-nearest neighbor graph (k-NN, k=15) on the scRNA-seq top 50 principal components with the cosine metric, and UMAP with the scanpy.tl.umap function in Scanpy30 version 1.7.2 with default parameters. Then, the Raman predicted expression profiles were projected on to the scRNA-seq UMAP embedding by scanpy.tl.ingest using k-NN as the labeling method and default parameters.

Feature Importance Analysis

To evaluate the contributions of Raman spectral features to expression profile prediction, Applicants used the get feature importance function in Catboost with default parameters. As the dimensions of Raman spectra were reduced by PCA prior to Catboost, feature importance scores were calculated for each principal component, and the weighted linear combination of the Raman PCA eigen vectors with feature scores as the weight were calculated to obtain the full spectrum.

TABLE 1

Leave-one-out cross-validation of Raman2rna Gene names show the genes left out, and the correlation coefficient r shows the correlation between the transcripts predicted from Raman2RNA and those measured from smFISH at the single-cell level.

| Gene name | Pearson correlation r | p-value |
|---|---|---|
| Nanog | 0.695 | $10^{-243}$ |
| Utf1 | 0.715 | $<10^{-308}$ |
| Epcam | 0.752 | $<10^{-308}$ |
| Krt7 | 0.712 | $<10^{-308}$ |

TABLE 1-continued

Leave-one-out cross-validation of Raman2rna Gene names show the genes left out, and the correlation coefficient r shows the correlation between the transcripts predicted from Raman2RNA and those measured from smFISH at the single-cell level.

| Gene name | Pearson correlation r | p-value |
|---|---|---|
| Peg10 | 0.716 | $<10^{-308}$ |
| Bgn | 0.465 | $10^{-137}$ |
| Colla1 | 0.441 | $10^{-122}$ |
| Fabp7 | 0.703 | $<10^{-308}$ |
| Nnat | 0.594 | $10^{-243}$ |

REFERENCES FOR EXAMPLES 1 AND 2

1. Tanay, A. & Regev, A. Scaling single-cell genomics from phenomenology to mechanism. *Nature* 541, 331-338 (2017).
2. Trapnell, C. et al. The dynamics and regulators of cell fate decisions are revealed by pseudotemporal ordering of single cells. *Nat. Biotechnol.* 32, 381-386 (2014).
3. Schiebinger, G. et al. Optimal-Transport Analysis of Single-Cell Gene Expression Identifies Developmental Trajectories in Reprogramming. *Cell* 176, 928-943.e22 (2019).
4. La Manno, G. et al. RNA velocity of single cells. *Nature* 560, 494-498 (2018).
5. Bergen, V., Lange, M., Peidli, S., Wolf, F. A. & Theis, F. J. Generalizing RNA velocity to transient cell states through dynamical modeling. *Nat. Biotechnol.* 38, 1408-1414 (2020).
6. Wagner, D. E. & Klein, A. M. Lineage tracing meets single-cell omics: opportunities and challenges. *Nat. Rev. Genet.* 21, 410-427 (2020).
7. Wei, L. et al. Super-multiplex vibrational imaging. *Nature* 544, 465-470 (2017).
8. Kobayashi-Kirschvink, K. J. et al. Linear Regression Links Transcriptomic Data and Cellular Raman Spectra. *Cell Systems* vol. 7 104-117.e4 (2018).
9. Singh, S. P. et al. Label-free characterization of ultra violet-radiation-induced changes in skin fibroblasts with Raman spectroscopy and quantitative phase microscopy. *Sci. Rep.* 7, 10829 (2017).
10. Ichimura, T. et al. Visualizing cell state transition using Raman spectroscopy. *PLOS One* 9, e84478 (2014).
11. Ho, C.-S. et al. Rapid identification of pathogenic bacteria using Raman spectroscopy and deep learning. *Nat. Commun.* 10, 4927 (2019).
12. Stadtfeld, M., Maherali, N., Borkent, M. & Hochedlinger, K. A reprogrammable mouse strain from gene-targeted embryonic stem cells. *Nat. Methods* 7, 53-55 (2010).
13. Choi, H. M. T. et al. Third-generation in situ hybridization chain reaction: multiplexed, quantitative, sensitive, versatile, robust. *Development* 145, (2018).
14. McInnes, L., Healy, J., Saul, N. & Großberger, L. UMAP: Uniform Manifold Approximation and Projection. *J. Open Source Softw.* 3, 861 (2018).
15. Prokhorenkova, L., Gusev, G., Vorobev, A., Dorogush, A. V. & Gulin, A. CatBoost: unbiased boosting with categorical features.
16. Biancalani, T. et al. Deep learning and alignment of spatially-resolved whole transcriptomes of single cells in the mouse brain with Tangram. bioRxiv 2020.08.29.272831 (2020) doi: 10.1101/2020.08.29.272831.

17. Germond, A., Panina, Y., Shiga, M., Niioka, H. & Watanabe, T. M. Following Embryonic Stem Cells, Their Differentiated Progeny, and Cell-State Changes During iPS Reprogramming by Raman Spectroscopy. *Anal. Chem.* 92, 14915-14923 (2020).
18. He, K., Zhang, X., Ren, S. & Sun, J. Deep residual learning for image recognition. in 2016 *IEEE Conference on Computer Vision and Pattern Recognition* (*CVPR*) (IEEE, 2016). doi: 10.1109/cvpr.2016.90.
19. Freudiger, C. W. et al. Label-free biomedical imaging with high sensitivity by stimulated Raman scattering microscopy. *Science* 322, 1857-1861 (2008).
20. Bai, Y. et al. Ultrafast chemical imaging by widefield photothermal sensing of infrared absorption. *Sci Adv* 5, eaav7127 (2019).
21. Tamamitsu, M., Toda, K., Horisaki, R. & Ideguchi, T. Quantitative phase imaging with molecular vibrational sensitivity. *Opt. Lett.* 44, 3729-3732 (2019).
22. Cleary, B., Cong, L., Cheung, A., Lander, E. S. & Regev, A. Efficient Generation of Transcriptomic Profiles by Random Composite Measurements. *Cell* 171, 1424-1436.e18 (2017).
23. Eng, C.-H. L. et al. Transcriptome-scale super-resolved imaging in tissues by RNA seqFISH. *Nature* 568, 235-239 (2019).
24. Chen, K. H., Boettiger, A. N., Moffitt, J. R., Wang, S. & Zhuang, X. RNA imaging. Spatially resolved, highly multiplexed RNA profiling in single cells. *Science* 348, aaa6090 (2015).
25. Wang, X. et al. Three-dimensional intact-tissue sequencing of single-cell transcriptional states. *Science* (2018) doi: 10.1126/science.aat5691.
26. Alon, S. et al. Expansion sequencing: Spatially precise in situ transcriptomics in intact biological systems. *Science* 371, (2021).
27. Yang, K. D. et al. Multi-domain translation between single-cell imaging and sequencing data using autoencoders. *Nat. Commun.* 12, 31 (2021).
28. Edelstein, A., Amodaj, N., Hoover, K., Vale, R. & Stuurman, N. Computer control of microscopes using uManager. Curr. Protoc. *Mol. Biol.* Chapter 14, Unit14.20 (2010).
29. Stuart, T. et al. Comprehensive Integration of Single-Cell Data. *Cell* 177, 1888-1902.e21 (2019).
30. Wolf, F. A., Angerer, P. & Theis, F. J. SCANPY: large-scale single-cell gene expression data analysis. *Genome Biol.* 19, 15 (2018).
31. Biancalani, T. et al. Deep learning and alignment of spatially-resolved whole transcriptomes of single cells in the mouse brain with Tangram. *bioRxiv* 2020.08.29.272831 (2020) doi: 10.1101/2020.08.29.272831.
32. Germond, A., Panina, Y., Shiga, M., Niioka, H. & Watanabe, T. M. Following Embryonic Stem Cells, Their Differentiated Progeny, and Cell-State Changes During iPS Reprogramming by Raman Spectroscopy. *Anal. Chem.* 92, 14915-14923 (2020).

Example 3—Raman Clock of Aging

Applicants aim to develop the first-ever "Raman clock of aging" by combining the recent advances in label-free hyperspectral Raman microscopy, spatially resolved single-cell muti-omics, and multi-domain integration and translation through machine learning to simultaneously measure chemical compositions, molecular vibrational energies, and whole-genome molecular dynamics during aging. This is based on the foundation and a series of innovative technologies that Applicants have developed to study aging and cellular reprogramming, including "Raman2RNA1" (the first report on predicting single-cell RNA-seq profiles from label-free Raman microscopy by machine learning), "WADDINGTON-OT$^{2}$" (a novel framework to reconstruct time information by optimal transport analysis; the most comprehensive characterization of iPSC reprogramming (reversing aging) at single-cell resolution). This innovative technology will enable multi-modal spatiotemporal characterization of the molecular dynamics during aging simultaneously and nondestructively in live cells, tissues, whole organisms, or humans.

Technical Plan

Problem-Different data modalities provide different (partial) perspectives on a population of cells and their integration is critical for studying cellular heterogeneity and its biological functions. To identify hallmarks/biomarkers of aging comprehensively, Applicants need new scalable technologies to map cellular phenotypes of aging simultaneously at single-cell resolution. Single-cell and spatial multi-omics are destructive: Single-cell multi-omics (e.g., scRNA-seq, single-cell ATAC-seq, and single-cell proteomics) and spatial transcriptomics (e.g., MERFISH, FISSEQ, SeqFISH, Slide-seq, STARmap) have opened new windows into understanding the properties, regulation, dynamics, and function of cells at unprecedented resolution. However, all these assays are inherently destructive, precluding tracking the temporal dynamics of live cells, in tissues, whole organisms, or humans. In particular, these assays face challenges in mapping large tissues and organs due to high cost and impossible instrument time and they cannot be applied to study humans in vivo.

Solution-Non-destructive high-throughput, high-dimensional chemical imaging at single-cell resolution: In contrast, chemical imaging (as quantitative-chemical mapping) is the analytical capability to create a visual image of distributions of molecular vibrations from simultaneous measurement of spectra and spatial, time information. Among these chemical imaging technologies, Raman microscopy offers a unique opportunity to comprehensively report on the vibrational energy levels of molecules inside cells in a label-free and non-destructive manner at a subcellular spatial resolution. Raman microscopy measures high-dimensional vibrational energy features which represent the chemical compositions inside a cell. It provides a multi-modal composite measurement of chemical molecules, including lipids, proteins, metabolites, and nucleic acids. Each imaging pixel can be up to 1000 peaks/features. Importantly, Applicants have recently developed Raman2RNA showing that the vibrational energy landscape of individual cells can be mapped to its transcriptome.

Bridging the gap by linking imaging with single-cell and spatial multi-omics: With the recent advancements in machine learning, Applicants can now integrate data from multiple domains and predict each other using multi-modal translation. Applicants aim to utilize an integrative strategy to significantly scale up the single-cell and spatial multi-omics technologies (up to ~60,000× increase in throughput) through label-free chemical imaging and machine learning to map the whole-genome multi-modal molecular dynamics simultaneously during aging.

Approach

Aim 1: Develop the "Raman clock of aging" by Raman microscopy and spatially resolved single-cell multi-omics (experimental framework). Applicants aim to develop an experimental system to measure and integrate Raman microscopy data with single-cell multi-omics (e.g., scRNA-seq, scATAC-seq, scMethylation-seq) and spatial transcriptomics (e.g., HCR, STARmap). Applicants have shown that Applicants can predict single-cell RNA-seq profiles from Raman microscopy by Raman2RNA. This is a natural extension to the Raman2RNA work. Applicants have established imaging, single-cell and spatial transcriptomics platforms in the lab. Applicants will use a well-established mouse model and focus on the skin to test the technology (young and aged skin). Hyperspectral Raman microscopy measures high-dimensional vibrational energy features which represent the chemical compositions inside a cell. It provides a multi-modal measurement of chemical molecules, including lipids, proteins, metabolites, and nucleic acids, nondestructively. Each imaging pixel at subcellular resolution can measure up to 1000 peaks/features. In addition, the subcellular spatial information of each measurement encodes much higher-dimension information of the cellular states of aging. Using feature learning and representation of the spatial information of each pixel, the feature space of the Raman information can be high compared to gene expression space.

Aim 2: Develop multi-modal integration and translation framework of the "Raman clock of aging" (computational framework). The concept of utilizing low-dimensional measurements to predict the full high-dimensional data is an emerging field in single-cell genomics[3-5]. Biological networks are also structured and can be reduced to lower-dimensional representations. The feasibility of this proposal is further supported by recent advances in machine learning and neural machine models, notably in multi-modal data integration and translation[6]. In computer vision, natural language processing, and chemistry, there are a number of exciting successes, such as image style transfer[7], AlphaFold's protein structure prediction from sequence®, image generation from text by DALL-E2[9], and cross-modality translation between multi-omic profiles at single-cell resolution[6], among others. In order to develop state-of-the-art methods for integrating and translating among a wide array of biological data modalities, Applicants aim to build new machine learning methods to analyze and build the "Raman clock of aging", improving on foundational neural machine frameworks to map each data modality into a common latent distribution. These include adversarial auto encoders[10], an ensemble of models encoding data to a common low-dimensional space for joint analysis, deep-metric/contrastive learning regimes[11], which map data from different modalities to a lower-dimensional space that preserves inter-modality structure, transformers[12], which learn to prioritize only important features of data to make improved and interpretable models, and generative adversarial networks[13], a game theoretic learning paradigm for the generation of high-quality synthetic data, among others. Applicants plan to evaluate the methods' performances on tasks including, but not limited to, spatially resolved single-cell omics data mining and inter-modal data clustering. Applicants have developed foundational computational frameworks to address 1) reconstruction of time information ("WADDINGTON-OT"); 2) predicting molecular dynamics and gene expression from imaging ("Raman2RNA"). Applicants have expertise and skillsets for the proposed analysis.

Aim 3: Test and validate "Raman clock of aging" in mouse skin aging. Applicants believe that an end-to-end iterative test-validate approach is more appropriate for technology development and in this developmental stage. Applicants will focus on skin as a starting point. Applicants will utilize the experimental and computational frameworks developed in Aims 1 and 2 to systematically map the molecular vibrational energies, composition, and dynamics in young and aged mice (newborn, 6 months, 14 months, and >24 months). Applicants will include both sexes for the different age groups.

Impact-Genomics is expensive and inherently destructive, precluding tracking the temporal dynamics of live cells in tissues and humans during aging. Imaging can be low-cost, non-destructive, scalable, applicable to humans in vivo and in vitro, but difficult to interpret. Applicants aim to build an "Raman clock of aging" by bridging the gap between imaging and genomics through AI/ML. "Raman clock of aging" will enable low-cost, fast, and scalable query and prediction of multi-modal omics information from imaging and will serve as a foundation for future development of more generalizable hallmarks/biomarkers of aging.

The technology will serve as a foundation for the future development of non-destructive multimodal measurement methods for monitoring aging. The technology will also enable massively scalable phenotypic screens for anti-aging drug discovery.

Applicants focus on the natural aging process in this proposal. Applicants look forward to testing and applying this technology to map the effects of interventions (e.g., chemicals, reprogramming) to delay/reverse aging.

REFERENCES FOR EXAMPLE 3

1 Kobayashi-Kirschvink K J, Gaddam S, James-Sorenson T, Grody E, Ounadjela J R, Ge B, et al. Raman2RNA: Live-cell label-free prediction of single-cell RNA expression profiles by Raman microscopy. BioRxiv 2021. https://doi.org/10.1101/2021.11.30.470655.

2 Schiebinger G, Shu J, Tabaka M, Cleary B, Subramanian V, Solomon A, et al. Optimal-transport analysis of single-cell gene expression identifies developmental trajectories in reprogramming. Cell 2019; 176:1517.

3 Cleary B, Cong L, Cheung A, Lander E S, Regev A. Efficient generation of transcriptomic profiles by random composite measurements. Cell 2017; 171:1424-1436.e18.

4 Cleary B, Simonton B, Bezney J, Murray E, Alam S, Sinha A, et al. Compressed sensing for highly efficient imaging transcriptomics. Nat Biotechnol 2021. https://doi.org/10.1038/s41587-021-00883-x.

5 Yu Z, Bian C, Liu G, Zhang S, Wong K-C, Li X. Elucidating transcriptomic profiles from single-cell RNA sequencing data using nature-inspired compressed sensing. Brief Bioinform 2021; 22: https://doi.org/10.1093/bib/bbab125.

6 Yang K D, Belyaeva A, Venkatachalapathy S, Damodaran K, Katcoff A, Radhakrishnan A, et al. Multi-domain translation between single-cell imaging and sequencing data using autoencoders. Nat Commun 2021; 12:31.

7 Gatys L A, Ecker A S, Bethge M. Image Style Transfer Using Convolutional Neural Networks. Presented at the 2016 IEEE Conference on Computer Vision and Pattern Recognition (CVPR), Las Vegas, N V, USA, 2016 Jun. 27-2016/6/30.

8 Jumper J, Evans R, Pritzel A, Green T, Figurnov M, Ronneberger O, et al. Highly accurate protein structure prediction with AlphaFold. Nature 2021; 596:583-9.

9 Ramesh A, Dhariwal P, Nichol A, Chu C, Chen M. Hierarchical text-conditional image generation with CLIP latents. ArXiv [CsCV] 2022.

10 Makhzani A, Shlens J, Jaitly N, Goodfellow I J. Adversarial autoencoders.CoRR. 2015.

11 Kaya, Bilge. Deep metric learning: A survey. Symmetry (Basel) 2019; 11:1066.

12 Wolf T, Debut L, Sanh V, Chaumond J, Delangue C, Moi A, et al. Transformers: State-of-the-Art Natural Language Processing. Presented at the Proceedings of the 2020 Conference on Empirical Methods in Natural Language Processing: System Demonstrations, Online.

13 Goodfellow I, Pouget-Abadie J, Mirza M, Xu B, Warde-Farley D, Ozair S, et al. Generative ad-versarial nets. In: Ghahramani Z, Welling M, Cortes C, Lawrence N, Weinberger Q, editors. Advances in Neural Information Processing Sys-tems, vol. 27. Curran Associates, Inc; 2014.

Example 4—ImageOmicsNet

Follow-Up Research Projects for Raman2RNA

The Applicants are fully committed to expand the Raman2RNA method. Applicants can begin to imagine an "ImageOmicsNet" by combing imaging with genomics and machine learning.

Applicants plan to develop Raman2Omics: Applicants plan to expand the Raman2RNA to infer single-cell ATAC-seq, single-cell proteomics, single-cell multi-omics, and spatial genomics;

Applicants plan to develop Raman2Microbe: Applicants plan to expand the Raman2Omics to characterize microbe (e.g., bacteria, virus, fungi) identities, metabolites, and host genomic information;

Applicants plan to develop Perturb-Raman: a new framework to combine perturbations such as chemical and genetic perturbations (e.g., by CRISPR, base editors) with Raman microscopy;

Applicants plan to test other high-throughput Raman microscopes such as Stimulated Raman Scattering (SRS) microscope;

Applicants plan to combine other imaging methods such as phase contrast, H&E, Cell Paint, FTIR (fourier-transform infrared spectroscopy) with genomics data;

Applicants plan to develop anchor-free inference method to predict genomics information through machine learning;

Applicants plan to apply above mentioned methods to study aging, cancer, infectious diseases, and immunity.

Commercial Opportunity for Raman2RNA and Follow-Up Research Projects.

Biomarker and Diagnosis: Raman2RNA can be used to identify biomarkers for many disease areas. For example, biomarkers/hallmarks/clocks of aging; biomarkers/hallmarks of cancer; quality check of sperm/egg/embryo for IVF; identification of pathogens; predicting preterm birth from blood. Raman2RNA can be used for clinical diagnosis. The first application could be early diagnosis of melanoma and other skin related cancers. Skin is a perfect demonstration area. It's an outer tissue barrier where Raman microscopy can access humans directly. Raman2Omics and Raman2Microbe can be utilized for the same applications.

Drug discovery (Perturbation): Perturb-Raman can be utilized for imaging-based live cell drug discovery. Applicants can use Raman microscopy to identify molecular signatures of drugs.

Beyond mammalian cells: Above mentioned technologies can be applied to imaging-based high-throughput phenotyping in other organisms such as protist, bacteria, plant.

Example 5—Raman2RNA: Live-Cell Label-Free Prediction of Single-Cell RNA Expression Profiles by Raman Microscopy Continued Single-cell RNA-Seq (scRNA-seq) and other profiling assays have opened new windows into understanding the properties, regulation, dynamics, and function of cells at unprecedented resolution and scale. However, these assays are inherently destructive, precluding Applicants from tracking the temporal dynamics of live cells in cell culture or whole organisms. Raman microscopy offers a unique opportunity to comprehensively report on the vibrational energy levels of molecules in a label-free and non-destructive manner at a subcellular spatial resolution, but it lacks genetic and molecular interpretability. Here, Applicants developed Raman2RNA (R2R), an experimental and computational framework to infer single-cell expression profiles in live cells through label-free hyperspectral Raman microscopy images and domain translation. Applicants demonstrate that deep neural networks, such as adversarial autoencoders, can integrate paired or unpaired measurements of two modalities and predict scRNA-seq profiles non-destructively from Raman images in multiple biological systems. In reprogramming of mouse fibroblasts into induced pluripotent stem cells (iPSCs), R2R accurately ($r>0.96$) inferred the expression profiles of various cell states and fates from Raman images, including iPSCs, mesenchymal-epithelial transition (MET) cells, stromal cells, epithelial cells, and fibroblasts. Furthermore, through live-cell tracking of mouse embryonic stem cells (ESCs) differentiating over time, R2R tracked emergence of lineage divergence and differentiation trajectories of ectoderm-like and extraembryonic endoderm (XEN)-like cells after 48 hours. Lastly, R2R outperformed inference from brightfield images, showing the importance of spectroscopic content afforded by Raman microscopy. Raman2RNA lays a foundation for future investigations into exploring single-cell genome-wide molecular dynamics through imaging data, in vitro, and in vivo.

Main

Cellular states and functions are determined by a dynamic balance between intrinsic and extrinsic programs. Dynamic processes such as cell growth, stress responses, differentiation, and reprogramming are not determined by a single gene but by the orchestrated temporal expression and function of multiple genes organized in programs and their interactions with other cells and the surrounding environment[1]. It is essential to decipher the dynamics of the underlying gene programs to understand how cells change their states in physiological and pathological conditions.

Despite significant advances in single-cell genomics and microscopy, Applicants still cannot track live cells and tissues at the genomic level. On the one hand, single cell and spatial genomics have provided a view of gene programs and cell states at unprecedented scale and resolution[1]. However, these measurement methods are destructive and involve tissue fixation and freezing or cell lysis, precluding Applicants from directly tracking the dynamics of full molecular profiles in live cells or organisms. While advanced computational methods such as pseudo-time algorithms (e.g., Monocle[2], Waddington-OT[3]) and velocity-based methods (e.g., velocyto[4], sc Velo[5]) can infer dynamics from snapshots of molecular profiles, they rely on assumptions such as Markov properties which is violated when epigenetic modifications occur or knowledge of splicing rates that remain challenging to obtain experimentally[6]. On the other hand, fluorescent reporters can be used to monitor the dynamics of individual genes and programs within live cells, but are limited in the number of targets they can report[7], must be chosen ahead of the experiment, and often involve genetically engineered cells. Moreover, the vast majority of dyes and reporters require fixation or can interfere with nascent biochemical processes and alter the natural state of the gene of interest[7]. Therefore, it remains technically challenging to dynamically monitor the activity of a large number of genes simultaneously.

Raman microscopy opens a unique opportunity for monitoring live cells and tissues, as it collectively reports on the vibrational energy levels of molecules in a label-free and non-destructive manner at a subcellular spatial resolution (<500 nm), thus providing molecular fingerprints of cells[8]. Pioneering research has demonstrated that Raman microscopy can be used for characterizing cell types and cell states[8], non-destructively diagnosing pathological specimens such as tumors[9], characterizing the developmental states of embryos[10], and identifying bacteria with antibiotic resistance[11]. However, the complex and high-dimensional nature of the spectra, the spectral overlaps of biomolecules such as proteins and nucleic acids, and the lack of unified computational frameworks have hindered the decomposition of the underlying molecular profiles[7,8].

To address this challenge and leverage the complementary strengths of Raman microscopy and scRNA-Seq, Applicants developed Raman2RNA (R2R), an experimental and computational framework for inferring single-cell RNA expression profiles from label-free non-destructive Raman hyperspectral images (FIG. 23). R2R takes spatially resolved hyperspectral Raman images (full Raman spectrum for each pixel in an image) from live cells, smFISH data of selected markers from the same cells, and scRNA-seq from the same biological system. R2R then learns a common latent space of the paired or unpaired Raman images and scRNA-seq using, for example, adversarial autoencoders. Finally, R2R translates Raman images into single-cell expression profiles, which are validated by smFISH data. When combined with a separate single live-cell tracking of time-lapse Raman imaging during ESCs differentiation, the result is a label-free live-cell inference of single-cell expression profiles over time.

To facilitate data acquisition, Applicants developed a high-throughput multimodal spontaneous Raman microscope that enables the automated acquisition of Raman spectra, brightfield, and fluorescent images. In particular, Applicants integrated Raman microscopy optics to a fluorescence microscope, where high-speed galvo mirrors and motorized stages were combined to achieve a large field of view (FOV) scanning, and where dedicated electronics automate measurements across multiple modalities (FIG. 27-28, Methods).

Applicants first demonstrated that R2R can infer profiles of two distinct cell types: mouse induced pluripotent stem cells (iPSCs) expressing an endogenous Oct4-GFP reporter and mouse fibroblasts[12]. To this end, Applicants mixed the cells in equal proportions, plated them in a gelatin-coated quartz glass-bottom Petri dish, and performed live-cell Raman imaging, along with fluorescent imaging of live-cell nucleus staining dye (Hoechst 33342) for cell segmentation and image registration, and an iPSC marker gene, Oct4-GFP (FIG. 24*a*). The excitation wavelength for the Raman microscope (785 nm) was distant enough from the GFP Stokes shift emission, such that there was no interference with the cellular Raman spectra (FIG. 29). Furthermore, there was no noticeable photo-toxicity induced in the cells (FIG. 30). After Raman and fluorescence imaging, Applicants fixed and permeabilized the cells and performed smFISH (with hybridization chain reaction (HCR[13]), Methods) of marker genes for mouse iPSCs (Nanog) and fibroblasts (Col1a1). Applicants registered the nuclei stains, GFP images, HCR images, and Raman images through either polystyrene control bead images or reference points marked under the glass bottom dishes (FIG. 31, Methods).

The Raman spectra distinguished the two cell populations in a manner congruent with the expression of their respective reporter (measured live or by smFISH in the same cells), as reflected by a low-dimensional embedding of hyperspectral Raman data (FIG. 24*b*). Specifically, Applicants focused on the fingerprint region of Raman spectra (600-1800 $cm^{-1}$, corresponding to 930 of the 1,340 features in a Raman spectrum), where most of the signatures from various key biomolecules, such as proteins, nucleic acids, and metabolites, lie[8]. After basic preprocessing, including cosmic-ray and background removal and normalization, Applicants aggregated Raman spectra that are confined to the nuclei, obtaining a 930-dimensional Raman spectroscopic representation for each cell's nucleus. Applicants then visualized these Raman profiles in an embedding in two dimensions using Uniform Manifold Approximation and Projection (UMAP)[14] and labeled cells with the gene expression levels that were concurrently measured by either an Oct4-GFP reporter or smFISH (FIG. 24*b*). The cells separated clearly in their Raman profiles in a manner consistent with their gene expression characteristics, forming two main subsets in the embedding, one with cells with high Oct4 and Nanog expression (iPSCs markers) and another with cells with relatively high Col1a1 expression (fibroblasts marker), indicating that Raman spectra reflect cell-intrinsic expression differences (FIG. 24*b*).

Applicants further successfully trained a classifier to classify the 'on' or 'off' expression states of Oct4, Nanog and Col1a1 in each cell based on its Raman profile (Methods). Applicants trained a logistic regression classifier with 50% of the data and held out 50% for testing. Applicants predicted Oct4 and Nanog expression states with high accuracy on the held-out test data (area under the receiver operating characteristic curve (AUROC)=0.98 and 0.95, respectively; FIG. 24*c*), indicating that expression of iPSC markers can be predicted confidently from Raman spectra of live, label-free cells. Applicants also successfully classified the expression state of the fibroblast marker Col1a1 (AUROC=0.87; FIG. 24*c*), albeit with lower confidence, which is consistent with the lower contrast in Col1a1 expression (FIG. 24*b*) between iPSC (Oct4+ or Nanog+ cells) vs. non-iPSCs, compared to Oct4 or Nanog. Most misclassifications occurred when the ground truth expression levels were near the threshold of the classifier, showing that misclassifications were likely due to the uncertainty in the ground truth expression level (FIG. 32).

Figure 25A:
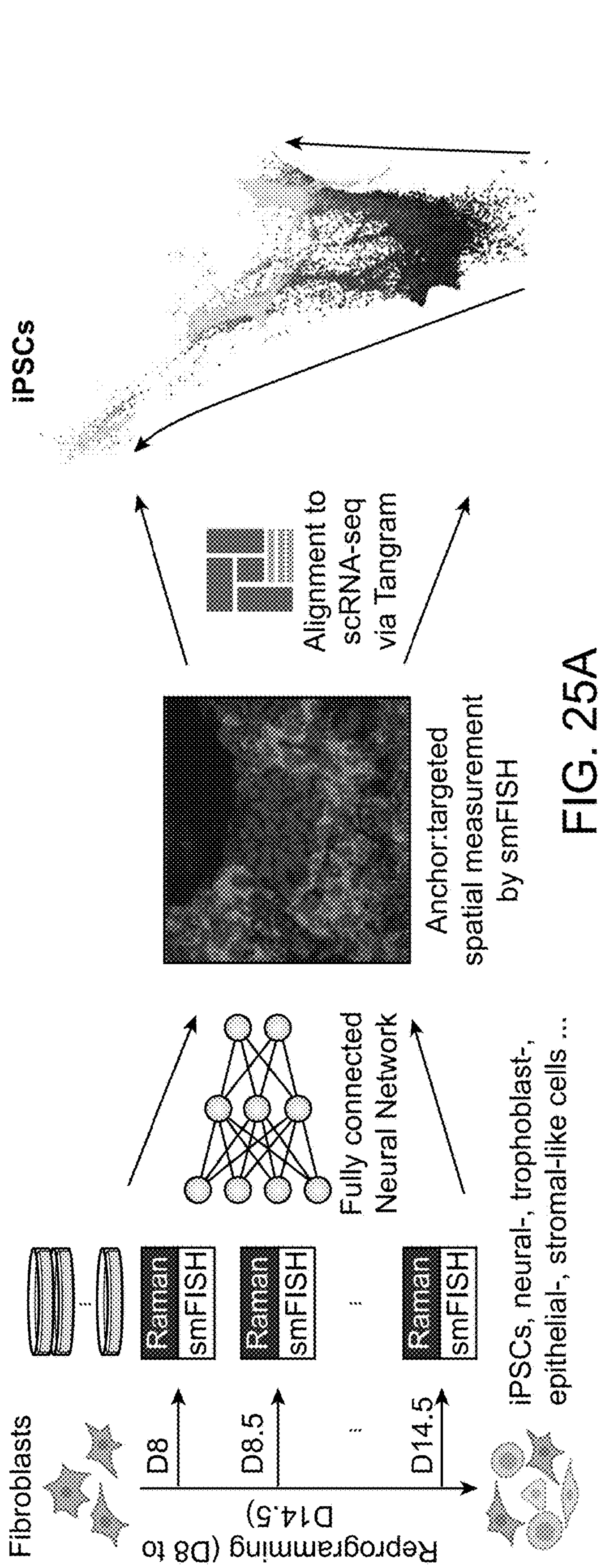
Figure 25B:
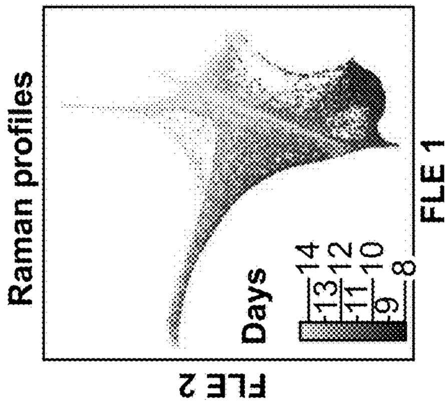
Figure 25C:
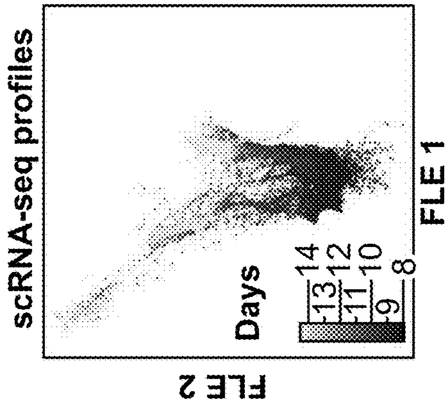
Figure 25D:
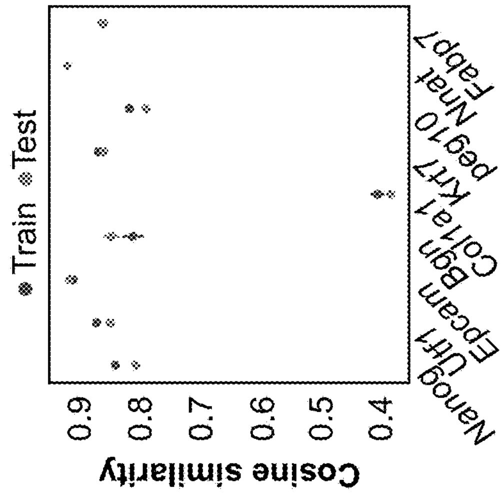
Figures 25E, 25F, 25G, 25H, 25I:
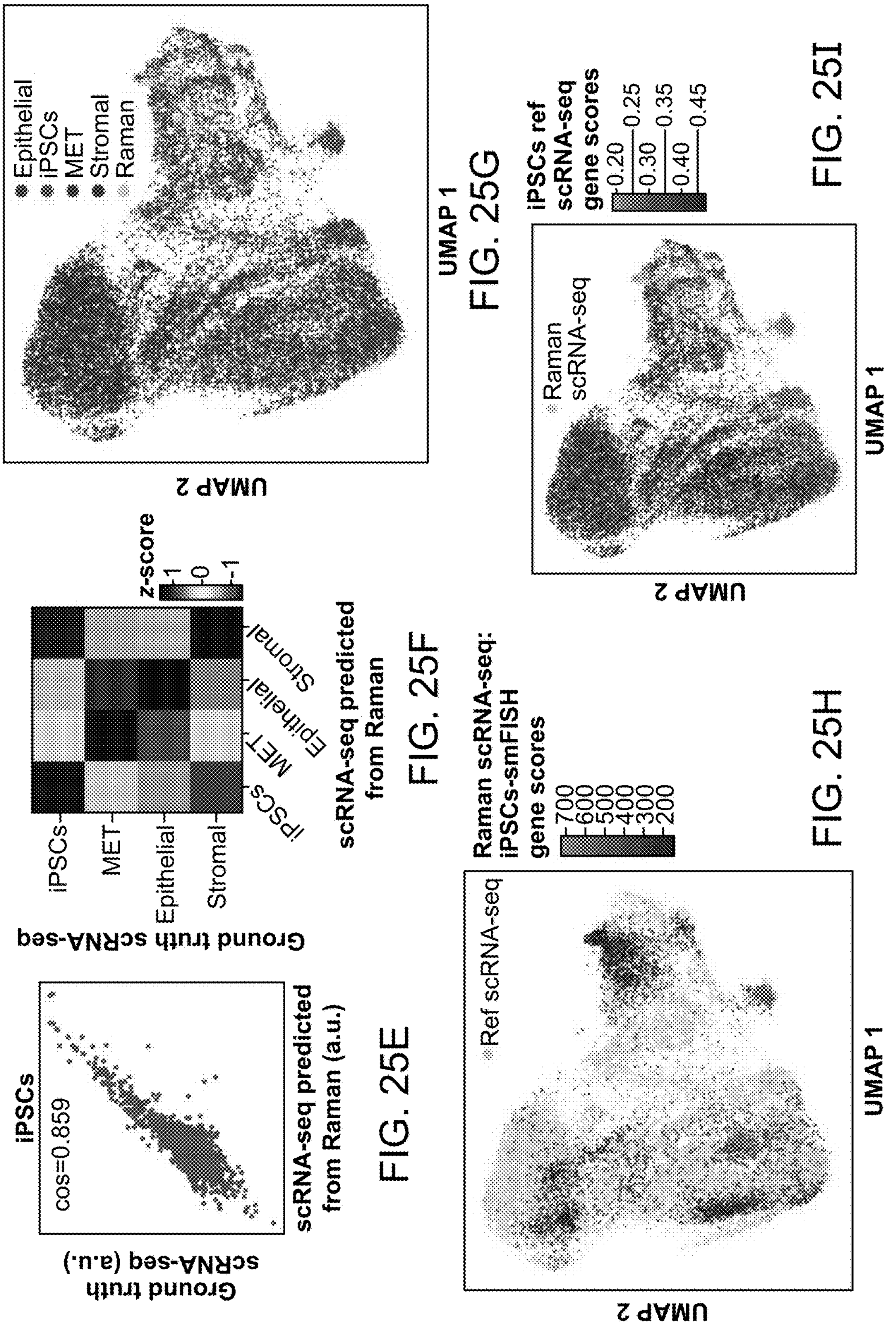

Next, Applicants asked if the Raman images could predict entire expression profiles non-destructively at single-cell resolution. To this end, Applicants aimed to reconstruct scRNA-seq profiles from Raman images by multimodal data integration and translation, using multiplex smFISH data to anchor between the Raman images and scRNA-seq profiles (FIG. 25*a*). As a test case, Applicants focused on the mouse iPSC reprogramming model system, where Applicants have previously generated ~250,000 scRNA-seq profiles at 1/2 day intervals throughout an 18 day, 36 time point time course of reprogramming[3] (Methods). Applicants used Waddington-OT[3] (WOT) to select from the scRNA-seq profiles nine anchor genes that represent diverse cell types that emerge during reprogramming (iPSCs: Nanog, Utf1 and Epcam; MET and neural: Nnat and Fabp7; epithelial: Krt7 and Peg10; stromal: Bgn and Col1a1; Methods). Applicants performed live-cell Raman imaging from day 8 of reprogramming, in which distinct cell types begin to emerge[3], up to day 14.5, at half-day intervals, totaling 14 time points (Methods). Applicants imaged ~500 cells per plate at 1 μm spatial resolution. Finally, Applicants fixed cells immediately after each Raman imaging time point followed by smFISH on the 9 anchor genes (Methods).

Strikingly, a low dimensional representation of the Raman profiles showed that they encoded similar temporal dynamics to those observed with scRNA-seq during reprogramming (FIG. 25*b,c*, FIG. 33), indicating that they may qualitatively mirror scRNA-seq.

Integrating Raman and scRNA-seq profiles (Methods), Applicants first explored whether Applicants can infer scRNA-seq profiles from Raman images in two-steps through a few marker genes as anchors measured by smFISH. Here, R2R learned a fully connected neural net that can predict smFISH anchors from the Raman profiles (Methods) and then used Tangram[16] method to map to full scRNA-seq profiles from the anchors (FIG. 23, FIG. 25*d-f*). In the first step, Applicants averaged the smFISH signal within a nucleus to represent a single nucleus's expression level. As Applicants conducted smFISH of 9 genes, the result was a 9-dimensional smFISH profile for each single nucleus. Then, Raman profiles were translated to these 9-dimensional profiles with the neural net using 50% of the Raman and smFISH profiles as training data.

In the second step, Applicants mapped these anchor smFISH profiles to full scRNA-seq profiles using Tangram, yielding well-predicted single cell RNA profiles, as supported by several lines of evidence. First, Applicants performed leave-one-out cross-validation (LOOCV) analysis, in which Applicants used eight out of the nine anchor genes to integrate Raman with scRNA-seq, and compared the predicted expression of the remaining genes to its smFISH measurements. The predicted left-out genes based on scRNA-seq showed a significant correlation with the measured smFISH expression for any left-out gene (cos similarity r~0.8, p-value<10-100, FIG. 25*d*). Notably, when Applicants analogously applied neural nets to either infer smFISH profiles or classify cell types from brightfield images, Applicants observed a poor, near-random prediction 9 genes in LOOCV (cos similarity<0.15) for regression, and f-scores iPSCs: 26.6%, epithelial: 27.9%, MET: 46.3%, stromal: 1.1% for classification (FIG. 45-46, Methods). This indicates that brightfield z-stack images, unlike Raman spectra, either do not have the necessary information to infer expression profiles or require significant modifications in the neural network architecture. Second, Applicants compared the real (scRNA-seq measured) and R2R predicted expression profiles averaged across cells of the same cell type ("pseudo-bulk" for each of iPSCs, epithelial cells, stromal cells, and MET). Here, Applicants obtained the "ground truth" cell types of the R2R profiles by transferring scRNA-seq annotations to the matching smFISH profiles using Tangram's label transfer function. Then, based on the labels, Applicants averaged R2R's predicted profiles across the cells of a single cell type. The two profiles (R2R-inferred and scRNA-seq pseudo-bulk per cell type) showed high correlations (cos similarity>0.95) (FIG. 25*e,f*, FIG. 34), demonstrating the accuracy of R2R at the cell type level. Furthermore, projecting the R2R predicted profiles of each cell onto an embedding learned from the real scRNA-seq shows that the predicted profiles span the key cell types as captured in real profiles (FIG. 25*g-i*, FIG. 35-39). Applicants note that the predicted profiles had lower variance compared to real scRNA-seq. As this is observed even when co-embedding only smFISH and scRNA-seq measurements (with no Raman data or projection, FIG. 40), Applicants believe it mostly reflects the limited number and domain maladaptation of the smFISH anchor genes used for integration.

In order to test how sensitive R2R was in tracking temporal changes during iPSC reprograming, Applicants trained a classifier with the day label given as ground truth. Confusion matrix confirmed that R2R can reliably detect changes occurring on the order of 0.5 days (FIG. 41). Furthermore, varying the number of cells and anchor genes used for training emperically confirmed that having around 600 cells and 4 genes is sufficient for a reliable transcriptome prediction (FIG. 42).

Figure 25J:
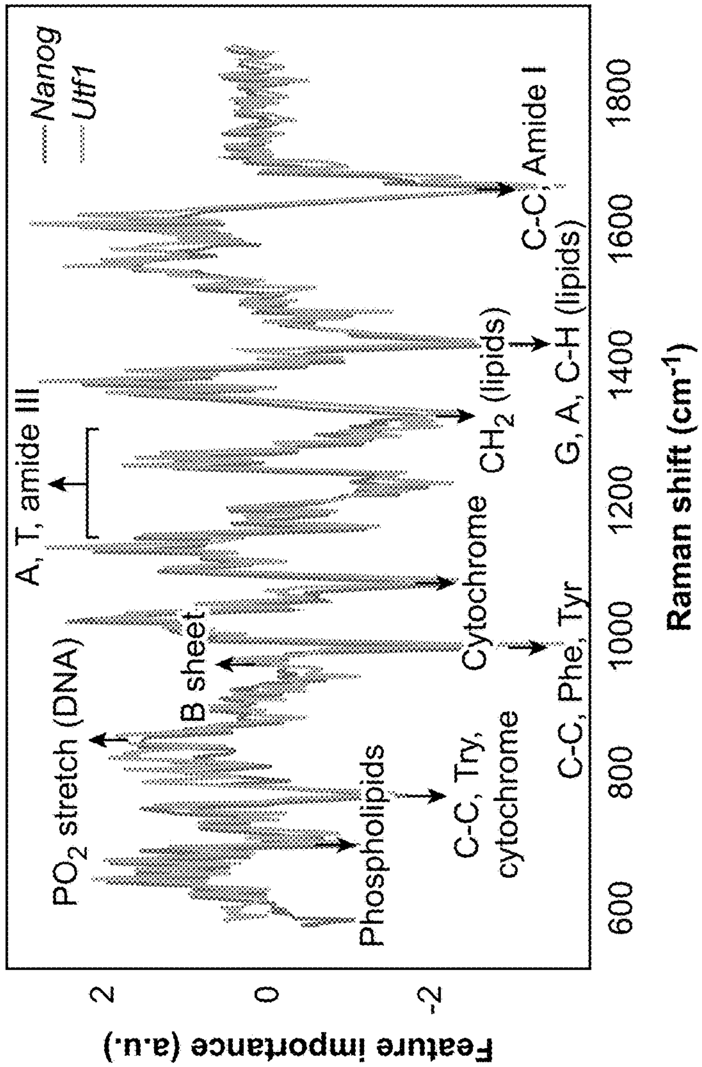
Figure 25K:
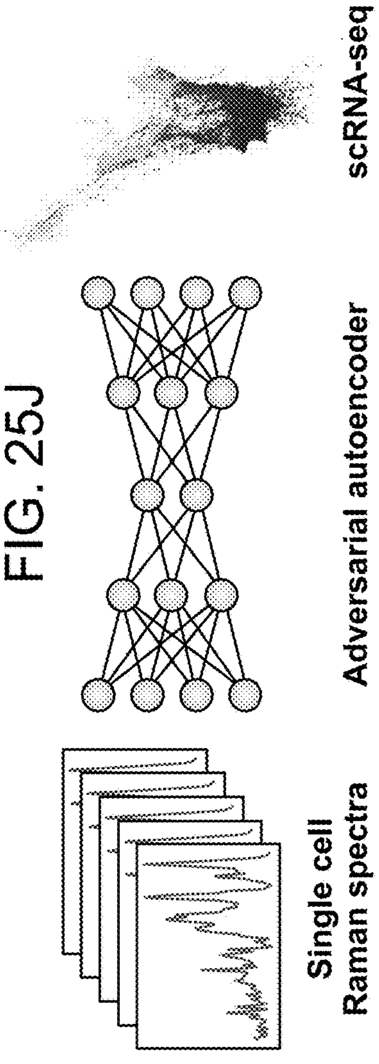
Figure 25L:
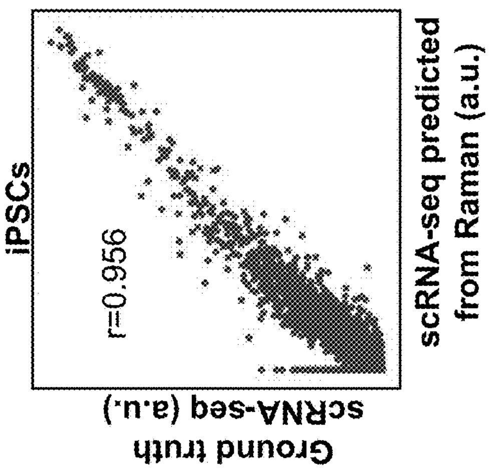
Figure 25M:
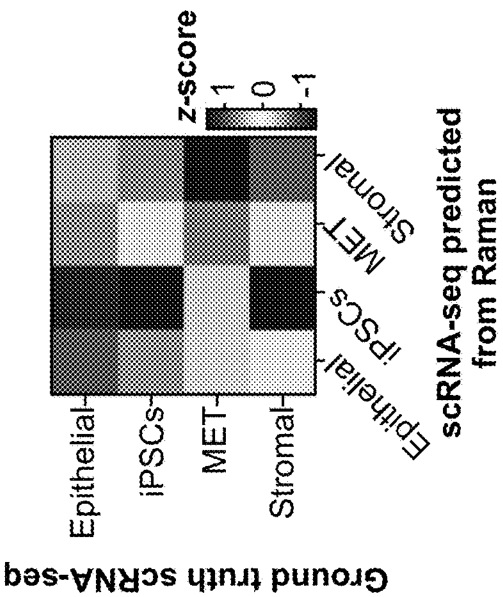

Next, Applicants identified Raman spectral features correlated with expression levels by calculating feature importance scores in R2R predictions (Methods, FIG. 25*j*, FIG. 43). For example, Raman bands at approximately 752 $cm^{-1}$ (C—C, Try, cytochrome), 1004 $cm^{-1}$ (CC, Phe, Tyr), and 1445 $cm^{-1}$ (G, A, C—H, lipids) contributed to predicting iPSCs-related expression profiles, which is consistent with previous research that employed single cell Raman spectra to identify mouse embryonic stem cells (ESCs) 18. The contributions of these bands were either suppressed or increased for other cell types, such as stromal or epithelial cells (FIG. 43).

In most biomedical systems, spatial gene expression measurements (e.g., by smFISH, various spatial transcriptomics technologies) are not paired with Raman measurements of the same cells. In addition, Applicants speculate that the anchor gene integration step causes domain maladaptation. Therefore, Applicants explored whether Applicants can obviate the smFISH anchor step and perform a 'one-step' translation model. To this end, Applicants developed a deep adversarial autoencoder that directly translates Raman images into expression profiles (Methods). Through adversarial training, which allows for integration of two different modalities of unpaired measurements, Applicants obtained accurate predictions (cosine similarity >0.94) (FIG. 251, m, FIG. 44). As expected, although the accuracy decreases compared to the 'two-step' prediction (~26% decrease in pair-wise correlation z-score relative to anchored), these results show promise for using referencing existing Cell Atlases for scRNA-seq profiles without the need for performing additional paired spatial gene expression measurements (e.g. smFISH) as anchors, which will have broader applications across various biomedical systems.

Figures 26A, 26B, 26C, 26D, 26E, 26F, 26G, 26H, 26I:
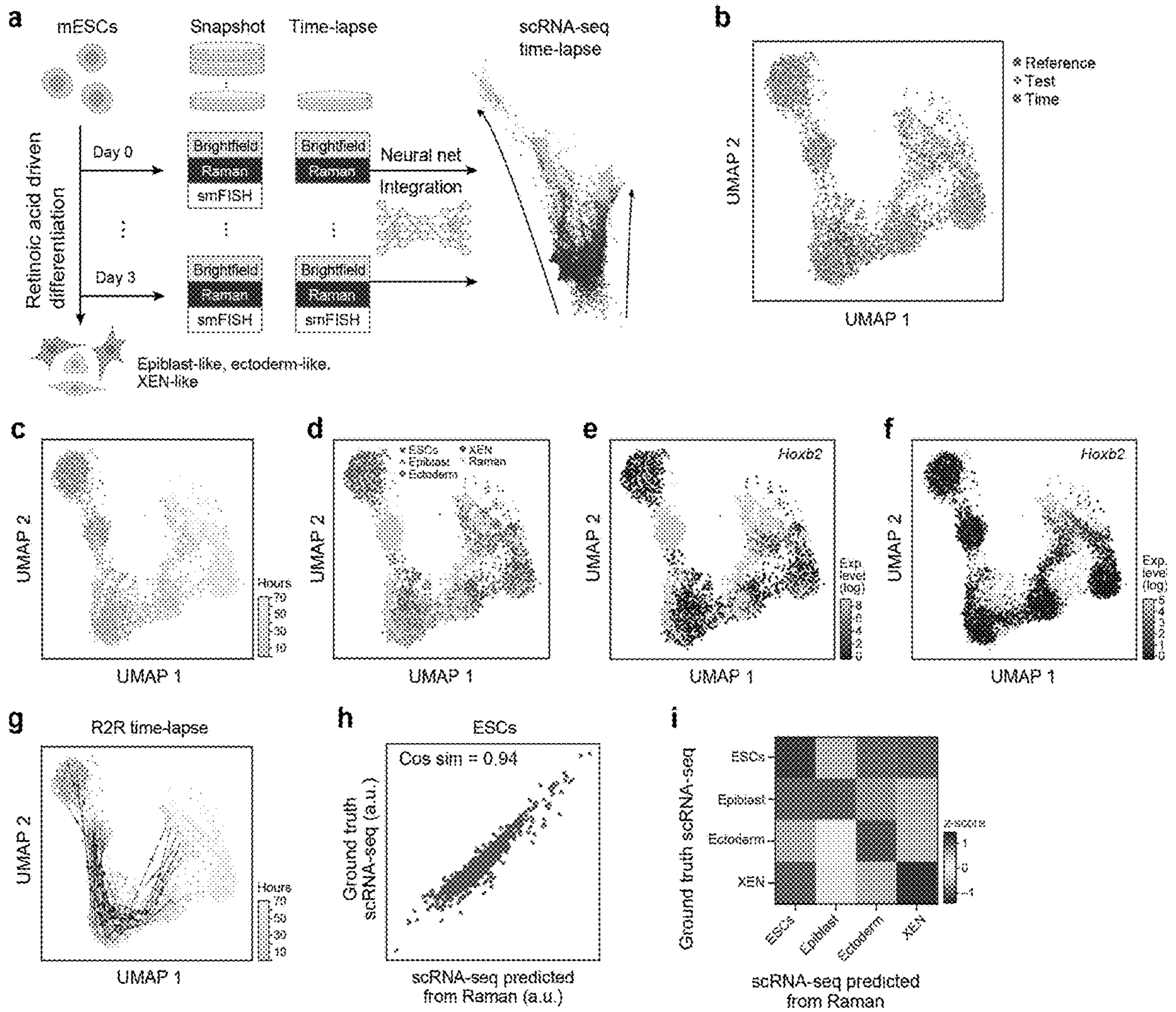

One unique strength of R2R is that one can track live cells and study their dynamics while providing genetic interpretability. On the contrary, almost all single-cell omics technologies are inhenrently desdructive, precluding measuring molecular dynamics in live cells over time. Lastly, Applicants demonstrated R2R in live-cell time-lapse measurements in a well established mouse embryonic stem cells (mESCs) differentiation model[18] (FIG. 26*a*). Applicants tracked mESCs differentiation process supplemented with retinoic acid (RA). Under RA, mESCs differentiate into epiblast, ectoderm or extraembryonic endoderm (XEN)-like cells over the course of 72 to 96 hours[18]. Applicants first took snapshot measurements across different time points (typically 12 hours apart, 7 time points, 1 plate per time point), followed by smFISH on 4 genes referring marker genes from literature (ESCs: Pou5f1, epiblastt: Dppa2, ectoderm: Hoxb2, XEN: Sox17)[18]. Then, on a separate plate, Applicants conducted Raman time-lapse measurements to track the differentiation process of same single cells over time (Methods). Through co-embedding of R2R predicted profiles and real scRNA-seq profiles (FIG. 26*b-d*), Applicants confirmed R2R predictions accurately predicted individual genes (FIG. 26*e-f*, FIG. 47) and expression profiles across various cell types compared with ground truth profiles[18] (FIG. 26*h-i*). Applicants then applied R2R to the Raman time-lapse measurements, which offered direct cell lineage transcriptome information enabled by cell tracking (Methods), once again showing the unique applicability of the method in tracking biological processes in live cells. Applicants found the transitioning of mESCs into epiblasts in around 24 hours, then to ectoderm-like or XEN-like cells (FIG. 26*e*). Notably, R2R detected the lineage divergence from as early as 48 hours which were not easily tracked in scRNA-seq-based studies[18]. The early lineage divergence in response to RA treatment is most likely associated with the activation of ectoderm- and XEN-like gene programs, which Raman time-lapse measurements could capture the early divergence while scRNA-seq may not have been sensitive enough. Applicants emphasize that these cell type transitions were detected agnostically through R2R and validated by literature[18], whereas computational methods such as pseudo-time algorithms or RNA velocity with default parameters produced non-sensical results such as epiblasts "reprogramming" to mESCs (FIG. 48). In summary, this assay demonstrates broad applications of R2R for understanding the molecular dynamics in live cells and uncovering new biological mechanisms.

In conclusion, Applicants reported R2R, a label-free non-destructive framework for inferring single-cell expression profiles from Raman spectra of live cells. The framework conceptually differs from approaches that gauge specific Raman spectral bands to specific molecules, but rather aims to associate spectral bands to RNA-based cell states. By integrating Raman hyperspectral images with scRNA-seq data through paired or unpaired smFISH measurements and multimodal data integration or adversarial autoencoders, Applicants inferred single-cell expression profiles with high accuracy based on both averages within cell types and co-embeddings of individual profiles. Applicants further showed that predictions using brightfield z-stacks had poor performance, indicating the importance of hyperspectral Raman microscopy for predicting expression profiles. Lastly, Applicants applied R2R in live-cell time-lapse measurements, and demonstrated that expression profiles of the same live cell can be inferred over time, where existing computational trajectories inference methods failed to reconstruct biologically reasonable results.

R2R can be further developed in several ways. First, the throughput of single-cell Raman microscopy is still limited. In this pilot study, Applicants profiled ~10,000 cells in total. By using emerging vibrational spectroscopy techniques, such as Stimulated Raman Scattering microscopy[19] or photo-thermal microscopy[20,21], Applicants envision increasing throughput by several orders of magnitude, to match the throughput of massively parallel single cell genomics. Second, because molecular circuits and gene regulation are structured, with strong co-variation in gene expression profiles across cells, Applicants can leverage the advances in computational microscopy to infer high-resolution data from low-resolution data, such as by using compressed sensing, to further increase throughput[22]. Third, increasing the number of anchor genes (e.g., by seqFISH[23], merFISH[24], STARmap[25], or ExSeq[26]) can increase the prediction accuracy and capture more single-cell variance. Forth, the adversarial networks that Applicants used for the unpaired training is unstable, and other domain translation architectures such as contrastive learning[27] could produce more stable results. Finally, with single-cell multi-omics, Applicants can project other modalities, such as scATAC-seq from Raman spectra. Overall, with further advances in single-cell genomics, imaging, and machine learning, Raman2RNA could allow Applicants to non-destructively investigate genome-wide molecular dynamics and complex biological processes through inferring omics profiles at scale in vitro, and possibly in vivo in living organisms.

Materials and Methods

Mouse Fibroblast Reprogramming

OKSM secondary mouse embryonic fibroblasts (MEFs) were derived from E13.5 female embryos with a mixed B6; 129 background. The cell line used in this study was homozygous for ROSA26-M2rtTA, homozygous for a polycistronic cassette carrying Oct4, Klf4, Sox2, and Myc at the Col1a1 3' end, and homozygous for an EGFP reporter under the control of the Oct4 promoter. Briefly, MEFs were isolated from E13.5 embryos from timed-matings by removing the head, limbs, and internal organs under a dissecting microscope. The remaining tissue was finely minced using scalpels and dissociated by incubation at 37 °C for 10 minutes in trypsin-EDTA (ThermoFisher Scientific). Dissociated cells were then plated in MEF medium containing DMEM (ThermoFisher Scientific), supplemented with 10% fetal bovine serum (GE Healthcare Life Sciences), non-essential amino acids (ThermoFisher Scientific), and GlutaMAX (ThermoFisher Scientific). MEFs were cultured at 37 °C and 4% $CO_2$ and passaged until confluent. All procedures, including maintenance of animals, were performed according to a mouse protocol (2006N000104) approved by the MGH Subcommittee on Research Animal Care[3].

For the reprogramming assay, 50,000 low passage MEFs (no greater than 3-4 passages from isolation) were seeded in 14 3.5 cm quartz glass-bottom Petri dishes (Waken B Tech) coated with gelatin. These cells were cultured at 37 °C and 5% $CO_2$ in reprogramming medium containing KnockOut DMEM (GIBCO), 10% knockout serum replacement (KSR, GIBCO), 10% fetal bovine serum (FBS, GIBCO), 1% GlutaMAX (Invitrogen), 1% nonessential amino acids (NEAA, Invitrogen), 0.055 mM 2-mercaptoethanol (Sigma), 1% penicillin-streptomycin (Invitrogen) and 1,000 U/ml leukemia inhibitory factor (LIF, Millipore). Day 0 medium was supplemented with 2 mg/mL doxycycline Phase-1 (Dox) to induce the polycistronic OKSM expression cassette. The medium was refreshed every other day. On day 8, doxycycline was withdrawn. Fresh medium was added every other day until the final time point on day 14. One plate was taken every 0.5 days after day 8 (D8-D14.5) for Raman imaging and fixed with 4% formaldehyde immediately after for HCR.

High-Throughput Multimodal Raman Microscope and Time-Lapse Imaging

Applicants developed an automated high-throughput multimodal microscope capable of multi-position and multi-timepoint fluorescence imaging and point scanning Raman microscopy (FIG. 27). A 749 nm short-pass filter was placed to separate brightfield and fluorescence from Raman scattering signal, and the fluorescence and Raman imaging modes were switched by swapping dichroic filters with auto-turrets. To realize a high-throughput Raman measurement, galvo mirror-based point scanning and stage scanning was combined to acquire each FOV and multiple different FOVs, respectively.

To realize this in an automated fashion, a MATLAB (2020b) script that communicates with Micro-manager28, a digital acquisition (DAQ) board, and Raman scattering detector (Princeton Instruments, PIXIS 100BR eXcelon) was written (FIG. 28). A 2D point scan Raman imaging sequence was regarded as a dummy image acquisition in Micro-manager, during which the script communicated via the DAQ board with 1. the detector to read out a spectrum, 2. the mirror to update the mirror angles, and 3. shutters to control laser exposure. All communications were realized using transistor-transistor logic (TTL) signaling. Updating of the galvo mirror angles was conducted during the readout of the detector. While the script ran in the background, Micro-manager initiated a multi-dimensional acquisition consisting of brightfield, DAPI, GFP, and dummy Raman channel at multiple positions and z-stacks.

An Olympus IX83 fluorescence microscope body was integrated with a 785 nm Raman excitation laser coupled to the backport, where the short-pass filter deflected the excitation to the sample through an Olympus UPLSAPO 60× NA 1.2 water immersion objective. The backscattered light was collimated through the same objective and collected with a 50 μm core multi-mode fiber, which was then sent to the spectrograph (Holospec f/1.8i 785 nm model) and detector. The fluorescence and brightfield channels were imaged by the Orca Flash 4.0 v2 sCMOS camera from Hamamatsu Photonics. The exposure time for each point in the Raman measurement was 20 msec, and laser power at the sample plane was 212 mW. Each FOV was $100\times10^0$ pixels, with each pixel corresponding to about 1 μm. The laser source was a 785 nm Ti-Sapphire laser cavity coupled to a 532 nm pump laser operating at 4.7 W.

The time to acquire Raman hyperspectral images was roughly 8 minutes per FOV. With 8 minutes, it is unrealistic to image an entire glass-bottom plate. Therefore, for reprogramming cells, Applicants visually chose representative FOVs that cover all representative cell types including iPSC-like, epithelial-like, stromal-like, and MET cells. 21 FOVs were chosen for each plate, where roughly 15 FOVs were from the boundaries of colonies, five from non-colonies, and one from non-cells to use for background correction in reprogramming cells. For mESCs differentiation, 20 FOVs were chosen that cover mESCs, epiblast-like, ectoderm-like, and XEN-like cells and one FOV for background correction.

Due to the extended Raman imaging time, evaporation of the immersion water was no longer negligible. Therefore, Applicants developed an automated water immersion feeder using syringe pumps and syringe needles glued to the tip of the objective lens. Here, water was supplied at a flow rate of 1 μL/min.

iPSC and MEF Mixture Experiment

Low passage iPSCs were first cultured in N2B27 2i media containing 3 mM CHIR99021, 1 mM PD0325901, and LIF. On the day of the experiment, 750,000 iPSCs and 750,000 MEFs were plated on the same gelatin-coated 3.5 cm quartz glass-bottom Petri dish. Cells were plated in the same reprogramming medium as previously described (with Dox) with the exception of utilizing DMEM without phenol red (Gibco) instead of KnockOut DMEM. 6 hours after plating, the quartz dishes were taken for Raman imaging and fixed with 4% formaldehyde immediately after for HCR.

mESCs Differentiation Experiment

For mESC differentiation, Applicants followed the protocol described by Semrau et. al [18]. Briefly, 40,000 V6.5 mESCs were plated onto 35 mm quartz bottom plates with a 10% gelatin coating and grown overnight, using modified 2i medium plus LIF. Modified 2i medium plus LIF (2i/L) contained no phenol-red DMEM/F12 (Life technologies) supplemented with 0.5×N2 supplement (Gibco), 0.5×B27 supplement (Gibco), 0.5 mM L-glutamine (Gibco), 20 μg/ml human insulin (Sigma-Aldrich), 1×100 U/ml penicillin/streptomycin (Gibco), 0.5×MEM Non-Essential Amino Acids (Gibco), 0.1 mM 2-Mercaptoethanol (Sigma-Aldrich), 1 μM MEK inhibitor (PD0325901, Stemgent), 3 μM GSK3 inhibitor (CHIR99021, Stemgent), and 1000 U/ml mouse LIF (ESGRO). The next day, cells were washed twice with PBS and differentiation medium was added. The differentiation medium used was basal N2B27 medium (2i/L without the inhibitors, LIF, and insulin) supplemented with all-trans retinoic acid (RA, Sigma-Aldrich) at 0.25 μM unless stated otherwise. Spent medium was exchanged with fresh medium every 48 hours.

Anchor Gene Selection by Waddington-OT

To select anchor genes for connecting spatial information to the full transcriptome data, Waddington-OT (WOT) 3, a probabilistic time-lapse algorithm that can reconstruct developmental trajectories, was used. Applicants applied WOT to mouse fibroblast reprogramming scRNA-seq data collected at matching time-points and culture condition (day 8-14.5 at 1/2 day intervals) 3. For each cell fate, Applicants calculated the transition probabilities of each cell and selected the top 10 percentile cells per time point (FIG. 32). Based on this, Applicants ran the FindMarker function in Seurat[29] to find genes differentially expressed in these cell subsets per time point. Through this approach, Applicants chose two genes per cell type that are both found by Seurat and commonly used for these cell types (iPSCs: Nanog, Utf1; epithelial: Krt7, Peg10; stromal: Bgn, Col1a1; MET and neural: Fabp7, Nnat), along with one gene that is an early marker of iPSCs, Epcam.

smFISH by Hybridization Chain Reaction (HCR)

Fixed samples were prepared for imaging using the HCR v3.0 protocol for mammalian cells on a chambered slide, incubating at the amplification step for 45 minutes in the dark at room temperature. Three probes with amplifiers conjugated to fluorophores Alexa Fluor 488, Alexa Fluor 546, and Alexa Fluor 647 were used. Samples were stained with DAPI prior to imaging. After imaging, probes were stripped from samples by washing samples once for 5 minutes in 80% formamide at room temperature and then incubating three times for 30 minutes in 80% formamide at 37 °C. Samples were washed once more with 80% formamide, then once with PBS, and reprobed with another panel of probes for subsequent imaging.

Image Registration of Raman Hyperspectral Images and Fluorescence/smFISH Images

Brightfield and fluorescence channels including DAPI and GFP, along with corresponding Raman images, were registered by using 5 μm polystyrene beads deposited on quartz glass-bottom Petri dishes (SF-S-D12, Waken B Tech) for calibration. The brightfield and fluorescence images of the beads were then registered by the scale-invariant template matching algorithm of the OpenCV (github.com/opencv/opencv) matchTemplate function followed by manual correction.

For the registration of smFISH and Raman images, four marks inscribed under the glass-bottom Petri dishes were used as reference points (FIG. 30). As the Petri dishes are temporarily removed from the Raman microscope after imaging to do smFISH measurements, the dishes cannot be placed back at the same exact location on the microscope. Therefore, the coordinates of these reference points were measured along with the different FOVs. When the dishes were placed again after smFISH measurements, the reference mark coordinates were measured, and an affine mapping was constructed to calculate the new FOV coordinates. Lastly, as smFISH consisted of 3 rounds of hybridization and imaging, the following steps were performed to register images across different rounds with a custom MATLAB script:

1. Maximum intensity projection of nuclei stain and RNA images
2. Automatic registration of round 1 images to rounds 2 and 3 based on nuclei stain images and MATLAB function imregtform. First, initial registration transformation functions were obtained with a similarity transformation model passing the 'multimodal' configuration. Then, those transformations were used as the initial conditions for an affine model-based registration with the imregtform function. Finally, this affine mapping transformation was applied to all the smFISH (RNA) images.
3. Use the protocol in (2) to register nuclei stain images obtained from the multimodal Raman microscope and the 1$^{st}$ round of images used for smFISH. Then, apply the transformation to the remaining 2$^{nd}$ and 3$^{rd}$ rounds.
4. Manually remove registration outliers in (3). Roughly 10% of the images were removed.

Fibroblast cells were mobile during the 2-class mixture experiment so that by the time Raman imaging finished, cells had moved far enough from their original position that the above semi-automated strategy could not be applied. Thus, Applicants manually identified roughly 100 cells present in both nuclei stain images before and after the Raman imaging.

Hyperspectral Raman Image Processing

Each raw Raman spectrum has 1,340 channels. Of those channels, Applicants extracted the fingerprint region (600-1800 $cm^{-1}$), which resulted in a total of 930 channels per spectrum. Thus, each FOV is a 100×100×930 hyperspectral image. As Applicants scanned the sample at 1 μm steps, the FOV corresponded to a 100-by-100 $\mu m^2$ region. The hyperspectral images were then preprocessed by a python script as follows:

1. Cosmic ray removal. Cosmic rays were detected by subtracting the median filtered spectra from the raw spectra, and any feature above 5 was classified as an outlier and replaced with the median value. The kernel window size for the median filter was 7.
2. Autofluorescence removal. The baseline function in rampy (github.com/charlesll/rampy), a python package for Raman spectral preprocessing, was used with the alternating least squares algorithm 'als'.
3. Savitzky-Golay smoothing. The scipy.signal.savgol_filter function was used with window size 5 and polynomial order 3.
4. Averaging spectra at the single-cell level. Nuclei stain images were segmented using NucleAlzer (github.com/spreka/biomagdsb) and averaged pixel-level spectra that fall within each nucleus.
5. Spectra standardization. Spectra were standardized to a mean of 0 and a standard deviation of 1.

Cell Segmentation and Cell Tracking of Raman Time-Lapse Images During mESC Differentiation Nuclei stains such as DAPI or Hoechst 33342 require UV excitation, which makes long-term time-lapse imaging not feasible in most cases. Therefore, Applicants performed cell segmentation of time-lapse measurements directly on brightfield z-stack images. To aid segmentation, Applicants used f-net, a deep learning model that predicts fluorescent images from brightfield images[30]. Ground truth nuclei stains of the corresponding brightfield images, which were obtained at snapshot timepoints, were used to train the U-net. Then, the neural net was applied to real time-lapse images to produce 'digital stains.' Then, Applicants applied Stardist[31] to carry out cell segmentation. This process was imperfect, so Applicants manually corrected segmentation errors using Napari (github.com/napari/napari). Lastly, Applicants conducted cell tracking by Bayesian Tracker[32].

Anchored Inference of the Transcriptome from Raman Spectra and smFISH

The anchored prediction consists of two steps: first to predict the anchor smFISH profiles from Raman profiles using a fully connected neural net, and second to integrate the predicted smFISH profile to scRNA-seq using Tangram.

The training for the neural net to predict smFISH profiles was carried out on an NVIDIA Tesla P100 GPU, according to a mean square error loss, for 100 epochs. The model was trained with a learning rate was 0.00001 on an Adam Optimizer and a batch size of 64. The smFISH were normalized, per gene, using min-max normalization before training. The model consisted of 3 Linear, BatchNorm, ReLU activation blocks in sequence. Letting n be the number of input spectra, the number of nodes in these three blocks were, in order, n, 512, 128, 10. To predict smFISH genes from Raman spectra, Applicants trained a neural network. The training was carried out on an NVIDIA Tesla P100 GPU, according to a mean square error loss, for 100 epochs. The model was trained with a learning rate was 0.00001 on an Adam Optimizer and a batch size of 64. The smFISH were normalized, per gene, using min-max normalization before training. The model consisted of 3 Linear, BatchNorm, ReLU activation blocks in sequence. Letting n be the number of input spectra, the number of nodes in these three blocks were, in order, n, 512, 128, 10.

To integrate the predicted smFISH to expression profiles, Applicants used Tangram[16]. Tangram enables the alignment of spatial measurements of a small number of genes to scRNA-seq measurements. Applicants used the map_cells_to_space function of Tangram (learning_rate=0.1, num_epochs=1000) on an Nvidia Tesla P100 GPU, followed by the project genes function in Tangram. Applicants used 50% of the data as training and the remaining 50% as test data.

When comparing different pseudo-bulk transcriptome predictions with the real scRNA-seq data, Applicants first transferred labels of annotated scRNA-seq profiles to the ground truth smFISH profiles using Tangram's label transfer function project_cell_annotations. Then, the average expression profiles across cells of a cell type were calculated by referring to the transferred labels and compared with those from the real scRNA-seq data[3].

For any classification tasks based on Raman spectra, Applicants ran Catboost, a decision tree-based non-linear regression[33]. The early stopping parameter was set to 5.

One-Step Anchor-Free Integration of Raman and scRNA-Seq Profiles Using Adversarial Autoencoders G, which reconstructs gene-expression profiles, was trained according a simple mean-square error loss function S, which outputs a probability vector of celltypes, was then trained with a simple weighted cross-entropy loss function with one-hot vectors for celltypes. R and A were then trained adversarially, taking turns between weight updates. A was trained according to a simple binary cross-entropy loss. R was trained according to the following loss function:

$$f(r)=\mathrm{MSE}(r,R(r))+\lambda_1(\mathrm{ADV}(A(\mathrm{ER}(r))))+\lambda_2(\mathrm{CE}(S(\mathrm{ER}(r)),c_r))$$

where r is a Raman spectrum, $c_r$ is r's celltype, $\lambda_1$ and $\lambda_2$ are regularizing constants, MSE(x, y) is a mean-square error loss between x and y, ADV(x) is the cross entropy loss against labels indicating x is a gene-expression encoding, and CE(x, y) is a cross entropy loss between x and y. G, a deep neural network, consisted of 10 Linear, BatchNorm, ReLU activation blocks in sequence. Letting n be the number of input genes, the number of nodes in these ten blocks are, in order, n, 2048, 2048, 2048, 2048, 512, 2048, 2048, 2048, 2048, n. R followed an architecture identical to G but with a different input dimension than that of G. A consisted of 4 Linear, Spectral Normalization, ReLU activation blocks. The number of nodes in each of these blocks are, in order, 128, 64, 32, 32, 2. All of these models were trained using the Adam optimizer, with G's having a learning rate of 0.00001, R's having 0.00005, and A's having 0.004. G was trained for 30 epochs while R and A were trained together, adversarially, for 100 epochs.

Inferring smFISH and Cell Types from Brightfield Images

Applicants applied deep learning to either regress or classify expression levels at the cellular level from brightfield z-stacks.

For cellular-level regression, Applicants created target cell masks where segmentation masks from nuclei stains were replaced with the average smFISH expression level, thereby averaging out any subcellular variations and thus making a fair comparison with R2R predictions. The goal here is to see if brightfield images can infer these 'blurred' smFISH images. Applicants trained a modified U-net with skip connections and residual blocks to estimate the corresponding smFISH image[16]. Due to the small size of the available training dataset, Applicants augmented the data by rotation and flipping. Furthermore, a subsample of each brightfield image was taken due to memory constraints (50×50 pixel region). The training was carried out on an NVIDIA Tesla P100 GPU, the number of epochs was 100, the learning rate was 0.01, and the batch size was 400. For each smFISH prediction, Applicants chose the epoch that gave the best validation score.

For cellular-level classification, Applicants first took registered smFISH-brightfield images and broke each of them into smaller "tiles," 32-by-32 pixel non-overlapping sections. Applicants then, for each tile, found the average smFISH gene-expression. Applicants then used Tangram and the single-cell RNA-seq data from the reprogramming system to map each tile's average smFISH vector to a cell type. Applicants then trained a Convolutional Neural Network (CNN) to map a brightfield tile to a cell type. This CNN consisted of a Convolutional layer with 11 input channels, 20 output channels, a kernel size of 5, and a stride 1, followed by a ReLU activation layer, followed by a maximum-pool layer with a kernel size of 2 and a stride of 2, followed by another convolutional layer with 20 input channels, 20 output channels, a kernel size of 5, and a stride 1, followed by another ReLU activation layer, followed by another maximum-pool layer with a kernel size of 2 and a stride of 2, followed by a reshaping layer to 500 nodes, another ReLU activation layer, and final fully-connected layer to 4 final nodes. The CNN is trained via a cross entropy loss with an Adam optimizer at a learning rate of 0.00003 for 20 epochs.

Dimensionality Reduction, Embedding and Projection

For dimension reduction and visualization of Raman and scRNA-seq profiles, Applicants performed forced layout embedding (FLE) using the Pegasus pipeline (github.com/klarman-cell-observatory/pegasus). First, Applicants performed principal component analysis on both Raman and scRNA-seq profiles independently, calculated diffusion maps on the top 100 principal components, and performed an approximated FLE graph using Deep Learning by pegasus.net_fle with default parameters.

To project Raman profiles to a scRNA-seq embedding, Applicants calculated a k-nearest neighbor graph (k-NN, k=15) on the scRNA-seq top 50 principal components with the cosine metric, and UMAP with the scanpy.tl.umap function in Scanpy[34] version 1.7.2 with default parameters. Then, the Raman predicted expression profiles were projected on to the scRNA-seq UMAP embedding by scanpy.tl.ingest using k-NN as the labeling method and default parameters.

Feature Importance Analysis

To evaluate the contributions of Raman spectral features to expression profile prediction, Applicants used the get_feature_importance function in Catboost. The early stopping parameter was set to 5. As the dimensions of Raman spectra were reduced by PCA prior to Catboost, feature importance scores were calculated for each principal component, and the weighted linear combination of the Raman PCA eigen vectors with feature scores as the weight were calculated to obtain the full spectrum.

REFERENCES FOR RAMAN2RNA CONTINUED

1. Tanay, A. & Regev, A. Scaling single-cell genomics from phenomenology to mechanism. *Nature* 541, 331-338 (2017).
2. Trapnell, C. et al. The dynamics and regulators of cell fate decisions are revealed by pseudotemporal ordering of single cells. *Nat. Biotechnol.* 32, 381-386 (2014).
3. Schiebinger, G. et al. Optimal-Transport Analysis of Single-Cell Gene Expression Identifies Developmental Trajectories in Reprogramming. *Cell* 176, 928-943.e22 (2019).
4. La Manno, G. et al. RNA velocity of single cells. *Nature* 560, 494-498 (2018).
5. Bergen, V., Lange, M., Peidli, S., Wolf, F. A. & Theis, F. J. Generalizing RNA velocity to transient cell states through dynamical modeling. *Nat. Biotechnol.* 38, 1408-1414 (2020).
6. Wagner, D. E. & Klein, A. M. Lineage tracing meets single-cell omics: opportunities and challenges. *Nat. Rev. Genet.* 21, 410-427 (2020).
7. Wei, L. et al. Super-multiplex vibrational imaging. *Nature* 544, 465-470 (2017).
8. Kobayashi-Kirschvink, K. J. et al. Linear Regression Links Transcriptomic Data and Cellular Raman Spectra. *Cell Systems* vol. 7 104-117.e4 Preprint at doi.org/10.1016/j.cels.2018.05.015 (2018).
9. Singh, S. P. et al. Label-free characterization of ultra violet-radiation-induced changes in skin fibroblasts with Raman spectroscopy and quantitative phase microscopy. *Sci. Rep.* 7, 10829 (2017).
10. Ichimura, T. et al. Visualizing cell state transition using Raman spectroscopy. *PLOS One* 9, e84478 (2014).

11. Ho, C.-S. et al. Rapid identification of pathogenic bacteria using Raman spectroscopy and deep learning. *Nat. Commun.* 10, 4927 (2019).
12. Stadtfeld, M., Maherali, N., Borkent, M. & Hochedlinger, K. A reprogrammable mouse strain from gene-targeted embryonic stem cells. *Nat. Methods* 7, 53-55 (2010).
13. Choi, H. M. T. et al. Third-generation in situ hybridization chain reaction: multiplexed, quantitative, sensitive, versatile, robust. Development 145, (2018).
14. McInnes, L., Healy, J., Saul, N. & Großberger, L. UMAP: Uniform Manifold Approximation and Projection. J. Open Source Softw. 3, 861 (2018).
15. Biancalani, T. et al. Deep learning and alignment of spatially resolved single-cell transcriptomes with Tangram. *Nat. Methods* 18, 1352-1362 (2021).
16. He, K., Zhang, X., Ren, S. & Sun, J. Deep residual learning for image recognition. in 2016 IEEE Conference on Computer Vision and Pattern Recognition (CVPR) (IEEE, 2016). doi: 10.1109/cvpr.2016.90.
17. Germond, A., Panina, Y., Shiga, M., Niioka, H. & Watanabe, T. M. Following Embryonic Stem Cells, Their Differentiated Progeny, and Cell-State Changes During iPS Reprogramming by Raman Spectroscopy. *Anal. Chem.* 92, 14915-14923 (2020).
18. Semrau, S. et al. Dynamics of lineage commitment revealed by single-cell transcriptomics of differentiating embryonic stem cells. *Nat. Commun.* 8, 1096 (2017).
19. Freudiger, C. W. et al. Label-free biomedical imaging with high sensitivity by stimulated Raman scattering microscopy. *Science* 322, 1857-1861 (2008).
20. Bai, Y. et al. Ultrafast chemical imaging by widefield photothermal sensing of infrared absorption. Sci Adv 5, eaav7127 (2019).
21. Tamamitsu, M., Toda, K., Horisaki, R. & Ideguchi, T. Quantitative phase imaging with molecular vibrational sensitivity. *Opt. Lett.* 44, 3729-3732 (2019).
22. Cleary, B., Cong, L., Cheung, A., Lander, E. S. & Regev, A. Efficient Generation of Transcriptomic Profiles by Random Composite Measurements. Cell 171, 1424-1436.e18 (2017).
23. Eng, C.-H. L. et al. Transcriptome-scale super-resolved imaging in tissues by RNA seqFISH. *Nature* 568, 235-239 (2019).
24. Chen, K. H., Boettiger, A. N., Moffitt, J. R., Wang, S. & Zhuang, X. RNA imaging. Spatially resolved, highly multiplexed RNA profiling in single cells. Science 348, aaa6090 (2015).
25. Wang, X. et al. Three-dimensional intact-tissue sequencing of single-cell transcriptional states. *Science* (2018) doi: 10.1126/science.aat5691.
26. Alon, S. et al. Expansion sequencing: Spatially precise in situ transcriptomics in intact biological systems. Science 371, (2021).
27. Radford, A. et al. Learning Transferable Visual Models From Natural Language Supervision. arXiv [cs.CV] (2021).
28. Edelstein, A., Amodaj, N., Hoover, K., Vale, R. & Stuurman, N. Computer control of microscopes using uManager. Curr. Protoc. *Mol. Biol.* Chapter 14, Unit14.20 (2010).
29. Stuart, T. et al. Comprehensive Integration of Single-Cell Data. *Cell* 177, 1888-1902.e21 (2019).
30. Ounkomol, C., Seshamani, S., Maleckar, M. M., Collman, F. & Johnson, G. R. Label-free prediction of three-dimensional fluorescence images from transmitted-light microscopy. *Nat. Methods* 15, 917-920 (2018).
31. Weigert, Schmidt, Haase, Sugawara & Myers. Star-convex Polyhedra for 3D Object Detection and Segmentation in Microscopy. in 2020 IEEE Winter Conference on Applications of Computer Vision (WACV) vol. 0 3655-3662 (2020).
32. Ulicna, K., Vallardi, G., Charras, G. & Lowe, A. R. Automated Deep Lineage Tree Analysis Using a Bayesian Single Cell Tracking Approach. Frontiers in Computer Science 3, (2021).
33. Prokhorenkova, L., Gusev, G., Vorobev, A., Dorogush, A. V. & Gulin, A. CatBoost: unbiased boosting with categorical features.
34. Wolf, F. A., Angerer, P. & Theis, F. J. SCANPY: large-scale single-cell gene expression data analysis. *Genome Biol.* 19, 15 (2018).

Example 6—Multimodal Tissue Data Analysis with the Single-Cell Omics from Histology Analysis Framework (SCHAF)

Tissue biology involves an intricate interplay between cell intrinsic processes and interactions between cells organized in specific spatial patterns, which can be respectively captured by single-cell profiling methods such as single-cell or single nucleus RNA-seq (sc/snRNA-seq), and histology imaging data, such as Hematoxylin-and-Eosin (H&E) stains. While single-cell profiles provide rich molecular information, they can be challenging to collect routinely and do not have spatial resolution. Conversely, histological H&E assays have been a cornerstone of tissue pathology for over a century, but do not directly report on molecular details, although the observed structure they capture arises from molecules and cells. Here, Applicants leverage advanced machine learning techniques to develop SCHAF (Single-Cell omics from Histology Analysis Framework), a framework for tissue data modality transfer. SCHAF uses adversarial-deep-learning to generate a tissue sample's spatially-resolved single-cell omics dataset from its H&E histology image. Applicants demonstrate SCHAF on two types of human tumors-from lung and metastatic breast cancer, each with samples analyzed by both sc/snRNA-seq and by H&E staining. Applicants demonstrate SCHAF's ability to generate appropriate single cell profiles from histology images in test data, relating them spatially, and comprehensively comparing them to ground-truth datasets in both spatial and non-spatial contexts. SCHAF opens the way to next-generation H&E2.0 analyses and to an integrated understanding of cell and tissue biology in health and disease.

Introduction

Advances in massively parallel, high-resolution molecular profiling now provide high resolution cellular and tissue level measurements at a genomic scale[1]. These include methods for massively parallel single-cell or single nucleus profiling of RNA, chromatin, proteins, and their multimodal combinations. Simultaneous advancements in data-driven analytics, largely in machine learning and deep learning[2], have allowed Applicants to derive biological insights from such rich data[3-7], as well as from key data modalities used in both research and routine clinical practice, especially H&E stains[8].

However, substantial challenges remain in realizing the promise of these methods in the context of tissue biology, especially for histopathology, a cornerstone of medicine. While the costs and complexity of single-cell omics have reduced dramatically[9], they remain relatively expensive and time consuming, and are not yet applied routinely in clinical settings. Experiments also remain prone to technical variations, leading to inter-sample discrepancies and batch effects[10,11]. Moreover, single cell genomics does not directly capture spatial information nor is it directly related to the rich legacy of histology. While spatial transcriptomic modalities, such as MERFISH[12], ISS[13], Barista-seq[14], smFISH[15], osmFISH[16], Targeted ExSeq[17], and seqFISH+[18], measure spatially-resolved expression data, their throughput is still limited, and they too involve high costs and complexities. Computational methods[19-21], such as [19] and [20], have used limited spatial signatures measured experimentally to project cell profiles to spatial positions, but they require some shared variables for such mapping (i.e., genes measured by both modalities) and cannot spatially resolve single-cell omics data given only the microscopic morphology in a histology image.

Recent advances in applied deep learning may open the way to address the challenge of mapping single cell profiles to histology. First, in other domains, deep learning methods have successfully related data modalities of the same entities even when they do not have nominally shared variables (such as audio and video[22-24]). Moreover, recent studies showed that a model can be trained to generate a tissue's bulk RNA-seq profile from its histology image[25]. Given these successes, Applicants hypothesized that deep learning could also be applied to the more difficult modality transfer problem inferring single cell expression profiles from histology.

To this end, Applicants present SCHAF, the Single-Cell omics from Histology Analysis Framework, an adversarial deep learning-based framework for transferring between histology images and single-cell omics data modalities. SCHAF is based on the assumption that a histology image and a single-cell omics dataset produced from the same tissue sample can be explained by a single, underlying latent distribution. Given a corpus of tissue data, where each sample has both a histology image and sc/snRNA-seq data, SCHAF discovers this common latent space from both modalities across different samples. SCHAF then leverages this latent space to construct an inference engine mapping a histology image to its corresponding single-cell profiles. This inferred dataset has genomic coverage, yielding expression information on all of the genes of the training corpus, and is spatially resolved, with each predicted cellular expression unit mapped to a radius of several dozen microns. Given the spatial information inherent in its predictions, SCHAF further produces a spatial portrait of a tissue's cell types with the help of an auxiliary annotator mapping from high-dimensional expression profiles to cell types. Applicants demonstrate SCHAF's success in these tasks on data spanning two different human tumor types and two different profiling technologies, through a series of criteria. SCHAF thus provides an important new tool for studies of tissue biology and disease.

Results

SCHAF: Single-Cell Omics from Histology Analysis Framework

SCHAF is trained to infer a tissue sample's single-cell omics dataset from its corresponding histological image by using a corpus of training samples with a matched histology image and single-cell omics dataset from each sample. The resulting predicted single cell dataset is spatially resolved, allowing it to be integrated with the input histology image to create a single powerful, spatial, genomic scale, morphologically informative tissue data modality from a single test histology image.

Briefly, SCHAF consists of the following steps (FIG. 49*a*): First, if necessary, Applicants reduce domain discrepancies between histology images via normalization techniques and between single-cell datasets via batch correction techniques (Methods). Applicants then decompose each histology image into many smaller tiles, roughly on the length scale of a single cell and its immediate neighborhood (but without explicit cell segmentation). Next, Applicants use adversarial machine learning to build a model to translate one histology image tile to one cell's profile. Finally, Applicants derive a tissue's full single-cell dataset by using this model to move each tile to a profile.

SCHAF Infers Single-Cell Profiles from Tiles in a Full Image

A first challenge for SCHAF is that single-cell profiling lacks an explicit spatial structure and-even if some spatial structure were available-state-of-the-art deep learning algorithms for image translation (e.g., Pix2Pix[26] or CycleGAN[27]) would exhaust standard resources given the high-dimensionality of omics data and the potentially large size of a histology image.

To address these challenges, SCHAF reduces the problem of predicting a collection of single cell profiles from a single macro-scalar image to the problem of predicting a collection of single cell profiles from a collection of smaller image "tiles", where each tile representing one cell and its immediate surroundings (FIG. 49*b*). To this end, SCHAF first decomposes the full histology image into many tiles of smaller images, by sliding a small window over the whole image and including any windowed-portions not composed of mostly whitespace in its final collection. SCHAF will then predict a tissue's single-cell omics dataset by first tiling the input histology image to a collection of appropriately small tiles and then predicting one single-cell's expression profile from each tile.

SCHAF Learns Histology-to-Single-Cell-Dataset Generation

SCHAF can effectively train an inference engine from a histology tile to a single cell's expression profile with domain discrepancy-reduced data. Specifically, if necessary, SCHAF first uses off-the-shelf histology image normalization[28] to move all histology images to a single domain (Methods). It then decomposes all histology images into tiles and trains a single reconstructing autoencoder on all samples' single-cell expression profiles. Applicants choose a tile size such that the total number of tiles of all training samples roughly equals the total number of cells of all training samples. Applicants then train a convolutional adversarial autoencoder on all samples' image tiles to both reconstruct the tiles and encode them to a latent space indistinguishable from that of the gene-expression reconstructing autoencoder. With these trained autoencoders, to predict a cell's expression profile from a tile, SCHAF encodes the tile with the histology image tile autoencoder's encoder and then decodes the encodings with the gene-expression autoencoder's decoder. As a result, every generated expression profile is also spatially positioned (to a tile) by definition.

One SCHAF is trained, Applicants construct an end-to-end way to generate a single-cell expression profiling dataset from its histology image (FIG. 49*d*). Applicants normalize the histology image to the same domain as the images used in training, break the normalized histology image into tiles, and generate for each tile a single cell's expression profile using the histology tile-to-expression profile inference mechanism.

A Framework to Assess SCHAF's Inference of Single-Cell Profiles from Histology in Tumors To demonstrate SCHAF Applicants applied it to three corpora of human tumor tissue, each consisting of matched single-cell or single-nucleus RNA-seq and H&E histology from adjacent portions of each specimen (FIG. 49*c*): a small cell lung cancer (SCLC) corpus with snRNA-seq data (sn-SCLC), a metastatic breast cancer (MBC) corpus with snRNA-seq data (sn-MBC), and an MBC corpus with scRNA-seq data (sc-MBC). The sn-SCLC corpus spanned 24 tumors (19 training, 5 for evaluation; XX and YY, unpublished data), the sn-MBC corpus had 8 tumors (6 for training, 2 for evaluation; XX and YY, unpublished data), and the sc-MBC corpus had 7 tumors (5 for training, 2 for evaluation; XX and YY, unpublished data) (Supplementary Table 1). These three corpora represent different tumor types and profiling techniques. Applicants demonstrate the results on two evaluation samples from the sn-SCLC dataset (MSKCC-146109 MSKCC-133396), one from the sn-MBC corpus (HTAPP-6760), and one from the sc-MBC corpus (HTAPP-932). Applicants analyze 6,244 common highly variable genes in the sn-SCLC corpus and 11,474 genes from the MBC corpora. For MBC, Applicants also had spatial transcriptomics data allowing Applicants to further assess the quality of spatial predictions, as Applicants present below.

Applicants evaluated the quality of SCHAF's inference of single cell profiles for each dataset by four criteria. To establish a performance baseline, for each of the three corpora, Applicants trained a Variational Autoencoder (VAE[29]) on the training sc/snRNA-seq dataset and compared each dataset inferred by SCHAF to an inferred "baseline" dataset generated from the corpus's VAE via random-sampling from a Gaussian latent space. Applicants considered their performance in correctly predicting the real test data based on four criteria: (1) pseudo-bulk expression profile proportions (the sum of all cells' expression profiles, normalized to unit sum); (2) gene-gene correlation matrices of the top-100 most highly variable genes across the entire dataset; (3) distribution of each gene's counts across the cells; and (4) annotated cell types and their organization in a low dimensional embedding.

SCHAF Accurately Predicts Pseudo-Bulk Expression Profiles

Figure 50A:
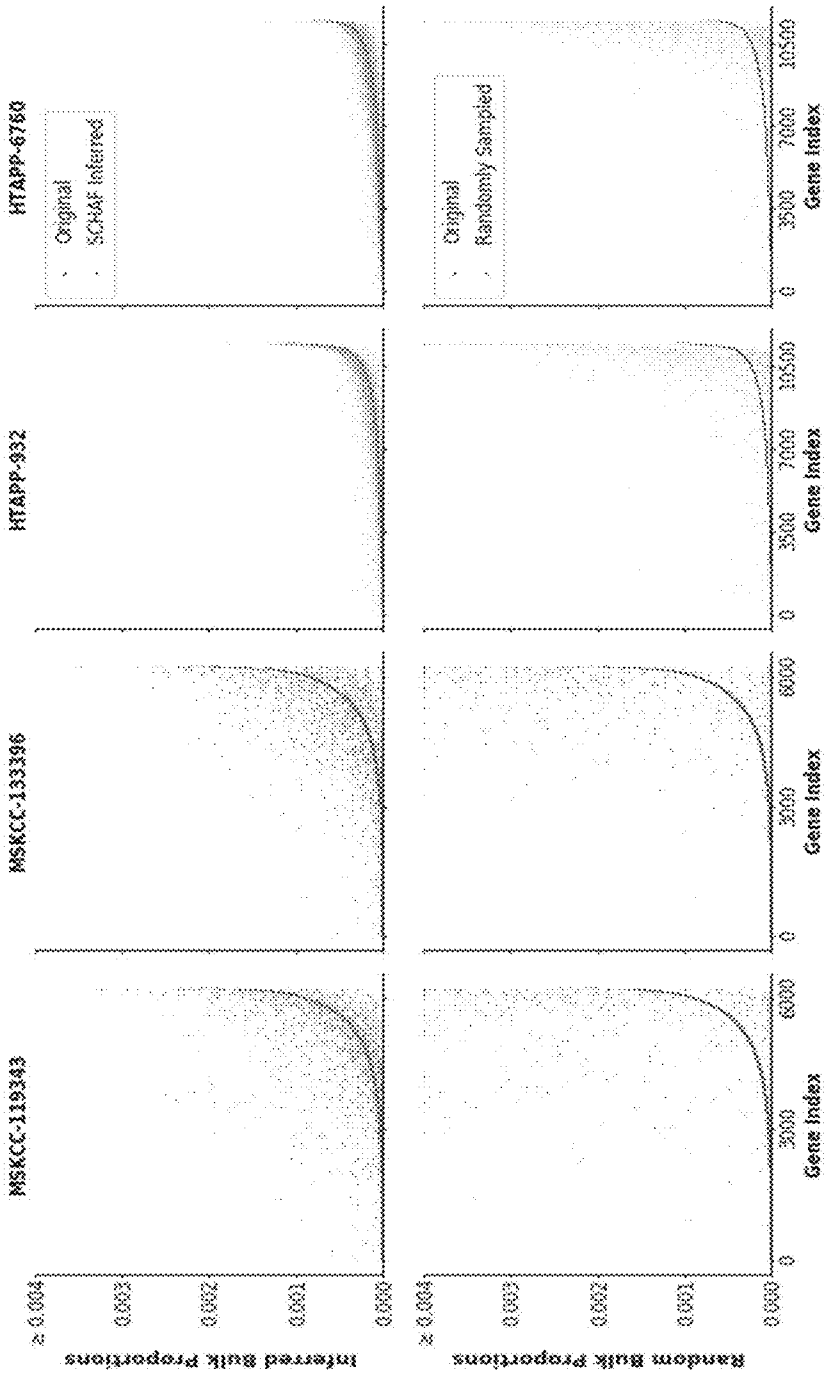
Figure 50B:
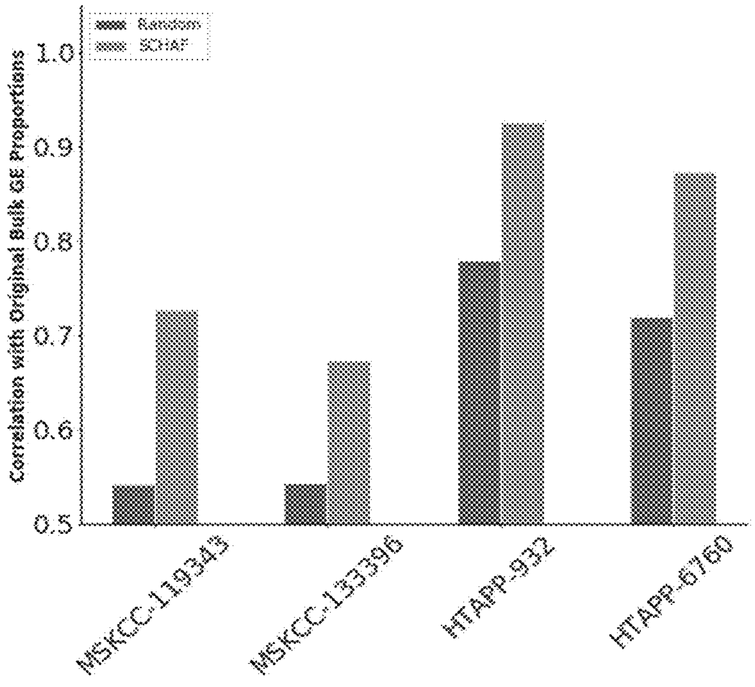
Figure 50C:
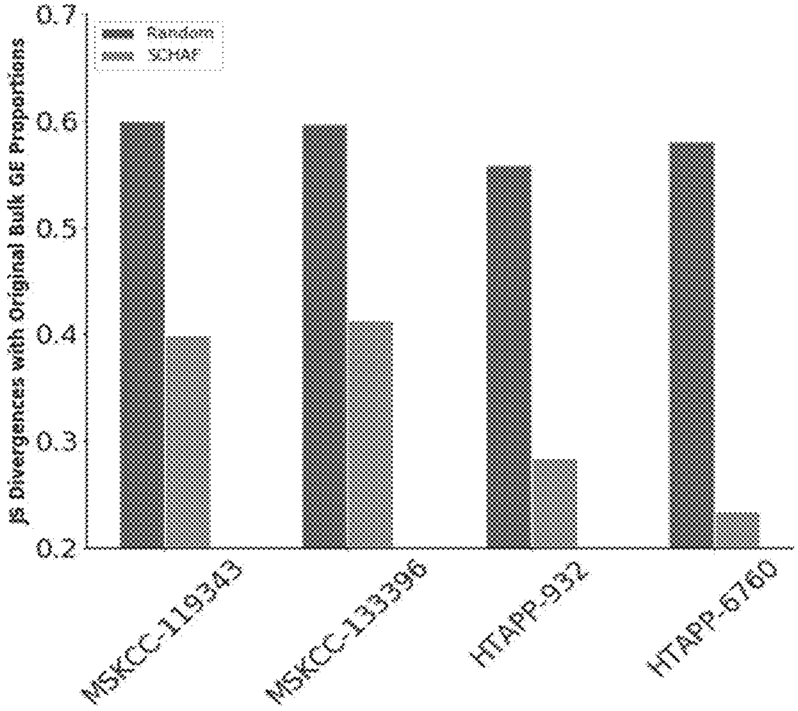

In all corpora, SCHAF's predicted pseudo-bulk expression proportions profiles (pseudo-bulk expression profiles normalized to unit sum; Methods) agreed closely with the corresponding real proportions (FIG. 50*a*), with higher gene-correlations (FIG. 50*b*, Pearson's r >0.67 for both sn-SCLC samples, r >0.87 for both the sn-MBC and the sc-MBC sample) than those of the VAE-sampled baseline (Fisher-Steiger improvement-of-correlation test[30] p-values of close-to 0 for all four samples, r<0.55 for both sn-SCLC samples' baselines, r<0.8 and <0.75 for the sc-MBC and sn-MBC samples' baselines, respectively) and far lower Jensen-Shannon divergence (FIG. 50*c*) than those of the VAE-sampled baseline. This is the case, despite the different cell numbers in the inferred, VAE-sampled baseline, and real datasets, and even given the relatively high correlation for the baseline (>0.5 for all four samples). Note that due to the sparsity of sc/snRNA-seq, SCHAF tended to under-predict the expression proportions of lowly expressed genes, and slightly over-predict those of more highly-expressed genes (FIG. 50*a*).

Gene-Gene Correlations in SCHAF-Predicted and Real Data are Well Aligned

Figure 50D:
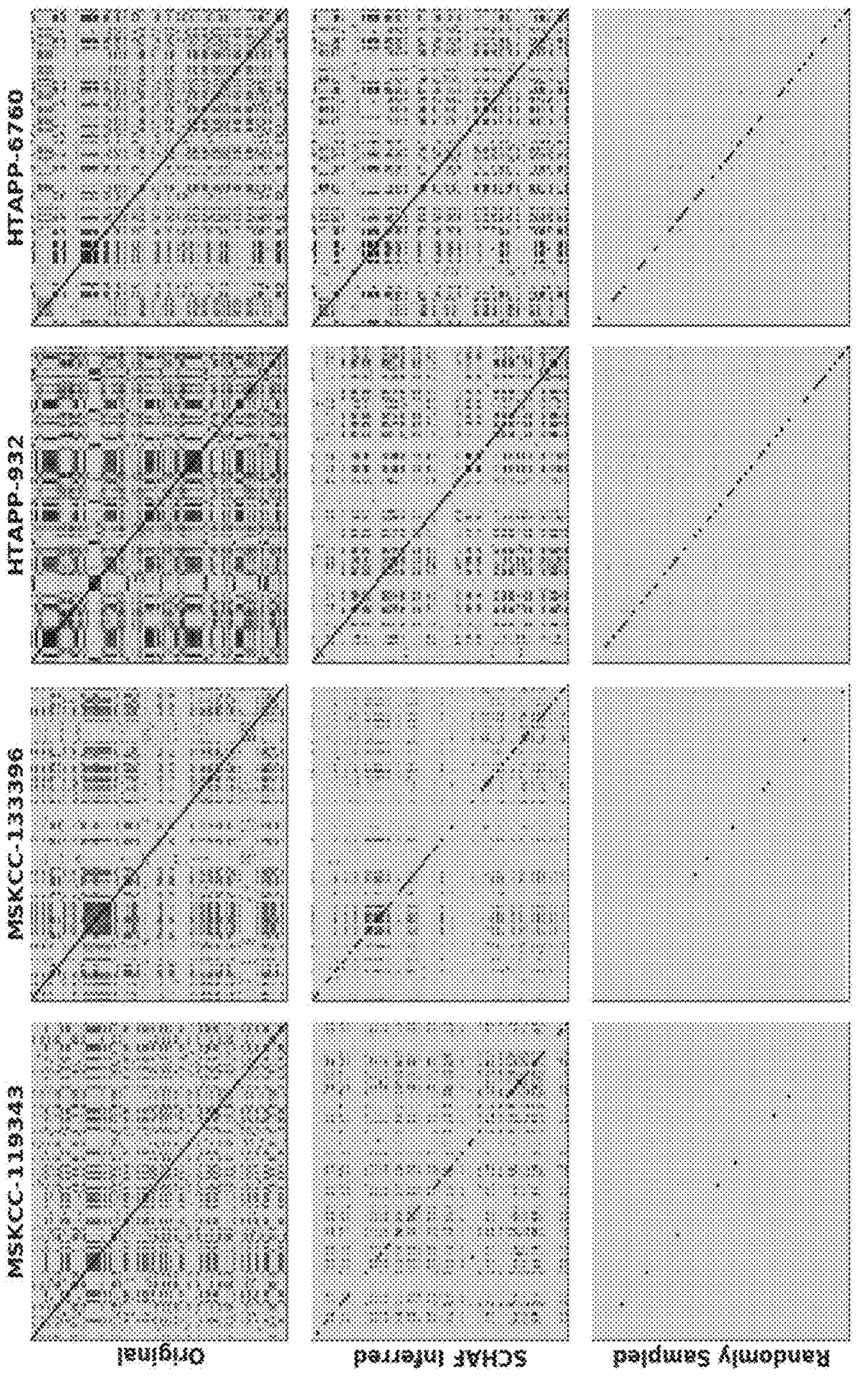
Figure 50E:
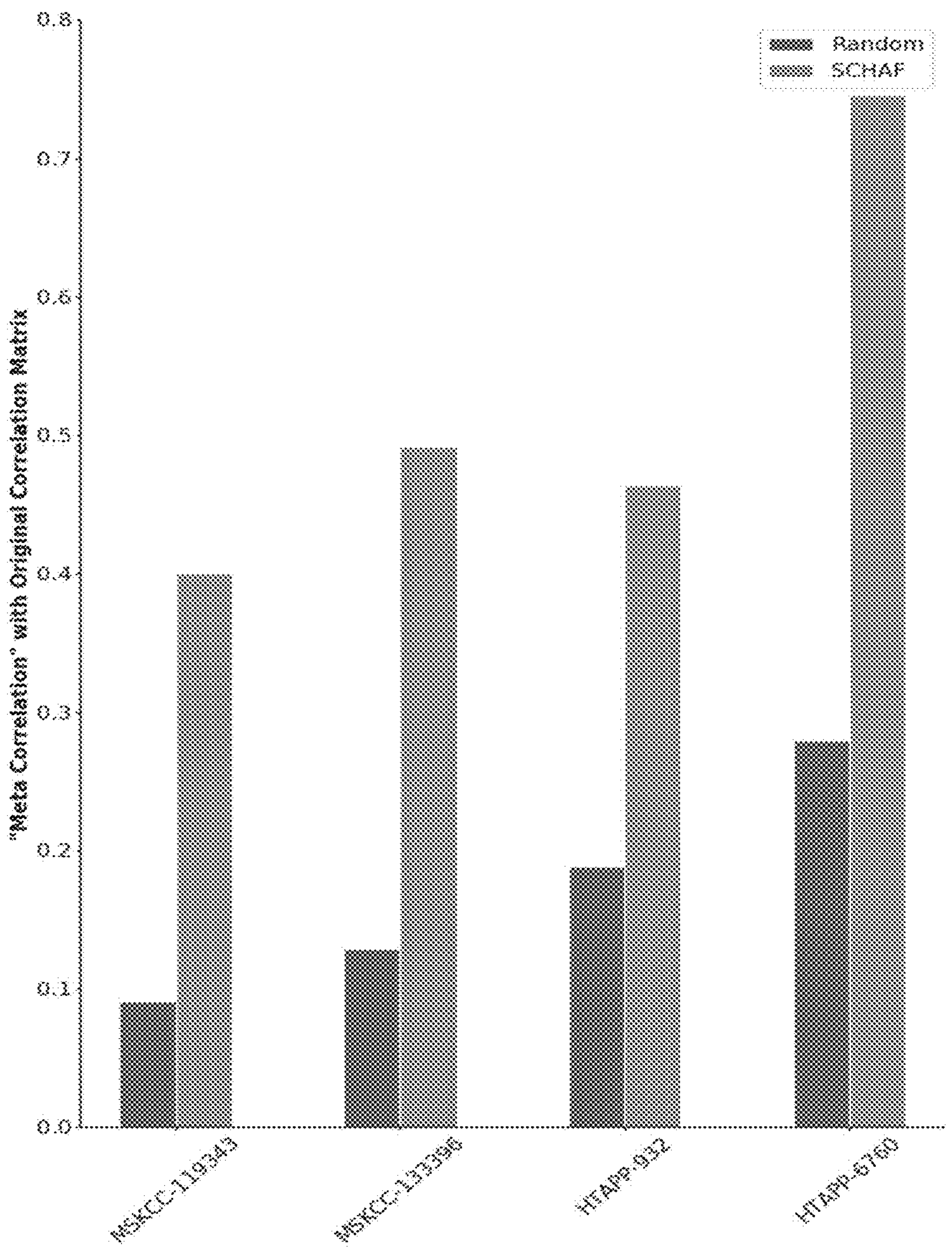

There was also good agreement in the gene-gene correlation across single cells between SCHAF-generated profiles and real scRNA-seq. First, visual comparison of the gene-gene correlation matrix for the top-100 highly variable genes in each sample shows strikingly similar patterns in real and SCHAF-generated data for each sample, but not in the VAE-sampled baseline, which yielded negligible gene-gene correlations in MBC and almost none in SCLC (FIG. 50*d*). Notably, the inferred datasets generally exaggerated the stronger correlations, while capturing more subtle correlations less well (FIG. 50*d*). Second, when calculating the correlation coefficient between corresponding top-100 highly variable genes' entries of the two flattened gene-gene correlation matrices, SCHAF showed much higher agreement with real data (FIG. 50*e*, *r*=0.40-0.49 in sc-SCLC; 0.46-0.74 in sn-MBC and sc-MBC) than the VAE-sampled baseline (r<0.13 in sn-SCLC; r=0.18-0.28 in sn-MBC and sc-MBC) yielding a significant improvement (p-values close-to 0, Fisher-Steiger improvement-of-correlation test for all four samples).

Figure 50F:
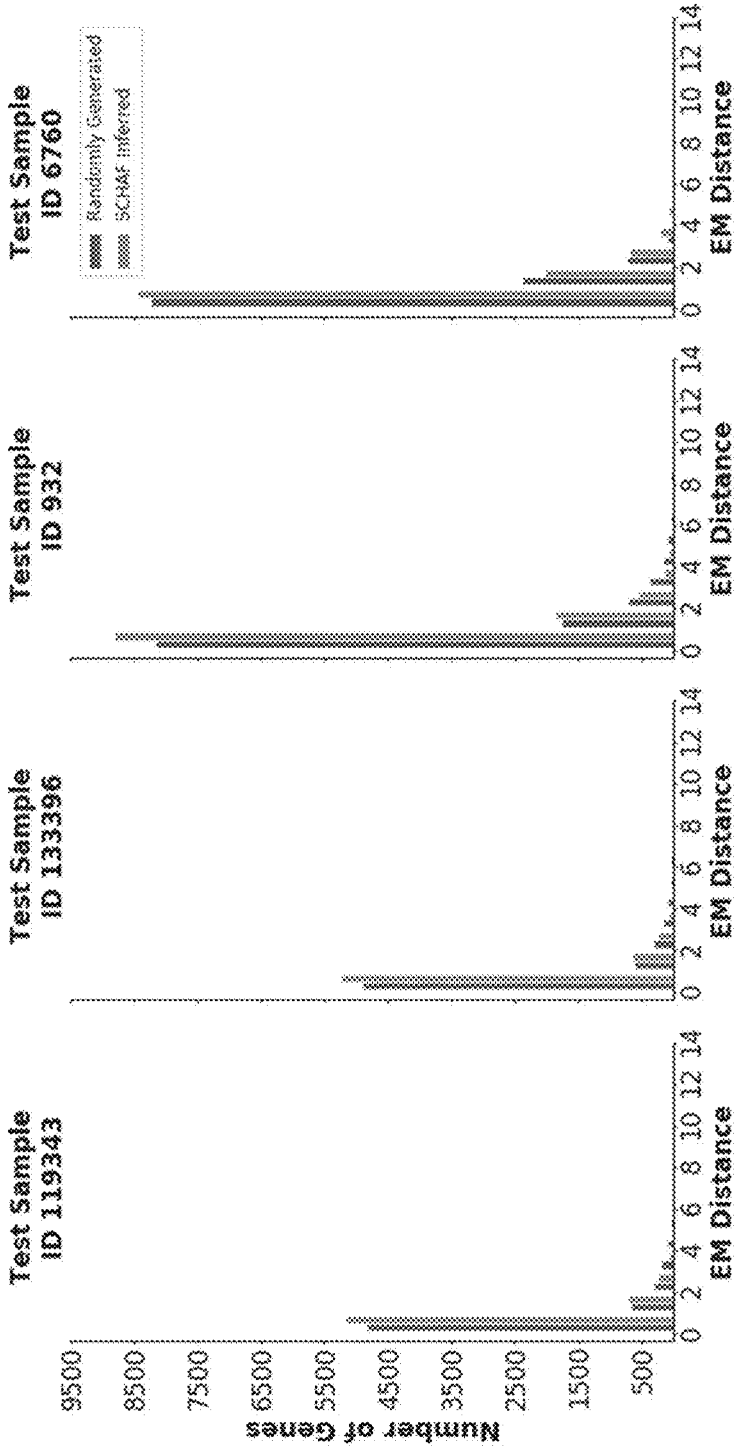

Single Cell Distributions of Gene Expression Agree in SCHAF-Predicted and Real scRNA-Seq Next, Applicants found that SCHAF's predicted datasets preserved the distribution of genes' expression levels (count values) well across the single cells. For each gene, Applicants calculated the Earth Mover's Distance between its distribution predicted by SCHAF and its distribution in the original target dataset (FIG. 50*f*). The SCHAF inferred data showed a higher similarity to the real data than the VAE-sampled baseline, with lower EMDs in three of three of the samples (p-values <10-12, Mann-Whitney U test, FIG. 50*f*), but not the fourth (p>0.08; sn-MBC HTAPP-6760). Furthermore, all EMDs between SCHAF predicted gene expression distributions and real ones were less than 11, far below the maximum possible of 50.

SCHAF Inference Preserves Cell Type Annotations and Clusters

To compare how well SCHAF generate profiles preserve cell types and their clusters, for each sample, Applicants first used the original scRNA-seq data to train a neural network to classify a cell-type from a single RNA-Seq profile, used this classifier to assign a cell-type label to each real, SCHAF-inferred, or VAE-sampled baseline profile, and then predicted how those labels organize when Applicants project the SCHAF-predicted, VAE-sampled baseline, or real single cell profiles in low dimensions using UMAP[31] and color each by its assigned cell type label. The cell type assignment probabilities of profiles to an existing annotation by the classifier were significantly higher for SCHAF-inferred data than for the VAE-sampled baseline ($p<<10^{-24}$ in each tested sample; Mann-Whitney U test, FIG. 51*d*). Furthermore, for each sample, within each cell type, the pseudo-bulk expression proportions profile (pseudobulk expression profiles normalized to unit sum) of cells assigned to a cell type agreed closely with that of real cell profiles of that cell type (r>0.63 in all cell types in both sn-SCLC samples, r>0.76 in all cell types in both MBC samples, FIG. 51*c*).

Figure 51A:
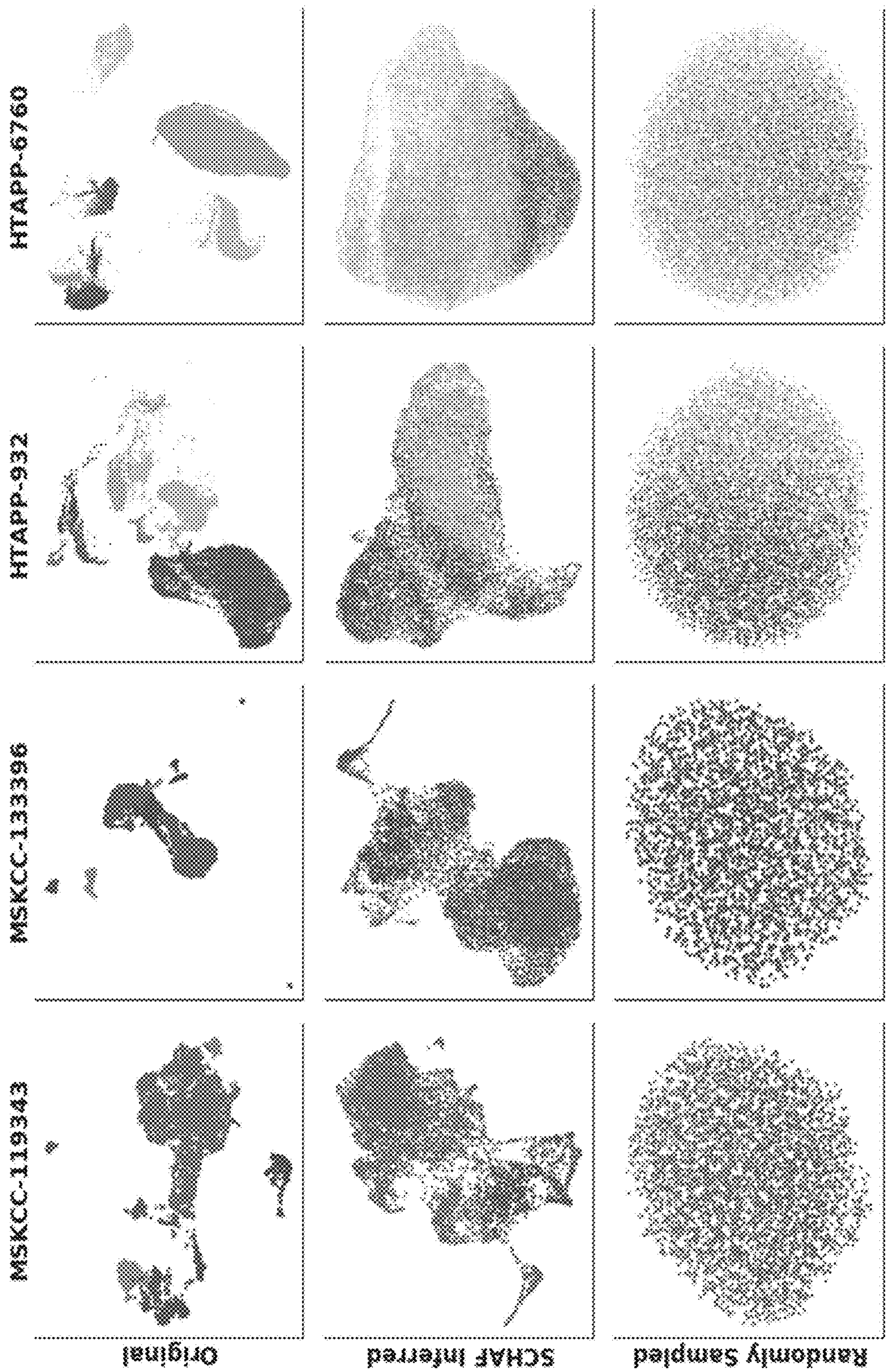
Figure 51B:
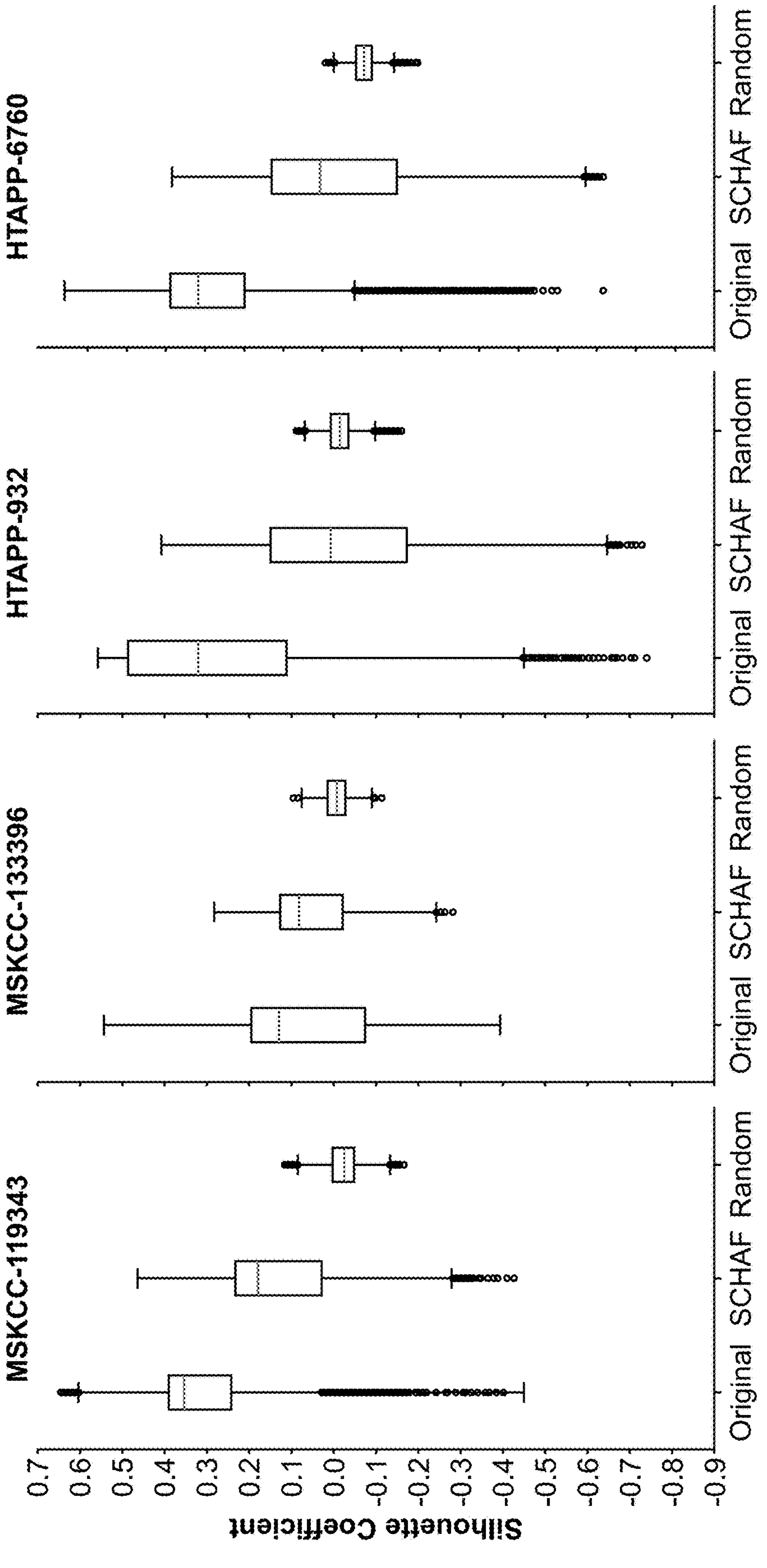
Figure 51C:
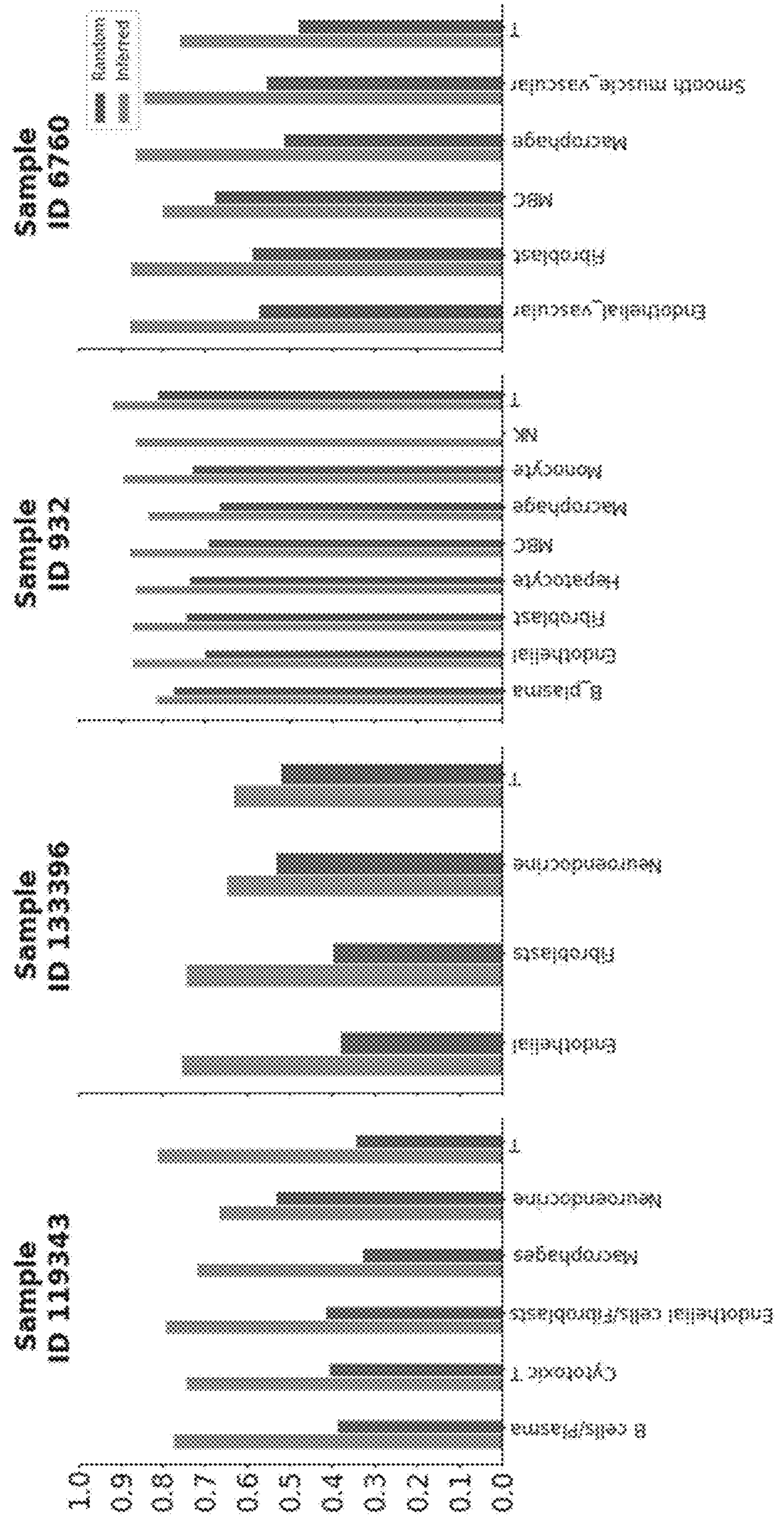
Figure 51D:
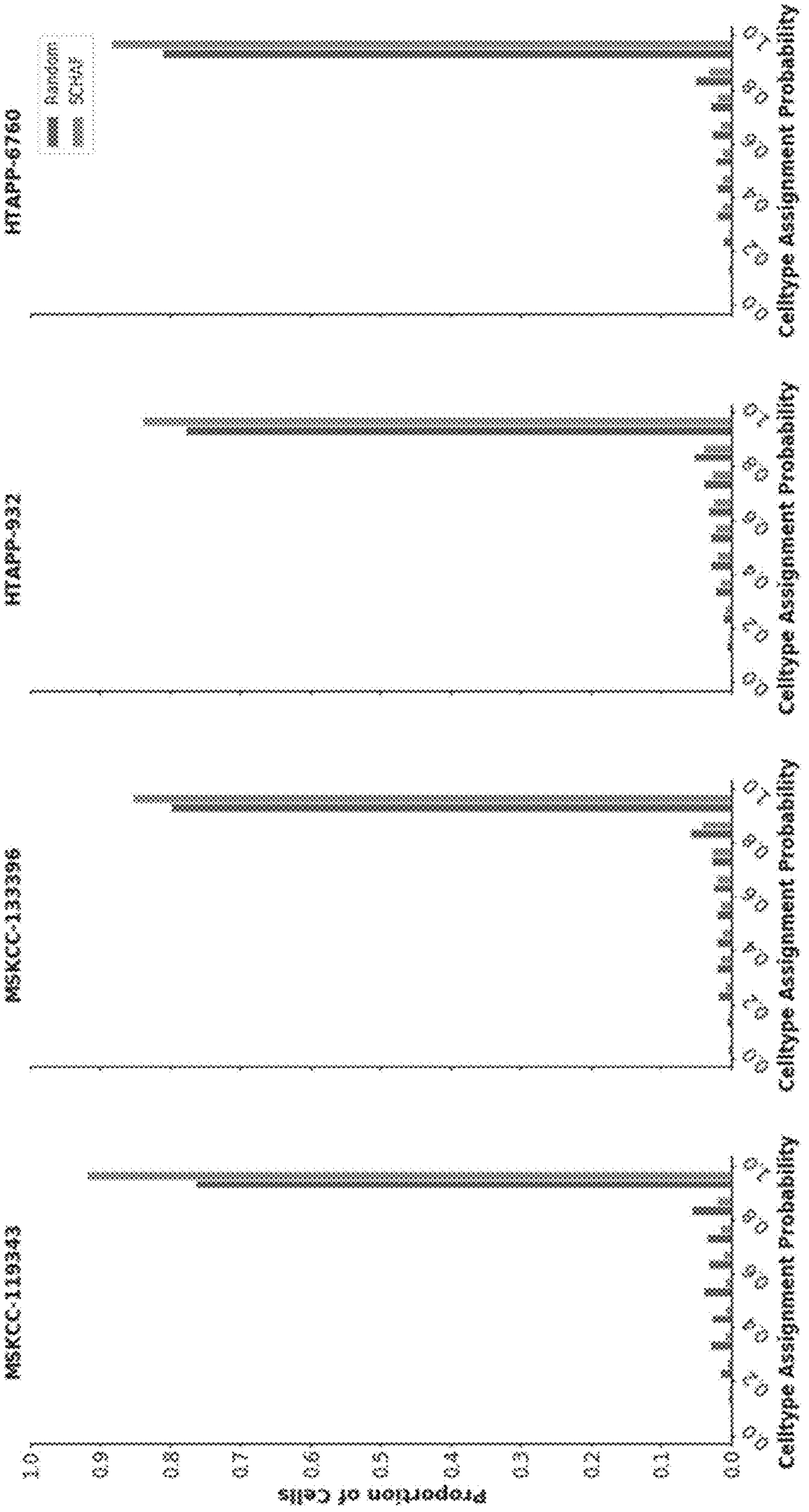

Strikingly, in all test samples across all corpora, the SCHAF-predicted datasets preserved cell-type clusters (FIG. 51*a*, middle) as distinct and mostly well-formed in a low dimensionality embedding; while these were not as well-separated as in the real datasets, they far exceeded the patterns in the VAE-sampled baseline (FIG. 51*a*, bottom). To quantify the quality of these clusters, Applicants compared the distributions of cells' cell-type silhouette coefficients between each sample's inferred, VAE-sampled baseline, and original (measured) sc/snRNA-seq profiles. In all samples, the distributions of the SCHAF-inferred profiles were significantly higher than those of the corresponding VAE-sampled baselines and quite close to those in the real data, supporting the qualitative conclusions from the embeddings (FIG. 51*b*, p-values close-to 0, Mann-Whitney U tests comparing the inferred and random silhouette coefficient distributions).

Evaluation of Spatial Mapping of Profiles by SCHAF

To evaluate SCHAF's performance in generating expression profiles at correct spatial positions (tiles), Applicants focused on the sn-MBC and sc-MBC samples, where Applicants had multiplex FISH measurements of 212 genes on a consecutive section measured by 12, as well as regional annotations on the H&E section performed by expert pathologists. Applicants devised two measures to assess the SCHAF's spatial inference: (1) the cross-tile (within sample) correlation between the SCHAF-predicted expression of a given gene in each tile, and its MERFISH measured expression in the tile; and (2) the agreement in high level cell type assignments (cancer, normal, fibrosis, immune, vasculature) between SCHAF-inferred and pathologist annotations.

Figure 52A:
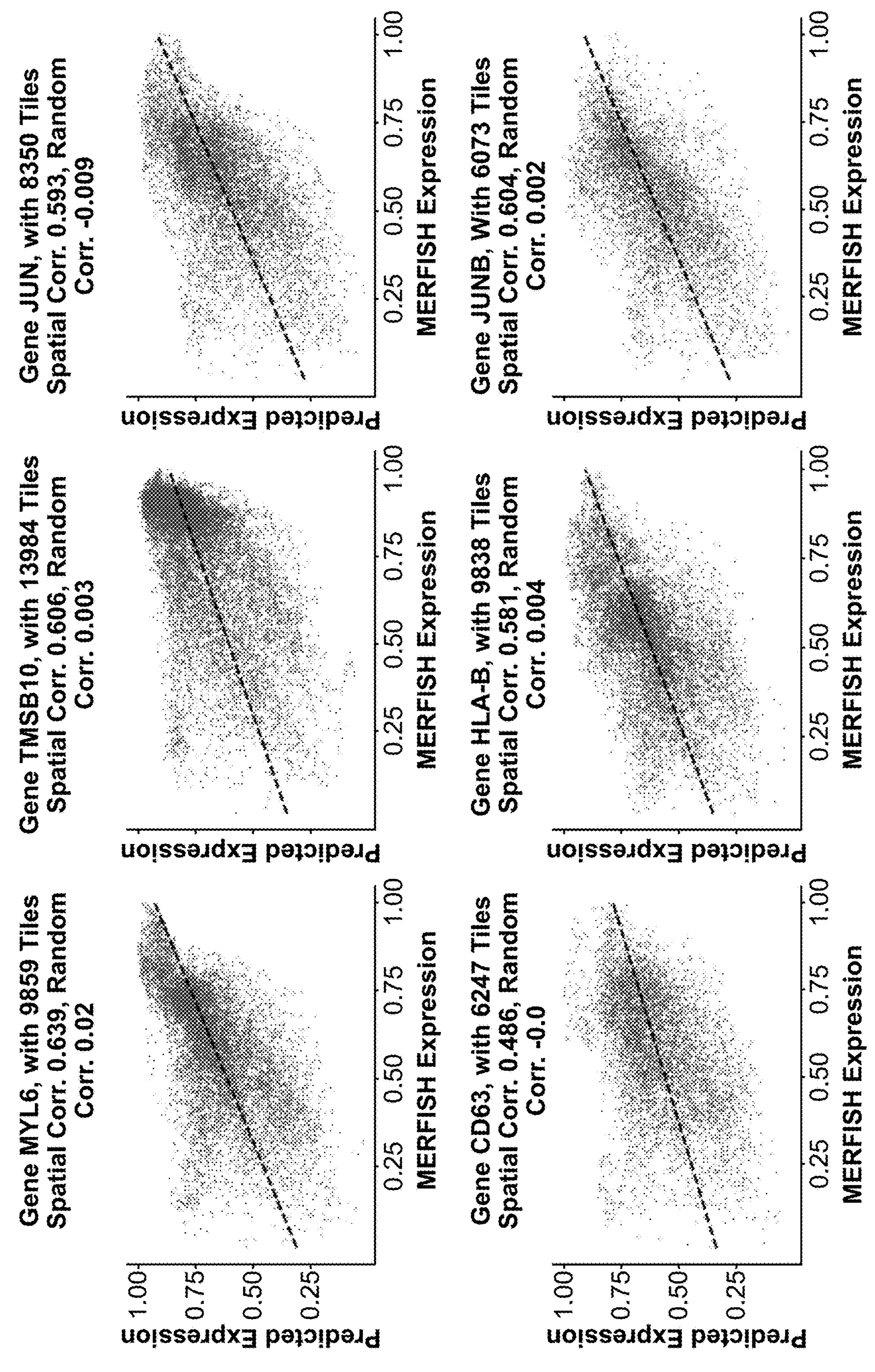
Figure 52A:
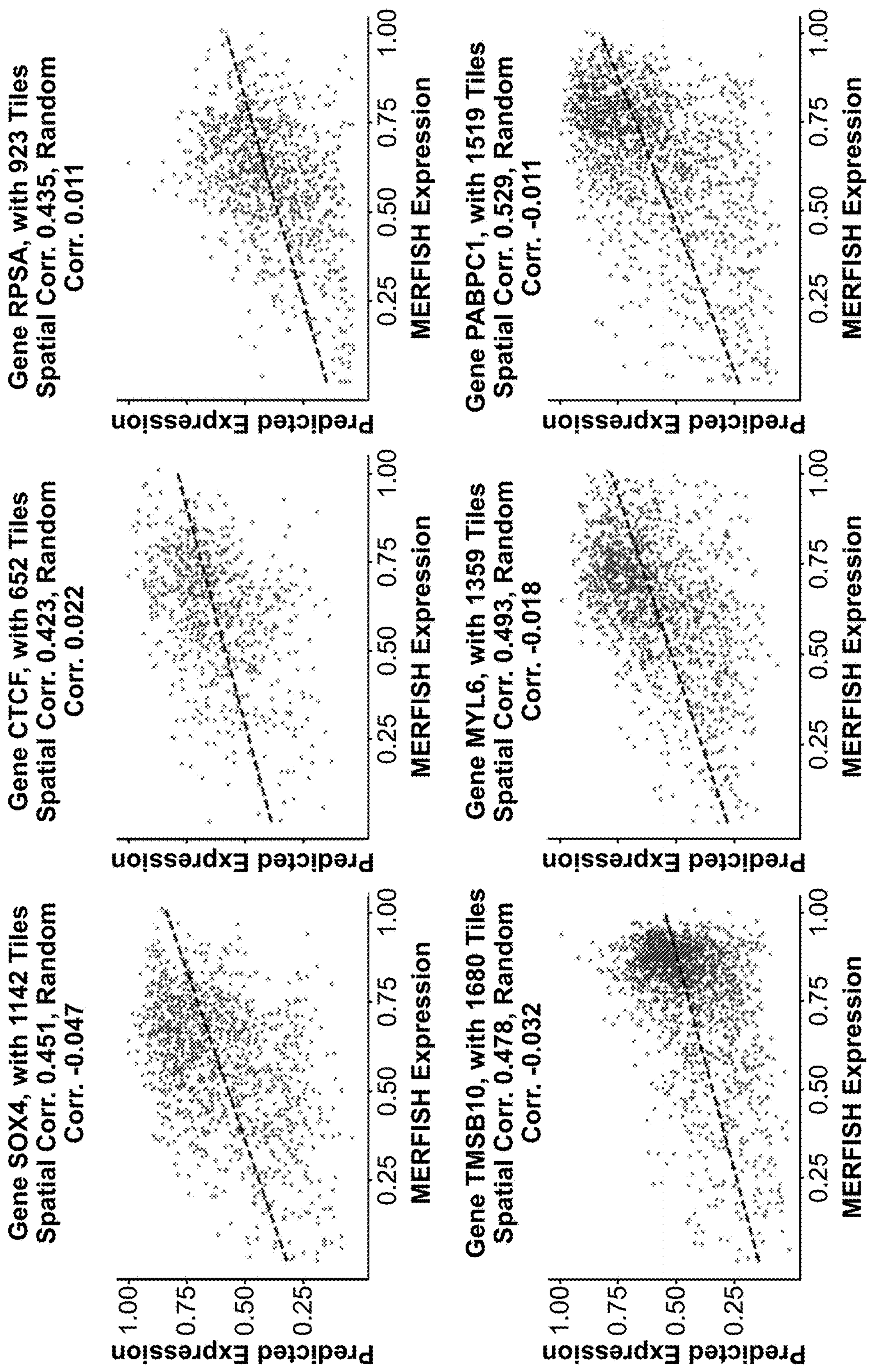
Figure 52B:
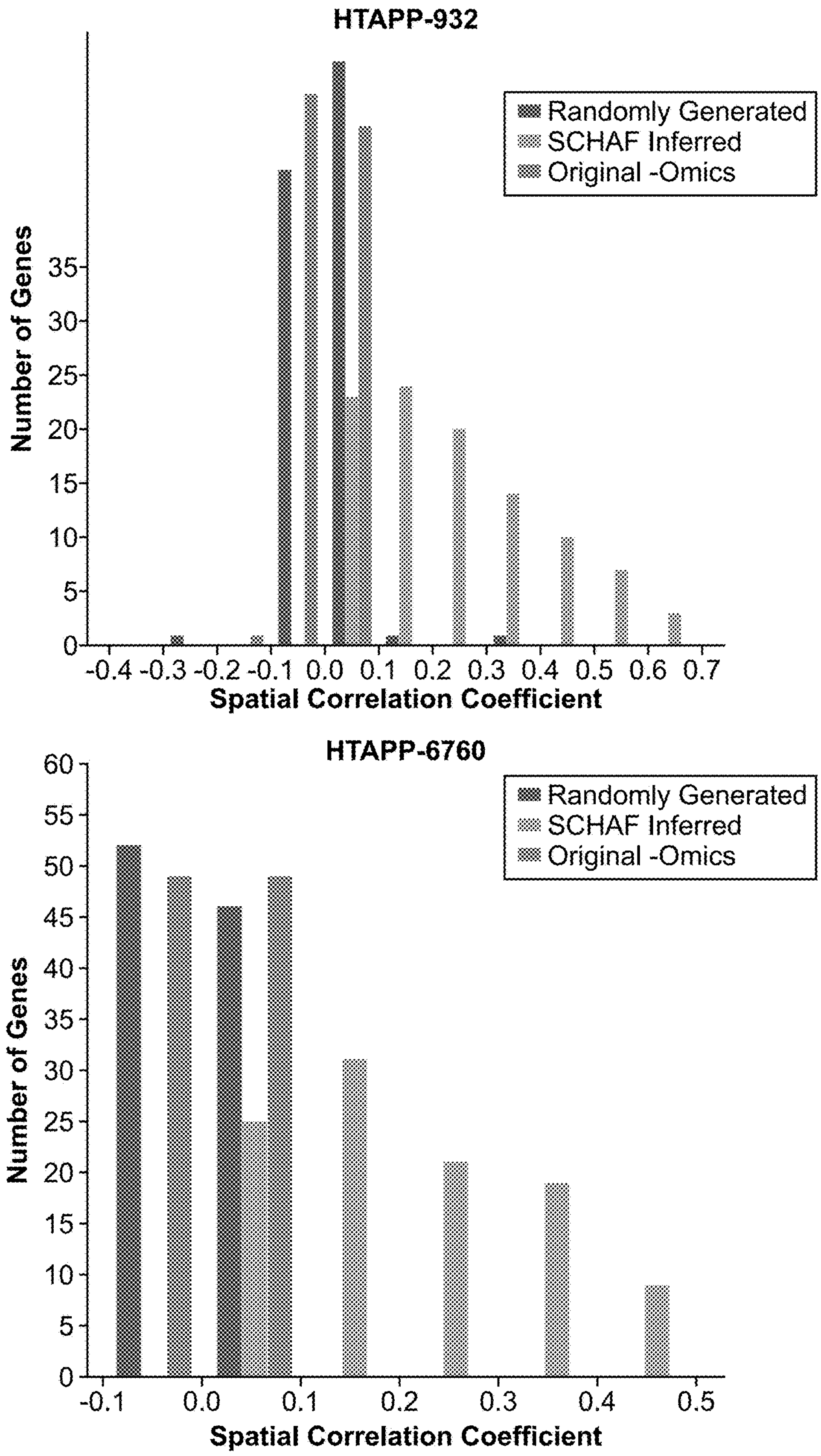
Figure 52C:
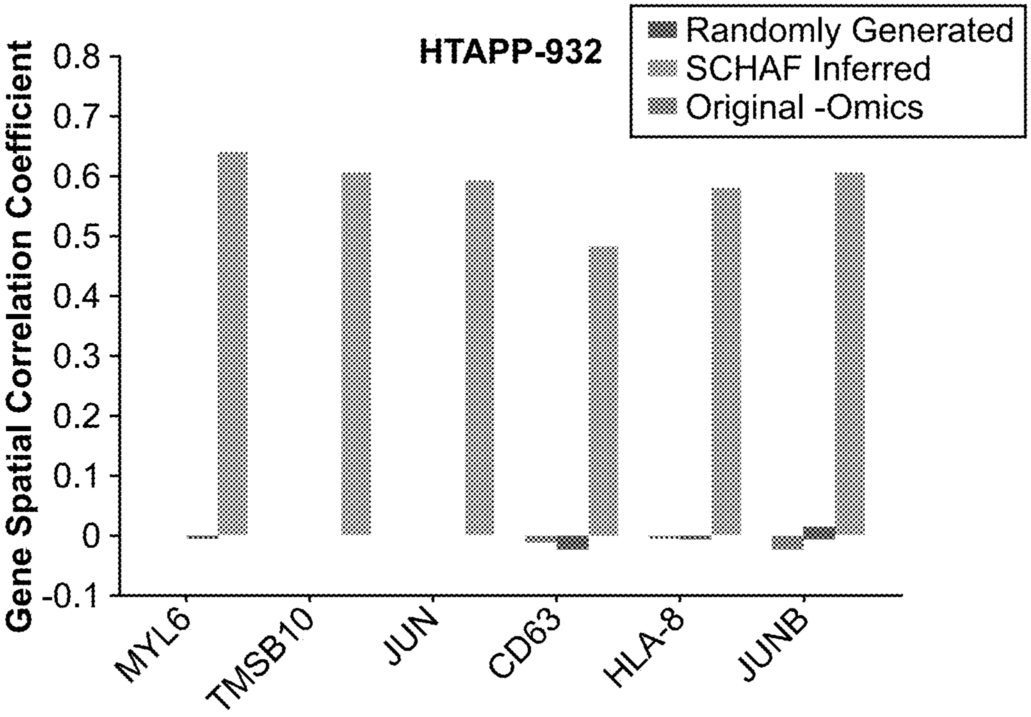
Figure 52C:
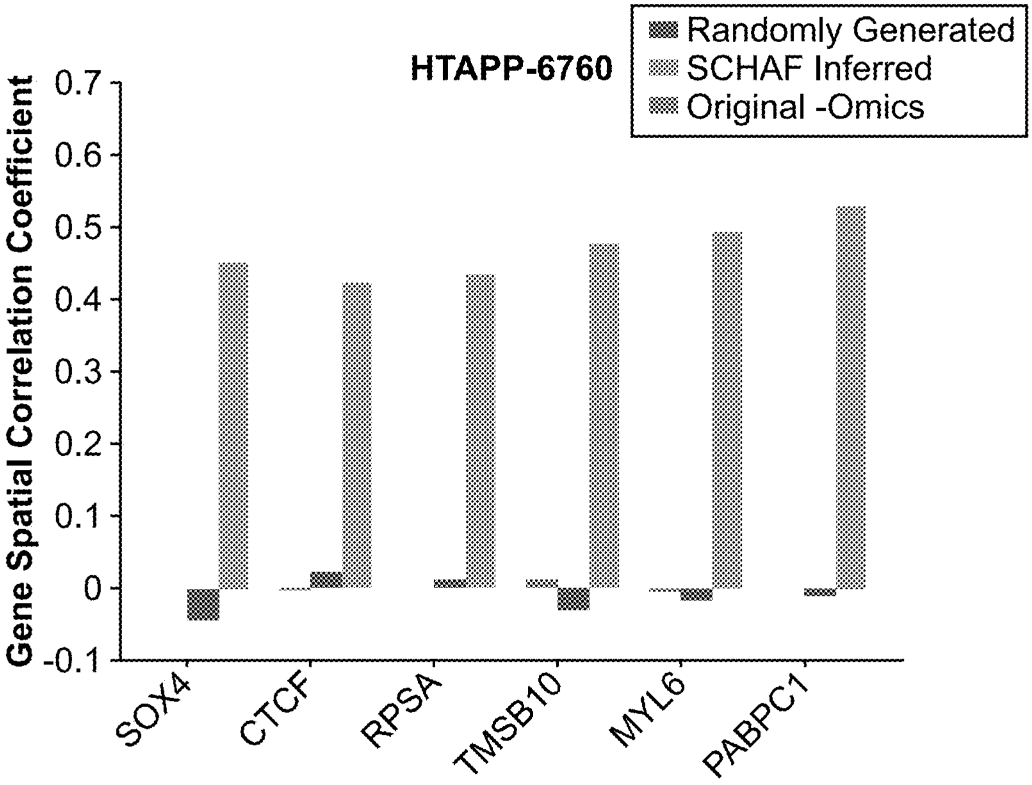

SCHAF Infers Accurate Spatial Gene Expression at the Tile Level and Agrees with Regional Annotations To compare SCHAF-inferred spatial expression to MERFISH measurements, Applicants "tiled" the aligned H&E (with SCHAF-inference) and MERFISH images (performed on consecutive sections) into multiple smaller tiles, each 1:1 between the two sections, and calculated, for each of the 212 genes measured by both scRNA-seq and MERFISH, the correlation coefficient between the mean SCHAF-expression and MERFISH-expression per tile across all the tiles. As null benchmarks, Applicants randomly assign spatial locations to either expression values from the VAE-sampled baseline (as above) or from the real scRNA-seq. Overall, the tile-level spatial correlation was higher for SCHAF-inferred compared to the null baseline (FIG. 52*b*), with 20-30 of the 212 genes where SCHAF had noticeable correlation (Pearson's r >0.3) with the original MERFISH data (FIG. 52*a,b*,). Conversely, there was virtually little to no correlation (all Pearson's rs between −0.1 and 0.1) in the two baseline cases (p-value <0.05 Fisher-Steiger improvement-of-correlation test in all cases, FIG. 52*c*).

Figure 52D:
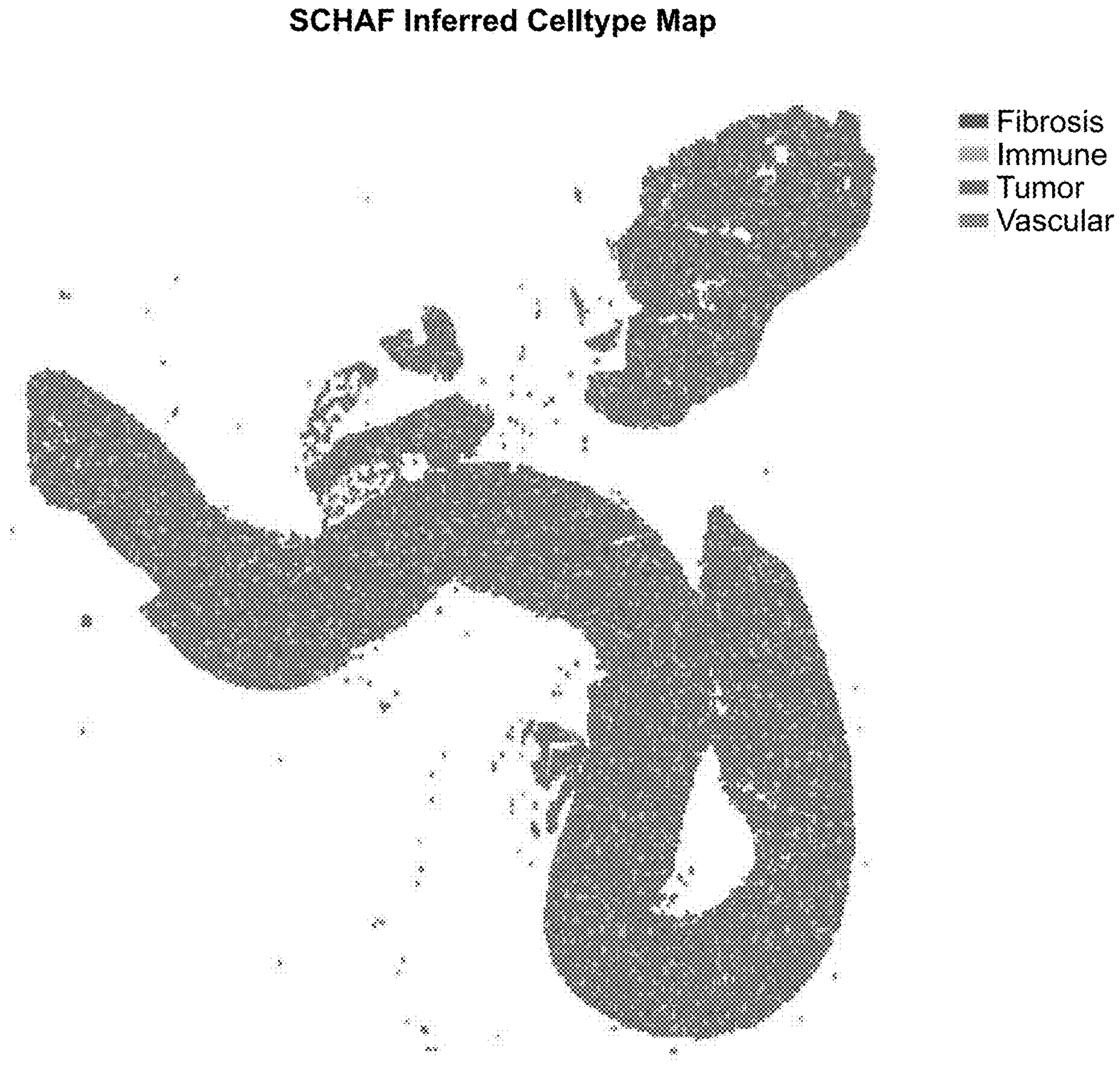
Figure 52E:
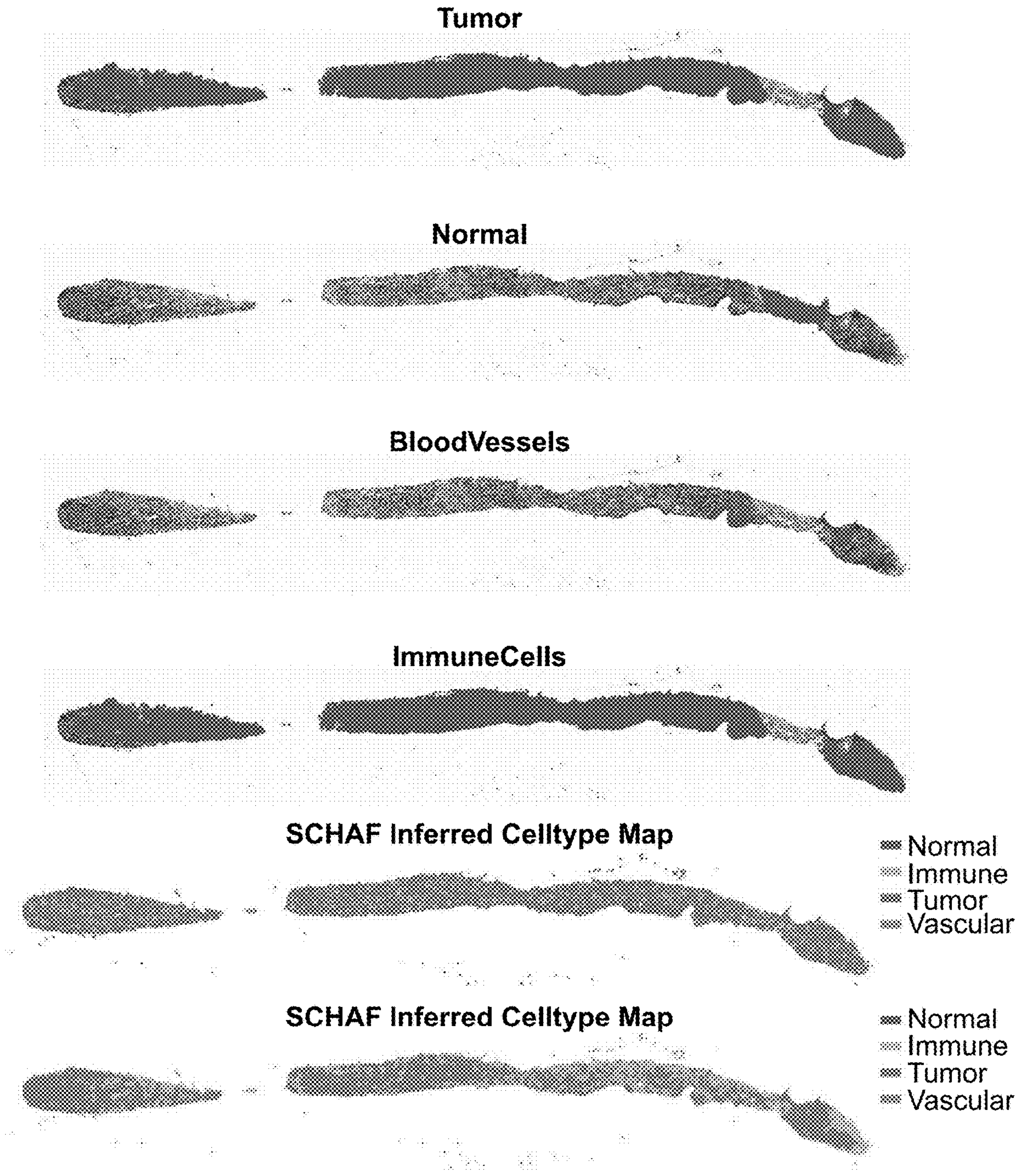

Applicants also compared regional annotations by pathologists (tumor, normal, immune, fibrosis, vasculature; FIG. 52*d* (left), 52*e* (top)) to annotations derived by mapping the cell-type assignments of single cell profiles (as above) to spatial locations of corresponding samples' histology images (FIG. 52*d* (right), 52*e*, (bottom)). Applicants assigned all pixels in each tile one color, according to the tile's assigned cell-type category, creating inferred spatial annotation (FIG. 52*d* (right), 52*e*, (bottom)) for both the sc-MBC sample and the sn-MBC sample. Applicants found good agreement between SCHAF-based and pathologist annotation distinguishing cancerous and non-cancer regions (sample HTAPP-932, FIG. 52*e*) and for the multiple detailed annotations available for one sn-MBC sample (HTAPP-6760). In this latter case, the pathology "Vasculature" annotation aligned with endothelial vascular and smooth muscle vascular portions in the SCHAF annotation maps (FIG. 52*d*), "Fibrosis" with SCAF's fibroblasts, "Immune Cells" with T cells, and "tumor" with parts of the SCHAF mapping consisting almost entirely of cancerous cells. In contrast, in both the sn-MBC and sc-MBC samples, the baseline annotations present an uninformative picture: a spatially uniform distribution dominated by cancerous cells with arbitrary "salt-and-pepper" patterns of other cell types. Overall, this shows strong evidence for the success of SCHAF's spatial mapping.

Discussion

Here, Applicants presented SCHAF as a computational framework to predict spatial single cell profiles from H&E images without the need for any molecular spatial data in the training. In-silico tissue-data modality transfer between histological imaging and single-cell RNA-Seq domains would significantly increase the accessibility of spatially resolved molecular profiles, not just in terms of time, effort and expense, but also in the ability to predict molecular information for the vast number of clinical samples archived over decades. To achieve this, SCHAF learns to use a tissue's histology image as a specification for inferring an associated single-cell expression dataset. More broadly, this can be seen as a biological application of a framework for inferring an entire dataset as opposed to a single output.

SCHAF is based on the framework of adversarial machine learning, with latent space representations of data in two modalities. These data-driven techniques underlying SCHAF prove powerful, such that it performs well even though it does not account for differences in cell sizes via segmentation, instead considering histology "tiles", each intended to encompass roughly one cell and its immediate surroundings, and intending to considering in each sample a number of tiles equal the number of cells profiled. SCHAF's success suggests that in-silico data generation is not only a viable path to augment laboratory measurements, but also that biological tissue data can be successfully represented by a modality-agnostic, lower-dimensional latent space, which can be exploited by adversarial machine learning techniques for a multitude of applications in data integration and modality transfer, as well as probed for understanding the principles of tissue organization, including how molecular information leads to tissue structures and vice versa.

Applicants showed that SCHAF is successful on corpora of matched H&E and sc/snRNA-seq data from two tumor types in three separate cases. As tumors are more variable and less canonical than healthy tissue, predicting a new tumor's profile, even of the same type, is a challenging task. Future studies are required to assess the ability to train a single model across a single corpus of multiple tissue types, tumor types, or technology types (snRNA-seq and scRNA-seq, or snRNA-Seq and scATAC-Seq, for example). Doing so would require additional datasets with matched single cell profiling and histology imaging, which are still surprisingly scarce, but are growing thanks to efforts such as the Human Tumor Atlas Network[32] and the Human Cell Atlas[3]. Such efforts also generate additional spatial genomics data, which as Applicants showed is not necessary for training SCHAF, but is crucial for validating its inferred patterns to gain confidence in its performance and introduce further improvements.

SCHAF's success should also motivate several further research directions. First, it suggests that inference should also be possible in the reverse direction: constructing histological images from single cell expression data, which can help with understanding tissue biology. Given the high dimensionality of single-cell profiles and the many ways histology images could manifest, this could be seen as designing a mechanism for the generation of imaging data conditioned on a very high-dimensional specification. Constructing such a gene-expression-to-histology mechanism presents several challenges, including choosing an appropriate size of the output histology data, the need to infer many different potential histological configuration from the same input single cell dataset, designing a generative model to be conditioned on a variable as high-dimensional as a transcriptome, departing from more traditional models (such as AC-GAN[33]), and validating the predicted images, which, especially in tumors, would likely require matching of features rather than direct pixel to pixel alignment.

Second, the underlying principles defining SCHAF can be extended to other cases in biology, both with similar data modalities (e.g., cell profiles and microscopy images measured in cultured cells), in different biological modalities (3D imaging[34] or temporal tracing[35]), and in non-biological settings. Finally, and more fundamentally, interpreting SCHAF's model could have implications for the understanding of tissue biology, by helping Applicants understand which cellular and gene programs and configuration relate to which tissue features.

Methods

Matched scRNA-Seq and H&E Images Data

Three corpora of tumors were used. A corpus of twenty-four (24) small cell lung cancer (SCLC) samples profiled by snRNA-seq and matching H&E stains were obtained from an unpublished study from Memorial Sloan Kettering Cancer Center (MSKCC). Two corpora of eight (8) and seven (7) metastatic breast cancer (MBC) tissue samples, with snRNA-seq and scRNA-seq data, respectively, were obtained from an unpublished study from the Human Tumor Atlas Project Pilot (HTAPP). In the MSKCC corpus. In the HTAPP corpora. The histology images were of definition and resolution. Further information about these datasets' dimensionalities are in Supplementary Table 1. Cell-types in the original datasets were manually annotated.

H&E Data Pre-Processing

To prepare the H&E stains for further analysis, all pixels that were sufficiently light (having a channel with pixel value >200 (255 being the maximum value)), indicating non-tissue, were replaced with pure white pixels.

sc/snRNA-Seq Data Pre-Processing

Cell profiles with less than 200 detected genes were removed, followed by removing genes expressed in less than 3 cells. Each cell's counts were normalized to have sum 10,000, followed by log 1p(f(x)=log(x+1)) transformation of each normalized count value, x. Each cell's counts were then normalized to sum to 1, and each entry was divided by 10, a constant larger than all counts of all cells in all samples. Lastly, within both all small-cell-lung cancer data and all breast-cancer data, all genes shared across all datasets were identified, followed by finding the 1,024 most highly variable of these common genes in each sample. Lastly, the union of all these genes (6,244 genes in sn-SCLC, and 11,474 genes in both of sn-MBC and sc-MBC) was retained for further analysis. Quality-control steps were performed with Python's scanpy[36] package (specifically the functions: pp.filter_cells with min genes=200, pp.filter_genes with min_cells=3, pp.normalize_total with target_sum=10,000, sc.pp.log 1p and pp.highly_variable_genes with n_top_genes=1024).

Discrepancy Correction in H&E Stains

To resolve domain-discrepancies between the different H&E stain samples, samples MSKCC-134537 (for SCLC) and HTAPP-6760 (for MBC) were used as references for the SCLC and both MBC datasets, respectively. The color normalization.reinhard function from the histomicstk (digitalslidearchive.github.io/HistomicsTK/index.html) package was used with default settings to normalize all histology images to occupy the same domain as the reference sample's image.

Histology Image Decomposition Via Tiling

After resolving domain discrepancies in imaging, histology images were tiled into smaller, potentially-overlapping histology image fragments called tiles. A square window of size tile_size X tile_size was slid over each histology image, starting at the top-left corner of each image, and moving the window tile_move_dist units at a time, first horizontally, then vertically once a row's tiles are exhausted, until each possible position of the window in each image is covered. A for tile_move_dist and for tile_size were found to yield a number of tiles closest to the number of cells profiled in each dataset across most samples. All tiles where the majority of pixels did not consist of whitespace were included in the image's set of tiles. This procedure was applied to tile each histology image.

Learning to Infer a Single-Cell-Omics Dataset from a Histology Image

All machine learning models were built and trained using the Python deep learning library pytorch[37].

Given a training dataset of tissue samples, each with a corresponding tiled H&E image and sc/snRNA-seq data, SCHAF learns to infer an entire sc/snRNA-seq dataset from a histology image. SCHAF, if necessary, first integrates all training histology images into a common discrepancy-free domain via image normalization as described above, and then tiles the histology images (as described above).

Next, a model is trained to learn a single-cell's expression profile from a single histology-image tile, using an adversarial autoencoder[38] based framework[39] for domain translation applied to image-tile and gene-expression domains. First, a standard autoencoder, G, is trained on all of the expression profiles of all samples. It was trained according to a mean-square-error (MSE) loss, optimized via [40], and trained for 50 epochs, with a batch size of 32, at a learning rate of. 0.00005. Let L be the latent space of such an autoencoder. A convolutional adversarial autoencoder Tis trained on all of the image-tiles of all of the samples, to simultaneously reconstruct image tiles and encode to a latent space indistinguishable from L via an adversarial training regime of the tile network against an adversarial discriminator. The adversarial discriminator was trained according to a binary-cross-entropy loss with-logits (BCE), optimized via [40], and trained for 25 epochs, with a batch size of 32, at a learning rate of 0.004. L was trained according to a regularized mean-square-error loss, given by the following function: given image input i, let i' be a reconstruction of i by L, t be labels signifying that a latent space comes from the gene-expression latent space, and z be the output of the adversarial discriminator an encoding of i by L. The loss was given by f (i', i, z)=MSE(i', i)+beta*BCE(z, t). L was trained with beta=0.001, optimized via [40], and trained for 25 epochs, with a batch size of 32, at a learning rate of 0.001. The adversarial discriminator and L were trained in adversarial fashion with alternating gradient updates.

G and T both had an encoder-decoder architecture, with the encoder being composed of four sequential [Linear, BatchNorm, ReLU] blocks, followed by one [Linear, BatchNorm] block, and the decoder being composed of four sequential [Linear, BatchNorm, ReLU] blocks, followed by one [Linear, ReLU] block. The dimensions of the five linear layers of the encoder were, in order, number_of_genes, 1024, 1024, 1024 and 128 neurons. The dimensions of the five linear layers of the decoder were, in order, 128, 1024, 1024, 1024, and number_of_genes neurons, where number of genes was the number of genes in each cell being considered. The adversarial discriminator had an architecture consisting of four [Linear, SpectralNorm, ReLU] blocks, followed by one [Linear, SpectralNorm] block. The dimensions of the five linear layers were, in order, 128, 64, 32, 32, and 2 neurons. The Linear, BatchNorm, ReLU, and SpectralNorm layers were implemented via pytorch's nn.Linear, nn.BatchNormID, nn.ReLU, and nn.utils.spectral_norm functions, respectively.

In order to translate from image-tile to a single cell expression profile, after training G and T, the tile is simply encoded with T's encoder and the encoding is decoded with G's decoder.

This provides the infrastructure for a final inference pipeline from H&E-stain to single-cell dataset. First, the input histology image is normalized to the same domain as the integrated images used in training using the histimoicstk package, the image is tiled with the same parameters used for training images, and a single cell expression profile is inferred for each tile.

Test Datasets for Evaluation of Non-Spatial Single Cell Profiles Predicted by SCHAF Two evaluation samples were withheld for testing and analyzed from the sn-SCLC corpus: MSKCC-146109 and MSKCC-133396. Similarly, HTAPP-6760 and HTAPP-932 were withheld for testing analyzed as evaluation samples from the sn-MBC and sc-MBC corpora, respectively. Each sample was evaluated based on four criteria (below) in comparison to a random (VAE sampled) baseline (also described below).

Generation of VAE-Sampled Baseline for Non-Spatial Evaluation

For each evaluation sample, the inferred dataset was compared to both the target (real) sc/snRNA-seq dataset as well as to a baseline dataset generated by sampling a variational autoencoder (VAE). First a variational autoencoder (VAE) was trained on training data from each corpus to both reconstruct expression profiles and encode to a Gaussian latent space. The VAE is trained according to a standard VAE loss: given data x, its reconstruction by a VAE, x', and its encoding, z', and sample from a unit Gaussian z, the loss is given by, $f(x', x, z)=MSE(x', x)+lambda*KL(z, z')$, where MSE is the mean-square-error and KL is the KL-Divergence. The VAEs all had architectures identical to that of the autoencoder G described above. After training, the VAE was used to generate a baseline dataset by sampling from the Gaussian latent-space of the VAE for each cell in the original dataset, and generating an expression profile. The VAEs were trained for 50 epochs, with a batch size of 32, optimized via 40, at a learning rate of 0.00005, with lambda=0.00000001.

Evaluation Based on Proportional Pseudo-Bulk Gene Expression

To calculate pseudo-bulk expression, in each of the SCHAF-inferred, VAE sampled baseline, or original (real) datasets, all of the constituent cells' vectors were first summed to a single pseudo-bulk expression vector, which was then divided by the sum of counts over all genes to yield a (proportional) pseudo-bulk expression probability distribution for each dataset, and then ordered the genes in the vector by increasing proportion in the original (real) dataset. The scipy.stats.pearsonr and scipy.spatial.distance.jensenshannon functions were used to calculate the Pearson correlation coefficient and the Jensen-Shannon divergence between these vectors. To test the significance of improvement in the Pearson correlation coefficient between the real data and the VAE sampled baseline vs. SCHAF, a Fisher-Steiger improvement-of-correlation test[30] was used (as implemented in github.com/psinger/CorrelationStats).

Evaluation Based on Gene-Gene Correlations

To compare the gene-gene relationships in the SCHAF-inferred, VAE sampled baseline, or original (real) datasets, the Pearson correlation coefficient was computed between each pair of genes in each dataset, and correlation matrices of the 100 most highly-variable genes in the original (real) dataset were plotted for each dataset using the numpy.corrcoef function (FIG. 53$a,b$). The "meta-correlations" between the SCHAF-inferred or VAE-sampled baseline and the original (real) datasets matrices were calculated by flattening the portion of each matrix corresponding to these 100 highly-variable genes to a one dimensional vector and calculating the Pearson correlation coefficient using the scipy.stats.pearsonr function.

Evaluation by Gene Count Distributions

To compare the distributions of each gene's expression across cells, for each gene, the distribution of counts over a dataset's cells was considered. For each dataset, and each gene, the distribution was found by first making fifty evenly-spaced bins of counts per cell, calculating the number of cells in each bin and divided each by the total number of cells, to creating a fifty-part discrete probability distribution. For each gene, such a distribution was calculated in SCHAF-inferred, VAE sampled baseline, or original (real) datasets. The Earth Mover's Distance, intuitively the minimum amount of work needed to make one distribution identical to the other, was calculated between the distribution in the original (real) dataset and the SCHAF-inferred or VAE sampled baseline datasets. The pyemd package's emd function was used to find these EMDs. In the setting, such a metric can take on a value anywhere in the interval [0, 50]. The distributions of these EMDs were plotted (FIG. 50$f$) and compared using a Mann-Whitney statistical test, with the scipy package's stats.mannwhitneyu function.

Evaluation by Cell Type Annotations, Composition and Relationship in Low Dimensions To compare cell type composition and clusters in the SCHAF-inferred, VAE sampled baseline, or original (real) datasets, a cell type classifier was first trained on labeled (cell type annotated) cell profiles in the target (real) dataset, and then applied to the SCHAF or random baseline inferred profiles to predict a cell type label for each profile. The classifier followed a vanilla linear neural network architecture, being composed of three sequential [Linear, BatchNorm, ReLU] blocks, followed by one [Linear, SoftMax] block. The dimensions of the four linear layers were, in order, num genes, 1024, 256, 64, and num_cell_types neurons, where num genes was the number of genes in consideration in each cell, and num_cell_types was the number of different celltypes present in the data. The Linear, BatchNorm, ReLU, and SoftMax layers were implemented via, respectively, pytorch's nn.Linear, nn.BatchNormID, nn.ReLU, and nn.Softmax functions. The model was trained according to a standard cross-entropy loss. Next, for each sample, the distribution of probabilities assigned to each cell's assignment by the classifier in the SCHAF-inferred or VAE sampled baseline were compared (FIG. 51$d$) and tested for significance using a Mann-Whitney U test.

To assess the relationship between cell profiles in low dimensions, Uniform Manifold Approximation and Projections (UMAPs[31]) were generated separately for the SCHAF-inferred, VAE sampled baseline, or original (real) datasets, with the scanpy[36] package with default parameters. First, Principal Components Analysis (PCA) was performed with the pp.pca function, retaining the top 50 PCs. Then, a k-nearest neighbor (k-NN) graph was computed (k=15) with the pp.neighbors function, and a UMAP was generated with the tl.umap function, and plotted in two dimensions using the pl.umap function, coloring by cell type annotations (for the real datasets) or classifier prediction (for SCHAF-inferred and VAE-sampled baseline) (FIG. 51*a*).

To quantify the quality of cell type groups, the distributions of cell-type silhouette scores were compared between the SCHAF-inferred, VAE sampled baseline, or original (real) datasets of each evaluation sample (FIG. 51*b*), using the sklearn library's metrics.silhouette_samples function on the principal components computed above.

To examine cell type-specific pseudo-bulk expression profiles (FIG. 51*c*), for each evaluation sample, within each cell type, the pseudo-bulk gene-expression vector was calculated, as described above, for cells annotated by that cell type in the original dataset, or assigned this annotation by the cell-type classifier in SCHAF-inferred or VAE-sampled datasets. The Pearson correlation coefficient was calculated for each cell type between the pseudo-bulk expression vectors of the original data and the the SCHAF-inferred or VAE-sampled datasets random baseline, using the scipy.stats.pearsonr function.

Evaluation of Spatial Gene Expression Compared to MERFISH Data

For samples HTAPP-932 and HTAPP-6760, segmented MERFISH data was converted into an image by first normalizing each cell's MERFISH counts to have sum 1,000, applying the log 1p($f(x)=\log(x+1)$) to each entry, and dividing each entry by 10, and then, starting from an empty image, filling in the 5-pixel-radius circle corresponding to an expression point's coordinates with the measured expression. This image was then resized using the imutis library's resize function and manually aligned with the sample's corresponding H&E image (and thus also with the SCHAF-inferred expression).

These MERFISH-SCHAF images were then tiled for each sample using the same tiling approach as above, but with a slightly larger tile size and stride size of MERFISH-_STRIDE_SIZE to compensate for potential shortcomings in image registration. In both samples, for the 212 genes that are in both SCHAF predictions and MERFISH measurements, the Pearson correlation coefficient between a tile's mean SCHAF expression value and mean MERFISH validation value was calculated, after discarding tiles without expression in both the gene's SCHAF and MERFISH channels. Two baselines were considered, based on the Pearson correlation between MERFISH and either profiles from the corresponding VAE sampled baseline dataset, or randomly placed profiles from the original (real) sc/snRNA-seq data.

Evaluation by Spatial Regional Annotation Compared to Expert Annotations

For samples HTAPP-932 and HTAPP-6760 (FIG. 52*d,e*), spatial annotations were compared between predicted cell-types assigned to each inferred cell by their respective classifiers (as above) and expert annotations of the H&E section. Each tile was colored by the corresponding predicted cell's assigned cell type, and compared to pathologist-assigned regional annotations (FIG. 52).

Data Availability

Links for accession of datasets used in figures can be found at the below links:

MSKCC-133396: MSKCC-146109: HTAPP-932: HTAPP-6760:

Datasets used in training will be published in their respective studies (XX and YY for SCLC; AA and BB for MBC).

REFERENCES FOR EXAMPLE 6

1. Tang, X., Huang, Y., Lei, J., Luo, H. & Zhu, X. The single-cell sequencing: new developments and medical applications. Cell Biosci. 9, 53 (2019).
2. Yan, L. C., Yoshua, B. & Geoffrey, H. Deep learning. Nature 521, 436-444 (2015).
3. Regev, A. et al. The Human Cell Atlas. Elife 6, (2017).
4. Rozenblatt-Rosen, O., Stubbington, M. J. T., Regev, A. & Teichmann, S. A. The Human Cell Atlas: from vision to reality. Nature 550, 451-453 (2017).
5. Regev, A. et al. The Human Cell Atlas White Paper. arXiv [q-bio.TO] (2018).
6. Biancalani, T. et al. Deep learning and alignment of spatially-resolved whole transcriptomes of single cells in the mouse brain with Tangram. bioRxiv 2020.08.29.272831 (2020) doi: 10.1101/2020.08.29.272831.
7 Ding, J. & Regev, A. Deep generative model embedding of single-cell RNA-Seq profiles on hyperspheres and hyperbolic spaces. bioRxiv (2019) doi: 10.1101/853457.
8. van der Laak, J., Litjens, G. & Ciompi, F. Deep learning in histopathology: the path to the clinic. Nat. Med. 27, 775-784 (2021).
9. Ziegenhain, C. et al. Comparative Analysis of Single-Cell RNA Sequencing Methods. Mol. Cell 65, 631-643.e4 (2017).
10. Lähnemann, D. et al. Eleven grand challenges in single-cell data science. Genome Biol. 21, 31 (2020).
11. Luecken, M. D. et al. Benchmarking atlas-level data integration in single-cell genomics. bioRxiv 2020.05.22.111161 (2020) doi: 10.1101/2020.05.22.111161.
12. Chen, K. H., Boettiger, A. N., Moffitt, J. R., Wang, S. & Zhuang, X. RNA imaging. Spatially resolved, highly multiplexed RNA profiling in single cells. Science 348, aaa6090 (2015).
13. Ke, R. et al. In situ sequencing for RNA analysis in preserved tissue and cells. Nat. Methods 10, 857-860 (2013).
14. Chen, X., Sun, Y.-C., Church, G. M., Lee, J. H. & Zador, A. M. Efficient in situ barcode sequencing using padlock probe-based BaristaSeq. Nucleic Acids Res. 46, e22 (2018).
15. Codeluppi, S. et al. Spatial organization of the somatosensory cortex revealed by cyclic smFISH. bioRxiv (2018) doi: 10.1101/276097.
16. Codeluppi, S. et al. Spatial organization of the somatosensory cortex revealed by osmFISH. Nat. Methods 15, 932-935 (2018).
17. Alon, S. et al. Expansion Sequencing: Spatially Precise In Situ Transcriptomics in Intact Biological Systems. bioRxiv 2020.05.13.094268 (2020) doi: 10.1101/2020.05.13.094268.
18. Eng, C.-H. L. et al. Transcriptome-scale super-resolved imaging in tissues by RNA seqFISH. Nature 568, 235-239 (2019).
19. Satija, R., Farrell, J. A., Gennert, D., Schier, A. F. & Regev, A. Spatial reconstruction of single-cell gene expression data. Nat. Biotechnol. 33, 495-502 (2015).
20. Biancalani, T. et al. Deep learning and alignment of spatially resolved single-cell transcriptomes with Tangram. Nat. Methods 18, 1352-1362 (2021).
21. Achim, K. et al. High-throughput spatial mapping of single-cell RNA-seq data to tissue of origin. Nat. Biotechnol. 33, 503-509 (2015).

22. Zhu, H., Luo, M.-D., Wang, R., Zheng, A.-H. & He, R. Deep Audio-visual Learning: A Survey. Int. J. Autom. Comput. 18, 351-376 (2021).
23. Kumar, L. A., Renuka, D. K., Rose, S. L., Shunmuga priya, M. C. & Wartana, I. M. Deep learning based assistive technology on audio visual speech recognition for hearing impaired. International Journal of Cognitive Computing in Engineering 3, 24-30 (2022).
24. Ngiam, J. et al. Multimodal Deep Learning. (2011).
25. Schmauch, B. et al. A deep learning model to predict RNA-Seq expression of tumours from whole slide images. Nat. Commun. 11, 3877 (2020).
26. Isola, P., Zhu, J.-Y., Zhou, T. & Efros, A. A. Image-to-image translation with conditional adversarial networks. in Proceedings of the IEEE conference on computer vision and pattern recognition 1125-1134 (2017).
27. Zhu, J.-Y., Park, T., Isola, P. & Efros, A. A. Unpaired image-to-image translation using cycle-consistent adversarial networks. in Proceedings of the IEEE international conference on computer vision 2223-2232 (2017).
29. Kingma, D. P. & Welling, M. Auto-Encoding Variational Bayes. arXiv [stat. ML] (2013).
30. Howell, D. C. Statistical Methods for Psychology. (Cengage Learning, 2012).
31. McInnes, L., Healy, J. & Melville, J. UMAP: Uniform Manifold Approximation and Projection for Dimension Reduction. arXiv [stat.ML] (2018).
32. Rozenblatt-Rosen, O. et al. The Human Tumor Atlas Network: Charting Tumor Transitions across Space and Time at Single-Cell Resolution. Cell 181, 236-249 (2020).
33. Odena, A., Olah, C. & Shlens, J. Conditional image synthesis with auxiliary classifier gans. in International conference on machine learning 2642-2651 (PMLR, 2017).
34. Wang, X. et al. Three-dimensional intact-tissue sequencing of single-cell transcriptional states. Science 361, (2018).
35. Schofield, J. A., Duffy, E. E., Kiefer, L., Sullivan, M. C. & Simon, M. D. TimeLapse-seq: adding a temporal dimension to RNA sequencing through nucleoside recoding. Nat. Methods 15, 221-225 (2018).
36. Wolf, F. A., Angerer, P. & Theis, F. J. SCANPY: large-scale single-cell gene expression data analysis. Genome Biol. 19, 15 (2018).
37. Paszke, A. et al. PyTorch: An Imperative Style, High-Performance Deep Learning Library. in Advances in Neural Information Processing Systems (eds. Wallach, H. et al.) vol. 32 (Curran Associates, Inc., 2019).
38. Makhzani, A., Shlens, J., Jaitly, N., Goodfellow, I. & Frey, B. Adversarial Autoencoders. arXiv [cs.LG] (2015).
39. Yang, K. D. & Uhler, C. Multi-Domain Translation by Learning Uncoupled Autoencoders. arXiv [cs.LG] (2019).
40. Kingma & Ba. Adam: A method for stochastic gradient descent. ICLR: International Conference on Learning.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

```
Sequence total quantity: 19
SEQ ID NO: 1            moltype = AA  length = 7
FEATURE                 Location/Qualifiers
source                  1..7
                        mol_type = protein
                        organism = Simian virus 40
SEQUENCE: 1
PKKKRKV                                                        7

SEQ ID NO: 2            moltype = AA  length = 10
FEATURE                 Location/Qualifiers
source                  1..10
                        mol_type = protein
                        organism = Simian virus 40
SEQUENCE: 2
PKKKRKVEAS                                                     10

SEQ ID NO: 3            moltype = AA  length = 16
FEATURE                 Location/Qualifiers
REGION                  1..16
                        note = Synthetic
source                  1..16
                        mol_type = protein
                        organism = synthetic construct
SEQUENCE: 3
KRPAATKKAG QAKKKK                                              16

SEQ ID NO: 4            moltype = AA  length = 9
FEATURE                 Location/Qualifiers
source                  1..9
                        mol_type = protein
```

```
                         organism = Homo sapiens
SEQUENCE: 4
PAAKRVKLD                                                          9

SEQ ID NO: 5             moltype = AA  length = 11
FEATURE                  Location/Qualifiers
source                   1..11
                         mol_type = protein
                         organism = Homo sapiens
SEQUENCE: 5
RQRRNELKRS P                                                       11

SEQ ID NO: 6             moltype = AA  length = 38
FEATURE                  Location/Qualifiers
source                   1..38
                         mol_type = protein
                         organism = Homo sapiens
SEQUENCE: 6
NQSSNFGPMK GGNFGGRSSG PYGGGGQYFA KPRNQGGY                          38

SEQ ID NO: 7             moltype = AA  length = 42
FEATURE                  Location/Qualifiers
source                   1..42
                         mol_type = protein
                         organism = Homo sapiens
SEQUENCE: 7
RMRIZFKNKG KDTAELRRRR VEVSVELRKA KKDEQILKRR NV                     42

SEQ ID NO: 8             moltype = AA  length = 8
FEATURE                  Location/Qualifiers
source                   1..8
                         mol_type = protein
                         organism = Homo sapiens
SEQUENCE: 8
VSRKRPRP                                                           8

SEQ ID NO: 9             moltype = AA  length = 8
FEATURE                  Location/Qualifiers
source                   1..8
                         mol_type = protein
                         organism = Homo sapiens
SEQUENCE: 9
PPKKARED                                                           8

SEQ ID NO: 10            moltype = AA  length = 8
FEATURE                  Location/Qualifiers
source                   1..8
                         mol_type = protein
                         organism = Homo sapiens
SEQUENCE: 10
PQPKKKPL                                                           8

SEQ ID NO: 11            moltype = AA  length = 12
FEATURE                  Location/Qualifiers
source                   1..12
                         mol_type = protein
                         organism = Mus sp.
SEQUENCE: 11
SALIKKKKKM AP                                                      12

SEQ ID NO: 12            moltype = AA  length = 5
FEATURE                  Location/Qualifiers
source                   1..5
                         mol_type = protein
                         organism = Influenza virus
SEQUENCE: 12
DRLRR                                                              5

SEQ ID NO: 13            moltype = AA  length = 7
FEATURE                  Location/Qualifiers
source                   1..7
                         mol_type = protein
                         organism = Influenza virus
SEQUENCE: 13
PKQKKRK                                                            7

SEQ ID NO: 14            moltype = AA  length = 10
FEATURE                  Location/Qualifiers
source                   1..10
```

-continued

```
                         mol_type = protein
                         organism = Hepatitis D virus
SEQUENCE: 14
RKLKKKIKKL                                                        10

SEQ ID NO: 15            moltype = AA  length = 10
FEATURE                  Location/Qualifiers
source                   1..10
                         mol_type = protein
                         organism = Mus sp.
SEQUENCE: 15
REKKKFLKRR                                                        10

SEQ ID NO: 16            moltype = AA  length = 20
FEATURE                  Location/Qualifiers
source                   1..20
                         mol_type = protein
                         organism = Homo sapiens
SEQUENCE: 16
KRKGDEVDGV DEVAKKKSKK                                             20

SEQ ID NO: 17            moltype = AA  length = 17
FEATURE                  Location/Qualifiers
source                   1..17
                         mol_type = protein
                         organism = Homo sapiens
SEQUENCE: 17
RKCLQAGMNL EARKTKK                                                17

SEQ ID NO: 18            moltype = AA  length = 288
FEATURE                  Location/Qualifiers
REGION                   1..288
                         note = Synthetic
source                   1..288
                         mol_type = protein
                         organism = synthetic construct
SEQUENCE: 18
MDPIRSRTPS PARELLSGPQ PDGVQPTADR GVSPPAGGPL DGLPARRTMS RTRLPSPPAP  60
SPAFSADSFS DLLRQFDPSL FNTSLFDSLP PFGAHHTEAA TGEWDEVQSG LRAADAPPPT  120
MRVAVTAARP PRAKPAPRRR AAQPSDASPA AQVDLRTLGY SQQQQEKIKP KVRSTVAQHH  180
EALVGHGFTH AHIVALSQHP AALGTVAVKY QDMIAALPEA THEAIVGVGK QWSGARALEA  240
LLTVAGELRG PPLQLDTGQL LKIAKRGGVT AVEAVHAWRN ALTGAPLN              288

SEQ ID NO: 19            moltype = AA  length = 183
FEATURE                  Location/Qualifiers
REGION                   1..183
                         note = Synthetic
source                   1..183
                         mol_type = protein
                         organism = synthetic construct
SEQUENCE: 19
RPALESIVAQ LSRPDPALAA LTNDHLVALA CLGGRPALDA VKKGLPHAPA LIKRTNRRIP  60
ERTSHRVADH AQVVRVLGFF QCHSHPAQAF DDAMTQFGMS RHGLLQLFRR VGVTELEARS  120
GTLPPASQRW DRILQASGMK RAKPSPTSTQ TPDQASLHAF ADSLERDLDA PSPMHEGDQT  180
RAS                                                               183
```

What is claimed is:

1. A computer-implemented method to determine an omics profile of a cell using microscopy imaging data, comprising:
   a. receiving, by at least one computing device, microscopy imaging data of a cell or a population of cells;
   b. determining, by the at least one computing device, a targeted expression profile of a set of target genes from the microscopy imaging data using a first machine learning model, the target genes identifying a cell type or cell state of interest;
   c. determining, by the at least one computing device, a single-cell omics profile for the cell or population of cells using a second machine learning model, wherein the targeted expression profile and a reference single-cell RNA-seq data set are used as input data for the second machine learning model.

2. The method of claim 1, wherein the targeted expression profile is targeted spatial expression profile.

3. The method of claim 1, wherein the microscopy imaging data is obtained from a label-free microscopy method or an in vivo imaging method.

4. The method of claim 1, wherein the cell or population of cells are live or fixed.

5. The method of claim 1, wherein the microscopy imaging data is vibrational hyperspectral imaging data.

6. The method of claim 1, wherein the microscopy imaging data comprises Cell Painting or Cell Profiler.

7. The method of claim 1, further comprising training the first machine learning model using Raman imaging spectra obtained from a sample cell or population of cells as training inputs, and gene expression data obtained for the set of target genes as ground truths.

8. The method of claim 1, further comprising training the first machine learning model using sequencing based omics data, imaging based omics data or spatial omics data.

9. The method of claim 1, wherein the first machine learning model comprises gradient boosting; and/or the second machine learning model comprises neural networks.

10. A system to determine an omics profile of a cell using microscopy imaging data, comprising:

a storage device; and a processor communicatively coupled to the storage device, wherein the processor executes application code instructions that are stored in the storage device to cause the system to:

a) receive microscopy imaging data of a cell or a population of cells;

b) determine a targeted expression profile of a set of target genes from the microscopy imaging data using a first machine learning model, the target genes identifying cell type or cell state of interest; and c) determine a single-cell omics profile for the cell or population of cells using a second machine learning model, wherein the targeted expression profile and a reference single-cell RNA-seq data set are used as input data for the second machine learning model.

11. The system of claim 10, wherein the targeted expression profile is targeted spatial expression profile.

12. The system of claim 10, wherein the microscopy imaging data is obtained from a label-free microscopy method or an in vivo imaging method.

13. The system of claim 10, wherein the microscopy imaging data is vibrational hyperspectral imaging data.

14. The system of claim of 10, wherein the microscopy imaging data comprises Cell Painting or Cell Profiler.

15. The system of claim 10, further comprising training the first machine learning model using Raman imaging spectra obtained from a sample cell or population of cells as training inputs, and gene expression data obtained for the set of target genes as ground truths.

16. The system of claim 10, wherein the first machine learning model is trained based at least on sequencing based omics data, imaging based omics data, or spatial omics data.

17. The system of claim 10, wherein the first machine learning model comprises gradient boosting; and/or the second machine learning model comprises neural networks.

18. A computer program product, comprising:

a non-transitory computer-readable storage device having computer-executable program instructions embodied thereon that when executed by a computer cause the computer to determine an omics profile of a cell using microscopy imaging data, the computer-executable program instructions comprising:

a) computer-executable program instructions to receive microscopy imaging data of a cell or a population of cells;

b) computer-executable program instructions to determine a targeted expression profile of a set of target genes from the microscopy imaging data using a first machine learning model, the target genes identifying cell type or cell state of interest; and c) computer-executable program instructions to determine a single-cell omics profile for the cell or population of cells using a second machine learning model, wherein the targeted expression profile and a reference single-cell RNA-seq data set are used as input data for the second machine learning model.

19. The computer program product of claim 18, wherein the targeted expression profile is targeted spatial expression profile.

20. The method of claim 1, wherein:

the targeted expression profile comprises spatial measurements of expression of the target genes; and determining the single-cell omics profile comprises aligning, by the at least one computing device using the second machine learning model, the spatial measurements to the reference single-cell RNA-seq data.

* * * * *